US009040279B2

(12) United States Patent
Breneman et al.

(10) Patent No.: US 9,040,279 B2
(45) Date of Patent: May 26, 2015

(54) SACCHARIFICATION ENZYME COMPOSITION AND METHOD OF SACCHARIFICATION THEREOF

(75) Inventors: Suzanne Breneman, Orfordville, CA (US); Sung Ho Lee, North Liberty, IA (US); Vivek Sharma, North Liberty, IA (US); Jayarama K. Shetty, Pleasanton, CA (US)

(73) Assignee: DANISCO US INC., Palo Alto, CA (US)

( * ) Notice: Subject to any disclaimer, the term of this patent is extended or adjusted under 35 U.S.C. 154(b) by 960 days.

(21) Appl. No.: 12/478,368

(22) Filed: Jun. 4, 2009

(65) Prior Publication Data

US 2009/0305360 A1 Dec. 10, 2009

Related U.S. Application Data

(60) Provisional application No. 61/059,535, filed on Jun. 6, 2008, provisional application No. 61/165,856, filed on Apr. 1, 2009.

(51) Int. Cl.
| | | |
|---|---|---|
| C12N 9/28 | (2006.01) | |
| C12P 19/14 | (2006.01) | |
| C12P 7/06 | (2006.01) | |
| C08B 37/00 | (2006.01) | |
| A21D 2/00 | (2006.01) | |
| C07H 21/04 | (2006.01) | |
| C12P 7/00 | (2006.01) | |

(52) U.S. Cl.
CPC ... *C12P 7/00* (2013.01); *Y02E 50/17* (2013.01)

(58) Field of Classification Search
None
See application file for complete search history.

(56) References Cited

U.S. PATENT DOCUMENTS

| 4,106,991 | A | 8/1978 | Markussen et al. |
|---|---|---|---|
| 4,435,307 | A | 3/1984 | Barbesgaard et al. |
| RE32,153 | E | 5/1986 | Tamura et al. |
| 4,643,736 | A | 2/1987 | Cholley |
| 4,661,452 | A | 4/1987 | Markussen et al. |
| 5,024,943 | A | 6/1991 | Van Ee |
| 5,112,518 | A | 5/1992 | Klugkist et al. |
| 5,141,664 | A | 8/1992 | Corring et al. |
| 5,240,632 | A | 8/1993 | Brumbaugh |
| 5,281,526 | A | 1/1994 | Good et al. |
| 5,457,046 | A | 10/1995 | Woldike et al. |
| 5,648,263 | A | 7/1997 | Schulein et al. |
| 5,686,593 | A | 11/1997 | Woldike et al. |
| 5,691,178 | A | 11/1997 | Schulein et al. |
| 5,763,254 | A | 6/1998 | Woldike et al. |
| 5,776,757 | A | 7/1998 | Schulein et al. |
| 5,827,718 | A | 10/1998 | Ishida et al. |
| 5,879,920 | A | 3/1999 | Dale et al. |
| 5,942,431 | A | 8/1999 | Yoneda et al. |
| 6,077,316 | A | 6/2000 | Lund et al. |
| 6,287,841 | B1 | 9/2001 | Mulleners et al. |
| 6,440,716 | B1 | 8/2002 | Svendsen et al. |
| 6,475,762 | B1 | 11/2002 | Stafford et al. |
| 7,037,704 | B2 | 5/2006 | Dunn-Coleman et al. |
| 7,332,319 | B2 | 2/2008 | Baldwin et al. |
| 2004/0018607 | A1* | 1/2004 | Callen et al. .................. 435/201 |
| 2006/0014265 | A1 | 1/2006 | Ferrari et al. |
| 2006/0134747 | A1 | 6/2006 | Baldwin et al. |
| 2008/0220498 | A1 | 9/2008 | Cervin et al. |
| 2009/0305360 | A1 | 12/2009 | Breneman et al. |
| 2009/0305935 | A1 | 12/2009 | Cascao-Pereira et al. |
| 2010/0003366 | A1 | 1/2010 | Cuevas et al. |
| 2010/0015686 | A1 | 1/2010 | Cascao-Pereira et al. |

FOREIGN PATENT DOCUMENTS

| AU | 198776638 A | 3/1988 |
|---|---|---|
| AU | 198782147 A | 6/1988 |
| CA | 2023529 | 2/1991 |
| CA | 2006687 C | 12/1994 |
| CA | 2202553 A1 | 4/1996 |
| DE | 37 27 911 A1 | 3/1988 |
| DE | 37 41 617 A1 | 7/1988 |
| DE | 38 33 047 A1 | 4/1990 |
| DE | 41 37 470 A1 | 5/1993 |
| DE | 42 05 071 A1 | 8/1993 |
| DE | 42 12 166 A1 | 10/1993 |
| EP | 0 135 138 A2 | 3/1985 |
| EP | 0 214 761 A2 | 3/1987 |
| EP | 0 218 272 A1 | 4/1987 |
| EP | 0 238 023 A2 | 9/1987 |
| EP | 0 238 216 A1 | 9/1987 |
| EP | 0 258 068 A2 | 3/1988 |
| EP | 0 260 105 A2 | 3/1988 |
| EP | 0 271 155 A2 | 6/1988 |
| EP | 0 271 156 A2 | 6/1988 |
| EP | 0 305 216 A1 | 3/1989 |

(Continued)

OTHER PUBLICATIONS

Sequence alignment of SEQ ID No. 2 with reference to Daiell H, WO2009/108941, publication Sep. 3, 2009 (see PTO892).*
Boel, E. et al. "Glucoamylases G1 and G2 from *Aspergillus niger* are synthesized from two different but closely related mRNAs." *The EMBO Journal* 3(5):1097-1102, 1984.
Cayot, P. et al. "The Quantification of Protein Amino Groups by the Trinitrobenzenesulfonic Acid Method: A Reexamination." *Analytical Biochemistry* 249(2):184-200, 1997.
Chen, H.M. et al. "Substitution of asparagine residues in *Aspergillus awamori* glucoamylase by site-directed mutagenesis to eliminate N-glycosylation and inactivation by deamidation." *Biochem. J.* 301(Pt 1):275-281, 1994.
Chen, H.-M. et al. "Identification and elimination by site-directed mutagenesis of thermolabile aspartyl bonds in *Aspergillus awamori* glucoamylase." *Protein Eng.* 8(6):575-582, 1995.

(Continued)

*Primary Examiner* — Iqbal H Chowdhury
(74) *Attorney, Agent, or Firm* — Danisco US Inc.

(57) ABSTRACT

The present disclosure relates to a *Bacillus subtilis* alpha-amylase (AmyE) or its variants thereof. AmyE or its variants thereof may be used to more efficiently produce fermentable sugars from starch. Also disclosed are a composition comprising a glucoamylase and AmyE or variant thereof and a method of processing starch utilizing the described enzyme composition.

24 Claims, 20 Drawing Sheets

(56) References Cited

FOREIGN PATENT DOCUMENTS

| | | |
|---|---|---|
| EP | 0 318 204 A1 | 5/1989 |
| EP | 0 318 279 A2 | 5/1989 |
| EP | 0 331 376 A2 | 9/1989 |
| EP | 0 346 136 A1 | 12/1989 |
| EP | 0 346 137 A1 | 12/1989 |
| EP | 0 407 225 A1 | 1/1991 |
| EP | 0 414 197 A2 | 2/1991 |
| EP | 0 429 124 A1 | 5/1991 |
| EP | 0 481 547 A1 | 4/1992 |
| EP | 0 495 257 A1 | 7/1992 |
| EP | 0 516 553 A2 | 12/1992 |
| EP | 0 516 554 A2 | 12/1992 |
| EP | 0 516 555 A2 | 12/1992 |
| EP | 0 518 719 A1 | 12/1992 |
| EP | 0 518 720 A1 | 12/1992 |
| EP | 0 518 721 A1 | 12/1992 |
| EP | 0 530 635 A2 | 3/1993 |
| EP | 0 530 870 A1 | 3/1993 |
| EP | 0 533 239 A2 | 3/1993 |
| EP | 0 554 943 A2 | 8/1993 |
| EP | 0 561 446 A2 | 9/1993 |
| EP | 0 561 452 A1 | 9/1993 |
| GB | 1372034 A | 10/1974 |
| GB | 1483591 A | 8/1977 |
| GB | 2200132 A | 7/1988 |
| GB | 2228945 A | 9/1990 |
| GB | 2234980 A | 2/1991 |
| IE | 911797 A1 | 12/1991 |
| JP | 64-074992 | 3/1989 |
| WO | WO 84/02921 A2 | 8/1984 |
| WO | WO 86/01831 A1 | 3/1986 |
| WO | WO 88/02775 A1 | 4/1988 |
| WO | WO 89/01032 A1 | 2/1989 |
| WO | WO 89/06270 A1 | 7/1989 |
| WO | WO 89/06279 A1 | 7/1989 |
| WO | WO 89/09259 A1 | 10/1989 |
| WO | WO 91/16422 A1 | 10/1991 |
| WO | WO 91/17243 A1 | 11/1991 |
| WO | WO 91/17244 A1 | 11/1991 |
| WO | WO 91/18977 A1 | 12/1991 |
| WO | WO 91/19782 A1 | 12/1991 |
| WO | WO 92/00381 A1 | 1/1992 |
| WO | WO 92/01793 A1 | 2/1992 |
| WO | WO 92/05249 A1 | 4/1992 |
| WO | WO 92/06154 A1 | 4/1992 |
| WO | WO 92/06157 A1 | 4/1992 |
| WO | WO 92/08777 A1 | 5/1992 |
| WO | WO 92/17573 A1 | 10/1992 |
| WO | WO 92/19708 A1 | 11/1992 |
| WO | WO 92/19709 A1 | 11/1992 |
| WO | WO 92/19729 A1 | 11/1992 |
| WO | WO 93/03129 A1 | 2/1993 |
| WO | WO 93/04153 A1 | 3/1993 |
| WO | WO93/10210 A1 | 5/1993 |
| WO | WO 93/17089 A1 | 9/1993 |
| WO | WO 93/18129 A1 | 9/1993 |
| WO | WO 93/21297 A1 | 10/1993 |
| WO | WO 93/21299 A1 | 10/1993 |
| WO | WO 93/24618 A1 | 12/1993 |
| WO | WO 93/25651 A1 | 12/1993 |
| WO | WO 94/01541 A1 | 1/1994 |
| WO | WO 94/07998 A1 | 4/1994 |
| WO | WO 94/25578 A1 | 11/1994 |
| WO | WO 94/25583 A1 | 11/1994 |
| WO | WO 95/00636 A1 | 1/1995 |
| WO | WO 95/06720 A1 | 3/1995 |
| WO | WO 95/10602 A1 | 4/1995 |
| WO | WO 95/14783 A1 | 6/1995 |
| WO | WO 95/22615 A1 | 8/1995 |
| WO | WO 95/24471 A1 | 9/1995 |
| WO | WO 95/26397 A1 | 10/1995 |
| WO | WO 95/30744 A2 | 11/1995 |
| WO | WO 95/35381 A1 | 12/1995 |
| WO | WO 96/00292 A1 | 1/1996 |
| WO | WO 96/11262 A1 | 4/1996 |
| WO | WO 96/12012 A1 | 4/1996 |
| WO | WO 96/13580 A1 | 5/1996 |
| WO | WO 96/27002 A1 | 9/1996 |
| WO | WO 96/29397 A1 | 9/1996 |
| WO | WO 96/34108 A2 | 10/1996 |
| WO | WO 97/04079 A1 | 2/1997 |
| WO | WO 97/07202 A1 | 2/1997 |
| WO | WO 98/08940 A1 | 3/1998 |
| WO | WO 98/12307 A1 | 3/1998 |
| WO | WO 98/15257 A1 | 4/1998 |
| WO | WO 98/20115 A1 | 5/1998 |
| WO | WO 98/22613 A1 | 5/1998 |
| WO | WO 99/01544 A1 | 1/1999 |
| WO | WO 99/25846 A2 | 5/1999 |
| WO | WO 99/28448 A1 | 6/1999 |
| WO | WO 99/49740 A1 | 10/1999 |
| WO | WO 00/04136 A1 | 1/2000 |
| WO | WO 01/14629 A1 | 3/2001 |
| WO | WO 01/34899 A1 | 5/2001 |
| WO | WO 02/068589 | 9/2002 |
| WO | WO 2004/091544 | 10/2004 |
| WO | WO 2005/056783 A1 | 6/2005 |
| WO | WO 2005/069849 | 8/2005 |
| WO | WO 2005/111203 A2 | 11/2005 |
| WO | WO 2006/043178 A2 | 4/2006 |
| WO | WO 2006/060062 A2 | 6/2006 |
| WO | 2007145912 A1 | 12/2007 |
| WO | WO2009-108941 * | 9/2009 |
| WO | WO 2009/014935 | 12/2009 |
| WO | WO 2009/149419 | 12/2009 |

OTHER PUBLICATIONS

Chen, H.-M. et al. "Effect of replacing helical glycine residues with alanines on reversible and irreversible stability and production of *Aspergillus awamori* glucoamylase." *Protein Eng.* 9(6):499-505, 1996.

Cho, H.-Y. et al. "Molecular characterization of a dimeric intracellular maltogenic amylase of *Bacillus subtilis* SUH4-2." *Biochimica et Biophysica Acta (BBA)—Protein Structure and Molecular Enzymology* 1478(2):333-340, 2000.

Christophersen, C. et al. "Enzymatic Characterisation of Novamyl, a Thermostable α-Amylase." *Starch—Stärke* 50(1):39-45, 1998.

Cleland, J. et al. "Baumé-Dry Substance Tables for Starch Suspensions." *Industrial & Engineering Chemistry Analytical Edition* 15(5):334-336, 1943.

Conti, M. et al. "Capillary isoelectric focusing: the problem of protein solubility." *Journal of Chromatography A* 757(1-2):237-245, 1997.

Dartois, V. et al. "Cloning, nucleotide sequence and expression in *Escherichia coli* of a lipase gene from *Bacillus subtilis* 168." *Biochimica et Biophysica Acta* 1131(3):253-260, 1992.

Engelen, A.J. et al. "Simple and rapid determination of phytase activity." *Journal of AOAC International* 77(3):760-764, 1994.

Fierobe, H-P et al. "Mutational Modulation of Substrate Bond-Type Specificity and Thermostability of Glucoamylase from *Aspergillus awamori* by Replacement with Short Homologue Active Site Sequences and Thiol/Disulfide Engineering." *Biochemistry* 35(26):8696-8704, 1996.

Fogarty, W.M. et al. "Starch degrading enzymes of microbial origin." *Progress in Industrial Microbiology* 15:87-150, particularly 112-115, 1979.

Fujimoto, Z. et al. "Crystal structure of a catalytic-site mutant [alpha]-amylase from *Bacillus subtilis* complexed with maltopentaose." *Journal of Molecular Biology* 277(2):393-407, 1998.

Hata, Y. et al. "The glucoamylase cDNA from *Aspergillus oryzae*: its cloning, nucleotide sequence, and expression in *Saccharomyces cerevisiae*." *Agric. Biol. Chem.* 55(4):941-949, 1991.

Kagawa, M. et al. "Crystal Structure of *Bacillus subtilis* {alpha}-Amylase in Complex with Acarbose." *J. Bacteriol.* 185(23):6981-6984, 2003.

Kaushik, J.K. et al. "Why Is Trehalose an Exceptional Protein Stabilizer?: An analysis of the thermal stability of proteins in the presence of the compatible osmolyte trehalose." *J. Biol. Chem.* 278(29):26458-26465, 2003.

(56) References Cited

OTHER PUBLICATIONS

Lassmann, T. et al. "Kalign—an accurate and fast multiple sequence alignment algorithm." *BMC Bioinformatics* 6(1):298, 2005.
Li, Y. et al. "Effect of introducing proline residues on the stability of *Aspergillus awamori*." *Protein Eng*. 10(10):1199-1204, 1997.
MacGregor, E.A. et al. "Relationship of sequence and structure to specificity in the [alpha]-amylase family of enzymes." *Biochimica et Biophysica Acta (BBA)—Protein Structure and Molecular Enzymology* 1546(1):1-20, 2001.
McKenzie, T. et al. "The nucleotide sequence of pUB110: some salient features in relation to replication and its regulation." *Plasmid* 15(2):93-103, 1986.
Morris, M.A. et al. "The Effect of Wash Temperature on Removal of Particulate and Oily Soil from Fabrics of Varying Fiber Content." *Textile Research Journal* 52(4):280-286, 1982.
Ohdan, K. et al. "Characteristics of Two Forms of alpha -Amylases and Structural Implication." *Appl. Environ. Microbiol*. 65(10):4652-4658, 1999.
Yang, M. et al. "Nucleotide sequence of the amylase gene from *Bacillus subtilis*." *Nucl. Acids Res*. 11(2):237-250, 1983.
Database UnitProt p. 1 1998, Ohdan et al: "Characteristic of two of alpha-amylases and structural implication", Database accession No. 082953.
Database UnitProt pp. 1-5 1986, Various Authors: "various titles". Database accession No. P00691.
Database UnitProt p. 1, Jan. 2008 Xin et al: "Cloning and expression of *Bacillus subtilis* FS321 alpha-amylase gene", Database accession No. A8W7J1.
De Moraes et al. "development of yeast strains for the efficient utilization of starch: evaluation of constructs that express alpha-amylase and glucoamylase separately or bifunctional fusion proteins", Applied Microbiology and Biotechnology, vol. 43, 1995, pp. 1067-1076.
Fujimoto et al. "Crystal structure of a catalytic-site mutant alpha-amylase from*Bacillus subtilis* complexed with maltopentaose", Journal of Molecular Biology, vol. 277, 1998, pp. 393-407.
Hayashida et al. "Production and characteristics of raw-potato-starch-digesting alpha-amylase from *Bacillus subtilis* 65", Applied and Environmental Microbiology, vol. 54, 1988, pp. 1516-1522.
Konsoula et al. "Alpha-amylases and glucoamylases free or immobilized in calcium alginate gel capsules for synergistic hydrolysis of crude starches", Amino Acids, vol. 33, 2007, pp. XIII.
Liu et al. "A novel raw starch digesting alpha-amylase from a newly isolated *Bacillus* sp. YX-1: Purification and characterization", Bioresource Technology, vol. 99, Oct. 24, 2007 pp. 4315-4320.
Sodhi et al. "Production of a thermostable alpha-amylase from *Bacillus* sp. PS-7 by solid state fermentation and its synergistic use in the hydrolysis of malt starch for alcohol production", Process Biochemistry, vol. 40, 2005.
Yeesang et al. "Sago starch as a low-cost carbon source for exopolysaccharide production by *Lactobacillus kefiranofaciens*" World Journal of Microbiology and Biotechnology, vol. 24, Nov. 15, 2007, pp. 1195-1201.
PCT Search Report for PCT Application No. PCT/US2009/046296, mailed Nov. 10, 2009.
PCT Search Report for PCT Application No. PCT/US2009/046279, 3 pages.
& Database Uniprot [Online]Jul. 21, 1986, "RecName: Full=Alpha-amylase; EC=<AHREF=" http://srs.ebi.ac.uk/srsbin/cgi-bin/wgetz?[enzyme-ECNumber:3.2.1.1]+-e">3.2.1.1.</A>;AltName: Full=1,4-alpha-D-glucan glucanohydrolase; Flags: Precurser; " retrieved from EBI accession No. UNIPROT:P00691 Database accession No. P00691 compound.
& Database UniProt [Online] May 1, 2000, "SubName: Full=Alpha-amylase;" retrieved from EBI accession No. UNIPROT:Q9R9H7.
Barbe et al. "From a consortium sequence to a unified sequence: the *Bacillus subtilis*168 reference genome a decade later," Microbiology 2009, 155 (PT 6), pp. 1758-1775.

Broun et al, Catalytic plasticity of fatty acid modification enzymes underlying chemical diversity of plant lipids. Science, 1998, vol. 282: 1315-1317.
Chico et al., Semi-rational approaches to engineering enzyme activity: combining the benefits of directed evolution and rational design. Curro Opi. Biotechnol., 2005, vol. 16: 378-384.
Cho et al., "Molecular characterization of a dimeric intracellular maltogenic amylase of *Bacillus subtilis*SUH4-2", Biochemica et Biophysica Acta 1478 (2000), pp. 333-340.
Devos et al., Practical limits of function prediction. Proteins: Structure, Function, and Genetics. 2000, vol. 41: 98-107.
Eichenberger et al, "The program of gene transcription for a single differentiating cell type during sporulation in *Bacillus subtilis*" PLoS biol. 2(10), E328 (2004).
Emori et al., "Molecular Cloning, Nucleotide Sequencing, and Expression of the *Bacillus subtilis*(*natto*) IAM1212 α-Amylase Gene, Which Encodes an α-Amylase Structurally Similar to but Enzymatically Distinct from That of *B. subtilis*2633," J. Bacteriol. (1990) 172(9): 4901-08.
Freire, E. (1995) Differential Scanning Calorimetry Methods. Mol. Biol. 41:191-218.
GenBank: ABK54355.1. Printed Jan. 27, 2012. http://www.ncbi.nlm.nih.gov/protein/117650733?report=genbank&log$=protalign&blast_rank=5&RID=HHEG2BRJ01N.
GenBank: ABS72727.1. Printed Jan. 27, 2012. http://www.ncbi.nlm.nih.gov/protein/154350648?report=genbank&log$=protalign&blast_rank=17&Rid=HHEG2BRJ01N.
GenBank: ABW34932.1. Printed Jan. 27, 2012. http://www.ncbi.nlm.nih.gov/protein/158342342?report=genbank&log$=protalign&blast_rank=33&RID=HHEG2BRJ01N.
GenBank: ABW75769.1. Printed Jan. 27, 2012. http://www.ncbi.nlm.nih.gov/protein/158633403?report=genbank&log$=protalign&blast_rank=7&RID=HHEG2BRJ01N.
GenBank: ABY73736.1. Printed Jan. 27, 2012. http://www.ncbi.nlm.nih.gov/protein/165909652?report=genbank&log$=protalign&blast_rank=21&Rid=HHEG2BRJ01N.
GenBank: ACD93218.3. Printed Jan. 27, 2012. http://www.ncbi.nlm.nih.gov/protein/288915565?report=genbank&log$=protalign&blast_rank=15&RID=HHEG2BRJ01N.
GenBank: ACK37366.1. Printed Jan. 27, 2012. http://www.ncbi.nlm.nih.gov/protein/217315807?report=genbank&log$=protalign&blast_rank=30&RID=HHEG2BRJ01N.
GenBank: ACM91731.1. Printed Jan. 27, 2012.
GenBank: ACU57501.1. Printed Jan. 27, 2012. http://www.ncbi.nlm.nih.gov/protein/256033945?report=genbank&log$=protalign&blast_rank=36&RID=HHEG2BRJ01N.
GenBank: ADB81848.1. Printed Jan. 27, 2012. http://www.ncbi.nlm.nih.gov/protein/284178231?report=genbank&log$=protalign&blast_rank=19&RID=HHEG2BRJ01N.
GenBank: ADF47479.1. Printed Jan. 27, 2012. http://www.ncbi.nlm.nih.gov/protein/294906521?report=genbank&log$=protalign&blast_rank=18&RID=HHEG2BRJ01N.
GenBank: ADH93703.1. Printed Jan. 27, 2012. http://www.ncbi.nlm.nih.gov/protein/296933182?report=genbank&log$=protalign&blast_rank=48RID=HHEG2BRJ01N.
GenBank: ADH93704.1. Printed Jan. 27, 2012. http://www.ncbi.nlm.nih.gov/protein/296933184?report=genbank&log8=protalign&blast_rank=2&RID=HHEG2BRJ01N.
GenBank: ADH93705.1. Printed Jan. 27, 2012. http://www.ncbi.nlm.nih.gov/protein/296933186?report=genbank&log8=protalign&blast_rank=3&RID=HHEG2BRJ01N.
GenBank: ADH93706.1. Printed Jan. 27, 2012. http://www.ncbi.nlm.nih.gov/protein/296933188?report=genbank&log8=protalign&blast_rank=10&RID=HHEG2BRJ01N.
GenBank: ADH93707.1. Printed Jan. 27, 2012. http://www.ncbi.nlm.nih.gov/protein/296933190?report=genbank&log8=protalign&blast_rank=24&RID=HHEG2BRJ01N.
GenBank: ADM36368.1. Printed Jan. 27, 2012. http://www.ncbi.nlm.nih.gov/protein/305411249?report=genbank&log8=protalign&blast_rank=14&RID=HHEG2BRJ01N.
GenBank: ADV95234.1. Printed Jan. 27, 2012. http://www.ncbi.nlm.nih.gov/protein/320020248?report=genbank&log8=protalign&blast_rank=1&RID=HHEG2BRJ01N.

(56) References Cited

OTHER PUBLICATIONS

GenBank: AEP85220.1. Printed Jan. 27, 2012. http://www.ncbi.nlm.nih.gov/protein/349597432?report=genbank&log8=protalign&blast_rank=13&RID=HHEG2BRJ01N.
GenBank: AEP89368.1. Printed Jan. 27, 2012. http://www.ncbi.nlm.nih.gov/protein/349593181?report=genbank&log8=protalign&blast_rank=9&RID=HHEG2BRJ01N.
GenBank: AL009126.3 region 90537-92086. Printed Jan. 27, 2012.
GenBank: BAA08938.1. Printed Jan. 27, 2012. http://www.ncbi.nlm.nih.gov/protein/1805376?report=genbank&log8=protalign&blast_rank=12&RID=HHEG2BRJ01N.
GenBank: BAA31528.1. Printed Jan. 27, 2012. http://www.ncbi.nlm.nih.gov/protein/3298505?report=genbank&log8=protalign&blast_rank=23&RID=HHEG2BRJ01N.
GenBank: BAI83766.1. Printed Jan. 27, 2012. http://www.ncbi.nlm.nih.gov/protein/291482691?report=genbank&log8=protalign&blast_rank=31&RID=HHEG2BRJ01N.
GenBank: CAA23437.1. Printed Jan. 27, 2012. http://www.ncbi.nlm.nih.gov/protein/39794?report=genbank&log8=protalign&blast_rank=12&RID=HHEG2BRJ01N.
GenBank: CAA26086.1. Printed Jan. 27, 2012. http://www.ncbi.nlm.nih.gov/protein/39796?report=genbank&log8=protalign&blast_rank=29&RID=HHEG2BRJ01N.
GenBank: CAA30643.1. Printed Jan. 27, 2012. http://www.ncbi.nlm.nih.gov/protein/39790?report=genbank&log8=protalign&blast_rank=28&RID=HHEG2BRJ01N.
GenBank: CAB12098.2. Printed Jan. 27, 2012. http://www.ncbi.nlm.nih.gov/protein/225184709?report=genbank&log8=protalign&blast_rank=1&RID=HHEG2BRJ01N.
GenBank: CAJ01439.1. Printed Jan. 27, 2012. http://www.ncbi.nlm.nih.gov/protein/67624833?report=genbank&log8=protalign&blast_rank=38&RID=HHEG2BRJ01N.
GenBank: CCF03805.1. Printed Jan. 27, 2012. http://www.ncbi.nlm.nih.gov/protein/371566955?report=genbank&log8=protalign&blast_rank=20&RID=HHEG2BRJ01N.
GenBank: EFG90830.1. Printed Jan. 27, 2012. http://www.ncbi.nlm.nih.gov/protein/296149941?report=genbank&log8=protalign&blast_rank=14&RID=HHEG2BRJ01N.
GenBank: EHA28753.1. Printed Jan. 27, 2012. http://www.ncbi.nlm.nih.gov/protein/351468537?report=genbank&log8=protalign&blast_rank=1&RID=HHEG2BRJ01N.
GenBank: EHM06463.1. Printed Jan. 27, 2012. http://www.ncbi.nlm.nih.gov/protein/363726325?report=genbank&log8=protalign&blast_rank=22&RID=HHEG2BRJ01N.
Gene ID: 11238201. Printed Jan. 27, 2012. http://www.ncbi.nlm.nih.gov/sites/entrez?db=gene&cmd=search&term=11238201&RID=HHEG2BRJ01N&log8=geneexplicitprot&blast_rank=13.
Gene ID: 5462160. Printed Jan. 27, 2012. http://www.ncbi.nlm.nih.gov/sites/entrez?db=gene&cmd=search&term=5462160&Rid=HHEG2BRJ01N&log$=geneexplicitprot&blast_rank=17.
Kunamneni, A., et al. "Response surface optimization of enzymatic hydrolysis of maize starch for higher glucose production" *Bichem EngJ*:27 (2005) pp. 179-190.
Kunst et al, "The complete genome sequence of the gram-positive bacterium *Bacillus subtilis*" Nature 390(6667), pp. 249-256 (1997).
Mäntsälä et al., "Membrane-bound and Soluble Extracellular α-Amylase from *Bacillus subtilis*," J. Biol. Chem. (1979) 254(17): 8540-47.
Mizuno et al., "Systematic sequence of the 263 kb 210 degrees-232 degrees region of the *Bacillus subtilis* genome containing the skin element and many sporulation genes", Microbiology 142 (PT 111), pp. 3103-3111 (1996); NCBI Genome Project, "Direct Submission", submitted ('Aug. 12, 2009) National Center for Biotechnology Information, NIH, Bethesda, MD 20894, USA.

Mizuno H. et al,. "Crystallization and preliminary X-ray studies of wild type and catalytic-site mutant alpha-amylase from *Bacillus subtilis*," J Mol Biol. Dec 20, 1993, 234(4). pp. 1282-1283.
NCBI Reference Sequence: NP_388186.2. Printed Jan. 27, 2012. http://www.ncbi.nlm.nih.gov/protein/255767082?report=genbank&log8=protalign&blast_rank=1&RID=HHEG2BRJ01N.
NCBI Reference Sequence: YP_001419958.1. Printed Jan. 27, 2012. http://www.ncbi.nlm.nih.gov/protein/154684797?report=genbank&log8=protalign&blast_rank=17&RID=HHEG2BRJ01N.
NCBI Reference Sequence: YP_003864677.1. Printed Jan. 27, 2012. http://www.ncbi.nlm.nih.gov/protein/305673005?report=genbank&log8=protalign&blast_rank=14&RID=HHEG2BRJ01N.
NCBI Reference Sequence: YP_004206261.1. Printed Jan. 27, 2012. http://www.ncbi.nlm.nih.gov/protein/321313974?report=genbank&log8=protalign&blast_rank=1&RID=HHEG2BRJ01N.
NCBI Reference Sequence: YP_004875852.1. Printed Jan. 27, 2012. http://www.ncbi.nlm.nih.gov/protein/350264545?report=genbank&log8=protalign&blast_rank=13&RID=HHEG2BRJ01N.
NCBI Reference Sequence: ZP_03598671.1. Printed Jan. 27, 2012. http://www.ncbi.nlm.nih.gov/protein/221317377?report=genbank&log8=protalign&blast_rank=11&RID=HHEG2BRJ01N.
NCBI Reference Sequence: ZP_06875121.1. Printed Jan. 27, 2012. http://www.ncbi.nlm.nih.gov/protein/296332661?report=genbank&log8=protalign&blast_rank=14&RID=HHEG2BRJ01N.
Orlando et al., "The purification of a novel amylase from *Bacillus subtilis* and its inhibition by wheat proteins," *Biochem. J.*(1983) 209: 561-64.
PDB: 1BAG_A. Printed Jan. 27, 2012. http://www.ncbi.nlm.nih.gov/protein/157830193?report=genbank&log8=protalign&blast_rank=35&RID=HHEG2BRJ01N.
PDB: 1 UA7_A. Printed Jan. 27, 2012. http://www.ncbi.nlm.nih.gov/protein/49259314?report=genbank&log8=protalign&blast_rank=37&RID=HHEG2BRJ01N.
PDB: 3DCO_A. Printed Jan. 27, 2012. http://www.ncbi.nlm.nih.gov/protein/190613740?report=genbank&log8=protalign&blast_rank=39&RID=HHEG2BRJ01N.
PRF: 226106. Printed Jan. 27, 2012. http://www.ncbi.nlm.nih.gov/protein/226106?report=genbank&log8=protalign&blast_rank=28&RID=HHEG2BRJ01N.
PRF: 352984. Printed Jan. 27, 2012. http://www.ncbi.nlm.nih.gov/protein/352984?report=genbank&log8=protalign&blast_rank=32&RID=HHEG2BRJ01N.
Rumbak et al. (J. Bacteriology, vol. 173, pp. 4203-4211, 1991).
Seffernick et al., Melamine deaminase and Atrazine chlorohydrolase: 98 percent identical but functionally different. J. Bacteriol., 2001, vol. 183 (8): 2405-2410.
Sen et al., Developments in directed evolution for improving enzyme functions. Appl. Biochem. Biotechnol., 2007, vol. 143: 212-223.
Swiss-Prot: P00691.2. Printed Jan. 27, 2012. http://www.ncbi.nlm.nih.gov/protein/239938593?report=genbank&log8=protalign&blast_rank=1&RID=HHEG2BRJ01N.
Whisstock et al., Prediction of protein function from protein sequence. Q. Rev. Biophysics., 2003, vol. 36 (3): 307-340.
Witkowski et al., Conversion of b-ketoacyl synthase to a Malonyl Decarboxylase by replacement of the active cysteine with glutamine. Biochemistry, 1999, vol. 38: 11643-11650.
Written Opinion of the International Search Authority for PCT/US2009/046506 dated Dec. 6, 2010.
Yamazaki et al., "α-Amylase Genes (*amyR2 and amyE*) from an α-Amylase-Hyperproducing *Bacillus subtilis* Strain: Molecular Cloning and Nucleotide Sequences", Journal of Bacteriology, Oct. 1983, pp. 327-337.

* cited by examiner

FIG. 1

```
B. stear    MLTFHRIIRKGWMFLLA---FLLTALLFCPTGQPAKAAAPFN---------GTMMQYFEW
B. lich     MKQQKRLYAR----LLT---LLFALIFLLP--HSAAAAANLN---------GTLMQYFEW
B. sub      --MFAKRFKTSLLPLFAGFLLLFHLVLAGPAAASAETANKSNELTAPSIKSGTILHAWNW B. stear    YLPDDGTLWTKVANEANNLSSLGITALWLPPAYK---GTSRSDVGYGVYDLYDLGEFNQK
B. lich     YMPNDGQHWKRLQNDSAYLAEHGITAVWIPPAYK---GTSQADVGYGAYDLYDLGEFHQK
B. sub      -------SFNTLKHNMKDIHDAGYTAIQTSPINQVKEGNQGDKSMSNWYWLYQPTSYQ--

B. stear    GAVRTKY-GTKAQYLQAIQAAHAAGMQVYADVVFDHKGGADGTEWVDAVEVNPSDRNQEI
B. lich     GTVRTKY-GTKGELQSAIKSLHSRDINVYGDVVINHKGGADATEDVTAVEVDPADRNRVI
B. sub      --IGNRYLGTEQEFKEMCAAAEEYGIKVIVDAVINH-------------TTSDYAAIS B. stear    SGTYQIQAWTKFDFPGRGNTYSSFKWRWYHFDGVDWDESRKLSRIYKFRGIGKAWDWEVD
B. lich     SGEHRIKAWTHFHFPGRGSTYSDFKWHWYHFDGTDWDESRKLNRIYKFQG--KAWDWEVS
B. sub      NEVKSIPNWTH------GNTQIK----------NWSDR--------------WDVTQN B. stear    TENGNYDYLMYADLDMDHPEVVTELKSWGKWYVNTTNIDGFRLDAVKHIKF----SFFPD
B. lich     NENGNYDYLMYADIDYDHPDVAAEIKRWGTWYANELQLDGFRLDAVKHIKF----SFLRD
B. sub      SLLGLYDW------NTQNTQVQSYLKRFLDRALND-GADGFRFDAAKHIELPDDGSYGSQ B. stear    WLSDVRSQTGKPLFTVGEYWSYDINKLHNYIMKTNGTMSLFDAPLHNKFYTASKSGGTFD
B. lich     WVNHVREKTGKEMFTVAEYWQNDLGALENYLNKTNFNHSVFDVPLHYQFHAASTQGGGYD
B. sub      FWPNITNTSAE--FQYGEILQDSASRDAAYANYMDVTASNYGHSIRSAL--KNRNLGVSN B. stear    MRTLMTNTLMKDQPTLAVTFVDNHDTEPGQALQSWVDPWFKP----LAYAFILTRQEGYP
B. lich     MRKLLNSTVVSKHPLKAVTFVDNHDTQPGQSLESTVQTWFKP----LAYAFILTRESGYP
B. sub      ISHYASDVSADK----LVTWVESHDTYANDDEES---TWMSDDDIRLGWAVIASRSGSTP B. stear    CVFYGDYYGI---PQYNIPSLKSKIDPLLIARRDYAYGTQHDYLDHSDIIGWTREGVTEK
B. lich     QVFYGDMYGTKGDSQREIPALKHKIEPILKARKQYAYGAQHDYFDHHDIVGWTREGDSSV
B. sub      -LFFSRPEG--GGNGVRFPGKSQIGDRGSALFEDQAITAVNRF---HNVMAGQPEELSNP B. stear    PGSGLAALITDGPGGSKWMYVGKQHAG-KVFYDLTGNRSDTVTINSDGWGEFKVNGGSVS
B. lich     ANSGLAALITDGPGGAKRMYVGRQNAG-ETWHDITGNRSEPVVINSEGWGEFHVNGGSVS
B. sub      NGNNQIFMNQRGSHGVVLANAGSSSVSINTATKLPDGRYD----NKAGAGSFQVNDGKLT B. stear    VWVPRKTTVSTIAWSITTRPWTDEFVRWTEPRLVAWP-----------------------
B. lich     IYVQR------------------------------------------------------
B. sub      GTINA-RSVAVL--------YPDDIAKAPHVFLENYKTGVTHSFNDQLTITLRADANTTK B. stear    ------------------------------------------------------------
B. lich     ------------------------------------------------------------
B. sub      AVYQINNGPDDRRLRMEINSQSEKEIQFGKTYTIMLKGTNSDGVTRTEKYSFVKRDPASA B. stear    ------------------------------------------------------------
B. lich     ------------------------------------------------------------
B. sub      KTIGYQNPNHWSQVNAYIYKHDGSRVIELTGSWPGKPMTKNADGIYTLTLPADTDTTNAK B. stear    ----------------------------------
B. lich     ----------------------------------
B. sub      VIFNNGSAQVPGQNQPGFDYVLNGLYNDSGLSGSLPH
```

FIG. 4

```
AmyE_FL      1  LTAPSIKSGTILHAWNWSFNTLKHNMKDIHDAGYTAIQTSPINQVKEGNQGDKSMSNWYW
Amy31A      42  VTASSVKNGTILHAWNWSFNTLTQNMKDIRDAGYAAIQTSPINQVKEGNQGDKSMSNWYW

AmyE_FL     61  LYQPTSYQIGNRYLGTEQEFKEMCAAAEEYGIKVIVDAVINHTISDYAAISNEVKSIPNW
Amy31A     102  LYQPTSYQIGNRYLGTEQEFKDMCAAAEKYGVKVIVDAVVNHTISDYGAISDEIKRIPNW

AmyE_FL    121  THGNTQIKNWSDRWDVTQNSLLGLYDWNTQNIQVQSYLKRFLDRAINDGADGFRFDAAKH
Amy31A     162  THGNTQIKNWSDRWDITQNALLGLYDWNTQNIEVQAYLKGFLERAINDGADGFRYDAAKH

AmyE_FL    181  IELPDDGSYGSQFWPNITNTSAEFQYGEILQDSASRDAAYANYMDVTASNYGHSIRSALK
Amy31A     222  IELPDDGNYGSQFWPNITNTSAEFQYGEILQDSASRDTAYANYMNVTASNYGHSIRSALK

AmyE_FL    241  NRNLGVSNISHYASDVSADKLVTWVESHDTYANDDEESTWMSDDDIRLGWAVIASRSGST
Amy31A     282  NRILSVSNISHYASDVSADKLVTWVESHDTYANDDEESTWMSDDDIRLGWAVIGSRSGST

AmyE_FL    301  PLFFSRPEGGGNGVRFPGKSQIGDRGSALFEDQAITAVNRFHNVMAGQPEEISNPNGNNQ
Amy31A     342  PLFFSRPEGGGNGVRFPGKSQIGDRGSALFKDQAITAVNQFHNEMAGQPEEISNPNGNNQ

AmyE_FL    361  IFMNQRGSHGVVLANAGSSSVSINTATKLPDGRYDNKAGAGSFQVNDGKLTGTINARSVA
Amy31A     402  IFMNQRGSKGVVLANAGSSSVTINTSTKLPDGRYDNRAGAGSFQVANGKLTGTINARSAA

AmyE_FL    421  VLYPDDIAKAPHVFLENYKTGVTHSFNDQLTITIRADANTTKAVYQINNGPETAFKDGDQ
Amy31A     462  VLYPDDIGNAPHVFLENYQTEAVHSFNDQLTVTIRANAKTTKAVYQINNGQETAFKDGDR

AmyE_FL    481  FTIGKGDPFGKTYTIMIKGTNSDGVTRTEKYSFVKRDPASAKTIGYQNPNHWSQVNAYIY
Amy31A     522  LTIGKEDPIGTTYNVKITGTNGEGASRTQEYTFVKKDPSQTNIIGYQNPDHWGNVNAYIY

AmyE_FL    541  KHDGSRVIELTGSWPGKPMTKNADGIYTLTLPADTDTTNAKVIFNNGSAQVPGQNQPGFD
Amy31A     582  KHDGGGAIELTGSWPGKAMTKNADGIYTLTLPANADTADAKVIFNNGSAQVPGQNHPGFD

AmyE_FL    601  YVLNGLYNDSGLSGSLPH (SEQ ID NO: 1)
Amy31A     642  YVQNGLYNNSGLNGYLPH (SEQ ID NO: 35; note that this is equivalent to
SEQ ID NO: 3 without the signal sequence)
```

SACCHARIFICATION ENZYME COMPOSITION AND METHOD OF SACCHARIFICATION THEREOF

CROSS-REFERENCE

This application claims priority to U.S. Provisional Patent Application Ser. Nos. 61/059,535 filed Jun. 6, 2008 and 61/165,856 filed Apr. 1, 2009, both of which are incorporated herein by reference.

SEQUENCE LISTING

A Sequence Listing, comprising SEQ ID NOs: 1-34, is attached and incorporated herein by reference in its entirety.

FIELD OF THE INVENTION

A composition comprising a glucoamylase and a *Bacillus subtilis* alpha-amylase (AmyE) or variant thereof is useful in producing fermentable sugars from starch substrate, for example. Methods of using a glucoamylase and an AmyE or variant thereof to produce ethanol from starch, for example, are also disclosed.

BACKGROUND

Vegetable starches, e.g., cornstarch, are widely used in the industrial manufacture of products such as syrups and biofuels. For example, high fructose corn syrup (HFCS) is a processed form of corn syrup having high fructose content and a sweetness comparable to sugar, making HFCS useful as a sugar substitute in soft drinks and other processed foods. HFCS production currently represents a billion dollar industry. Similarly, the production of ethanol from vegetable starches is a rapidly expanding industry. Ethanol has widespread applications as an industrial chemical, a gasoline additive, or a liquid fuel by itself. The use of ethanol as a fuel or fuel additive significantly reduces air emissions while maintaining or even improving engine performance. On the other hand, ethanol is a renewable fuel, so that its use may reduce dependence on finite fossil fuel sources. Furthermore, use of ethanol may decrease the net accumulation of carbon dioxide in the atmosphere.

Syrups and biofuels can be produced from starch by an enzymatic process that catalyzes the breakdown of starch into glucose. This enzymatic process typically involves a sequence of enzyme-catalyzed reactions:

(1) Liquefaction: Alpha-amylases (EC 3.2.1.1) first catalyze the degradation of a starch suspension, which may contain 30-40% w/w dry solids (ds), to maltodextrans. Alpha-amylases are endohydrolases that catalyze the random cleavage of internal $\alpha$-1,4-D-glucosidic bonds. Because liquefaction typically is conducted at high temperatures, e.g., 90-100° C., thermostable alpha-amylases, such as an alpha-amylase from *Bacillus* sp., are preferred for this step. Alpha-amylases currently used for this step, e.g., alpha-amylases from *B. licheniformis* (AmyL), *B. amyloliquefaciens*, and *Geobacillus stearothermophilus* (AmyS), do not produce significant amounts of glucose. Instead, the resulting liquefact has a low dextrose equivalent (DE) and contains maltose and sugars with high degrees of polymerization (DPn).

(2) Saccharification: Glucoamylases and/or maltogenic alpha-amylases catalyze the hydrolysis of non-reducing ends of the maltodextrans formed after liquefaction, releasing D-glucose, maltose and isomaltose. Saccharification produces either glucose-rich or high-maltose syrups. In the former case, glucoamylases typically catalyze saccharification under acidic conditions at elevated temperatures, e.g., 60° C., pH 4.3. Glucoamylases used in this process typically are obtained from fungi, e.g., *Aspergillus niger* glucoamylase used in Optidex® L400 or *Humicola grisea* glucoamylase. De-branching enzymes, such as pullulanases, can aid saccharification.

Maltogenic alpha-amylases alternatively may catalyze saccharification to form high-maltose syrups. Maltogenic alpha-amylases typically have a higher optimal pH and a lower optimal temperature than glucoamylase, and maltogenic amylases typically require $Ca^{2+}$. Maltogenic alpha-amylases currently used for this application include *B. subtilis* alpha-amylases, plant amylases, and the alpha-amylase from *Aspergillus oryzae*, the active ingredient of Clarase® L. Exemplary saccharification reactions used to produce various products are depicted below:

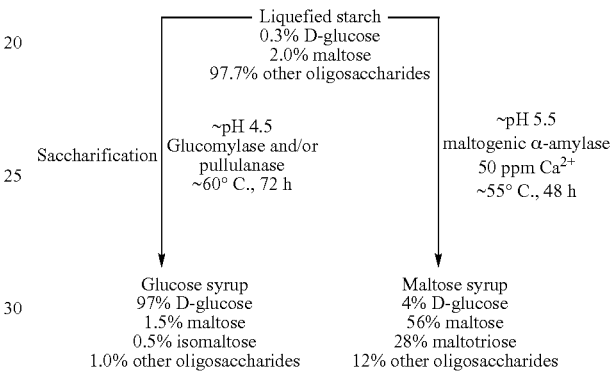

(3) Further processing: A branch point in the process occurs after the production of a glucose-rich syrup, shown on the left side of the reaction pathways above. If the final desired product is a biofuel, yeast can ferment the glucose-rich syrup to ethanol. On the other hand, if the final desired product is a fructose-rich syrup, glucose isomerase can catalyze the conversion of the glucose-rich syrup to fructose.

Saccharification is the rate-limiting step in the production of a glucose-rich syrup. Saccharification typically occurs over 48-72 hours, by which time many fungal glucoamylases lose significant activity. Moreover, it takes a significant portion, e.g., more than 70%, of saccharification time for the glucose yield to increase from 85% to 96%. This is mainly due to the inefficient hydrolysis of low molecular weight oligosaccharides by the glucoamylase. Accordingly, maximization of glucose production would require a relatively high dose of glucoamylase and/or a longer saccharification period. Furthermore, although maltogenic alpha-amylases and glucoamylases both can catalyze saccharification, the enzymes typically operate at different optimal pH and temperatures, as shown above. If both enzymes are used sequentially, the difference in reaction conditions between the two enzymes necessitates adjusting the pH and temperature, which slows down the overall the process and may give rise to the formation of insoluble amylose aggregates.

Accordingly, there is a need in the art for an improved starch processing method to make industrial products. In particular, there is a need for improved efficiencies in a saccharification step.

SUMMARY

Starch processing is useful, for example, in producing sweeteners, producing alcohol for fuel or drinking (i.e., potable alcohol), producing beverages, processing cane sugar, or producing desired organic compounds, e.g., citric acid, itaconic acid, lactic acid, gluconic acid, ketones, amino acids, antibiotics, enzymes, vitamins, and hormones. To facilitate starch processing, an alpha-amylase from *Bacillus subtilis* (AmyE) is provided. AmyE exhibits properties different from the Termamyl-like alpha-amylases, such as the alpha-amylases from *Bacillus licheniformis* and *Bacillus stearothermophilus*. AmyE has a previously unrecognized transglucosidase activity and is able to synthesize maltotriose from maltose. In addition, AmyE is able to hydrolyze maltose, high DP substrates, or even uncooked granular starch to glucose. Adding AmyE or variant thereof and a glucoamylase to saccharification results in, among other things, a higher level of fermentable sugars, and a reduced level of higher sugars. The dose of glucoamylase is significantly reduced in saccharification supplemented with AmyE. In addition, AmyE or variant thereof is able to mitigate the "glucose surge" in simultaneous saccharification and fermentation catalyzed by *Trichoderma reesei* glucoamylase. Furthermore, use of AmyE or variant thereof in saccharification, for example, significantly improves production of high fructose corn syrup (HFCS) or ethanol from starch.

The present disclosure provides a composition for saccharifying a starch comprising a glucoamylase and an alpha-amylase. The alpha-amylase is a *Bacillus subtilis* alpha-amylase (AmyE) or an AmyE variant having an amino acid sequence with at least about 80%, about 85%, about 90%, about 95%, or about 98% identity to an AmyE having an amino acid sequence of SEQ ID NO: 1. In one aspect, the alpha-amylase may have a similar level of transglucosidase activity as an AmyE having an amino acid sequence of SEQ ID NO: 1. In another aspect, the AmyE may comprise an amino acid sequence set forth in: SEQ ID NO: 1, SEQ ID NO: 2, SEQ ID NO: 3, SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 34. In a further aspect, the alpha-amylase may be an AmyE variant that may have one or more altered properties compared to the AmyE enzyme having an amino acid sequence of SEQ ID NO: 1. The altered properties can be substrate specificity, substrate binding, substrate cleavage pattern, thermal stability, pH/activity profile, pH/stability profile, stability towards oxidation, stability at lower level of calcium ion, specific activity, or any combination thereof. The composition may further comprise a phytase, a pullulanase, a beta-amylase, a fungal alpha-amylase, a protease, a cellulose, a hemicellulase, a lipase, a cutinase, and/or an isoamylase. Also disclosed is a method of processing a starch comprising admixing the described composition. In one aspect, the composition may be used to produce high fructose corn syrup by further admixing a glucose isomerase at a pH of about 6.0 to about 8.0, e.g., pH 7.5. In another aspect, the composition may be used to produce ethanol. For the ethanol production, the saccharifying and fermenting may be performed simultaneously. The produced ethanol may be recovered. The ethanol production may further comprise distilling the ethanol. The fermenting and the distilling may be carried out simultaneously, separately, or sequentially.

In another aspect, the present disclosure provides a method of processing starch comprising administering a glucoamylase and an alpha-amylase for a time sufficient to saccharify the starch. The alpha-amylase is a *Bacillus subtilis* alpha-amylase (AmyE) or an AmyE variant having an amino acid sequence with at least about 80%, about 85%, about 90%, about 95%, or about 98% identity to an AmyE having an amino acid sequence of SEQ ID NO: 1. In another aspect, the AmyE may comprise an amino acid sequence set forth in: SEQ ID NO: 1, SEQ ID NO: 2, SEQ ID NO: 3, SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 34. In one aspect, the alpha-amylase may be an AmyE variant that may have one or more altered properties compared to the AmyE enzyme having an amino acid sequence of SEQ ID NO: 1. The altered properties can be substrate specificity, substrate binding, substrate cleavage pattern, thermal stability, pH/activity profile, pH/stability profile, stability towards oxidation, stability at lower level of calcium ion, specific activity, or any combination thereof. The glucoamylase may be used at an amount no higher than about 0.22, about 0.19, about 0.17, about 0.15, about 0.13, or about 0.11 glucoamylase unit per gram dry solid (GAU/g ds). In another aspect, the method may further comprise contacting the starch substrate with a phytase, a pullulanase, a beta-amylase, a fungal alpha-amylase, a protease, a cellulose, a hemicellulase, a lipase, a cutinase, and/or an isoamylase. In yet another aspect, the starch saccharifying method may further comprise producing high fructose corn syrup (HFCS). The production of high fructose corn syrup may be achieved by admixing a glucose isomerase at a pH of about 6.0 to about 8.0, e.g., pH 7.5. In one embodiment, the product contains about 40-45% fructose. In another aspect, the starch saccharifying method may further comprise fermenting the saccharified starch to produce ethanol. The saccharifying and fermenting may be performed simultaneously for ethanol production. Also provided is a method further comprising recovering the ethanol. The ethanol production may comprise distilling the ethanol. The fermenting and the distilling may be carried out simultaneously, separately, or sequentially.

BRIEF DESCRIPTION OF THE DRAWINGS

The accompanying drawings are incorporated into the specification and provide non-limiting illustrations of various embodiments. In the drawings:

FIG. 1 depicts amino acid sequence alignment of full-length alpha-amylases (with intact signal sequences from *Geobacillus stearothermophilus* (SEQ ID NO: 25; AmyS; "*B. stear*"), *Bacillus licheniformis* (SEQ ID NO: 26; AmyL; "*B. lich*"), and *Bacillus subtilis* (SEQ ID NO: 27; AmyE; "*B. sub*").

FIG. 4 depicts a sequence alignment between the AmyE having the amino acid sequence of SEQ ID NO: 1 ("AmyE full length") and the AmyE having the amino acid sequence of SEQ ID NO: 35 (mature "Amy31A"). Differences in the amino acid sequences are shown in bold font. Residues are numbered from the first amino acid in the mature form of the enzymes.

DETAILED DESCRIPTION

Figure 2:
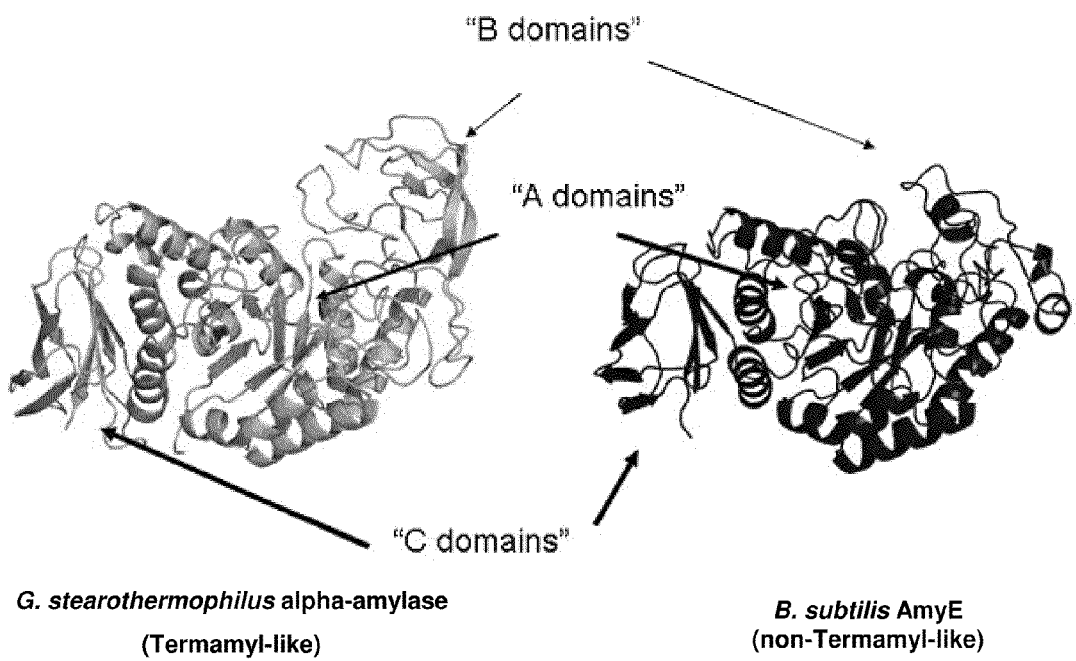
FIG. 2 depicts a three-dimensional structure comparison between *B. subtilis* alpha-amylase (AmyE; Protein Data Bank Accession No. 1UA7) and *G. stearothermophilus* alpha-amylase (AmyS; Protein Data Bank Accession No. 1HVX).

The present disclosure relates to a *Bacillus subtilis* alpha-amylase (AmyE). The AmyE or its variants thereof may be used to more efficiently produce fermentable sugars from starch. Also disclosed include a composition comprising a glucoamylase and the described alpha-amylase and a method of processing starch utilizing a glucoamylase supplemented with the described alpha-amylase.

1. DEFINITIONS AND ABBREVIATIONS

In accordance with this detailed description, the following abbreviations and definitions apply. It should be noted that as used herein, the singular forms "a," "an," and "the" include plural referents unless the context clearly dictates otherwise. Thus, for example, reference to "an enzyme" includes a plurality of such enzymes and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

1.1. DEFINITIONS

As used herein, "amino acid sequence" is synonymous with the term "polypeptide" and/or the term "protein." In some instances, the term "amino acid sequence" is synonymous with the term "peptide"; in some instances, the term "amino acid sequence" is synonymous with the term "enzyme."

As used herein, "hybridization" includes the process by which a strand of nucleic acid joins with a complementary strand through base pairing, as well as the process of amplification as carried out in polymerase chain reaction (PCR) technologies. Hybridized nucleic acid may exist as single- or double-stranded DNA or RNA, an RNA/DNA heteroduplex, or an RNA/DNA copolymer. As used herein, "copolymer" refers to a single nucleic acid strand that comprises both ribonucleotides and deoxyribonucleotides. Nucleic acids include those that hybridize under "highly stringent conditions" to a nucleic acid disclosed herein. Highly stringent conditions are defined as hybridization at 50° C. in 0.2×SSC or at 65° C. in 0.1×SSC (1×SSC=0.15 M NaCl, 0.015 M sodium citrate, pH 7.0).

As used herein, "nucleotide sequence" or "nucleic acid sequence" refer to a sequence of genomic, synthetic, or recombinant origin and may be double-stranded or single-stranded, whether representing the sense or anti-sense strand. As used herein, the term "nucleic acid" may refer to genomic DNA, cDNA, synthetic DNA, or RNA. The residues of a nucleic acid may contain any of the chemically modifications commonly known and used in the art.

"Isolated" means that the material is at least substantially free from at least one other component that the material is naturally associated and found in nature.

"Purified" means that the material is in a relatively pure state, e.g., at least about 90% pure, at least about 95% pure, or at least about 98% pure.

"Thermostable" means the enzyme retains activity after exposure to elevated temperatures. The thermostability of an alpha-amylase is measured by its half-life ($t_{1/2}$), where half of the enzyme activity is lost by the half-life. The half-life is measured by determining the specific alpha-amylase activity of the enzyme remaining over time at a given temperature, particularly at a temperature used for a specific application.

As used herein, "food" includes both prepared food, as well as an ingredient for a food, such as flour, that is capable of providing any beneficial effect to the consumer. "Food ingredient" includes a formulation that is or can be added to a food or foodstuff and includes formulations used at low levels in a wide variety of products that require, for example, acidifying or emulsifying. The food ingredient may be in the form of a solution or as a solid, depending on the use and/or the mode of application and/or the mode of administration.

"Oligosaccharide" means a carbohydrate molecule composed of 3-20 monosaccharides.

"Homologue" means an entity having a certain degree of identity or "homology" with the subject amino acid sequences or the subject nucleotide sequences. A "homologous sequence" includes an amino acid sequence having at least 85% sequence identity to the subject sequence, e.g., at least 85%, 90%, 95%, 96%, 97%, 98% or 99% identity to the subject sequence. Typically, homologues will comprise the same active site residues as the subject amino acid sequence.

As used herein, "transformed cell" includes cells that have been transformed by use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

As used herein, "operably linked" means that the described components are in a relationship permitting them to function in their intended manner. For example, a regulatory sequence operably linked to a coding sequence is ligated in such a way that expression of the coding sequence is achieved under condition compatible with the control sequences.

As used herein, "biologically active" refers to a sequence having a similar structural, regulatory, or biochemical function as the naturally occurring sequence, although not necessarily to the same degree.

As used herein, "starch" refers to any material comprised of the complex polysaccharide carbohydrates of plants, comprised of amylose and amylopectin with the formula $(C_6H_{10}O_5)_x$, wherein "X" can be any number. In particular, the term refers to any plant-based material including but not limited to grains, grasses, tubers and roots and more specifically wheat, barley, corn, rye, rice, sorghum, brans, cassava, millet, potato, sweet potato, and tapioca.

As used herein, "granular starch" refers to uncooked (raw) starch, which has not been subject to gelatinization.

As used herein, "starch gelatinization" means solubilization of a starch molecule to form a viscous suspension.

As used herein, "gelatinization temperature" refers to the lowest temperature at which gelatinization of a starch substrate occurs. The exact temperature depends upon the specific starch substrate and further may depend on the particular variety and the growth conditions of plant species from which the starch is obtained.

"DE" or "dextrose equivalent" is an industry standard for measuring the concentration of total reducing sugars, calculated as the percentage of the total solids that have been converted to reducing sugars. The granular starch that has not been hydrolyzed has a DE that is essentially 0, and D-glucose has a DE of 100.

As used herein, "starch substrate" refers to granular starch or liquefied starch using refined starch, whole ground grains, or fractionated grains.

As used herein, "liquefied starch" refers to starch that has gone through solubilization process, for example, the conventional starch liquefaction process.

As used herein, "glucose syrup" refers to an aqueous composition containing glucose solids. Glucose syrup will have a DE of at least 20. In some embodiments, glucose syrup may contain no more than 21% water while at least 25% reducing sugar calculated as dextrose. In one embodiment, glucose syrup may include at least 90% D-glucose, and in another embodiment, glucose syrup may include at least 95% D-glucose. In some embodiments, the terms glucose and glucose syrup are used interchangeably.

As used herein, "fermentable sugars" refer to saccharides that are capable of being metabolized under yeast fermentation conditions. These sugars mainly refer to glucose, maltose, and maltotriose (DP1, DP2 and DP3).

As used herein, "total sugar content" refers to the total sugar content present in a starch composition.

As used herein, "ds" refers to dissolved solids in a solution.

"Brix" refers to a well-known hydrometer scale for measuring the sugar content of a solution at a given temperature. The Brix scale measures the grams of sucrose dissolved, or the total solubilized solid content, per 100 grams of aqueous sugar solution. Brix measurements are frequently made by using a hydrometer or refractometer.

As used herein, "Baumé degrees" refer to the specific gravity of a liquid. At 20° C., the relationship between specific gravity (s.g.) and Baumé degrees is: for liquids heavier than water: s.g.=145÷(145−Baumé degrees); and for liquids lighter than water: s.g.=140÷(Baumé degrees+130).

For starch suspensions, e.g., slurries and starch hydrolysates, the Baumé-dry substance relationship is disclosed in Cleland J. et al., "Baumé-Dry Substance Tables for Starch Suspensions," *Ind. Eng. Chem. anal. Ed.*, 15: 334-36 (1943). See also, "Critical Data Tables," Corn Refiners Association, Inc. (1991). Baumé degrees are useful in the corn wet milling industry for both process control and commercial sale of hydrolysis products.

As used herein, "starch-liquefying enzyme" refers to an enzyme that catalyzes the hydrolysis or breakdown of granular starch. Exemplary starch liquefying enzymes include alpha-amylases (EC 3.2.1.1).

"Amylase" means an enzyme that is, among other things, capable of catalyzing the degradation of starch.

"Alpha-amylases (EC 3.2.1.1)" refer to endo-acting enzymes that cleave α-D-(1→4) O-glycosidic linkages within the starch molecule in a random fashion. In contrast, the exo-acting amylolytic enzymes, such as beta-amylases (EC 3.2.1.2; α-D-(1→4)-glucan maltohydrolase) and some product-specific amylases like maltogenic alpha-amylase (EC 3.2.1.133) cleave the starch molecule from the non-reducing end of the substrate. These enzymes have also been described as those effecting the exo- or endohydrolysis of 1,4-α-D-glucosidic linkages in polysaccharides containing 1,4-α-linked D-glucose units. Another term used to describe these enzymes is glycogenase. Exemplary enzymes include alpha-1,4-glucan 4-glucanohydrolase.

As used herein, "glucoamylases" refer to the amyloglucosidase class of enzymes (EC 3.2.1.3, glucoamylase, α-1,4-D-glucan glucohydrolase). These are exo-acting enzymes that release glucosyl residues from the non-reducing ends of amylose and/or amylopectin molecules. The enzymes are also capably of hydrolyzing α-1,6 and α-1,3 linkages, however, at much slower rates than the hydrolysis of α-1,4 linkages.

As used herein, the "transglucosidase activity" of AmyE or its variants thereof is characterized by the formation of maltotriose upon incubation with maltose. Specifically, the transglucosidase activity refers to the alpha-1,4-glucosyl transferase activity.

As used herein, "iodine-positive saccharide" or "IPS" refers to the amylose that is not hydrolyzed after liquefaction and saccharification. When saccharified starch is tested with iodine, the high DPn amylose binds iodine and produces a characteristic blue color. IPS is highly undesirable in starch processing applications, because its presence reflects incomplete starch hydrolysis.

As used herein, "insoluble residual starch" or "IRS" refers to incompletely hydrolyzed starch that shows as sediments after saccharification. A high level of sediments is undesirable in sweetener applications, because they may substantially interfere with the efficiency of production and reduce the output. IRS also contributes to an undesirable texture of foods containing such sweeteners.

As used herein, "glucose surge" refers to the significantly increased glucose level at the lag (yeast growth) phase of the fermentation.

As used herein, "hydrolysis of starch" refers to the cleavage of glucosidic bonds with the addition of water molecules.

"Degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP4+(>DP4) denotes polymers with a degree of polymerization of greater than 4.

As used herein, "contacting" or "admixing" refers to the placing of the respective enzyme(s) in sufficiently close proximity to the respective substrate to enable the enzyme(s) to convert the substrate to the end-product. Those skilled in the art will recognize that mixing solutions of the enzyme with the respective substrates can effect contacting or admixing.

1.2. ABBREVIATIONS

The following abbreviations apply unless indicated otherwise:
AE alcohol ethoxylate
AEO alcohol ethoxylate
AEOS alcohol ethoxysulfate
AES alcohol ethoxysulfate
GAU glucoamylase activity unit
AkAA *Aspergillus kawachii* alpha-amylase
AmyE *Bacillus subtilis* alpha-amylase
AmyE-tr AmyE truncated
AmyE FL full length AmyE
AmyL *Bacillus licheniformis* alpha-amylase
AmyR SPEZYME® XTRA amylase
AmyS *Geobacillus stearothermophilus* alpha-amylase
AS alcohol sulfate
BAA bacterial alpha-amylase
cDNA complementary DNA
CMC carboxymethylcellulose
DE Dextrose Equivalent
DI distilled, deionized
DNA deoxyribonucleic acid
DP3 degree of polymerization with three subunits
DPn degree of polymerization with n subunits
DS or ds dry solid
DTMPA diethyltriaminepentaacetic acid
EC enzyme commission for enzyme classification
EDTA ethylenediaminetetraacetic acid
EDTMPA ethylenediaminetetramethylene phosphonic acid
EO ethylene oxide
F&HC fabric and household care
gpm gallon per minute
GAU glucoamylase units
HFCS high fructose corn syrup
HFSS high fructose starch based syrup
HGA *Humicola grisea* glucoamylase
HPLC high pressure liquid chromatography
IPS iodine-positive saccharide
IPTG isopropyl β-D-thiogalactoside
IRS insoluble residual starch
kg kilogram
LA Lauria agar
LB Lauria broth
LIT leucine (L) residue at position 1 is replaced with a threonine (T) residue, where amino acids are designated by single letter abbreviations commonly known in the art
LU lipase unit
MOPS 3-(N-morpholino)propanesulfonic acid
MT metric ton
MW molecular weight
NCBI National Center for Biotechnology Information
nm nanometer
NOBS nonanoyloxybenzenesulfonate
NTA nitrilotriacetic acid
OD optical density
PCR polymerase chain reaction
PEG polyethylene glycol
pI isoelectric point
ppm parts per million
PVA poly(vinyl alcohol)
PVP poly(vinylpyrrolidone)
RAU Reference Amylase Units
RMSD root mean square deviation
RNA ribonucleic acid
rpm revolutions per minute
SAS secondary alkane sulfonates
1×SSC 0.15 M NaCl, 0.015 M sodium citrate, pH 7.0
SSF simultaneous saccharification and fermentation
SSU soluble starch unit, equivalent to the reducing power of 1 mg of glucose released per minute
TAED tetraacetylethylenediamine
TNBS trinitrobenzenesulfonic acid
TrGA *Trichoderma reesei* glucoamylase
w/v weight/volume
w/w weight/weight
wt wild-type
μL microliter
μNm microNewton×meter
XTRA SPEZYME® XTRA (Danisco US Inc., Genencor Division)

2. ALPHA-AMYLASES

2.1. Structure and Function

Alpha-amylases constitute a group of enzymes present in microorganisms and tissues from animals and plants. They are capable of hydrolyzing alpha-1,4-glucosidic bonds of glycogen, starch, related polysaccharides, and some oligosaccharides. Although all alpha-amylases possess the same catalytic function, their amino acid sequences vary greatly. The sequence identity between different amylases can be virtually non-existent, e.g., falling below 25%. Despite considerable amino acid sequence variation, alpha-amylases share a common overall topological scheme that has been identified after the three-dimensional structures of alpha-amylases from different species have been determined. The common three-dimensional structure reveals three domains: (1) a "TIM" barrel known as domain A, (2) a long loop region known as domain B that is inserted within domain A, and (3) a region close to the C-terminus known as domain C that contains a characteristic beta-structure with a Greek-key motif.

The TIM barrel of domain A consists of eight alpha-helices and eight parallel beta-strands, i.e., $(\beta/\alpha)_8$, that alternate along the peptide backbone. This structure, named after a conserved glycolytic enzyme triosephosphate isomerase, has been known to be common among conserved protein folds. Domain B is a loop region inserted between $\beta_{A3}$ and $\alpha_{A3}$ (the third β-strand and α-helix in domain A). Both domain A and domain B are directly involved in the catalytic function of an alpha-amylase, because the three-dimensional structure indicates that domain A flanks the active site and domain overlays the active site from on side. Furthermore, domain A is considered the catalytic domain, as amino acid residues of the active site are located in loops that link beta-strands to the adjacent alpha-helices. Domain B is believed to determine the specificity of the enzyme by affecting substrate binding. MacGregor et al., *Biochim. Biophys. Acta.* 1546:1-20 (2001).

"Termamyl-like" alpha-amylases refer to a group of alpha-amylases widely used in the starch-processing industry. The *B. licheniformis* alpha-amylase having an amino acid sequence of SEQ ID NO: 2 of U.S. Pat. No. 6,440,716 is commercially available as Termamyl®. Termamyl-like alpha-amylases commonly refer to a group of highly homologous alpha-amylases produced by *Bacillus* spp. Other members of the group include the alpha-amylases from *Geobacillus stearothermophilus* (previously known as *Bacillus stearothermophilus*; both names are used interchangeably in the present disclosure) and *B. amyloliquefaciens*, and those derived from *Bacillus* sp. NCIB 12289, NCIB 12512, NCIB 12513, and DSM 9375, all of which are described in detail in U.S. Pat. No. 6,440,716 and WO 95/26397, and incorporated herein by reference.

Although alpha-amylases universally contain the three domains discussed above, the three-dimensional structures of some alpha-amylases, such as AmyE from *B. subtilis*, differ significantly from Termamyl-like alpha-amylases. These enzymes are collectively referred as non-Termamyl-like alpha-amylases. FIG. 1 depicts a sequence alignment of alpha-amylases from *Geobacillus stearothermophilus* (SEQ ID NO: 25; AmyS), *Bacillus licheniformis* (SEQ ID NO: 26), and *Bacillus subtilis* (SEQ ID NO: 27; AmyE). The sequence alignment was generated by the Kalign 2.0 program (available at http://www.ebi.ac.uk/Tools/kalign/index.html; see also Lassmann & Sonnhammer, *BMC Bioinformatics* 6: 298 (2005)). The Termamyl-like AmyS and AmyL share approximately 63% identity and approximately 77% similarity, while AmyE shares approximately 15% identity and less than 25% similarity with AmyL or AmyS.

The crystal structure of *Bacillus subtilis* alpha-amylase (AmyE) or its truncated variant has been determined, and it shares the common features of other alpha-amylases. Fujimoto et al., *J. Mol. Biol.* 277: 393-407 (1998)(Protein Data Bank Accession No. 1BAG); Kagawa et al., *J. Bacteriol.* 185:6981-84 (2001)(Protein Data Bank Accession No. 1UA7). It is of particular interest to compare the crystal structure of AmyE with those "Termamyl-like alpha-amylases." As indicated in FIG. 2, a common topological scheme is identified by comparing the three-dimensional structures between AmyE and AmyS. Both amylases display a similar overall structure with three domains. See, e.g., Protein Data Bank Accession Nos. 1UA7 and 1HVX, respectively.

Figure 3A:
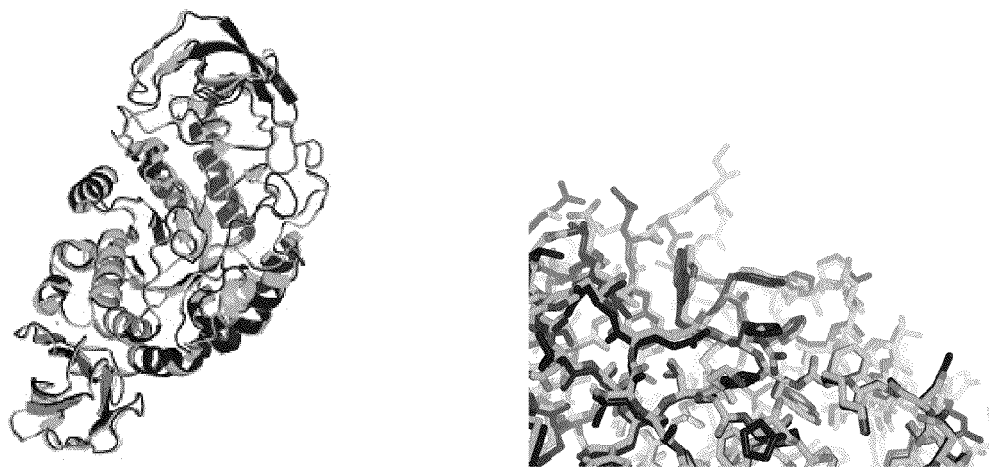
FIG. 3A depicts the superposed structures of *G. stearothermophilus* alpha-amylase (AmyS; Protein Data Bank Accession No. 1HVX) (gray shaded) and *B. licheniformis* (AmyL; Protein Data Bank Accession No. 1BLI) (dark shaded). The left panel shows an overall comparison, while the right panel shows a magnified view of selected amino acid side chains.
Figure 3B:
FIG. 3B depicts a stereographic view of the superposed structures of *G. stearothermophilus* alpha-amylase (AmyS; Protein Data Bank Accession No. 1HVX) (gray shaded) and *B. subtilis* alpha-amylase (AmyE; Protein Data Bank Accession No. 1UA7) (dark shaded).

A close examination of the three-dimensional structures of AmyS, AmyL, and AmyE, however, reveals considerable structural difference between AmyE and the Termamyl-like alpha-amylases. When AmyS and AmyL are superposed together, these two amylases almost overlap for each of the three domains. Significant differences are present only at the amino acid side chain level. See FIG. 3A. FIG. 3B, on the other hand, provides superimposed three-dimensional structures of AmyS and AmyE. There are considerable structural differences between AmyS and AmyE. The most dramatic difference can be located in the domain B. Since domain B is commonly believed to form a large portion of the catalytic site, it is expected that AmyE may display enzymatic properties different from those of the Termamyl-like alpha-amylases.

A more quantitative measure for structural similarity is through determining the root mean square deviation (RMSD) based on a given three-dimensional alignment. RMSD is the measure of the average distance between the backbones of superimposed proteins. Typically, one may measure the similarity in three-dimensional structure by the RMSD of the alpha-carbon atomic coordinates after optimal rigid body superposition. When the three-dimensional structure of AmyL (Protein Data Bank Accession No. 1BLI) is superimposed to that of AmyS (Protein Data Bank Accession No. 1HVX), the RMSD is 0.408 angstrom among 419 amino acid residues based on PyMOL (available at http://pymol.org). The three-dimensional structure comparison between AmyE (Protein Data Bank Accession No. 1UA7) and AmyS (Protein Data Bank Accession No. 1HVX), however, generates a RMSD of 8.134 angstroms among 311 amino acid residues.

2.2. AmyE and Variants

AmyE enzymes and variants thereof are provided, which are useful for carrying out the applications disclosed herein. Nucleic acids encoding AmyE and variants thereof also are provided, as are vectors and host cells comprising the nucleic acids.

"AmyE" for the purpose of this disclosure means a naturally occurring alpha-amylase (EC 3.2.1.1; 1,4-α-D-glucan glucanohydrolase) from *B. subtilis*. A representative AmyE sequence is set forth in SEQ ID NO: 1 or 27. The amino acid sequence of AmyE shown in SEQ ID NO: 1 is that of the mature form, without the native signal sequence. The amino acid sequence of AmyE shown in SEQ ID NO: 27 contains a signal sequence consisting of 41 amino acid residues. The amino acid sequence of the native signal sequence of this AmyE is shown in SEQ ID NO: 17. The mature form of this AmyE is referred to elsewhere in the present disclosure as "AmyE full-length." Other AmyE sequences have at least about 80%, about 85%, about 90%, about 95%, or about 98% sequence identity to the AmyE of SEQ ID NO: 1, using the BLAST sequence alignment algorithm with default alignment parameters. For example, an AmyE known as Amy31A, disclosed in UniProtKB/TrEMBL Accession No. 082953 (SEQ ID NO: 3), has an 86% sequence identity to the AmyE of SEQ ID NO: 1. The N-terminal 45 amino acid residues of SEQ ID NO: 3 are the signal sequence of Amy31A. A sequence alignment between AmyE (SEQ ID NO: 1) and Amy31A (SEQ ID NO: 3 without the signal sequence) is depicted in FIG. 4. AmyE enzymes include, but are not limited to, the AmyE having the amino acid sequence disclosed in NCBI Accession No. ABW75769 (SEQ ID NO: 28). Further AmyE protein sequences include those disclosed in NCBI Accession Nos. ABK54355 (SEQ ID NO: 29), AAF14358 (SEQ ID NO: 30), AAT01440 (SEQ ID NO: 31), AAZ30064 (SEQ ID NO: 32), AAQ83841 (SEQ ID NO: 33), and BAA31528 (SEQ ID NO: 34), the contents of which are incorporated herein by reference.

An AmyE "variant" comprises an amino acid sequence modification of a naturally occurring AmyE sequence. As used herein, a naturally occurring AmyE is also a "parent enzyme," "parent sequence," "parent polypeptide," or "wild-type AmyE." The amino acid modification may comprise an amino acid substitution, addition, or deletion. The amino acid modification in the AmyE variant may be the result of a naturally occurring mutation or the result of deliberate modification of the amino sequence using one of the well-known methods in the art for this purpose, described further below. Representative AmyE variants are disclosed in U.S. Provisional Application 61/059,513, filed Jun. 6, 2008, which is incorporated herein by reference in its entirety.

An AmyE variant, unless otherwise specified, has at least one amino acid modification, but the variant retains at least about 80%, about 85%, about 90%, about 95%, or about 98% amino acid sequence identity to the AmyE of SEQ ID NO: 1, measured by a BLAST alignment of the protein sequences with default alignment parameters. For example, the variant may have one, two, three, up to five, up to ten, or up to 20 amino acid substitutions compared to the amino acid sequence of SEQ ID NO: 1. Typically, modifications are made to amino acid residues that are not required for biological function. The selection of amino acid residues to be modified may be guided by sequence homology among AmyE sequences. Generally, amino acids that are well conserved in AmyE sequences are more likely to be required for biological activity. Conversely, amino acid positions that vary among AmyE sequences are less likely to be required for biological activity. For example, amino acid residues that differ in the alignment between AmyE and Amy31A, shown in bold font in FIG. 4, likely can be modified in an AmyE variant without loss of biological activity.

A variant AmyE may display substantial structural identity to a naturally occurring AmyE within the B domain, e.g., amino acid residues 101-151 of SEQ ID NO: 1. In one embodiment, a variant AmyE may comprises 1-3 amino acid substitutions as to the amino acid residues of the B domain of a naturally occurring AmyE. In another embodiment, a variant AmyE may have a three-dimensional structure that overlaps that of a naturally occurring AmyE, either overall or only the B domain, within 2 angstroms on average.

In some embodiments, a variant AmyE may display one or more altered properties compared to those of the parent enzyme. The altered properties may result in improved performance of the variant compared to its parent. These properties may include substrate specificity, substrate binding, substrate cleavage pattern, thermal stability, pH/activity profile, pH/stability profile, stability towards oxidation, stability at lower levels of calcium ion ($Ca^{2+}$), and/or specific activity.

AmyE or variants thereof may be expressed as a fusion protein that comprises sequences at the N- and/or C-terminus of the mature form of AmyE that facilitate expression, detection, and/or purification, e.g., a signal sequence or a His-tag. Such a sequence includes a signal sequence, which facilitates secretion and expression of the AmyE in a host organism. Additional amino acid residues may be cleaved from the N-terminus of an AmyE, following cleavage of the signal sequence, as discussed in Yang et al., "Nucleotide sequence of the amylase gene from *Bacillus subtilis*," *Nucleic Acids Res.* 11: 237-49 (1983). A "mature form" of an AmyE is defined as the product of all such post-translational modifications of the expressed AmyE sequence. Sequences found at the N-terminus of the primary translation product that are cleaved to form the mature AmyE may be designated alternatively as a "signal sequence," "leader sequence," or "pro-sequence."

The signal sequence may encoded by the same gene as the AmyE. For example, the AmyE set forth in SEQ ID NO: 1 is expressed naturally with a signal sequence and additional N-terminal amino acids having the sequence MFAKRFKTSLLPLFAGFLLLFHLVLAG-PAAASAETANKSNE (SEQ ID NO: 17). The signal sequence alternatively may be a *B. subtilis* sp. signal sequence from a different AmyE or even a different protein. Further, the signal sequence may be from a different species, e.g., *B. licheniformis*. The signal sequence may be chosen to provide optimal expression of the AmyE or variant thereof in a particular host cell, for example. The mature AmyE may be produced as a result of proteolytic cleavage of additional sequences from the N-terminus that are not signal sequences. For example, a 31-amino acid residue signal sequence from *B. licheniformis* ("LAT leader sequence") may be fused in frame with an AmyE sequence.

An AmyE variant for the purpose of this disclosure has at least partial or similar 1,4-α-D-glucan glucanohydrolase activity, compared to a naturally occurring AmyE. Furthermore, an AmyE variant for the purpose of this disclosure may also have a similar level of transglucosidase activity compared to the AmyE having an amino acid sequence of SEQ ID NO: 1. The transglucosidase activity is measured based on the enzymatic synthesis of maltotriose from maltose as described in Example 2.2. Variants may have the same activity and properties as a wild-type AmyE, or variants may have an altered property, compared to the AmyE having an amino acid sequence of SEQ ID NO: 1. The altered property may be an altered, e.g., two- or three-fold higher, specific activity toward maltoheptaose and/or maltotriose substrates. The thermostability of the protein alternatively or additionally may be altered. For example, the variant may be more thermostable than AmyE. The altered property alternatively or additionally may be the optimal pH for enzymatic activity. For example, the variant may have a more acidic or alkaline optimum pH.

A "truncated" AmyE ("AmyE-tr") means an AmyE with a sequence deletion of all or part of the C-terminal starch binding domain. In the AmyE-tr of SEQ ID NO: 2, for example, the AmyE of SEQ ID NO: 1 is truncated at residue D425. A 2.5 Å resolution crystal structure of this AmyE-tr is available at Protein Databank Accession No. 1BAG, which is disclosed in Fujimoto et al., "Crystal structure of a catalytic-site mutant alpha-amylase from *B. subtilis* complexed with maltopentaose," *J. Mol. Biol.* 277: 393-407 (1998). AmyE-tr may be truncated at other positions, e.g., Y423, P424, D426 or I427 of the AmyE of SEQ ID NO: 1, provided all or part of the C-terminal starch binding domain is removed.

Nucleic acids encoding AmyE or a variant thereof include, but are not limited to, the polynucleotide disclosed in SEQ ID NO: 9 and NO: 10, which encode the AmyE of SEQ ID NO: 1 and AmyE-tr (SEQ ID NO: 2), respectively. Further representative polynucleotides include that disclosed in SEQ ID NO: 11, which encodes Amy31A (SEQ ID NO: 3). The AmyE disclosed in NCBI Accession Nos. ABK54355, AAF14358, AAT01440, AAZ30064, NP_388186, AAQ83841, and BAA31528 likewise are encoded by polynucleotides disclosed in publicly accessible databases, which sequences are incorporated herein by reference. Nucleic acids may be DNA, mRNA, or cDNA sequences. Nucleic acids further include "degenerate sequences" of any of the aforementioned nucleic acids. A degenerate sequence contains at least one codon that encodes the same amino acid residue but has a different nucleotide sequence from the aforementioned nucleic acid sequences. For example, nucleic acids include any nucleic acid sequence that encodes an AmyE or variant thereof. Degenerate sequences may be designed for optimal expression by using codons preferred by a particular host organism.

Vectors comprising the nucleic acids encoding AmyE or variants thereof also are provided. Host cells comprising the vectors are provided. The host cell may express the polynucleotide encoding the AmyE variant. The host may be a *Bacillus* sp., e.g., *B. subtilis*.

2.3. Characterization of AmyE Variants

AmyE variants can be characterized by their nucleic acid and primary polypeptide sequences, by 3D structural modeling, and/or by their specific activity. Additional characteristics of the AmyE variant include stability, $Ca^{2+}$ dependence, pH range, oxidation stability, and thermostability. In one aspect, the AmyE variants are expressed at higher levels than the wild-type AmyE, while retaining the performance characteristics of the wild-type AmyE. Levels of expression and enzyme activity can be assessed using standard assays known to the artisan skilled in this field. In another aspect, variants demonstrate improved performance characteristics relative to the wild-type enzyme, such as improved stability at high temperatures or improved activity at various pH values, e.g., pH 4.0 to 6.0 or pH 8.0 to 11.0.

The AmyE variant may be expressed at an altered level in a host cell compared to AmyE. Expression generally relates to the amount of active variant that is recoverable from a fermentation broth using standard techniques known in this art over a given amount of time. Expression also can relate to the amount or rate of variant produced within the host cell or secreted by the host cell. Expression also can relate to the rate of translation of the mRNA encoding the variant enzyme.

In a further aspect, important mutations exhibit altered stability or specific activity, especially at temperatures around 60° C., e.g., 50-70° C., for use in saccharification, for example. Variants may have altered stability or specific activity at other temperatures, depending on whether the variant is to be used in other applications or compositions. For example, in baking products, variant may exhibit altered specific activity at higher temperature ranges.

AmyE variants also may have altered oxidation stability, in particular higher oxidation stability, in comparison to the parent AmyE. For example, increased oxidation stability is advantageous in detergent compositions, and decreased oxidation stability may be advantageous in composition for starch liquefaction.

The AmyE variants described herein can also have mutations that extend half-life relative to the parent enzyme by 10%, 20%, 30%, 40%, 50%, 60%, 70%, 80%, 90%, 100%, 200%, or more, particularly at elevated temperatures of about 55° C. to about 95° C. or more, particularly at about 80° C. In one embodiment, the AmyE variant can be heated for about 1-10 minutes at 80° C. or higher.

The AmyE variants may have exo-specificity, measured by exo-specificity indices described herein, for example. AmyE variants include those having higher or increased exo-specificity compared to the parent enzymes or polypeptides from which they were derived, optionally when measured under identical conditions. Thus, for example, the AmyE variant polypeptides may have an exo-specificity index 10%, 20%, 30%, 40%, 50%, 60%, 70%, 80%, 90%, 100%, 150%, 200%, 500%, 1000%, 5000%, 10,000% or higher compared to their parent polypeptides.

In one aspect, the AmyE variant has the same pH stability as the parental sequence. In another aspect, the variant comprises a mutation that confers a greater pH stability range or shifts the pH range to a desired area for the end commercial purpose of the enzyme. For example, in one embodiment, the variant can degrade starch at about pH 5.0 to about pH 10.5. The AmyE variant polypeptide may have a longer half-life or higher activity (depending on the assay) compared to the parent polypeptide under identical conditions, or the AmyE variant may have the same activity as the parent polypeptide. The AmyE variant polypeptide also may have about 10%, 20%, 30%, 40%, 50%, 60%, 70%, 80%, 90%, 100%, 200% or longer half-life compared to their parent polypeptide under identical pH conditions. Alternatively, or in addition, the AmyE variant may have higher specific activity compared to the parent polypeptide under identical pH conditions.

In another aspect, a nucleic acid complementary to a nucleic acid encoding any of the AmyE variants set forth herein is provided. Additionally, a nucleic acid capable of hybridizing to the complement is provided. In another embodiment, the sequence for use in the methods and compositions described herein is a synthetic sequence. It includes, but is not limited to, sequences made with optimal codon usage for expression in a particular host organism.

3. PRODUCTION OF ALPHA-AMYLASES

A DNA sequence encoding the alpha-amylase produced by methods described herein, or by any alternative methods known in the art, can be expressed, in enzyme form, using an expression vector which typically includes control sequences encoding a suitable promoter, operator, ribosome binding site, translation initiation signal, and, optionally, a repressor gene or various activator genes.

3.1. Vectors

The recombinant expression vector carrying the DNA sequence encoding the alpha-amylase may be any vector that may conveniently be subjected to recombinant DNA procedures, and the choice of vector will often depend on the host cell into which it is to be introduced. Thus, the vector may be an autonomously replicating vector, i.e., a vector that exists as an extrachromosomal entity, the replication of which is independent of chromosomal replication, e.g., a plasmid, a bacteriophage or an extrachromosomal element, mini-chromosome or an artificial chromosome. Alternatively, the vector may be one which, when introduced into a host cell, is integrated into the host cell genome and replicated together with the chromosome(s) into which it has been integrated. The integrated gene may also be amplified to create multiple copies of the gene in the chromosome by use of an amplifiable construct driven by antibiotic selection or other selective pressure, such as an essential regulatory gene or by complementation of an essential metabolic pathway gene.

An expression vector typically includes the components of a cloning vector, e.g., an element that permits autonomous replication of the vector in the selected host organism and one or more phenotypically detectable markers for selection purposes. The expression vector normally comprises control nucleotide sequences encoding a promoter, operator, ribosome binding site, translation initiation signal and optionally, a repressor gene or one or more activator genes. In one aspect, all the signal sequences used target the material to the cell culture media for easier enzyme collection and optionally purification. The procedures used to ligate the DNA construct encoding an alpha-amylase described herein, the promoter, the terminator and other elements, respectively, and to insert them into suitable vectors containing the information necessary for replication, are well known to persons skilled in the art (see e.g., Sambrook et al., MOLECULAR CLONING: A LABORATORY MANUAL, $2^{nd}$ ed., Cold Spring Harbor, 1989 and $3^{rd}$ ed., 2001).

In the vector, the DNA sequence should be operably connected to a suitable promoter sequence. The promoter may be any DNA sequence that shows transcriptional activity in the host cell of choice and may be derived from genes encoding proteins either homologous or heterologous to the host cell. Suitable promoters for directing the transcription of the DNA sequence encoding an alpha-amylase described herein, especially in a bacterial host, include various Bacillus-derived promoters, such as an alpha-amylase promoter derived from B. subtilis, B. licheniformis, B. stearothermophilus, or B. amyloliquefaciens, the promoter of the lac operon of E. coli, the Streptomyces coelicolor agarase gene dagA or celA promoters, and the promoters of the *Bacillus subtilis* xylA and xylB genes, etc. For transcription in a fungal host, examples of useful promoters are those derived from the gene encoding *Aspergillus oryzae* TAKA amylase, *Rhizomucor miehei* aspartic proteinase, *Aspergillus niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase, or *A. nidulans* acetamidase. When the gene encoding an alpha-amylase described herein is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the AOX1 and AOX2 promoters of *Pichia pastoris*.

The expression vector may also comprise a suitable transcription terminator and, in eukaryotes, polyadenylation sequences operably connected to the DNA sequence encoding the alpha-amylase variant. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1, pICatH, and pIJ702.

The vector may also comprise a selectable marker, e.g., a gene the product of which complements a defect in the host cell, such as the dal genes from *B. subtilis* or *B. licheniformis*, or a gene which confers antibiotic resistance, e.g., ampicillin, kanamycin, chloramphenicol or tetracyclin resistance. Furthermore, the vector may comprise *Aspergillus* selection markers such as amdS, argB, niaD, and xxsC, a marker giving rise to hygromycin resistance, or the selection may be accomplished by co-transformation as known in the art. See, e.g., WO 91/17243.

3.2 Variant Expression and Host Organisms

It is generally advantageous if the alpha-amylase is secreted into the culture medium, when expressed in a host cell. To this end, the alpha-amylase may comprise a signal sequence that permits secretion of the expressed enzyme into the culture medium. If desirable, this original signal sequence may be replaced by a different signal sequence, which is conveniently accomplished by substitution of the DNA sequences encoding the respective signal sequence. For example, a nucleic acid encoding AmyE is operably linked to a *B. licheniformis* signal sequence in the expression vector shown in FIG. 5. Signal sequences are discussed in more detail above.

An isolated cell, comprising either a DNA construct or an expression vector, is advantageously used as a host cell in the recombinant production of the alpha-amylase. The cell may be transformed with the DNA construct encoding the alpha-amylase, optionally by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram-positive bacterial species such as *Bacillaceae*, including *B. subtilis*, *B. licheniformis*, *B. lentus*, *B. brevis*, *B. stearothermophilus*, *B. alkalophilus*, *B. amyloliquefaciens*, *B. coagulans*, *B. lautus*, *B. megaterium*, and *B. thuringiensis*; *Streptomyces* sp., such as *S. murinus*; lactic acid bacterial species including *Lactococcus* sp., such as *L. lactis*; *Lactobacillus* sp., including *L. reuteri*; *Leuconostoc* sp.; *Pediococcus* sp.; and *Streptococcus* sp. Still other useful hosts include *Bacillus* sp. A 7-7, for example. Alternatively, strains of a Gram-negative bacterial species belonging to *Enterobacteriaceae*, including *E. coli*, or to *Pseudomonadaceae* can be selected as the host organism.

A suitable yeast host organism can be selected from biotechnologically relevant yeasts species, such as, but not limited to, *Pichia* sp., *Hansenula* sp., *Kluyveromyces* sp., *Yarrowinia* sp., *Saccharomyces* sp., including *S. cerevisiae*, or a species belonging to *Schizosaccharomyces*, such as *S. pombe*. A strain of the methylotrophic yeast species *Pichia pastoris* can be used as the host organism. Alternatively, the host organism can be a *Hansenula* species. Suitable host organisms among filamentous fungi include species of *Aspergillus*, e.g., *A. niger*, *A. oryzae*, *A. tubigensis*, *A. awamori*, or *A. nidulans*. Alternatively, a strain of *Fusarium* sp., e.g., *Fusarium oxysporum* or *Rhizomucor* sp., such as *R. miehei*, can be used as the host organism. Other suitable yeasts include *Thermomyces* sp. and *Mucor* sp. Fungal cells may be transformed by a process involving protoplast formation and transformation of the protoplasts followed by regeneration of the cell wall in a manner known in the art. A suitable procedure for transforming *Aspergillus* host cells, for example, is described in EP 238023.

In a yet further aspect, a method of producing an alpha-amylase is provided, which method comprises cultivating a host cell as described above under conditions conducive to the production of the variant and recovering the variant from the cells and/or culture medium. The medium used to cultivate the cells may be any conventional medium suitable for growing the host cell in question and obtaining expression of the alpha-amylase. Suitable media and media components are available from commercial suppliers or may be prepared according to published recipes, e.g., as described in catalogues of the American Type Culture Collection (ATCC). Exemplary culture media include, but are not limited to, those for fed-batch fermentations performed in a three thousand liter (3,000 L) stirred tank fermentor. The growth medium in that case can consist of corn steep solids and soy flour as sources of organic compounds, along with inorganic salts as a source of sodium, potassium, phosphate, magnesium and sulfate, as well as trace elements. Typically, a carbohydrate source such as glucose is also part of the initial medium. Once the culture has established itself and begins growing, the carbohydrate is metered into the tank to maintain the culture as is known in the art. Samples are removed from the fermentor at regular intervals to measure enzyme titer using, for example, a colorimetric assay method. The fermentation process is halted when the enzyme production rate stops increasing according to the measurements.

The alpha-amylase secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

Host cells may be cultured under suitable conditions that allow expression of the alpha-amylase. Expression of the proteins may be constitutive such that they are continually produced, or inducible, requiring a stimulus to initiate expression. In the case of inducible expression, protein production can be initiated when required by addition of an inducer substance, e.g., dexamethasone, IPTG, or Sepharose, to the culture medium, for example. Polypeptides can also be produced recombinantly in an in vitro cell-free system, such as the TnT™ (Promega) rabbit reticulocyte system.

A host for expressing the alpha-amylase can be cultured under aerobic conditions in the appropriate medium for the host. Shaking or a combination of agitation and aeration can be provided, with production occurring at the appropriate temperature for that host, e.g., from about 30° C. to about 75° C., depending on the needs of the host and production of the desired alpha-amylase variant. Culturing can occur from about 12 to about 100 hours or greater (and any hour value there between) or more particularly from 24 to 72 hours. Typically, the culture broth is at a pH of about 5.5 to about 8.0, again depending on the culture conditions needed for the host cell relative to production of the desired alpha-amylase.

The amylolytic activity of the expressed enzyme may be determined using potato starch as substrate, for example. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

4. PURIFICATION OF THE ALPHA-AMYLASE

Conventional methods can be used in order to prepare a purified alpha-amylase described herein. After fermentation, a fermentation broth is obtained, and the microbial cells and various suspended solids, including residual raw fermentation materials, are removed by conventional separation techniques to obtain an amylase solution. Filtration, centrifugation, microfiltration, rotary vacuum drum filtration, followed by ultra-filtration, extraction or chromatography, or the like are generally used.

It is desirable to concentrate the solution containing the expressed alpha-amylase described herein to optimize recovery, since the use of un-concentrated solutions requires increased incubation time to collect precipitates containing the purified enzyme. The solution is concentrated using conventional techniques until the desired enzyme level is obtained. Concentration of the enzyme containing solution may be achieved by any of the techniques discussed above. In one embodiment, rotary vacuum evaporation and/or ultrafiltration is used. Alternatively, ultrafiltration can be used.

By "precipitation agent" for purposes of purification is meant a compound effective to precipitate the alpha-amylase described herein from solution, whatever the nature of the precipitate may be, i.e., crystalline, amorphous, or a blend of both. Precipitation can be performed using, for example, a metal halide precipitation agent. Metal halide precipitation agents include: alkali metal chlorides, alkali metal bromides and blends of two or more of these metal halides. The metal halide may be selected from the group consisting of sodium chloride, potassium chloride, sodium bromide, potassium bromide and blends of two or more of these metal halides. Suitable metal halides include sodium chloride and potassium chloride, particularly sodium chloride, which can further be used as a preservative. The selection of conditions of the precipitation for maximum recovery, including incubation time, pH, temperature and concentration of an alpha-amylase described herein, will be readily apparent to one of ordinary skill in the art after routine testing.

Generally, at least about 5% w/v (weight/volume) to about 25% w/v of metal halide is added to the concentrated enzyme variant solution, and usually at least 8% w/v. Generally, no more than about 25% w/v of metal halide is added to the concentrated enzyme variant solution and usually no more than about 20% w/v. The optimal concentration of the metal halide precipitation agent will depend, among others, on the nature of the specific alpha-amylase described herein and on its concentration in solution.

Another alternative to effect precipitation of the enzyme is to use of organic compounds, which can be added to the concentrated enzyme variant solution. The organic compound precipitating agent can include: 4-hydroxybenzoic acid, alkali metal salts of 4-hydroxybenzoic acid, alkyl esters of 4-hydroxybenzoic acid, and blends of two or more of these organic compounds. The addition of said organic compound precipitation agents can take place prior to, simultaneously with or subsequent to the addition of the metal halide precipitation agent, and the addition of both precipitation agents, organic compound and metal halide, may be carried out sequentially or simultaneously. For further descriptions, see, e.g., U.S. Pat. No. 5,281,526 to Danisco US, Inc., Genencor Division, for example.

Generally, the organic compound precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitations agents can be for example linear or branched alkyl esters of 4-hydroxybenzoic acid, wherein the alkyl group contains from 1 to 10 carbon atoms, and blends of two or more of these organic compounds. Suitable organic compounds include linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl ester of 4-hydroxybenzoic acid, butyl ester of 4-hydroxybenzoic acid, ethyl ester of 4-hydroxybenzoic acid and blends of two or more of these organic compounds can also be used. Additional organic compounds also include, but are not limited to, 4-hydroxybenzoic acid methyl ester (methyl PARABEN) and 4-hydroxybenzoic acid propyl ester (propyl PARABEN), which are also amylase preservative agents. Addition of the such an organic compound precipitation agent provides the advantage of high flexibility of the precipitation conditions with respect to pH, temperature, enzyme concentration, precipitation agent concentration, and time of incubation. Generally, at least 0.01% w/v of organic compound precipitation agent is added to the concentrated enzyme variant solution and usually at least 0.02% w/v. Generally, no more than 0.3% w/v of organic compound precipitation agent is added to the concentrated enzyme variant solution and usually no more than 0.2% w/v.

The concentrated enzyme solution, containing the metal halide precipitation agent and, in one aspect, the organic compound precipitation agent, is adjusted to a pH that necessarily will depend on the enzyme variant to be purified. Generally, the pH is adjusted to a level near the isoelectric point (pI) of the amylase. For example, the pH can be adjusted within a range of about 2.5 pH units below the pI to about 2.5 pH units above the pI. The pH may be adjusted accordingly if the pI of the variant differs from the wild-type pI.

The incubation time necessary to obtain a purified enzyme precipitate depends on the nature of the specific enzyme, the concentration of enzyme, and the specific precipitation agent(s) and its (their) concentration. Generally, the time effective to precipitate the enzyme variant is between about 1 to about 30 hours; usually it does not exceed about 25 hours. In the presence of the organic compound precipitation agent, the time of incubation can still be reduced to less than about 10 hours, and in most cases even about 6 hours.

Generally, the temperature during incubation is between about 4° C. and about 50° C. Usually, the method is carried out at a temperature between about 10° C. and about 45° C., and particularly between about 20° C. and about 40° C. The optimal temperature for inducing precipitation varies according to the solution conditions and the enzyme or precipitation agent(s) used.

The overall recovery of purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

The purified enzyme may be further purified by conventional separation techniques, such as filtration, centrifugation, microfiltration, rotary vacuum filtration, ultrafiltration, press filtration, cross membrane microfiltration, cross flow membrane microfiltration, or the like. Cross membrane microfiltration can be one method used. Further purification of the purified enzyme precipitate can be obtained by washing the precipitate with water. For example, the purified enzyme precipitate may be washed with water containing the metal halide precipitation agent, for example, with water containing the metal halide and the organic compound precipitation agents.

During culturing, expressed enzyme may accumulate in the culture broth. For the isolation and purification of the expressed enzyme, the culture broth may be centrifuged or filtered to eliminate cells, and the resulting cell-free liquid may be used for the purification of the enzyme. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme active fraction. For further purification, a conventional procedure such as ion exchange chromatography may be used.

Purified enzymes are useful for all applications in which the enzymes are generally utilized. For example, they can be used in laundry detergents and spot removers, in the food industry, in starch processing and baking, and in pharmaceutical compositions as digestive aids. They can be made into a final product that is either liquid (solution, slurry) or solid (granular, powder).

Alternatively, the enzyme product can be recovered and a flocculating agent is added to the media in order to remove cells and cell debris by filtration or centrifugation without further purification of the enzyme.

The alpha-amylase that is produced and purified by the methods described above can be used in a variety of useful industrial applications. The enzymes possess valuable properties facilitating applications related to fabric and household care (F&HC). For example, an alpha-amylase described herein can be used as a component in washing, dishwashing and hard-surface cleaning detergent compositions. Alpha-amylases described herein also are useful in the production of sweeteners and ethanol from starch, and/or for textile desizing. The described alpha-amylases are particularly useful in starch-conversion processes, including starch liquefaction and/or saccharification processes, as described, for example, in WO 2005/111203 and U.S. Published Application No. 2006/0014265, published Jan. 19, 2006 (Danisco US, Inc., Genencor Division). These uses of described alpha-amylases are described in more detail below.

5. COMPOSITIONS FOR STARCH PROCESSING

5.1. Liquefaction and Saccharification

In one aspect, compositions with the alpha-amylase can be utilized for starch processing, for example, liquefaction and/or saccharification. The process may comprise hydrolysis of a slurry of gelatinized or granular starch, in particular hydrolysis of granular starch into a soluble starch hydrolysate at a temperature below the initial gelatinization temperature of the granular starch. Starch processing is useful for producing sweetener, producing alcohol for fuel or drinking (i.e., potable alcohol), producing a beverage, processing cane sugar, or producing desired organic compounds, e.g., citric acid, itaconic acid, lactic acid, gluconic acid, ketones, amino acids, antibiotics, enzymes, vitamins, and hormones. Conversion of starch to fructose syrups normally consists of three consecutive enzymatic processes: a liquefaction process, a saccharification process, and an isomerization process.

As used herein, the term "liquefaction" or "liquefy" means a process by which starch is converted to less viscous and shorter chain dextrins. Generally, this process involves gelatinization of starch simultaneously with or followed by the addition of an alpha-amylase described herein. As used herein, the term "primary liquefaction" refers to a step of liquefaction when the slurry's temperature is raised to or near its gelatinization temperature. Subsequent to the raising of the temperature, the slurry is sent through a heat exchanger or jet to temperatures from about 90-150° C., e.g., 100-110° C. Subsequent to application to a heat exchange or jet temperature, the slurry is held for a period of 3-10 minutes at that temperature. This step of holding the slurry at 90-150° C. is termed primary liquefaction.

As used herein, the term "secondary liquefaction" refers the liquefaction step subsequent to primary liquefaction (heating to 90-150° C.), when the slurry is allowed to cool to room temperature. This cooling step can be 30 minutes to 180 minutes, e.g. 90 minutes to 120 minutes. As used herein, the term "minutes of secondary liquefaction" refers to the time that has elapsed from the start of secondary liquefaction to the time that the Dextrose Equivalent (DE) is measured.

After the liquefaction process, the dextrins typically may be converted into dextrose by addition of a glucoamylase (e.g., AMG™ from Novozymes, A/S) and optionally a debranching enzyme, such as an isoamylase or a pullulanase (e.g., Promozyme® from Novozymes, A/S). Before this step, the pH typically is reduced to a value below about 4.5, while maintaining the temperature at 95° C. or more, so that the liquefying alpha-amylase variant activity is denatured. The temperature then is lowered to 60° C., and a glucoamylase and a debranching enzyme are added. The saccharification process proceeds typically for about 24 to about 72 hours.

An advantage of alpha-amylase described herein is their ability to catalyze the breakdown of complex sugars, such as maltose, maltotriose, and maltoheptaose. For this reason, saccharification can be catalyzed by AmyE or a variant thereof with a glucoamylase. A further advantage of the alpha-amylases described herein is that dextrins may be converted into dextrose by the action or one or more alpha-amylases described herein under the same reaction conditions that are optimal for glucoamylase. This advantageous property of AmyE and variants thereof is disclosed in U.S. Provisional Application 61/059,618, filed Jun. 6, 2008, incorporated herein by reference in its entirety. Because AmyE and variants thereof operate at the same pH and temperature as glucoamylase, AmyE and variants thereof may be added before or after additional catalysis with a glucoamylase, or by a cocktail of AmyE or a variant thereof and a glucoamylase. The delays necessitated by adjusting the pH and temperature of the reaction to accommodate the use of a glucoamylase thus are avoided.

Glucoamylases, when used alone in saccharification, typically are present in an amount of no more than, or even less than, 0.5 glucoamylase activity unit (GAU)/g DS (i.e., glucoamylase activity units per gram of dry solids). Glucoamylases may be added in an amount of 0.02-2.0 GAU/g DS or 0.1-1.0 GAU/g DS, e.g., 0.2 GAU/g DS. Glucoamylases are derived from a microorganism or a plant. For example, glucoamylases can be of fungal or bacterial origin. Exemplary bacterial glucoamylases are *Aspergillus* glucoamylases, in particular *A. niger* G1 or G2 glucoamylase (Boel et al., *EMBO J.* 3(5): 1097-1102 (1984)), or variants thereof, such as disclosed in WO 92/00381 and WO 00/04136; *A. awamori* glucoamylase (WO 84/02921); *A. oryzae* glucoamylase (Hata et al., *Agric. Biol. Chem.* 55(4): 941-949 (1991)), or variants or fragments thereof. In one embodiment, the process also comprises the use of a carbohydrate-binding domain of the type disclosed in WO 98/22613. Other contemplated *Aspergillus* glucoamylase variants include variants to enhance the thermal stability: G137A and G139A (Chen et al., *Prot. Eng.* 9: 499-505 (1996)); D257E and D293E/Q (Chen et al., *Prot. Eng.* 8: 575-582 (1995)); N182 (Chen et al., *Biochem. J.* 301: 275-281 (1994)); disulphide bonds, A246C (Fierobe et al., *Biochemistry*, 35: 8698-8704 (1996)); and introduction of Pro residues in positions A435 and S436 (Li et al., *Protein Eng.* 10: 1199-1204 (1997)). Other contemplated glucoamylases include *Talaromyces* glucoamylases, in particular derived from *T. emersonii* (WO 99/28448), *T. leycettanus* (U.S. Pat. No. RE 32,153), *T. duponti*, or *T. thermophilus* (U.S. Pat. No. 4,587,215). Contemplated bacterial glucoamylases include glucoamylases from the genus *Clostridium*, in particular *C. thermoamylolyticum* (EP 135138) and *C. thermohydrosulfuricum* (WO 86/01831). Suitable glucoamylases include the glucoamylases derived from *Aspergillus oryzae*, such as a glucoamylase having 50%, 55%, 60%, 65%, 70%, 75%, 80%, 85%, or even 90% homology to the amino acid sequence shown in SEQ ID NO: 2 in WO 00/04136. Also suitable are commercial glucoamylases, such as AMG 200L; AMG 300 L; SAN™ SUPER and AMG™ E (Novozymes); OPTIDEX® 300 (Danisco US, Inc., Genencor Division); AMIGASE™ and AMIGASE™ PLUS (DSM); G-ZYME® G900 (Enzyme Bio-Systems); and G-ZYME® G990 ZR (*A. niger* glucoamylase and low protease content).

Alpha-amylases described herein can be advantageously combined with a glucoamylase in a composition for process starch, e.g., as a composition for saccharification. Because of the advantageous properties of AmyE or its variants thereof, a reduced amount of glucoamylase, for example, about 50%, about 45%, about 40%, about 35%, about 30%, about 25%, about 20%, about 15%, or about 10% less, may be sufficient to achieve an equivalent saccharification result as using glucoamylase alone.

In another embodiment, other alpha- or beta-amylases, or other enzymes to provide a "cocktail" with a broad spectrum of activity. For example, the starch may be contacted with one or more enzyme selected from the group consisting of a fungal alpha-amylase (EC 3.2.1.1), a bacterial alpha-amylase, e.g., a *Bacillus* alpha-amylase or a non-Bacillus alpha-amylase, and/or a beta-amylase (EC 3.2.1.2). In an embodiment further another amylolytic enzyme or a debranching enzyme, such as an isoamylase (EC 3.2.1.68), or a pullulanases (EC 3.2.1.41) may be added to the alpha-amylase described herein. Isoamylase hydrolyses α-1,6-D-glucosidic branch linkages in amylopectin and β-limit dextrins and can be distinguished from pullulanases by the inability of isoamylase to attack pullulan and by the limited action of isoamylase on α-limit dextrins. Debranching enzymes may be added in effective amounts well known to the person skilled in the art.

Phytases are useful for the present disclosure as they are capable of hydrolyzing phytic acid under the defined conditions of the incubation and liquefaction steps. In some embodiments, the phytase is capable of liberating at least one inorganic phosphate from an inositol hexaphosphate (phytic acid). Phytases can be grouped according to their preference for a specific position of the phosphate ester group on the phytate molecule at which hydrolysis is initiated (e.g., as 3-phytases (EC 3.1.3.8) or as 6-phytases (EC 3.1.3.26)). A typical example of phytase is myo-inositol-hexakisphosphate-3-phosphohydrolase.

Phytases can be obtained from microorganisms such as fungal and/or bacterial organisms. Some of these microorganisms include e.g., *Aspergillus* (e.g., *A. niger, A. terreus, A. ficum* and *A. fumigatus*), *Myceliophthora* (*M. thermophila*), *Talaromyces* (*T. thermophilus*) *Trichoderma* spp (*T. reesei*). and *Thermomyces* (WO 99/49740). Phytases are also available from *Penicillium* species, e.g., *P. hordei* (ATCC No. 22053), *P. piceum* (ATCC No. 10519), or *P. brevi-compactum* (ATCC No. 48944). See, e.g., U.S. Pat. No. 6,475,762. In addition, phytases are available from *Bacillus* (e.g., *B. subtilis*), *Pseudomonas, Peniophora, E. coli, Citrobacter, Enterbacter,* and *Buttiauxella* (see WO2006/043178)).

Commercial phytases are available such as NATUPHOS (BASF), RONOZYME P (Novozymes A/S), PHZYME XP (Danisco A/S), and FINASE (AB Enzymes). The method for determining microbial phytase activity and the definition of a phytase unit has been published by Engelen et al., *J. of AOAC Int.*, 77: 760-764 (1994). The phytase may be a wild-type phytase, a variant, or a fragment thereof.

In one embodiment, the phytase is one derived from the bacterium *Buttiauxella* spp. The *Buttiauxella* spp. includes *B. agrestis, B. brennerae, B. ferragutiase, B. gaviniae, B. izardii, B. noackiae,* and *B. warmboldiae*. Strains of *Buttiauxella* species are available from DSMZ, the German National Resource Center for Biological Material (Inhoffenstrabe 7B, 38124 Braunschweig, Germany). *Buttiauxella* sp. strain P1-29 deposited under accession number NCIMB 41248 is an example of a particularly useful strain from which a phytase may be obtained and used according to the present disclosure. In some embodiments, the phytase is BP-wild-type, a variant thereof (such as BP-11) disclosed in WO 06/043178, or a variant as disclosed in US 2008/0220498, published Sep. 11, 2008. For example, a BP-wild-type and variants thereof are disclosed in Table 1 of WO 06/043178, wherein the numbering is in reference to SEQ ID NO: 3 of the published PCT application.

Beta-amylases are exo-acting maltogenic amylases, which catalyze the hydrolysis of 1,4-α-glucosidic linkages into amylose, amylopectin, and related glucose polymers, thereby releasing maltose. Beta-amylases have been isolated from various plants and microorganisms (Fogarty et al., PROGRESS IN INDUSTRIAL MICROBIOLOGY, Vol. 15, pp. 112-115, 1979). These beta-amylases are characterized by having optimum temperatures in the range from 40° C. to 65° C., and optimum pH in the range from about 4.5 to about 7.0. Contemplated beta-amylases include, but are not limited to, beta-amylases from barley SPEZYME® BBA 1500, SPEZYME® DBA, Optimalt™ ME, Optimalt™ BBA (Danisco A/S); and Novozym™ WBA (Novozymes A/S).

After the saccharification process, the dextrose syrup may be converted into high fructose syrup using an immobilized glucose isomerase (such as Sweetzyme®), for example. In one regard, the soluble starch hydrolysate of the process is subjected to conversion into high fructose starch-based syrup (HFSS), such as high fructose corn syrup (HFCS). This conversion can be achieved using a glucose isomerase, particularly a glucose isomerase immobilized on a solid support. Contemplated isomerases included the commercial products Sweetzyme® IT (Novozymes A/S); G-zyme® IMGI, and G-zyme® G993, Ketomax®, G-zyme® G993 liquid, and GenSweet® IGI (Danisco US Inc., Genencor Division).

While addition of 1 mM $Ca^{2+}$ or more is typically required to ensure adequately high stability of the alpha-amylase, the free $Ca^{2+}$ strongly inhibits the activity of the glucose isomerase. The $Ca^{2+}$ is thus typically removed prior to isomerization, by means of an expensive unit operation, so that the level of free $Ca^{2+}$ concentration is below 3-5 ppm. Cost savings could be obtained if such an operation were avoided.

Alpha-amylases described herein advantageously require less or no added $Ca^{2+}$ for stability. For this reason, the $Ca^{2+}$ added to a liquefaction and/or saccharification reaction may be reduced or eliminated altogether. The removal of $Ca^{2+}$ by ion exchange prior to contacting the reaction mixture with glucose isomerase thus may be avoided, saving time and cost and increasing the efficiency of a process of producing a high fructose syrup.

The starch to be processed may be obtained from tubers, roots, stems, legumes, cereals or whole grain. More specifically, the granular starch may be obtained from corns, cobs, wheat, barley, rye, milo, sago, cassava, tapioca, sorghum, rice, peas, bean, banana, or potatoes. Specially contemplated are both waxy and non-waxy types of corn and barley. The starch may be a highly refined starch quality, for instance, at least 90%, at least 95%, at least 97%, or at least 99.5% pure. Alternatively, the starch can be a more crude starch containing material comprising milled whole grain, including nonstarch fractions such as germ residues and fibers. The raw material, such as whole grain, is milled to open up the structure and allow further processing.

Two milling processes are suitable: wet and dry milling. In dry milling, the whole kernel is milled and used. Wet milling gives a good separation of germ and meal (starch granules and protein) and is usually used in the production of syrups. Both dry and wet milling are well known in the art of starch processing and also are contemplated for use with the compositions and methods disclosed. The process may be conducted in an ultrafiltration system where the retentate is held under recirculation in presence of enzymes, raw starch and water, where the permeate is the soluble starch hydrolysate. Another method is the process conducted in a continuous membrane reactor with ultrafiltration membranes, where the retentate is held under recirculation in presence of enzymes, raw starch and water, and where the permeate is the soluble starch hydrolysate. Also contemplated is the process conducted in a continuous membrane reactor with microfiltration membranes and where the retentate is held under recirculation in presence of enzymes, raw starch and water, and where the permeate is the soluble starch hydrolysate.

Dry milled grain will comprise significant amounts of non-starch carbohydrate compounds, in addition to starch. When such a heterogeneous material is processed by jet cooking, often only a partial gelatinization of the starch is achieved. Accordingly, the described alpha-amylases having a high activity towards ungelatinized starch are advantageously applied in a process comprising liquefaction and/or saccharification jet cooked dry milled starch.

The starch slurry to be used in any of the above aspects may have about 20% to about 55% dry solids granular starch, about 25% to about 40% dry solids granular starch, or about 30% to about 35% dry solids granular starch. The enzyme variant converts the soluble starch into a soluble starch hydrolysate of the granular starch in the amount of at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In another embodiment, an alpha-amylase described herein is used in starch processing further comprising fermentation to produce a fermentation product, e.g., ethanol. Such a process for producing ethanol from starch-containing material by fermentation comprises: (i) liquefying the starch-containing material; (ii) saccharifying the liquefied mash obtained; and (iii) fermenting the material obtained in step (ii) in the presence of a fermenting organism. Optionally the process further comprises recovery of the ethanol. During the fermentation, the ethanol content reaches at least about 7%, at least about 8%, at least about 9%, at least about 10% such as at least about 11%, at least about 12%, at least about 13%, at least about 14%, at least 15%, or at least 16% ethanol.

The saccharification and fermentation processes may be carried out as a simultaneous saccharification and fermentation (SSF) process. When fermentation is performed simultaneously with the hydrolysis, the temperature can be between 30° C. and 35° C., particularly between 31° C. and 34° C. The process may be conducted in an ultrafiltration system where the retentate is held under recirculation in presence of enzymes, raw starch, yeast, yeast nutrients and water and where the permeate is an ethanol containing liquid. Also contemplated is the process conducted in a continuous membrane reactor with ultrafiltration membranes and where the retentate is held under recirculation in presence of enzymes, raw starch, yeast, yeast nutrients and water and where the permeate is an ethanol containing liquid.

The soluble starch hydrolysate of the process may also be used for production of a fermentation product comprising fermenting the treated starch into a fermentation product, such as citric acid, monosodium glutamate, gluconic acid, sodium gluconate, calcium gluconate, potassium gluconate, glucono delta-lactone, or sodium erythorbate.

5.2. Ethanol Production from Starch

In general, alcohol production (ethanol) from whole grain can be separated into four main steps: milling, liquefaction, saccharification, and fermentation. A glucoamylase and an alpha-amylase described herein may be used in saccharification.

The grain is milled in order to open up the structure and allow for further processing. The two processes generally used are wet or dry milling. In dry milling the whole kernel is milled and used in the remaining part of the process. Wet milling gives a very good separation of germ and meal (starch granules and protein) and is, with a few exceptions, applied at locations where there is a parallel production of syrups.

In the liquefaction process, the starch granules are solubilized by hydrolysis to maltodextrins mostly of a DP higher than 4. The hydrolysis may be carried out by acid treatment or enzymatically by alpha-amylase. Acid hydrolysis is used on a limited basis. The raw material can be milled whole grain or a side stream from starch processing. Enzymatic liquefaction is typically carried out as a three-step hot slurry process. The slurry is heated to between about 60-95° C., typically about 80-85° C., and the enzyme(s) is (are) added. Then the slurry is jet-cooked at between about 95-140° C., typically about 105-125° C., cooled to about 60-95° C. and more enzyme(s) is (are) added to obtain the final hydrolysis. The liquefaction process is carried out at about pH 4.5-6.5, typically at a pH about between about 5.0 and about 6.0. Milled and liquefied grain is also known as mash.

To produce low molecular sugars $DP_{1-3}$ that can be metabolized by yeast, the maltodextrin from the liquefaction must be further hydrolyzed or saccharified. The hydrolysis is typically performed enzymatically using glucoamylases, alternatively alpha-glucosidases, or acid alpha-amylases. In one embodiment, a glucoamylase and an AmyE or variant thereof are used in saccharification. A full saccharification step may last up to 72 hours, however, it is common only to do a pre-saccharification of typically 40-90 minutes and then complete saccharification during fermentation (SSF). Saccharification is generally carried out at temperatures from about 30-65° C., typically around about 60° C., and at about pH 4.5.

Yeast typically from *Saccharomyces* spp. is added to the mash and the fermentation is ongoing for 24-96 hours, such as typically 35-60 hours. The temperature is between about 26-34° C., typically at about 32° C., and the pH is from about pH 3-6, typically around about pH 4-5. Note that the most widely used process is a simultaneous saccharification and fermentation (SSF) process where there is no holding stage for the saccharification, meaning that yeast and enzyme is added together. When doing SSF, it is common to introduce a pre-saccharification step at a temperature above 50° C., just prior to the fermentation.

Following the fermentation the mash is distilled to extract the ethanol. The ethanol obtained according to the process of the disclosure may be used as, e.g., fuel ethanol; drinking ethanol, i.e., potable neutral spirits or industrial ethanol. Left over from the fermentation is the grain, which is typically used for animal feed either in liquid form or dried. Further details on how to carry out liquefaction, saccharification, fermentation, distillation, and recovery of ethanol are well known to the skilled person. According to the process of the disclosure, the saccharification and fermentation may be carried out simultaneously or separately.

Although the present invention has been described in detail with reference to examples below, it is understood that various modifications can be made without departing from the spirit of the invention, and would be readily known to the skilled artisan.

5.3. Cleaning and Dishwashing Compositions and Use

The AmyE or variants thereof discussed herein can be formulated in detergent compositions for use in cleaning dishes or other cleaning compositions, for example. These can be gels, powders or liquids. The compositions can comprise the alpha-amylase variant alone, other amylolytic enzymes, other cleaning enzymes, and other components common to cleaning compositions.

Thus, a dishwashing detergent composition can comprise a surfactant. The surfactant may be anionic, non-ionic, cationic, amphoteric or a mixture of these types. The detergent can contain 0% to about 90% by weight of a non-ionic surfactant, such as low- to non-foaming ethoxylated propoxylated straight-chain alcohols.

In the detergent applications, AmyE or variants thereof are usually used in a liquid composition containing propylene glycol. The AmyE or variants thereof can be solubilized in propylene glycol, for example, by circulating in a 25% volume/volume propylene glycol solution containing 10% calcium chloride.

The dishwashing detergent composition may contain detergent builder salts of inorganic and/or organic types. The detergent builders may be subdivided into phosphorus-containing and non-phosphorus-containing types. The detergent composition usually contains about 1% to about 90% of detergent builders. Examples of phosphorus-containing inorganic alkaline detergent builders, when present, include the water-soluble salts, especially alkali metal pyrophosphates, orthophosphates, and polyphosphates. An example of phosphorus-containing organic alkaline detergent builder, when present, includes the water-soluble salts of phosphonates. Examples of non-phosphorus-containing inorganic builders, when present, include water-soluble alkali metal carbonates, borates, and silicates, as well as the various types of water-insoluble crystalline or amorphous alumino silicates, of which zeolites are the best-known representatives.

Examples of suitable organic builders include the alkali metal; ammonium and substituted ammonium; citrates; succinates; malonates; fatty acid sulphonates; carboxymethoxy succinates; ammonium polyacetates; carboxylates; polycarboxylates; aminopolycarboxylates; polyacetyl carboxylates; and polyhydroxsulphonates.

Other suitable organic builders include the higher molecular weight polymers and co-polymers known to have builder properties, for example appropriate polyacrylic acid, polymaleic and polyacrylic/polymaleic acid copolymers, and their salts.

The cleaning composition may contain bleaching agents of the chlorine/bromine-type or the oxygen-type. Examples of inorganic chlorine/bromine-type bleaches are lithium, sodium or calcium hypochlorite, and hypobromite, as well as chlorinated trisodium phosphate. Examples of organic chlorine/bromine-type bleaches are heterocyclic N-bromo- and N-chloro-imides such as trichloroisocyanuric, tribromoisocyanuric, dibromoisocyanuric, and dichloroisocyanuric acids, and salts thereof with water-solubilizing cations such as potassium and sodium. Hydantoin compounds are also suitable.

The cleaning composition may contain oxygen bleaches, for example in the form of an inorganic persalt, optionally with a bleach precursor or as a peroxy acid compound. Typical examples of suitable peroxy bleach compounds are alkali metal perborates, both tetrahydrates and monohydrates, alkali metal percarbonates, persilicates, and perphosphates. Suitable activator materials include tetraacetylethylenediamine (TAED) and glycerol triacetate. Enzymatic bleach activation systems may also be present, such as perborate or percarbonate, glycerol triacetate and perhydrolase, as disclosed in WO 2005/056783, for example.

The cleaning composition may be stabilized using conventional stabilizing agents for the enzyme(s), e.g., a polyol such as, e.g., propylene glycol, a sugar or a sugar alcohol, lactic acid, boric acid, or a boric acid derivative (e.g., an aromatic borate ester). The cleaning composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescent agents, thickeners, and perfumes.

Finally, the AmyE or variants thereof may be used in conventional dishwashing detergents, e.g., in any of the detergents described in the following patent publications, with the consideration that the AmyE or variants thereof disclosed herein are used instead of, or in addition to, any alpha-amylase disclosed in the listed patents and published applications: CA 2006687, GB 2200132, GB 2234980, GB 2228945, DE 3741617, DE 3727911, DE 4212166, DE 4137470, DE 3833047, DE 4205071, WO 93/25651, WO 93/18129, WO 93/04153, WO 92/06157, WO 92/08777, WO 93/21299, WO 93/17089, WO 93/03129, EP 481547, EP 530870, EP 533239, EP 554943, EP 429124, EP 346137, EP 561452, EP 318204, EP 318279, EP 271155, EP 271156, EP 346136, EP 518719, EP 518720, EP 518721, EP 516553, EP 561446, EP 516554, EP 516555, EP 530635, EP 414197, and U.S. Pat. Nos. 5,112,518; 5,141,664; and 5,240,632.

5.4. Laundry Detergent Compositions and Use

According to the embodiment, one or more AmyE or variant thereof may be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products; (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB Patent No. 1,483,591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in U.S. Pat. No. 5,879,920 (Danisco A/S) or EP 238216, for example. Polyols have long been recognized as stabilizers of proteins as well as for improving the solubility of proteins. See, e.g., Kaushik et al., *J. Biol. Chem.* 278: 26458-65 (2003) and references cited therein; and M. Conti et al., *J. Chromatography* 757: 237-245 (1997).

The detergent composition may be in any convenient form, e.g., as gels, powders, granules, pastes, or liquids. A liquid detergent may be aqueous, typically containing up to about 70% of water, and 0% to about 30% of organic solvent, it may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate; α-olefinsulfonate; alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide, as described in WO 92/06154, for example.

The detergent composition may additionally comprise one or more other enzymes, such as lipase, cutinase, protease, cellulase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylentriaminepentaacetic acid (DTMPA), alkyl- or alkenylsuccinic acid, soluble silicates or layered silicates (e.g., SKS-6 from Hoechst). The detergent may also be unbuilt, i.e., essentially free of detergent builder. Enzymes may be used in any composition compatible with the stability of the enzyme. Enzymes can be protected against generally deleterious components by known forms of encapsulation, as by granulation or sequestration in hydro gels, for example. Enzymes and specifically alpha-amylases either with or without the starch binding domains are not limited to laundry and dishwashing applications, but may bind use in surface cleaners and ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate optionally combined with a peracid-forming bleach activator, such as TAED or nonanoyloxybenzenesulfonate (NOBS). Alternatively, the bleaching system may comprise peroxy acids of the amide, imide, or sulfone type, for example. The bleaching system can also be an enzymatic bleaching system where a perhydrolase activates peroxide, such as that described in WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative, such as an aromatic borate ester; and the composition may be formulated as described in WO 92/19709 and WO 92/19708, for example.

The detergent may also contain other conventional detergent ingredients such as fabric conditioners including clays, foam boosters, suds suppressors, anti-corrosion agents, soil-suspending agents, anti-soil redeposition agents, dyes, bactericides, optical brighteners, or perfume, for example. The pH (measured in aqueous solution at use concentration) is usually neutral or alkaline, e.g., pH about 7.0 to about 11.0.

The alpha-amylase variant may be incorporated in concentrations conventionally employed in detergents. It is at present contemplated that, in the detergent composition, the alpha-amylase variant may be added in an amount corresponding to 0.00001-1.0 mg (calculated as pure enzyme protein) of alpha-amylase variant per liter of wash liquor. Particular forms of detergent compositions comprising the alpha-amylase variants can be formulated to include:

(1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate, about 2 to about 6%; zeolite (e.g., NaAlSiO$_4$) about 15% to about 22%; sodium sulfate (e.g., Na$_2$SO$_4$) 0% to about 6%; sodium citrate/citric acid (e.g., C$_6$H$_5$Na$_3$O$_7$/C$_6$H$_8$O$_7$) about 0% to about 15%; sodium perborate (e.g., NaBO$_3$.H$_2$O) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

(2) A detergent composition formulated as a granulate having a bulk density of at least 600 g/L comprising linear alkylbenzenesulfonate (calculated as acid) about 6% to about 11%; alcohol ethoxysulfate (e.g., C$_{12-18}$ alcohol, 1-2 EO) or alkyl sulfate (e.g., C$_{16-18}$) about 1% to about 3%; alcohol ethoxylate (e.g., C$_{14-15}$ alcohol, 7 EO) about 5% to about 9%; sodium carbonate (e.g., Na$_2$CO$_3$) about 15% to about 21%; soluble silicate, about 1% to about 4%; zeolite (e.g., NaAlSiO$_4$) about 24% to about 34%; sodium sulfate (e.g., Na$_2$SO$_4$) about 4% to about 10%; sodium citrate/citric acid (e.g., C$_6$H$_5$Na$_3$O$_7$/C$_6$H$_8$O$_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

(3) A detergent composition formulated as a granulate having a bulk density of at least 600 g/L comprising linear alkylbenzenesulfonate (calculated as acid) about 5% to about 9%; alcohol ethoxylate (e.g., C$_{12-15}$ alcohol, 7 EO) about 7% to about 14%; Soap as fatty acid (e.g., C$_{16-22}$ fatty acid) about 1 to about 3%; sodium carbonate (as Na$_2$CO$_3$) about 10% to about 17%; soluble silicate, about 3% to about 9%; zeolite (as NaAlSiO$_4$) about 23% to about 33%; sodium sulfate (e.g., Na$_2$SO$_4$) 0% to about 4%; sodium perborate (e.g., NaBO$_3$.H$_2$O) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

(4) A detergent composition formulated as a granulate having a bulk density of at least 600 g/L comprising linear alkylbenzenesulfonate (calculated as acid) about 8% to about 12%; alcohol ethoxylate (e.g., C$_{12-15}$ alcohol, 7 EO) about 10% to about 25%; sodium carbonate (as Na$_2$CO$_3$) about 14% to about 22%; soluble silicate, about 1% to about 5%; zeolite (e.g., NaAlSiO$_4$) about 25% to about 35%; sodium sulfate (e.g., Na$_2$SO$_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

(5) An aqueous liquid detergent composition comprising linear alkylbenzenesulfonate (calculated as acid) about 15% to about 21%; alcohol ethoxylate (e.g., C$_{12-15}$ alcohol, 7 EO or C$_{12-15}$ alcohol, 5 EO) about 12% to about 18%; soap as fatty acid (e.g., oleic acid) about 3% to about 13%; alkenylsuccinic acid (C$_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., B$_4$O$_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

(6) An aqueous structured liquid detergent composition comprising linear alkylbenzenesulfonate (calculated as acid) about 15% to about 21%; alcohol ethoxylate (e.g., C$_{12-15}$ alcohol, 7 EO, or C$_{12-15}$ alcohol, 5 EO) 3-9%; soap as fatty acid (e.g., oleic acid) about 3% to about 10%; zeolite (as NaAlSiO$_4$) about 14% to about 22%; potassium citrate about 9% to about 18%; borate (e.g., B$_4$O$_7$) 0% to about 2%; carboxymethylcellulose (CMC) 0% to about 2%; polymers (e.g., PEG, PVP) 0% to about 3%; anchoring polymers (e.g., lauryl methacrylate/acrylic acid copolymer); molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

(7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., Na$_2$CO$_3$) about 5% to about 10%; soluble silicate, about 1% to about 4%; zeolite (e.g., NaAlSiO$_4$) about 20% to about 40%; sodium sulfate (e.g., Na$_2$SO$_4$) about 2% to about 8%; sodium perborate (e.g., NaBO$_3$.H$_2$O) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

(8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., Na$_2$CO$_3$) about 4% to about 10%; soluble silicate, about 1% to about 4%; zeolite (e.g., NaAlSiO$_4$) about 30% to about 50%; sodium sulfate (e.g., Na$_2$SO$_4$) about 3% to about 11%; sodium citrate (e.g., C$_6$H$_5$Na$_3$O$_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

(9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., Na$_2$CO$_3$) about 14% to about 22%; zeolite (e.g., NaAlSiO$_4$) about 18% to about 32%; sodium sulfate (e.g., Na$_2$SO$_4$) about 5% to about 20%; sodium citrate (e.g., C$_6$H$_5$Na$_3$O$_7$) about 3% to about 8%; sodium perborate (e.g., NaBO$_3$.H$_2$O) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

(10) An aqueous liquid detergent composition comprising linear alkylbenzenesulfonate (calculated as acid) about 15% to about 23%; alcohol ethoxysulfate (e.g., C$_{12-15}$ alcohol, 2-3 EO) about 8% to about 15%; alcohol ethoxylate (e.g., C$_{12-15}$ alcohol, 7 EO, or C$_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., B$_4$O$_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

(11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer, such as lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

(12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates, about 5% to about 15%; sodium sulfate (e.g., $Na_2SO_4$) 0% to about 5%; zeolite ($NaAlSiO_4$) about 15% to about 28%; sodium perborate (e.g., $NaBO_3H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

(13) Detergent compositions as described in compositions 1)-12) supra, wherein all or part of the linear alkylbenzenesulfonate is replaced by ($C_{12}$-$C_{18}$) alkyl sulfate.

(14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate, 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

(15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate, 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

(16) Detergent formulations as described in 1)-15) supra, which contain a stabilized or encapsulated peracid, either as an additional component or as a substitute for already specified bleach systems.

(17) Detergent compositions as described supra in 1), 3), 7), 9), and 12), wherein perborate is replaced by percarbonate.

(18) Detergent compositions as described supra in 1), 3), 7), 9), 12), 14), and 15), which additionally contains a manganese catalyst.

(19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

In another embodiment, the 2,6-β-D-fructan hydrolase can be incorporated in detergent compositions and used for removal/cleaning of biofilm present on household and/or industrial textile/laundry.

The detergent composition may for example be formulated as a hand or machine laundry detergent composition, including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the detergent composition can comprise 2,6-O-D-fructan hydrolase, one or more alpha-amylase variants, and one or more other cleaning enzymes, such as a protease, a lipase, a cutinase, a carbohydrase, a cellulase, a pectinase, a mannanase, an arabinase, a galactanase, a xylanase, an oxidase, a laccase, and/or a peroxidase, and/or combinations thereof. In general the properties of the chosen enzyme(s) should be compatible with the selected detergent, (e.g., pH-optimum, compatibility with other enzymatic and non-enzymatic ingredients, etc.), and the enzyme(s) should be present in effective amounts.

Proteases: suitable proteases include those of animal, vegetable or microbial origin. Chemically modified or protein engineered mutants are also suitable. The protease may be a serine protease or a metalloprotease, e.g., an alkaline microbial protease or a trypsin-like protease. Examples of alkaline proteases are subtilisins, especially those derived from *Bacillus* sp., e.g., subtilisin Novo, subtilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729 and WO 98/20115. Suitable commercially available protease enzymes include Alcalase®, Savinase®, Primase™, Duralase™, Esperase®, and Kannase™ (Novo Nordisk A/S); Maxatase®, Maxacal™, Maxapem™, Properase™, Purafect®, Purafect OXP™, FN2™, and FN3™ (Danisco A/S).

Lipases: suitable lipases include those of bacterial or fungal origin. Chemically modified or protein engineered mutants are included. Examples of useful lipases include, but are not limited to, lipases from *Humicola* (synonym *Thermomyces*), e.g. *H. lanuginosa* (*T. lanuginosus*) (see, e.g., EP 258068 and EP 305216) and *H. insolens* (see, e.g., WO 96/13580); a *Pseudomonas* lipase (e.g., from *P. alcaligenes* or *P. pseudoalcaligenes*;see, e.g., EP218272), *P. cepacia* (see, e.g., EP331 376), *P. stutzeri* (see, e.g., GB 1,372,034), *P. fluorescens, Pseudomonas* sp. strain SD 705 (see, e.g., WO 95/06720 and WO 96/27002), *P. wisconsinensis* (see, e.g., WO 96/12012); a *Bacillus* lipase (e.g., from *B. subtilis*; see, e.g., Dartois et al. *Biochemica Biophysica Acta,* 1131: 253-360 (1993)), *B. stearothermophilus* (see, e.g., JP 64/744992), or *B. pumilus* (see, e.g., WO 91/16422). Additional lipase variants contemplated for use in the formulations include those described, for example, in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include Lipolase® and Lipolase® Ultra (Novo Nordisk A/S).

Polyesterases: Suitable polyesterases include, but are not limited to, those described in WO 01/34899 (Danisco A/S)

and WO 01/14629 (Danisco A/S), and can be included in any combination with other enzymes discussed herein.

Amylases: The compositions can be combined with other alpha-amylases, such as a non-variant alpha-amylase. These can include commercially available amylases, such as but not limited to Duramyl®, Termamyl™, Fungamyl® and BAN™ (Novo Nordisk A/S), Rapidase®, and Purastar® (Danisco A/S).

Cellulases: Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307; 5,648,263; 5,691,178; 5,776,757; and WO 89/09259, for example. Exemplary cellulases contemplated for use are those having color care benefit for the textile. Examples of such cellulases are cellulases described in EP 0495257; EP 531 372; WO 99/25846 (Danisco A/S), WO 96/34108 (Danisco A/S), WO 96/11262; WO 96/29397; and WO 98/08940, for example. Other examples are cellulase variants, such as those described in WO 94/07998; WO 98/12307; WO 95/24471; PCT/DK98/00299; EP 531 315; U.S. Pat. Nos. 5,457,046; 5,686,593; and 5,763,254. Commercially available cellulases include Celluzyme® and Carezyme® (Novo Nordisk A/S); Clazinase™ and Puradax® HA (Danisco A/S); and KAC-500(B)™ (Kao Corporation).

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novo Nordisk A/S), for example.

The detergent enzyme(s) may be included in a detergent composition by adding separate additives containing one or more enzymes, or by adding a combined additive comprising all of these enzymes. A detergent additive, i.e., a separate additive or a combined additive, can be formulated as a granulate, liquid, slurry, etc. Suitable granulate detergent additive formulations include non-dusting granulates.

Non-dusting granulates may be produced, e.g., as disclosed in U.S. Pat. Nos. 4,106,991 and 4,661,452 and optionally may be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591, for example. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238 216.

The detergent composition may be in any convenient form, e.g., a bar, tablet, gel, powder, granule, paste, or liquid. A liquid detergent may be aqueous, typically containing up to about 70% water, and 0% to about 30% organic solvent. Compact detergent gels containing 30% or less water are also contemplated. The detergent composition comprises one or more surfactants, which may be non-ionic, including semipolar, anionic, cationic, or zwitterionic, or any combination thereof. The surfactants are typically present at a level of from 0.1% to 60% by weight.

When included therein the detergent typically will contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose (CMC), poly(vinylpyrrolidone) (PVP), poly(ethylene glycol) (PEG), poly (vinyl alcohol) (PVA), poly(vinylpyridine-N-oxide), poly(vinylimidazole), polycarboxylates, e.g., polyacrylates, maleic/acrylic acid copolymers), and lauryl methacrylate/acrylic acid copolymers.

The detergent may contain a bleaching system that may comprise a source of $H_2O_2$, such as perborate or percarbonate, which may be combined with a peracid-forming bleach activator (e.g., tetraacetylethylenediamine or nonanoyloxybenzenesulfonate). Alternatively, the bleaching system may comprise peroxyacids (e.g., the amide-, imide-, or sulfone-type peroxyacids). The bleaching system can also be an enzymatic bleaching system.

The enzyme(s) of the detergent composition may be stabilized using conventional stabilizing agents, e.g., polyol (e.g., propylene glycol or glycerol), a sugar or sugar alcohol, lactic acid, boric acid, a boric acid derivative (e.g., an aromatic borate ester), or a phenyl boronic acid derivative (e.g., 4-formylphenyl boronic acid). The composition may be formulated as described in WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is contemplated that in the detergent compositions, the enzyme variants may be added in an amount corresponding to about 0.01 to about 100 mg of enzyme protein per liter of wash liquor, particularly about 0.05 to about 5.0 mg of enzyme protein per liter of wash liquor, or even more particularly in 0.1 to about 1.0 mg of enzyme protein per liter of wash liquor.

A representative assay that may be used to test the efficacy of a cleaning composition comprising AmyE or a variant thereof includes a swatch test. A "swatch" is a piece of material such as a fabric that has a stain applied thereto. The material can be, for example, fabrics made of cotton, polyester or mixtures of natural and synthetic fibers. Alternatively, the material can be paper, such as filter paper or nitrocellulose, or a piece of a hard material, such as ceramic, metal, or glass. For alpha-amylases, the stain is starch based, but can include blood, milk, ink, grass, tea, wine, spinach, gravy, chocolate egg, cheese, clay, pigment, oil, or mixtures of these compounds. In one embodiment, the AmyE or variant thereof is tested in a BMI (blood/milk/ink) assay.

A "smaller swatch" is a piece of the swatch that has been cut with a single hole punch device, or a custom manufactured 96-hole punch device, where the pattern of the multi-hole punch is matched to standard 96-well microtiter plates, or has been otherwise removed from the swatch. The swatch can be of textile, paper, metal, or other suitable material. The smaller swatch can have the stain affixed either before or after it is placed into the well of a 24-, 48- or 96-well microtiter plate. The smaller swatch also can be made by applying a stain to a small piece of material. For example, the smaller swatch can be a piece of fabric with a stain ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived to deliver simultaneously swatches to any format plate, including, but not limited to, 24-well, 48-well, and 96-well plates. In another conceivable method, the soiled test platform can be a bead made of either metal, plastic, glass, ceramic, or other suitable material that is coated with the soil substrate. The one or more coated beads are then placed into wells of 96-, 48-, or 24-well plates or larger formats, containing suitable buffer and enzyme. In this case, supernatant can be examined for released soil either by direct absorbance measurement or after a secondary color development reaction. Analysis of the released soil might also be taken by mass spectral analysis.

In one embodiment, a treatment protocol provides control over degree of fixation of a stain. As a result, it is possible to produce swatches that, for example, release varying amounts of stain when washed in the absence of the enzyme being tested. The use of fixed swatches leads to a dramatic improvement of the signal-to-noise ratio in the wash assays. Furthermore, by varying the degree of fixation, one can generate stains that give optimum results under the various cleaning conditions.

Swatches having stains of known "strength" on various types of material are commercially available (EMPA, St. Gallen, Switzerland; wfk—Testgewebe GmbH, Krefeld Germany; or Center for Test Materials, Vlaardingen, The Netherlands) and/or can be made by the practitioner (Morris and Prato, *Textile Research Journal* 52(4): 280-286 (1982)). Swatches can comprise, for example, a cotton-containing fabric containing a stain made by blood/milk/ink (BMI), spinach, grass, or chocolate/milk/soot. A BMI stain can be fixed to cotton with 0.0003% to 0.3% hydrogen peroxide, for example. Other combinations include grass or spinach fixed with 0.001% to 1% glutaraldehyde, gelatin and Coomassie stain fixed with 0.001% to 1% glutaraldehyde, or chocolate, milk and soot fixed with 0.001% to 1% glutaraldehyde.

The swatch can also be agitated during incubation with the enzyme and/or detergent formulation. Wash performance data is dependent on the orientation of the swatches in the wells (horizontal versus vertical), particularly in the 96-well plate. This would indicate that mixing was insufficient during the incubation period. Although there are a number of ways to ensure sufficient agitation during incubation, a plate holder in which the microtiter plate is sandwiched between two plates of aluminum can be constructed. This can be as simple as placing, for example, an adhesive plate sealer over the wells then clamping the two aluminum plates to the 96-well plate with any type of appropriate, commercially available clamps. It can then be mounted in a commercial incubator shaker. Setting the shaker to about 400 rpm results in very efficient mixing, while leakage or cross-contamination is efficiently prevented by the holder.

Trinitrobenzenesulfonic acid (TNBS) can be used to quantify the concentration of amino groups in the wash liquor. This can serve as a measure of the amount of protein that was removed from the swatch (see, e.g., Cayot and Tainturier, *Anal. Biochem.* 249: 184-200 (1997)). However, if a detergent or an enzyme sample leads to the formation of unusually small peptide fragments (for example, from the presence of peptidases in the sample), then one will obtain a larger TNBS signal, i.e., more "noise."

Another means of measuring wash performance of blood/milk/ink that is based on ink release that can be quantified by measuring the absorbance of the wash liquor. The absorbance can be measured at any wavelength between 350 and 800 nm. In one embodiment, the wavelength is measured at 410 nm or 620 nm. The wash liquor can also be examined to determine the wash performance on stains containing grass, spinach, gelatin or Coomassie stain. Suitable wavelengths for these stains include and 670 nm for spinach or grass and 620 nm for gelatin or Coomassie. For example, an aliquot of the wash liquor (typically 100-150 μL from a 96-well microplate, for example) is removed and placed in a cuvette or multiwell microplate. This is then placed in a spectrophotometer and the absorbance is read at an appropriate wavelength. The system also can be used to determine a suitable enzyme and/or detergent composition for dish washing, for example, using a blood/milk/ink stain on a suitable substrate, such as cloth, plastic or ceramic.

In one aspect, a BMI stain is fixed to cotton by applying 0.3% hydrogen peroxide to the BMI/cotton swatch for 30 minutes at 25° C. or by applying 0.03% hydrogen peroxide to the BMI/cotton swatch for 30 minutes at 60° C. Smaller swatches of approximately 0.25" are cut from the BMI/cotton swatch and placed in the wells of a 96-well microtiter plate. Into each well, a known mixture of a detergent composition and an enzyme, such as a variant protein, is placed. After placing an adhesive plate sealer onto the top of the microtiter plate, the microtiter plate is clamped to an aluminum plate and agitated on an orbital shaker at approximately 250 rpm for about 10 to 60 minutes. At the end of this time, the supernatants are transferred to wells in a new microtiter plate and the absorbance of the ink at 620 nm is measured. This can be similarly tests with spinach stains or grass stains fixed to cotton by applying 0.01% glutaraldehyde to the spinach/cotton swatch or grass/cotton swatch for 30 minutes at 25° C. The same can be done with chocolate, milk, and/or soot stains.

5.5. Textile Desizing Compositions and Use

Also contemplated are compositions and methods of treating fabrics (e.g., to desize a textile) using one or more AmyE or variant thereof. The AmyE or variants thereof can be used in any fabric-treating method, which are well known in the art (see, e.g., U.S. Pat. No. 6,077,316). For example, in one aspect, the feel and appearance of a fabric is improved by a method comprising contacting the fabric with an enzyme variant in a solution. In one aspect, the fabric is treated with the solution under pressure.

In one aspect, the enzymes are applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The AmyE or variants thereof can be applied to remove these sizing starch or starch derivatives. After the textiles have been woven, a fabric can proceed to a desizing stage. This can be followed by one or more additional fabric processing steps. Desizing is the act of removing size from textiles. After weaving, the size coating should be removed before further processing the fabric in order to ensure a homogeneous and wash-proof result. Also provided is a method of desizing comprising enzymatic hydrolysis of the size by the action of an enzyme variant.

The AmyE or variants thereof can be used alone or with other desizing chemical reagents and/or desizing enzymes to desize fabrics, including cotton-containing fabrics, as detergent additives, e.g., in aqueous compositions. The AmyE or variants thereof also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. The alpha-amylase variant can be used in methods of finishing denim garments (e.g., a "bio-stoning process"), enzymatic desizing and providing softness to fabrics, and/or finishing process.

It will be apparent to those skilled in the art that various modifications and variation can be made to the compositions and methods of using same without departing from the spirit or scope of the intended use. Thus, it is the modifications and variations provided they come within the scope of the appended claims and their equivalents.

EXAMPLES

Example 1

1.1. Plasmid Construction

Figure 5:
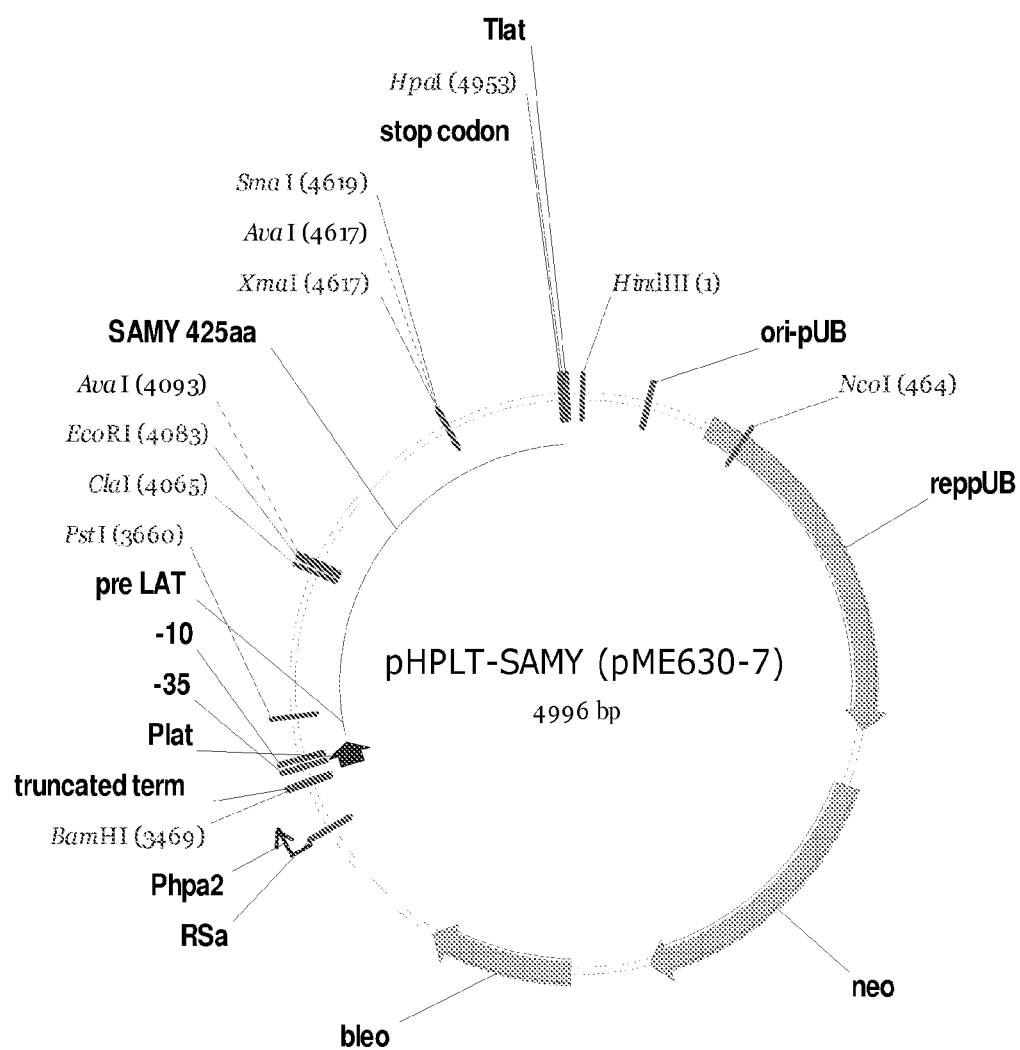
FIG. 5 depicts plasmid pME630-7, which comprises a polynucleotide (labeled "SAMY 425aa") that encodes AmyE-tr (SEQ ID NO: 2). The plasmid comprises a polynucleotide in-frame with the SAMY gene that encodes a signal sequence from *B. licheniformis* alpha-amylase (labeled "pre LAT").

Nucleic acids encoding the AmyE of SEQ ID NO: 1 or a C-terminal truncated AmyE variant, AmyE-tr (SEQ ID NO: 2), were cloned into the *B. subtilis* pHPLT expression vector, disclosed in U.S. Pat. No. 5,024,943. FIG. 5 depicts the vector comprising a nucleic acid encoding AmyE-tr.

Referring to FIG. 5, the pHPLT vector contains the *B. licheniformis* LAT promoter ("Plat"), a sequence encoding the LAT signal peptide ("preLAT"), followed by PstI and HpaI restriction sites for cloning. Additional plasmid elements from plasmid pUB110 disclosed in McKenzie et al., *Plasmid* 15(2): 93-103 (1986): "ori-pUB" is the origin of replication from pUB110; "reppUB" is the replicase gene from pUB110, "neo" is the neomycin/kanamycin resistance gene from pUB110; "bleo" is the bleomycin resistance marker, "Tlat" is the transcriptional terminator from *B. licheniformis* amylase.

Plasmid constructs for the expression of AmyE and AmyE-tr were assembled using the AmyE-encoding sequence described by Yang et al, "Nucleotide sequence of the amylase gene from *Bacillus subtilis*," *Nucleic Acids Res.* 11(2): 237-49 (1983). Plasmid pME629.5 contains the nucleic acid encoding the full-length AmyE of SEQ ID NO: 1. The gene has a three base deletion in the sequence encoding the starch binding domain, compared to the sequence described by Yang et al.

Plasmid pME630.7 contains the truncated AmyE sequence, AmyE-tr, and is shown in FIG. 5. AmyE-tr is truncated at D425 of SEQ ID NO: 1. AmyE-tr was designed from a crystal structure of an AmyE variant that lacks the starch binding domain, disclosed in Fujimoto et al., "Crystal structure of a catalytic-site mutant alpha-amylase from *Bacillus subtilis* complexed with maltopentaose," *J. Mol. Biol.* 277: 393-407 (1998). See RCSB Protein Data Bank© Accession No. 1BAG, "Alpha-Amylase From *Bacillus Subtilis* Complexed With Maltopentaose."

For expression plasmid construction, the nucleic acid encoding AmyE was PCR-amplified using Herculase® (Stratagene, Calif.). The PCR products were purified using a column provided in a Qiagen QIAquik™ PCR purification kit (Qiagen, Valencia, Calif.), and resuspended in 50 µL of Milli-Q™-purified water. 50 µL of the purified DNA was digested sequentially with HpaI (Roche) and PstI (Roche), and the resultant DNA resuspended in 30 µL of Milli-Q™-purified water. 10-20 ng/µL DNA was cloned into plasmid pHPLT using PstI and HpaI cloning sites. The ligation mixtures were directly transformed into competent *B. subtilis* cells (genotype: DaprE, DnprE, degUHy32 oppA, DspoIIE3501, amyE::xylRPxylAcomK-phleo). SC6.1 *B. subtilis* cells have a competency gene (comK) that is placed under a xylose-inducible promoter. Competency for DNA binding and uptake is induced by the addition of xylose. Because the AmyE gene in the parent plasmid has two PstI sites, a PCR fusion reaction was carried out to remove these sites before cloning. PCR fusion was done after two separate PCR reactions. The following primers were used for making the pHPLT construct using HpaI and PstI sites:

```
SEQ ID NO: 18: Primer PSTAMYE-F
5' CTTCTTGCTGCCTCATTCTGCAGCTTCAGCACTTACAGCACCGTCGAT
CAAAAGCGGAAC 3'

SEQ ID NO: 19: Primer AMYENOPST-R
5' CTGGAGGCACTATCCTGAAGGATTTCTCCGTATTGGAACTCTGCTGAT
GTATTTGTG 3'

SEQ ID NO: 20: Primer AMYENOPST-F
5' CACAAATACATCAGCAGAGTTCCAATACGGAGAAATCCTTCAGGATA
GTGCCTCCAG 3'

SEQ ID NO: 21: Primer HPAIAMYE-R
5' CAGGAAATCCGTCCTCTGTTAACTCAATGGGGAAGAGAACCGCTTAA
GCCCGAGTC 3'

SEQ ID NO: 22: Primer HPAIAMYE466-R
5' CAGGAAATCCGTCCTCTGTTAACTCAATCAGGATAAAGCACAGCTAC
AGACCTGG 3'

SEQ ID NO: 23: Primer AMYE SEQ-F1
5' TACACAAGTACAGTCCTATCTG 3'

SEQ ID NO: 24: Primer AMYE SEQ-F2
5' CATCCTCTGTCTCTATCAATAC 3'
```

The plasmids pME629.5 and pME630.7 express AmyE with a 31 residue signal sequence, which is cleaved post-translationally. The subsequent 10 N-terminal amino acids are processed separately as proposed by Yang et al. (1983) supra.

1.2. Protein Expression

Transformants for AmyE full-length and truncated clones were selected on LA with 10 µg/mL neomycin, 1% insoluble starch and incubated overnight at 37° C. Transformants showing a clearing (or halo) around the colony were selected, and vials were made for further studies. Pre-cultures of the transformants were grown for 8 h in LB with 10 μg/mL neomycin. Then, 30 L of this pre-culture were added into a 250 mL flask filled with 30 mL of cultivation media (described below) supplemented with 10 μg/mL neomycin and 5 mM $CaCl_2$. The cultivation media was an enriched semi-defined media based on MOPS buffer, with urea as the major nitrogen source, glucose as the main carbon source, and supplemented with 1% soytone for robust cell growth. The shake flasks were incubated for 60-65 hours at 37° C., with mixing at 250 rpm. Cultures were harvested by centrifugation at 5000 rpm for 20 minutes in conical tubes. Since both AmyE full-length and AmyE truncated proteins expressed at high levels, the culture supernatants were used for assays without further purification.

Example 2

The following assays were used in the examples described below. Any deviations from the protocols provided below are indicated in the examples. In these experiments, a spectrophotometer was used to measure the absorbance of the products formed after the completion of the reactions.

2.1. Bradford Assay for Protein Content Determination in 96-Well Microtiter Plate Protein concentration in sample supernatants was determined using the Bradford QuickStart™ Dye Reagent (Bio-Rad, California). Samples were obtained by filtration of broths from cultures grown in microtiter plates (MTPs) for 3 days at 37° C. with shaking at 280 rpm and humidified aeration. A 10 μL sample of the culture filtrate was combined with 200 μL Bradford QuickStart™ Dye Reagent in a well of a second MTP. After thorough mixing, the MTP's were incubated for at least 10 minutes at room temperature. Air bubbles were removed and the OD (optical density) was measured at 595 nm. To determine the protein concentration, the background reading (from uninoculated wells) was subtracted from the sample readings.

2.2. Determination of AmyE Activity

Figure 6:
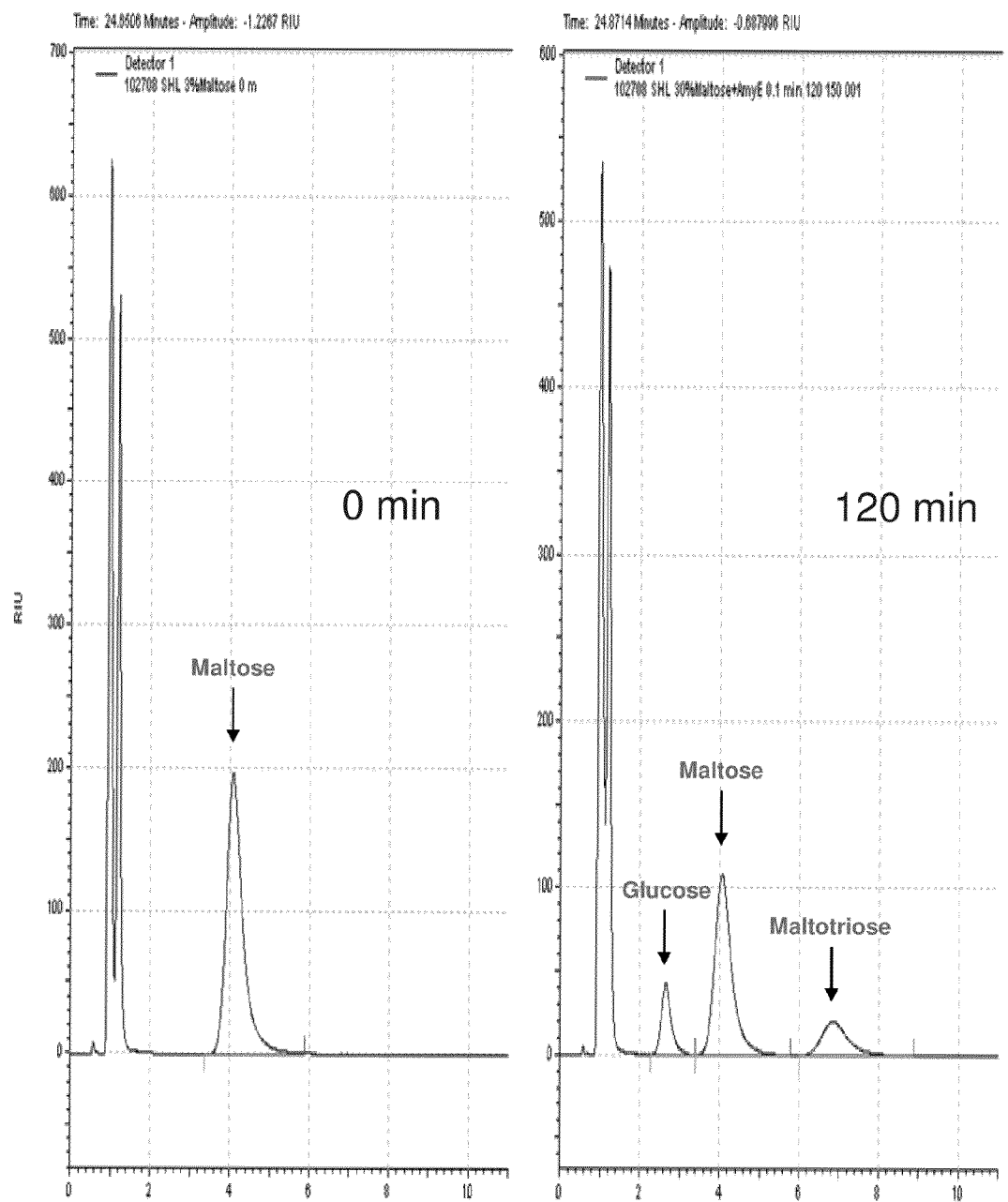
FIG. 6 depicts the HPLC analysis of reaction products catalyzed by AmyE during incubation with maltose.
Figure 7:
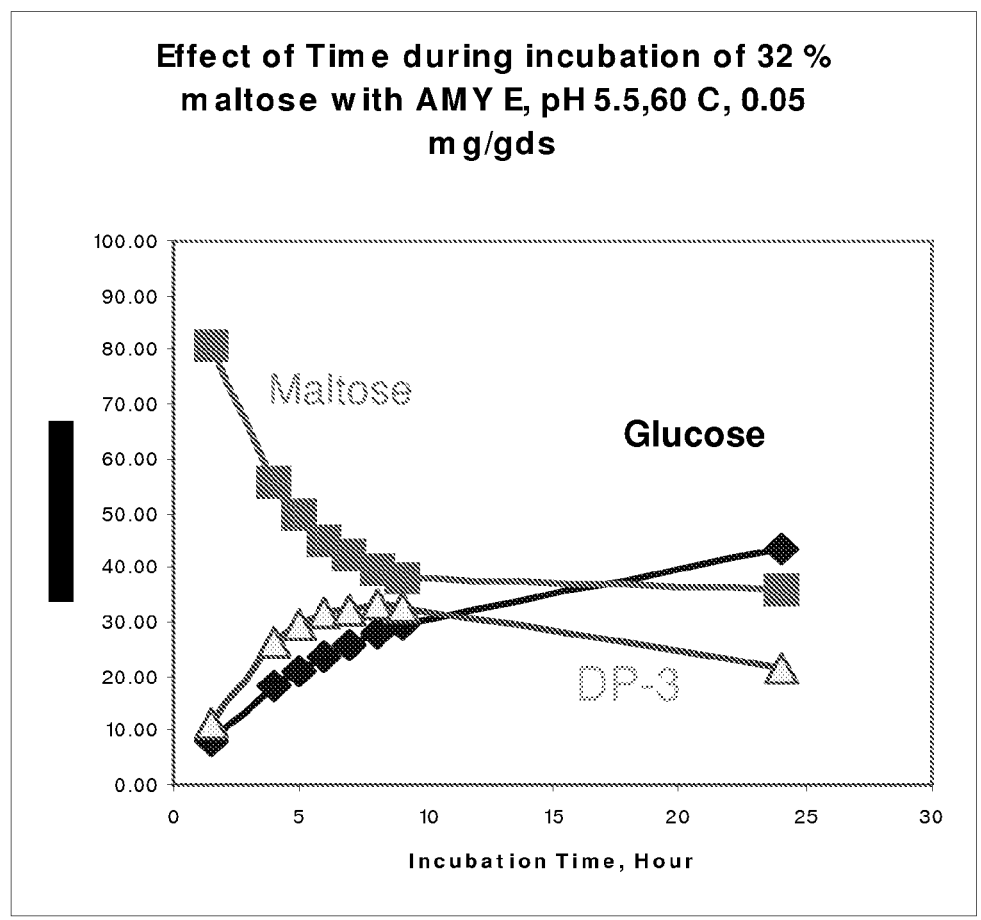
FIG. 7 depicts the reaction composition of AmyE-mediated maltotriose synthesis (glucose, maltose, and maltotriose) over time.

AmyE displays transglucosidase activity, i.e., AmyE catalyzes the formation of the tri-saccharide from maltose. FIG. 6 depicts the HPLC detection of the tri-saccharide after incubating AmyE with maltose. FIG. 7 depicts the reaction composition of AmyE-mediated maltotriose synthesis over time. The enzyme activity of AmyE was measured based on its transglucosidase activity. One unit of AmyE is defined as the amount of enzyme required under assay condition to produce one micromole of tri-saccharide from maltose per minute. In a typical assay, an aliquot sample of AmyE, 0.1 ml, was added to 5 ml of 30% maltose in phosphate buffer, pH 4.5, and incubated for 60 min at 60° C. The reaction was terminated by placing the sample in a boiling water bath for 10 min. The amount of tri-saccharide present in the sample was determined by HPLC.

2.3. Determination of Glucoamylase Activity

Glucoamylase activity was measured using an assay based on its ability to catalyze the hydrolysis of p-nitrophenyl-alpha-D-glucopyranoside (PNPG) to glucose and p-nitrophenol. At an alkaline pH, the released nitrophenol displays a yellow color that is proportional to glucoamylase activity and is monitored at 400 nm. One glucoamylase activity unit (GAU) is defined as the amount of enzyme that produce 1 μmole of reducing sugar, calculated as glucose, per hour from a soluble starch substrate (4%) at pH 4.2 and 60° C.

2.4. Determination of Pullulanase Activity

The pullulanase activity was determined by a colorimetric method that utilizes a soluble red-pullan substrate. The pullulanase is able to catalyze the hydrolysis of the red-pullan substrate, which results in the release of soluble fragments from the dyed substrate. Enzyme reaction is terminated by precipitating the substrate with 95% ethanol solution. The supernatant is measured spectrophotometrically at 501 nm. The degree of color intensity is proportional to the enzyme activity. One acid stable pullulanase unit (ASPU) is defined as the amount of the enzyme that releases one equivalent reducing potential as glucose from pullulan per minute at pH 4.5 and 60° C.

2.5. Conventional Ethanol Fermentation

Two batches of liquefact (31% DS) obtained from Illinois River Energy, containing 400 ppm urea were adjusted to pH 4.3 and pH 5.8 (using $5NH_2SO_4$). 100 g substrate was added to a 125 mL Erlenmeyer flask. AmyE-tr and SPEZYME® XTRA amylase were dosed at 0.20 mg/g DS. Fermentations were inoculated with 0.2 ml of 10% (w/v) Red Star Ethanol Red yeast pre-hydrated ~45 min in DI water. Flasks were incubated at 32° C. with stir bars at 320 rpm for a 48 h fermentation.

2.6. Ethanol Fermentation on Whole Ground Corn

Two batches of 32% DS corn flour substrate with 400 ppm urea were prepared at pH 4.3 and pH 5.8 (adjusted with $5NH_2SO_4$). 100 g substrate was added to a 125 ml Erlenmeyer flask. Full length AmyE (SEQ ID NO: 1) and AmyE-tr (SEQ ID NO: 2) were dosed at 0.20 mg/g DS, *A. kawachii* alpha-amylase (AkAA; SEQ ID NO: 6) was dosed at 1.5 SSU/g DS. The amino acid sequence of AkAA is disclosed in SEQ ID NO: 4 of U.S. Pat. No. 7,332,319. The ability of AmyE and AmyE-tr to hydrolyze whole ground corn was also compared to a mixture of *T. reesei* glucoamylase (TrGA; SEQ ID NO: 7) dosed at 0.5 GAU/g plus *A. kawachii* alpha-amylase dosed at 1.5 SSU/g DS. The amino acid sequence of TrGA was disclosed in SEQ ID NO: 3 of WO 06/060062. Fermentations were inoculated with 0.2 ml of 10% (w/v) Red Star Ethanol Red yeast prehydrated ~45 min in DI water. Flasks were incubated at 32° C. with stir bars at 300 rpm for 72 h fermentation.

2.7. Glucose Formation Determination by HPLC Measurement

Hydrolysis of Maltose and Maltoheptaose 0.5% maltose or maltoheptaose solutions were prepared in 50 mM sodium acetate, pH 4.5 or 5.6, or in 50 mM malic acid pH 5.6, as specified for each experiment. All enzyme samples were initially diluted to 1 mg/mL. Reaction mixtures were prepared by diluting the enzyme using the appropriate substrate solutions to give a final enzyme concentration of 1 ppm, then 200 μL aliquots were transferred to sterile screw top tubes and place in a 37° C. incubator. The reactions were stopped at the indicated times by diluting 10-fold into 10 mM sodium hydroxide.

Hydrolysis of Insoluble Starch

For measuring the hydrolysis of insoluble granular starch, purified AmyE (24.5 g/L) was diluted to a final concentration of 20.4 ppm in malic acid buffer, pH 5.6. The protein was then added to a 5% corn flour solution prepared in malic acid buffer, pH 5.6, to a final concentration of 1 ppm, and the mixture was incubated in a shaker at 32° C. Samples were periodically removed and diluted 10 fold into 50 mM NaOH to quench the reaction.

HPLC Detection Method

The composition of saccharification products was measured by a HPLC system (Beckman System Gold 32 Karat Fullerton, Calif.). The system, maintained at 50° C., was equipped with a Rezex 8 u8% H Monosaccharides column and a refractive index (RI) detector (ERC-7515A, Anspec Company, Inc.). Diluted sulfuric acid (0.01 N) was applied as the mobile phase at a flow rate of 0.6 ml/min. 20 µl of 4.0% solution of the reaction mixture was injected onto the column. Elution profiles were obtained over 45 minutes. The distribution of saccharides and the amount of each saccharide were determined from previously run standards.

2.8. Sediment Test

Samples of saccharified syrup were incubated in a 60° C. water bath for 10-30 minutes to bring them to a constant temperature. The incubation, however, should not be longer than one hour. If necessary, the DS value was adjusted to 35%±0.5% prior to testing. Samples were mixed well on a magnetic stirrer, and transferred to a centrifuge tube with a syringe. Samples were centrifuged at 2,500 rpm (1,350×g) for 10 minutes. The sediment, if present, is visible at the bottom of the centrifuge tube.

2.9. Preparation of Filtrate from Saccharified Starch

Column jackets were maintained at 60° C. Two filter paper discs were inserted and screwed in the fitting until snug against the O-ring gasket. While a tared 250 ml vacuum flask was in place, 100 ml of water was added to the column with the exit plugged. Vacuum pump was turned on till a steady vacuum of 23-24 inches is achieved. The tube exit was turned on and a timer was started. The 100 ml of water should filter in 1 min 10 seconds to 1 min 30 seconds. If the time is too long to too short, check the papers to make sure they are tight. After the papers were pulled to dryness, the exit tube was clamped. The pump was left running with the clamp off the exit tube. The flask was replaced with a tared 250 ml filter flask. Approximately 2.0 grams of filter aid was mixed with 100 grams of test liquor in a 250 ml beaker. While the sample was stirring on the magnetic plate, a syringe was used to remove the sample with targeted quantity. A top loading balance may be used for this step. While keeping the particulates in suspension, the entire quantity was rapidly transferred to the column with the aid of a funnel. The exit tube clamp was turned on, and a timer was started. The filtrate was collected until the liquor reaches the top of the filter bed, and the time was recorded. The collected filtrate would be suitable for further testing, e.g., iodine test.

2.10. Iodine Test

For saccharide liquor iodine test, 0.2 ml saccharide liquor was diluted with 10 ml of DI water. The diluted saccharide liquor was boiled for 10 minutes and then cooled in an ice bath. 0.5 ml iodine solution (0.02 M) was added to the cooled saccharide liquor sample.

For filtrate test, 0.5 ml filtrate as obtained in Example 2.9 was diluted with 10 ml of DI water. The diluted filtrate was boiled for 10 minutes and cooled in an ice bath. 0.5 ml iodine solution (0.02 M) was added to the cooled filtrate sample.

Example 3

Figure 8:
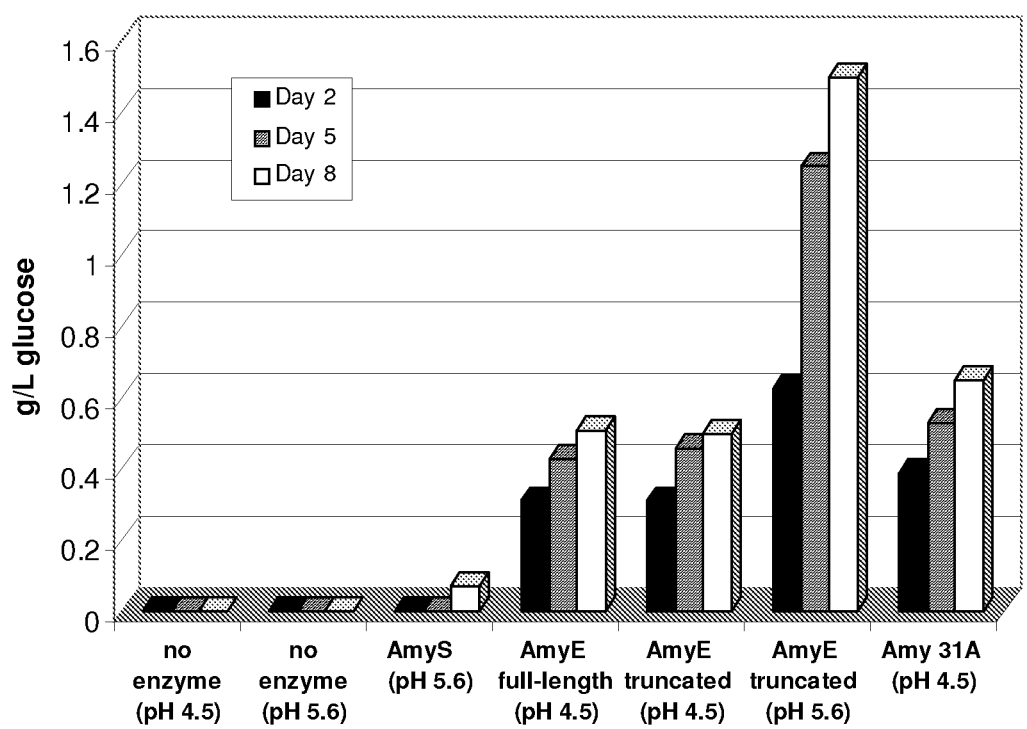
FIG. 8 depicts glucose formation by AmyE ("AmyE full-length"), AmyE-tr ("AmyE truncated"), and Amy 31A compared to *Geobacillus stearothermophilus* alpha-amylase (AmyS; SEQ ID NO: 4) at pH 4.5 and 5.6.

The ability of AmyE to convert maltose to glucose at pH 4.5 and 5.6 (using sodium acetate buffer) was tested, using the glucose formation assay described in Example 2.7. The reactions were analyzed after 2,5, and 8 days. As shown in FIG. 8, AmyE (SEQ ID NO: 1), AmyE-tr (SEQ ID NO: 2), and Amy 31A (SEQ ID NO: 3) effectively converted maltose to glucose, whereas *Geobacillus stearothermophilus* alpha-amylase, AmyS (SEQ ID NO: 4, shown with a 34-amino-acid leader sequence), showed only a minimal amount of glucose formation under these conditions.

Example 4

The ability of AmyE (SEQ ID NO: 1) and AmyE-tr (SEQ ID NO: 2) to catalyze the hydrolysis of DP7 or an insoluble, uncooked granular starch was tested. The HPLC method used for detection of saccharides produced from insoluble starch is described in Example 2.7. Degradation products were quantified by HPLC analysis at various times after the reaction was initiated.

Figure 9:
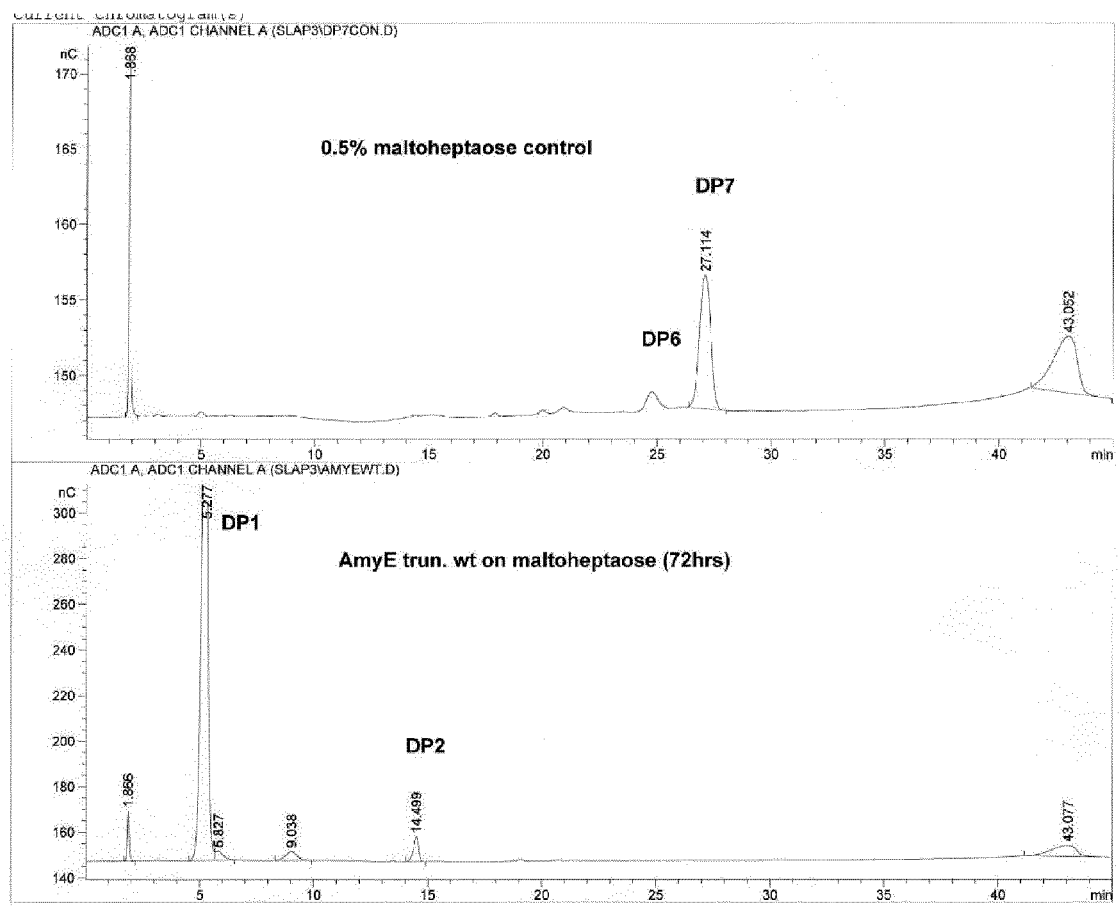
FIG. 9 depicts breakdown products detected by HPLC following a 0 h (top panel) and 72 h incubation (bottom panel) of AmyE-tr with maltoheptaose (DP7).

FIG. 9 depicts hydrolysis products obtained after incubating a 0.5% maltoheptaose substrate in the presence of 1 ppm AmyE-tr for 72 hours. As can be seen in the bottom panel of FIG. 9, AmyE-tr converts nearly all of the DP7 substrate to glucose by 72 hours. The results demonstrate that AmyE is capable of degrading a DP7 substrate to glucose efficiently.

Figure 10:
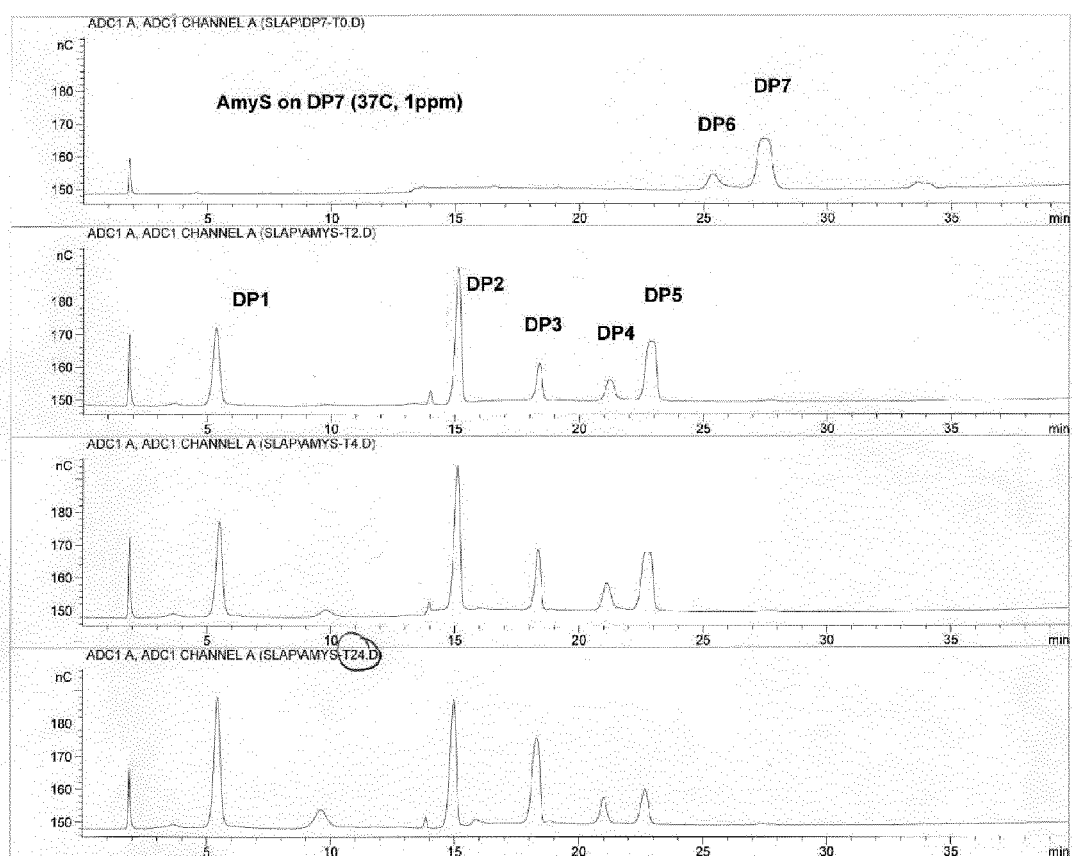
FIG. 10 depicts breakdown products detected by HPLC following a 0 h, 2 h, 4 h, and 24 h (panels from top to bottom) incubation of AmyS with a DP7 substrate.
Figure 11:
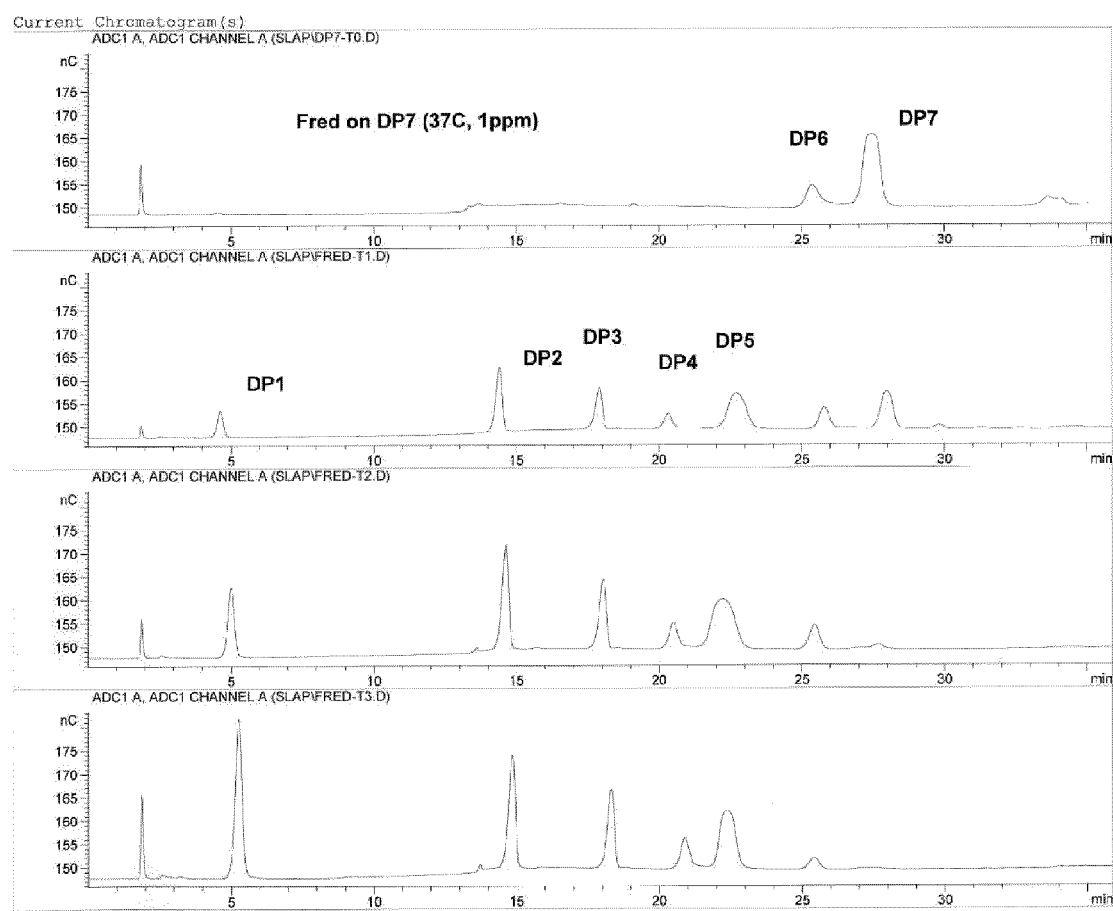
FIG. 11 depicts breakdown products detected by HPLC following a 0 h, 1 h, 2 h, and 3 h (panels from top to bottom) incubation of SPEZYME® FRED ("Fred") with a DP7 substrate.

By comparison, the degradation of a DP7 substrate by 1 ppm of either AmyS (SEQ ID NO: 4) or SPEZYME® FRED ("Fred"; SEQ ID NO: 8) is depicted in FIG. 10 and FIG. 11, respectively. Samples from reactions were analyzed using the HPLC procedure set forth in Example 2.4 above. The panels in FIG. 10 from top to bottom represent the reaction products at 0 hours, 2 hours, 4 hours and 24 hours after addition of AmyS. The panels in FIG. 11 from top to bottom represent the reaction products at 0 hours, 1 hours, 2 hours and 3 hours after addition of SPEZYME® FRED. The results show that a considerable portion of the DP7 substrate remains at a degree of polymerization of DP2 or greater in the presence of AmyS or SPEZYME® FRED at the times indicated.

Figure 12:
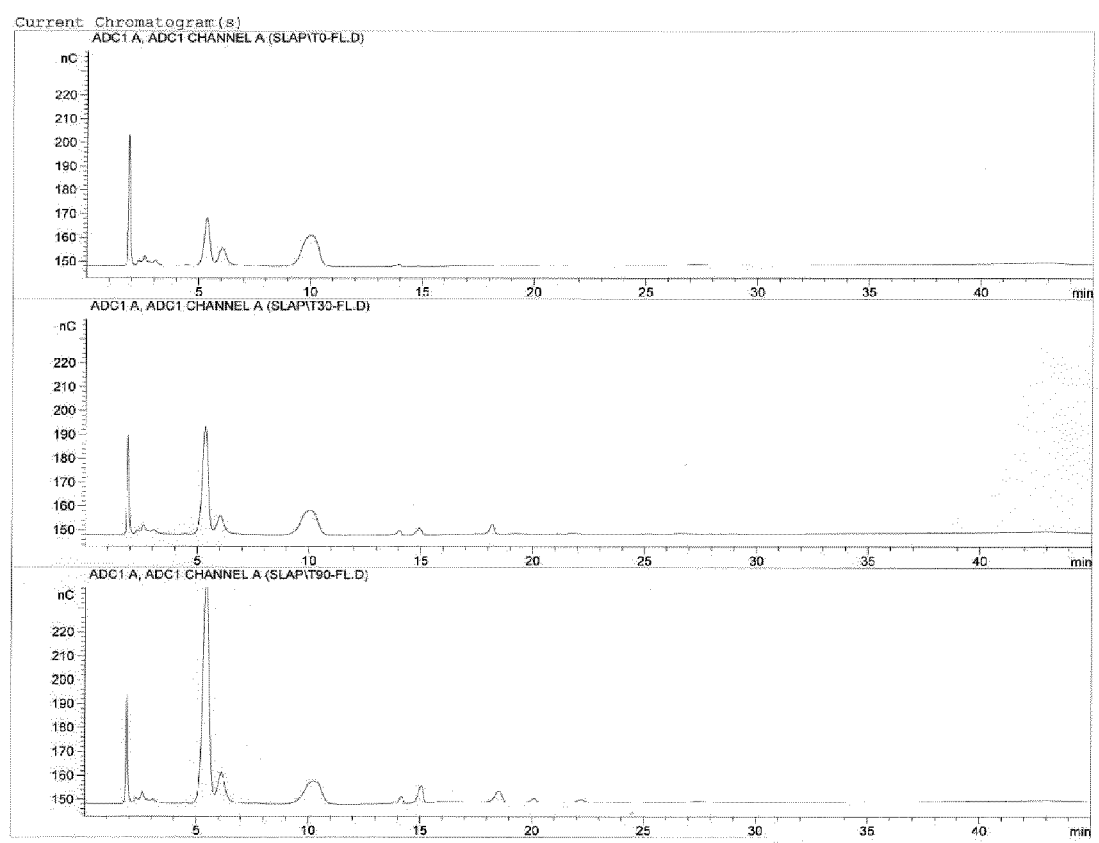
FIG. 12 depicts breakdown products detected by HPLC following a 0 min, 30 min, and 90 min (panels from top to bottom) incubation of AmyE (SEQ ID NO: 1) with raw corn flour starch.

FIG. 12 depicts the results of incubating a 5% corn flour solution with 1 ppm AmyE (SEQ ID NO: 1) at 32° C., according to the procedure set forth in Example 2.4. The results show that AmyE by itself can convert insoluble granular starch efficiently to glucose.

Example 5

Figure 13:
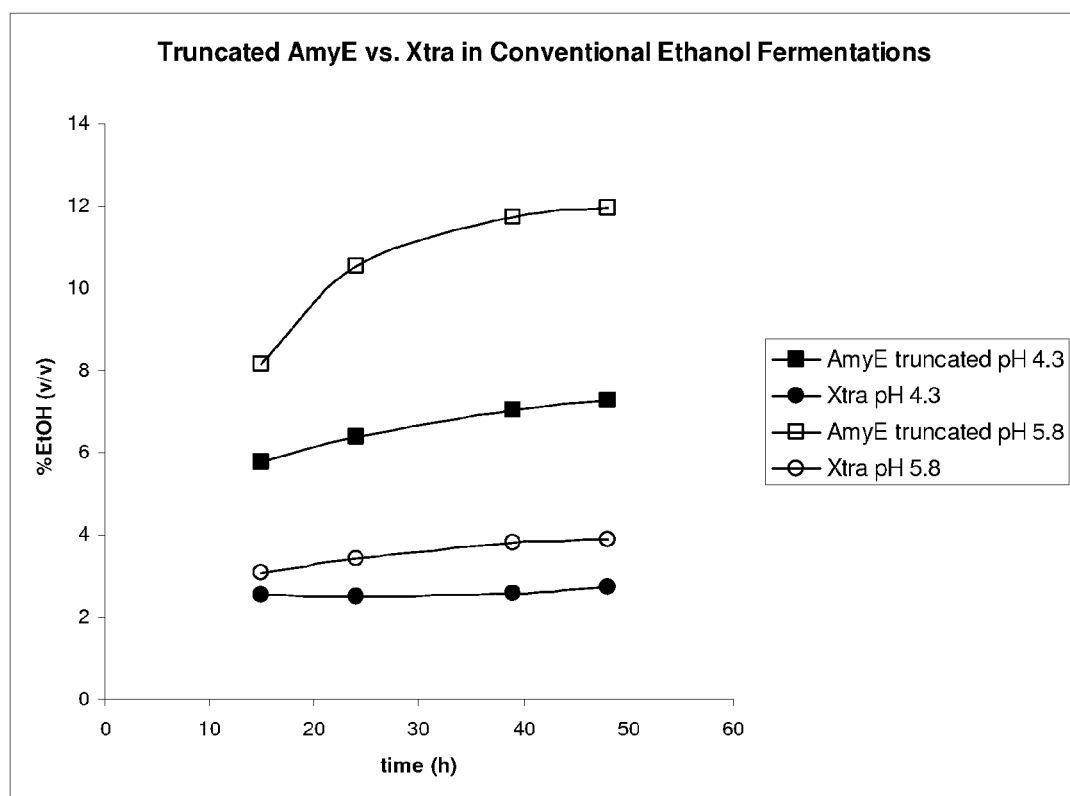
FIG. 13 depicts ethanol formation by AmyE-tr ("AmyE truncated") and SPEZYME® XTRA amylase ("XTRA") in conventional fermentation at pH 4.3 and pH 5.8.

The performance of truncated AmyE in conventional ethanol fermentation was tested on Illinois River Energy liquefact (31% DS), using the conventional ethanol fermentation assay described in Example 2.5. The performance of AmyE-tr (SEQ ID NO: 2) was compared to SPEZYME® XTRA amylase (Danisco US Inc., Genencor Division; AmyR; SEQ ID NO: 5) at pH 4.3 and pH 5.8. Fermentations were carried out for 48 h. AmyE-tr and SPEZYME® XTRA amylase were dosed at 0.2 mg/g DS. As shown in FIG. 13, the final ethanol yield produced by AmyE-tr at pH 5.8 is 12.0% (v/v). AmyE-tr at pH 4.3 produced a final ethanol yield of 7.3% (v/v). Final ethanol yields in the presence of SPEZYME® XTRA amylase were 2.7% (v/v) at pH 4.3 and 3.9% (v/v) at pH 5.8. AmyE-tr thus produces significantly more ethanol in conventional ethanol fermentation of liquefact than SPEZYME® XTRA amylase. This example also demonstrates that AmyE-tr produces more ethanol at pH 5.8 than at pH 4.3.

Example 6

The ability of AmyE (SEQ ID NO: 1) and AmyE-tr (SEQ ID NO: 2) to catalyze the hydrolysis of insoluble granular (uncooked) starch into ethanol at pH 4.3 and pH 5.8 was compared, using the ethanol fermentation on whole ground corn assay described in Example 2.7. The ethanol forming performance of AmyE and AmyE-tr was compared to *A. kawachii* alpha-amylase (AkAA, SEQ ID NO: 6), dosed at 1.5 SSU/g, a mixture of *T. reesei* glucoamylase (TrGA; SEQ ID NO: 7) dosed at 0.5 GAU/g plus *A. kawachii* alpha-amylase dosed at 1.5 SSU/g DS. Both AmyE full-length and truncated AmyE were dosed at 0.2 mg/g DS.

Figure 14:
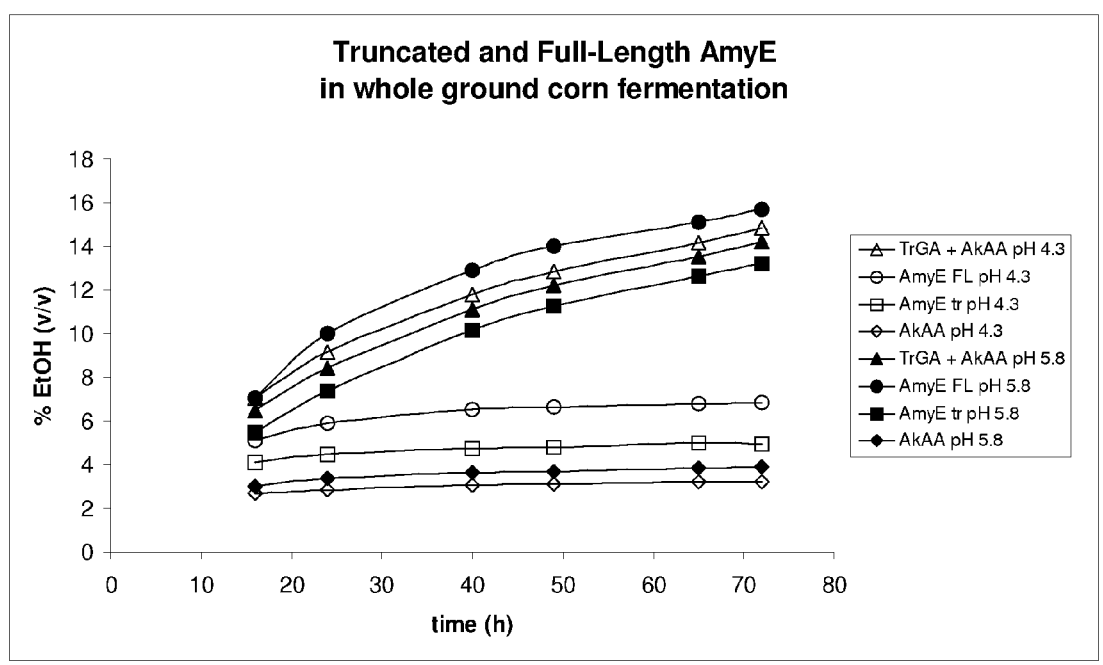
FIG. 14 depicts hydrolysis of insoluble granular (uncooked) starch into ethanol by full length AmyE ("AmyE FL") and AmyE-tr compared to *Aspergillus kawachii* alpha-amylase (AkAA) alone or a mixture of *A. kawachii* alpha-amylase and *Trichoderma reesei* glucoamylase (TrGA), at pH 4.3 and pH 5.8.

FIG. 14 shows the final ethanol yield produced by the enzymes at pH 4.3 and pH 5.8. When tested at pH 5.8, both AmyE (-●-) and AmyE-tr (-■-) performed comparably to the TrGA/AkAA (-▲-), with AmyE actually surpassing the ethanol yields observed for TrGA/AkAA. AmyE (-○-) and AmyE-tr (-□-) produced ethanol at pH 4.3, but the yield was not as high as obtained with TrGA/AkAA (-Δ-). In comparison, AkAA performed poorly at both pHs tested (-♦ ◊ -). This example demonstrates that AmyE can completely replace glucoamylase in a saccharification reaction at around pH 5.8. It also demonstrates that AmyE can replace glucoamylase partially or completely in a saccharification reaction at pH 4.3.

Example 7

The capability of AmyE as a supplementary enzyme in saccharification was tested by applying various combinations of AmyE and TrGA to a liquefied starch substrate. An aqueous slurry containing 32% ds refined starch (Cargill, Minneapolis, Minn.), 10 ppm of $Ca^{2+}$, and 100 ppm of sulfur dioxide ($SO_2$) were mixed overnight with constant stirring. The pH of the slurry was adjusted to about 5.8 with sodium carbonate (20% w/v). The Baumé degrees of the slurry were approximately 22.3. Thermostable alpha-amylase SPEZYME® FRED (Danisco US, Inc., Genencor Division) was subsequently added at 0.56 kg/MT ds corn. The slurry was sent through a pilot plant jet equipped with a M101 hydro-heater at 0.5 gpm with 6 min residence time, cooked at an average temperature about 107-109° C. for the primary cook. Samples were collected at the outlet and placed in a 95° C. water bath. Secondary liquefaction was further carried out at 95° C. without any additional enzyme. The secondary liquefaction was continued until a final DE of the starch substrate reached 10 DE. The liquefaction was then terminated by lowering the pH of the starch slurry to pH 4.5 at 95° C. The processed slurry, also called starch liquefact or liquefied starch substrate, was used in the following saccharification experiments.

Saccharification was conducted at 32% solids with varying levels of TrGA and AmyE under commercial yeast fermentation conditions, i.e., pH 5.3 and 32° C. The composition of saccharides (fermentable and higher sugars) was determined by HPLC or iodine staining from samples drawn at different time intervals. The results were compiled in Table 1.

TABLE 1

Effect of AmyE on the production of fermentable sugars

| Serial | TrGA (GAUs/g) | AmyE (AMYE units/g) | Hours (hr) | DP1 (w/v %) | DP2 (w/v %) | DP3 (w/v %) | Total Fermentable Sugars (DP1 + DP2 + DP3; w/v %) | Higher Sugars (DP4+; w/v %) |
|---|---|---|---|---|---|---|---|---|
| 1 | 0.4 | 0 | 6 | 46.84 | 8.92 | 0.74 | 56.50 | 43.50 |
| 2 | 0.4 | 0 | 18 | 64.86 | 3.69 | 0.42 | 68.97 | 31.04 |
| 3 | 0.4 | 0 | 24 | 69.45 | 1.99 | 0.45 | 71.90 | 28.10 |
| 4 | 0.4 | 0 | 54 | 78.09 | 1.33 | 0.35 | 79.77 | 20.23 |
| 5 | 0 | 0.8 | 6 | 10.76 | 17.74 | 14.99 | 43.49 | 55.56 |
| 6 | 0 | 0.8 | 18 | 21.00 | 23.21 | 15.29 | 59.51 | 39.72 |
| 7 | 0 | 0.8 | 24 | 27.60 | 24.51 | 14.02 | 66.13 | 33.12 |
| 8 | 0 | 0.8 | 54 | 47.97 | 20.57 | 8.00 | 76.54 | 22.68 |
| 9 | 0.3 | 0 | 6 | 28.29 | 6.65 | 2.93 | 37.86 | 62.14 |
| 10 | 0.3 | 0 | 18 | 54.52 | 6.83 | 0.62 | 61.97 | 38.03 |
| 11 | 0.3 | 0 | 24 | 63.32 | 4.33 | 0.45 | 68.10 | 31.91 |
| 12 | 0.3 | 0 | 54 | 75.07 | 1.25 | 0.46 | 76.78 | 23.22 |
| 13 | 0.3 | 0.2 | 6 | 25.73 | 11.44 | 7.94 | 45.10 | 54.90 |
| 14 | 0.3 | 0.2 | 18 | 48.76 | 17.61 | 4.52 | 70.89 | 29.11 |
| 15 | 0.3 | 0.2 | 24 | 58.43 | 14.37 | 3.82 | 76.62 | 22.76 |
| 16 | 0.3 | 0.2 | 54 | 81.36 | 6.13 | 2.74 | 90.23 | 9.77 |
| 17 | 0.3 | 0.4 | 6 | 28.36 | 17.27 | 10.88 | 56.52 | 42.84 |
| 18 | 0.3 | 0.4 | 18 | 52.56 | 18.11 | 5.14 | 75.80 | 23.65 |
| 19 | 0.3 | 0.4 | 24 | 63.71 | 13.40 | 4.41 | 81.52 | 18.04 |
| 20 | 0.3 | 0.4 | 54 | 83.63 | 6.57 | 3.02 | 93.23 | 6.78 |
| 21 | 0.3 | 0.8 | 6 | 31.83 | 20.78 | 11.77 | 64.38 | 35.62 |
| 22 | 0.3 | 0.8 | 18 | 57.05 | 17.06 | 5.88 | 79.99 | 19.59 |
| 23 | 0.3 | 0.8 | 24 | 67.67 | 13.10 | 4.79 | 85.57 | 13.61 |
| 24 | 0.3 | 0.8 | 54 | 83.81 | 7.65 | 3.20 | 94.66 | 5.11 |
| 25 | 0.2 | 0 | 6 | 19.78 | 4.99 | 3.40 | 28.17 | 71.83 |
| 26 | 0.2 | 0 | 18 | 43.78 | 8.20 | 1.29 | 53.27 | 46.73 |
| 27 | 0.2 | 0 | 24 | 54.51 | 7.65 | 0.51 | 62.67 | 37.33 |
| 28 | 0.2 | 0 | 54 | 69.77 | 1.66 | 0.45 | 71.88 | 28.09 |
| 29 | 0.2 | 0.2 | 6 | 23.90 | 13.25 | 9.26 | 46.41 | 53.59 |
| 30 | 0.2 | 0.2 | 18 | 42.38 | 19.70 | 5.51 | 67.58 | 32.42 |
| 31 | 0.2 | 0.2 | 24 | 51.83 | 16.94 | 3.97 | 72.74 | 26.50 |
| 32 | 0.2 | 0.2 | 54 | 75.74 | 7.97 | 3.03 | 86.74 | 12.53 |
| 33 | 0.2 | 0.4 | 6 | 20.42 | 13.96 | 11.06 | 45.43 | 53.61 |
| 34 | 0.2 | 0.4 | 18 | 41.16 | 21.56 | 7.18 | 69.90 | 29.96 |
| 35 | 0.2 | 0.4 | 24 | 51.18 | 18.86 | 5.89 | 75.92 | 23.49 |
| 36 | 0.2 | 0.4 | 54 | 76.99 | 9.16 | 3.67 | 89.82 | 10.18 |
| 37 | 0.2 | 0.8 | 6 | 25.65 | 20.39 | 13.34 | 59.38 | 39.87 |
| 38 | 0.2 | 0.8 | 18 | 49.14 | 20.16 | 6.95 | 76.26 | 23.25 |
| 39 | 0.2 | 0.8 | 24 | 58.76 | 16.60 | 5.82 | 81.18 | 17.92 |
| 40 | 0.2 | 0.8 | 54 | 80.85 | 9.06 | 3.40 | 93.32 | 6.69 |
| 41 | 0.1 | 0 | 6 | 11.20 | 7.46 | 3.84 | 22.49 | 77.51 |
| 42 | 0.1 | 0 | 18 | 24.34 | 6.24 | 3.47 | 34.05 | 65.95 |
| 43 | 0.1 | 0 | 24 | 33.46 | 7.88 | 2.46 | 43.80 | 56.20 |
| 44 | 0.1 | 0 | 54 | 58.44 | 5.99 | 0.40 | 64.84 | 35.16 |
| 45 | 0.1 | 0.2 | 6 | 12.65 | 10.12 | 9.36 | 32.13 | 66.53 |
| 46 | 0.1 | 0.2 | 18 | 24.89 | 17.38 | 10.68 | 52.94 | 47.06 |

TABLE 1-continued

Effect of AmyE on the production of fermentable sugars

| Serial | TrGA (GAUs/g) | AmyE (AMYE units/g) | Hours (hr) | DP1 (w/v %) | DP2 (w/v %) | DP3 (w/v %) | Total Fermentable Sugars (DP1 + DP2 + DP3; w/v %) | Higher Sugars (DP4+; w/v %) |
|---|---|---|---|---|---|---|---|---|
| 47 | 0.1 | 0.2 | 24 | 32.01 | 21.60 | 9.44 | 63.05 | 36.95 |
| 48 | 0.1 | 0.2 | 54 | 55.97 | 16.92 | 3.81 | 76.71 | 22.70 |
| 49 | 0.1 | 0.4 | 6 | 14.62 | 13.31 | 11.65 | 39.57 | 59.32 |
| 50 | 0.1 | 0.4 | 18 | 28.64 | 22.25 | 11.69 | 62.58 | 37.42 |
| 51 | 0.1 | 0.4 | 24 | 36.90 | 23.21 | 9.21 | 69.32 | 29.95 |
| 52 | 0.1 | 0.4 | 54 | 63.53 | 14.07 | 4.18 | 81.78 | 17.31 |
| 53 | 0.1 | 0.8 | 6 | 18.27 | 18.03 | 13.96 | 50.26 | 48.91 |
| 54 | 0.1 | 0.8 | 18 | 36.29 | 23.32 | 10.41 | 70.02 | 29.21 |
| 55 | 0.1 | 0.8 | 24 | 46.10 | 21.07 | 7.99 | 75.15 | 24.29 |
| 56 | 0.1 | 0.8 | 54 | 71.43 | 12.29 | 4.18 | 87.90 | 12.10 |

Based on the data presented in Table 1, a combination of TrGA and AmyE is more efficient than TrGA alone in saccharification. The combination of TrGA and AmyE resulted in (1) a higher level of fermentable sugars (DP1, DP2, and DP3 altogether), and (2) an elevated rate of hydrolysis of higher sugars (>DP4+). Thus, supplementation of AmyE to TrGA is capable of producing more fermentable sugars than a conventional process that uses only glucoamylases.

Example 8

Other *Bacillus* alpha-amylases, e.g., SPEZYME® FRED and GC358 (both from Danisco US Inc., Genencor Division), were characterized in saccharification as Example 7. The saccharification of liquefied starch substrate was carried out at pH 5.2 and at 32° C. with the presence of TrGA. The composition of saccharides (both fermentable and higher sugars) was determined from samples drawn at 6, 18, 24, and 54 hours. The result, shown in Table 2, indicates that supplementation of AmyE to glucoamylase is able to produce more fermentable sugars than the supplementation of equivalent amounts of other *Bacillus* alpha-amylases. This observation is consistent with what is described in Examples 5-6 as to AmyE's superior ability to convert maltose to glucose and hydrolyze DP7. Accordingly, the advantageous properties of AmyE are not universally shared by other *Bacillus* alpha-amylases.

Example 9

Figure 15:
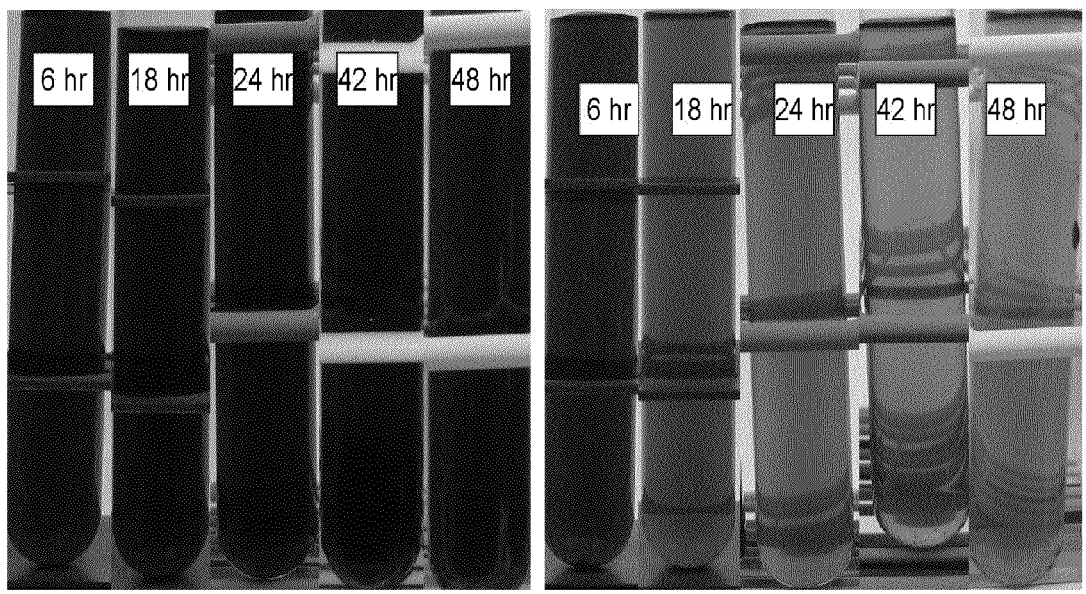
FIG. 15 depicts the presence of iodine-positive saccharide (IPS) in filtrate over time in saccharification catalyzed by TrGA alone or TrGA supplemented with AmyE.

When saccharified starch is tested with iodine, any amylose that escapes hydrolysis would bind with iodine and produce a characteristic blue color. This is termed iodine-positive saccharide (IPS), which is an indicator for liquefaction/saccharification efficiency. IPS is highly undesirable in starch processing applications, because its presence reflects incomplete starch hydrolysis. FIG. 15 shows that supplementation of AmyE to TrGA significantly reduced the presence of IPS in the filtrate.

Figure 16:
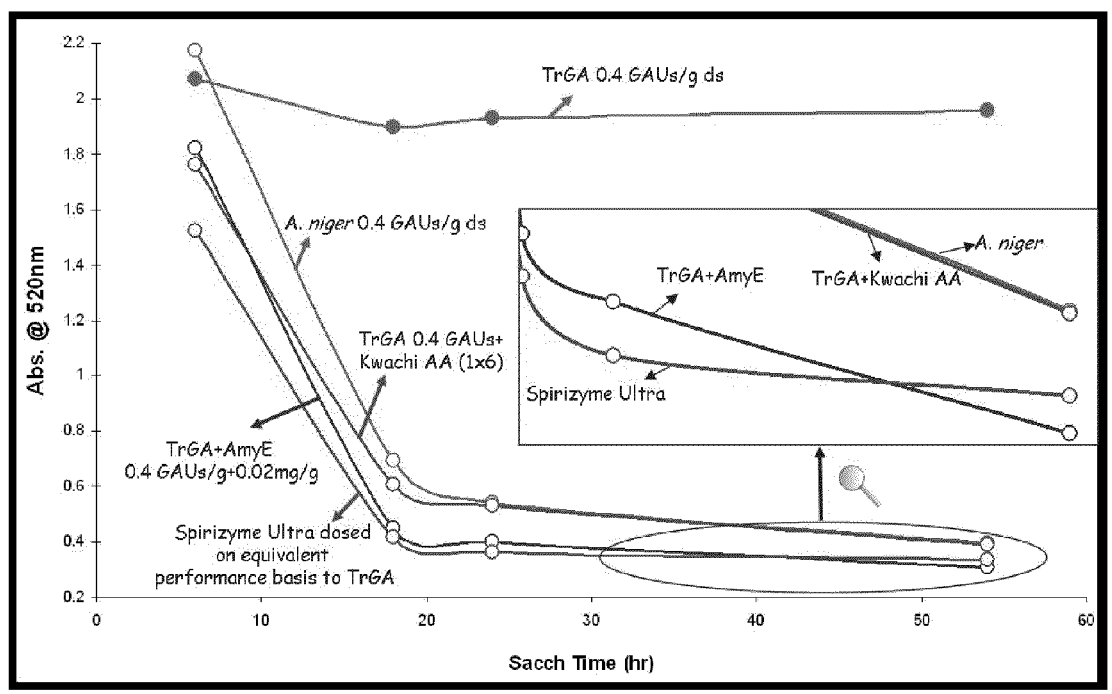
FIG. 16 depicts the presence of iodine-positive saccharide (IPS) in filtrate over time in saccharification catalyzed by various enzyme combinations. The absorbance at 520 nm was plotted against the time for various saccharification reactions.

In addition, FIG. 16 shows the presence of IPS (as reflected by absorbance at 520 nm) over time in saccharification catalyzed by various enzyme combinations. Supplementation of AmyE at 0.02 mg/g to TrGA significantly reduced the IPS to a level similar to that with an equivalent amount of Spirizyme Ultra™ (Novozymes A/S).

Figure 17:
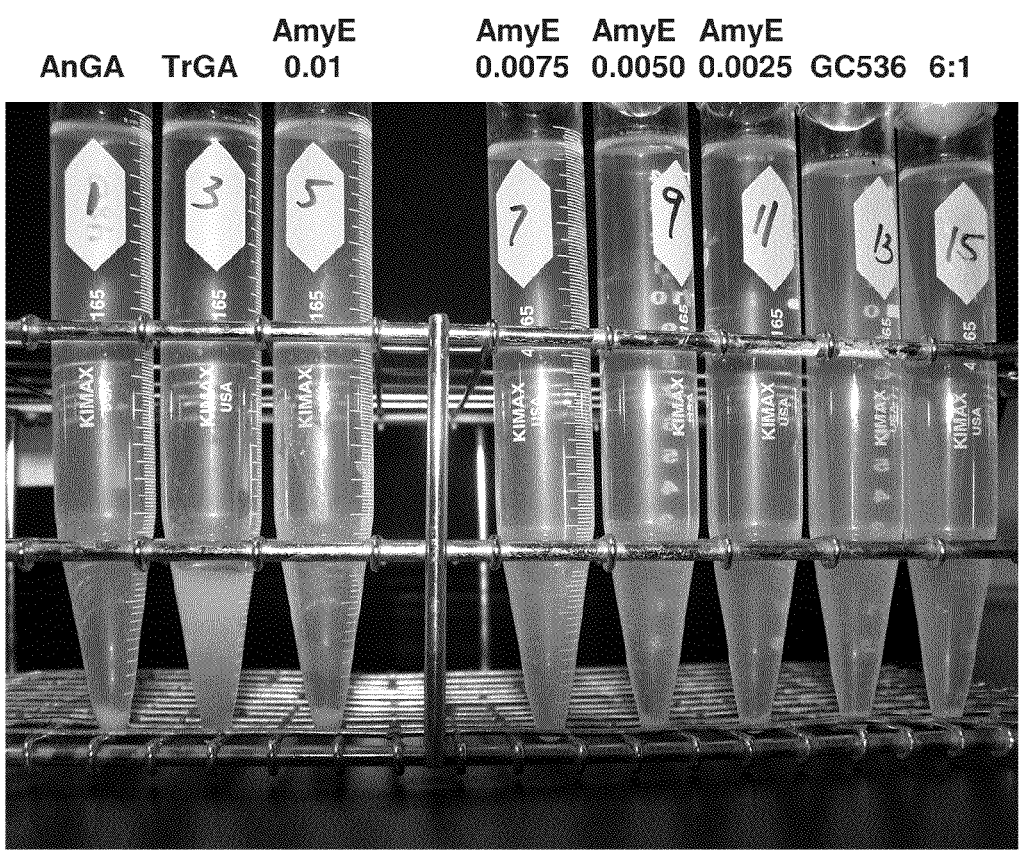
FIG. 17 depicts the detection of insoluble residual starch (IRS) in saccharification catalyzed by various enzyme combinations.

Furthermore, it was observed that a lower level of insoluble residual starch (IRS) is present in saccharification reactions supplemented with AmyE. Insoluble residual starch refers to incompletely hydrolyzed starch that shows as sediments after saccharification. A high level of sediments is particularly undesirable in sweetener applications, because they may substantially interfere with the efficiency of production and reduce the output. FIG. 17 indicates that the presence of a significant amount of IRS in saccharification catalyzed by TrGA alone. Supplementation of AmyE, as low as 0.0025 mg/g ds, dramatically reduced the amount of IRS. Accord-

TABLE 2

Effect of other *Bacillus* alpha-amylases on the production of fermentable sugars

| Enzyme Treatments | Hours (hr) | DP1; w/v % | DP2; w/v % | DP3; w/v % | Total Fermentable Sugars (DP1 + DP2 + DP3; w/v %) | Higher Sugars (DP4+; w/v %) | Higher Sugars (DP10+; w/v %) |
|---|---|---|---|---|---|---|---|
| TrGA 0.4 GAUs/g + Fred 5 µg/g | 6 | 29.80 | 8.74 | 6.47 | 45.01 | 54.99 | 35.29 |
|  | 18 | 60.84 | 10.26 | 2.04 | 73.13 | 26.87 | 15.40 |
|  | 24 | 66.82 | 8.19 | 1.59 | 76.59 | 23.41 | 11.42 |
|  | 54 | 79.90 | 2.95 | 1.29 | 84.14 | 15.86 | 6.80 |
| TrGA 0.4 GAUs/g + GC358 5 µg/g | 6 | 28.90 | 12.44 | 8.58 | 49.92 | 50.08 | 23.06 |
|  | 18 | 61.13 | 13.01 | 1.27 | 75.41 | 24.59 | 12.58 |
|  | 24 | 66.72 | 10.16 | 1.16 | 78.04 | 21.96 | 10.22 |
|  | 54 | 79.99 | 3.19 | 1.16 | 84.33 | 15.67 | 6.67 |
| TrGA 0.4 GAUs/g + AmyE 5 µg/g | 6 | 36.79 | 9.29 | 3.44 | 49.52 | 50.48 | 42.02 |
|  | 24 | 71.45 | 4.58 | 1.00 | 77.03 | 22.97 | 19.73 |
|  | 54 | 84.69 | 3.16 | 1.01 | 88.86 | 11.14 | 7.66 | ingly, saccharification by TrGA supplemented with AmyE is more efficient, and the saccharified starch is suitable for a range of applications as described herein.

Example 10

Saccharification was further conducted on the liquefied starch substrate (32% ds) at pH 4.5 and 60° C. with varying levels of (1) AmyE, (2) AnGA (OPTDEX L-400, Danisco US, Inc., Genencor Division), and (3) a pullulanase (OPTI-MAX™ L-1000, Danisco US, Inc., Genencor Division). The composition of saccharides (both fermentable and higher sugars) was determined by HPLC or iodine staining from samples drawn at 6, 18, 24, 48, and 72 hours. The results are compiled in Table 3.

AmyE may be able to replace at least 50% of glucoamylase in the saccharification. Furthermore, the addition of the debranching enzyme to AmyE and glucoamylase resulted in a higher level of fermentable sugars and a significantly reduced level of non-fermentable sugars (DP4+), both of which are indications of an efficient saccharification process.

Example 11

To further characterize the capability of AmyE as an enzyme usable in saccharification, AmyE combined with different glucoamylases, as well as a glucoamylase blend, was applied to a liquefied starch substrate. The saccharification was performed at pH 5.2 and 32° C. The composition of saccharides (both fermentable and higher sugars) was deter-

TABLE 3

Effect of AnGA, AmyE, and pullulanase concentrations on the production of fermentable sugars

| Serial No. | Optidex L 400 (GAUs/g) | AmyE (Units/g) | Optimax L1000 (ASPUs/g) | Time (hr) | DP1 | DP2 | DP3 | Total Fermentable Sugars (DP1 + DP2 + DP3; w/v %) | Higher Sugars (DP4+; w/v %) |
|---|---|---|---|---|---|---|---|---|---|
| 1 | 0.22 | 0 | 0 | 6 | 70.60 | 6.44 | 0.33 | 77.38 | 22.47 |
| 2 | 0.22 | 0 | 0 | 18 | 89.04 | 1.85 | 0.38 | 91.27 | 8.68 |
| 3 | 0.22 | 0 | 0 | 24 | 92.10 | 1.99 | 0.36 | 94.45 | 5.50 |
| 4 | 0.22 | 0 | 0 | 48 | 94.59 | 2.81 | 0.32 | 97.72 | 2.09 |
| 5 | 0.22 | 0 | 0 | 72 | 94.30 | 3.31 | 0.32 | 97.94 | 1.77 |
| 6 | 0.11 | 0 | 0 | 6 | 47.86 | 10.76 | 2.88 | 61.50 | 38.17 |
| 7 | 0.11 | 0 | 0 | 18 | 76.94 | 4.05 | 0.40 | 81.38 | 18.52 |
| 8 | 0.11 | 0 | 0 | 24 | 83.75 | 2.23 | 0.45 | 86.43 | 13.50 |
| 9 | 0.11 | 0 | 0 | 48 | 91.46 | 2.07 | 0.38 | 93.91 | 6.03 |
| 10 | 0.11 | 0 | 0 | 72 | 93.20 | 2.37 | 0.35 | 95.92 | 3.34 |
| 11 | 0.11 | 0.2 | 0 | 6 | 38.04 | 25.82 | 10.16 | 74.02 | 25.90 |
| 12 | 0.11 | 0.2 | 0 | 18 | 72.05 | 13.72 | 1.66 | 87.43 | 12.53 |
| 13 | 0.11 | 0.2 | 0 | 24 | 82.88 | 7.88 | 1.27 | 92.03 | 7.93 |
| 14 | 0.11 | 0.2 | 0 | 48 | 92.22 | 4.10 | 0.75 | 97.06 | 2.53 |
| 15 | 0.11 | 0.2 | 0 | 72 | 93.54 | 4.35 | 0.61 | 98.50 | 1.19 |
| 16 | 0.11 | 0.2 | 0.16 | 6 | 36.93 | 25.65 | 11.16 | 73.74 | 26.18 |
| 17 | 0.11 | 0.2 | 0.16 | 18 | 71.54 | 16.09 | 2.33 | 89.96 | 9.73 |
| 18 | 0.11 | 0.2 | 0.16 | 24 | 82.94 | 9.43 | 2.03 | 94.40 | 5.45 |
| 19 | 0.11 | 0.2 | 0.16 | 48 | 93.36 | 3.97 | 1.32 | 98.65 | 1.32 |
| 20 | 0.11 | 0.2 | 0.16 | 72 | 93.35 | 4.25 | 1.03 | 98.62 | 0.65 |
| 21 | 0.11 | 0.4 | 0 | 6 | 44.23 | 26.41 | 7.89 | 78.53 | 21.42 |
| 22 | 0.11 | 0.4 | 0 | 18 | 78.24 | 10.67 | 1.58 | 90.48 | 9.49 |
| 23 | 0.11 | 0.4 | 0 | 24 | 86.37 | 6.79 | 1.24 | 94.40 | 4.97 |
| 24 | 0.11 | 0.4 | 0 | 48 | 91.78 | 5.03 | 0.75 | 97.56 | 1.86 |
| 25 | 0.11 | 0.4 | 0 | 72 | 92.56 | 5.65 | 0.69 | 98.91 | 0.72 |
| 26 | 0.11 | 0.4 | 0.16 | 6 | 43.92 | 26.99 | 8.62 | 79.53 | 20.42 |
| 27 | 0.11 | 0.4 | 0.16 | 18 | 78.31 | 11.95 | 2.34 | 92.61 | 7.23 |
| 28 | 0.11 | 0.4 | 0.16 | 24 | 87.88 | 7.30 | 1.85 | 97.03 | 2.94 |
| 29 | 0.11 | 0.4 | 0.16 | 48 | 92.13 | 5.35 | 1.22 | 98.70 | 1.26 |
| 30 | 0.11 | 0.4 | 0.16 | 72 | 92.10 | 5.63 | 0.98 | 98.71 | 1.06 |

The data presented in Table 3 show that supplementation of 0.2 units/g of AmyE to 0.11 GAUs/g of AnGA is capable of (1) producing a higher level of fermentable sugars, and (2) reducing higher sugars at an elevated rate than the hydrolysis by 0.22 GAUs/g of AnGA alone. This result suggests that mined from samples drawn at 6, 18, 24, and 48 hours. As shown in Table 4, the addition of AmyE to other glucoamylases or the glucoamylase blend resulted in an increased level of total fermentable sugars and a significantly reduced level of non-fermentable sugars.

TABLE 4

Effect of AmyE combined with various glucoamylase on saccharification

| Enzyme Treatments | Hours (hr) | DP1; w/v % | DP2; w/v % | DP3; w/v % | Total Fermentable Sugars (DP1 + DP2 + DP3; w/v %) | Higher Sugars (DP4+; w/v %) | Higher Sugars (DP10+; w/v %) |
|---|---|---|---|---|---|---|---|
| 0.4 GAUs A. niger; | 6 | 28.09 | 7.15 | 6.63 | 41.86 | 58.14 | 47.50 |
|  | 18 | 58.57 | 10.93 | 0.31 | 69.81 | 30.19 | 26.92 |

TABLE 4-continued

Effect of AmyE combined with various glucoamylase on saccharification

| Enzyme Treatments | Hours (hr) | DP1; w/v % | DP2; w/v % | DP3; w/v % | Total Fermentable Sugars (DP1 + DP2 + DP3; w/v %) | Higher Sugars (DP4+; w/v %) | Higher Sugars (DP10+; w/v %) |
|---|---|---|---|---|---|---|---|
|  | 24 | 64.11 | 8.45 | 0.18 | 72.75 | 27.25 | 24.14 |
|  | 48 | 79.71 | 1.62 | 0.26 | 81.59 | 18.41 | 15.28 |
| 0.4 GAUs TrGA; | 6 | 30.00 | 7.37 | 3.42 | 40.79 | 59.21 | 50.93 |
|  | 18 | 62.52 | 5.70 | 0.41 | 68.64 | 31.36 | 30.18 |
|  | 24 | 66.94 | 3.90 | 0.42 | 71.26 | 28.74 | 28.14 |
|  | 48 | 75.72 | 1.39 | 0.33 | 77.44 | 22.56 | 22.24 |
| 0.4 GAUs HGA | 6 | 14.49 | 3.25 | 5.39 | 23.13 | 76.87 | 58.63 |
|  | 18 | 41.61 | 9.19 | 3.76 | 54.55 | 45.45 | 41.08 |
|  | 24 | 52.00 | 10.67 | 0.79 | 63.46 | 36.55 | 34.07 |
|  | 48 | 78.36 | 1.97 | 0.38 | 80.71 | 19.29 | 18.96 |
| 0.4 GAUs A. niger + 0.01 mg/g AmyE | 6 | 26.48 | 8.97 | 8.43 | 43.89 | 56.11 | 44.48 |
|  | 18 | 54.76 | 16.28 | 1.22 | 72.26 | 27.74 | 23.04 |
|  | 24 | 60.44 | 13.34 | 0.88 | 74.66 | 25.34 | 19.78 |
|  | 48 | 79.06 | 4.14 | 0.74 | 83.93 | 16.07 | 9.93 |
| 0.4 GAUs TrGA + 0.01 mg/g AmyE | 6 | 32.36 | 10.79 | 5.20 | 48.35 | 51.65 | 43.28 |
|  | 18 | 60.76 | 10.67 | 1.32 | 72.75 | 27.25 | 22.66 |
|  | 24 | 65.87 | 9.21 | 1.42 | 76.50 | 23.50 | 18.53 |
|  | 48 | 80.37 | 4.95 | 1.37 | 86.69 | 13.31 | 8.75 |
| 0.4 GAUs HGA + 0.01 mg/g AmyE | 6 | 13.90 | 5.41 | 7.09 | 26.40 | 73.60 | 54.69 |
|  | 18 | 39.44 | 13.69 | 5.89 | 59.03 | 40.97 | 34.43 |
|  | 24 | 49.35 | 16.28 | 2.29 | 67.92 | 32.08 | 26.04 |
|  | 48 | 79.82 | 5.06 | 1.09 | 85.97 | 14.03 | 9.49 |
| A. niger + TrGA + HGA Each 0.13 GAUs/g | 6 | 25.82 | 6.26 | 5.13 | 37.21 | 62.79 | 51.83 |
|  | 18 | 58.85 | 8.84 | 0.37 | 68.05 | 31.95 | 29.78 |
|  | 24 | 65.13 | 5.89 | 0.35 | 71.36 | 28.64 | 26.51 |
|  | 48 | 80.69 | 1.52 | 0.38 | 82.60 | 17.40 | 15.96 |
| A. niger + TrGA + HGA Each 0.13 GAUs/g + AmyE 0.01 mg/g | 6 | 25.14 | 8.54 | 7.33 | 41.01 | 58.99 | 46.85 |
|  | 18 | 55.86 | 13.90 | 1.31 | 71.07 | 28.93 | 23.83 |
|  | 24 | 62.70 | 11.08 | 1.24 | 75.02 | 24.98 | 18.91 |
|  | 48 | 83.32 | 4.06 | 1.11 | 88.48 | 11.52 | 7.26 |

Figure 18:
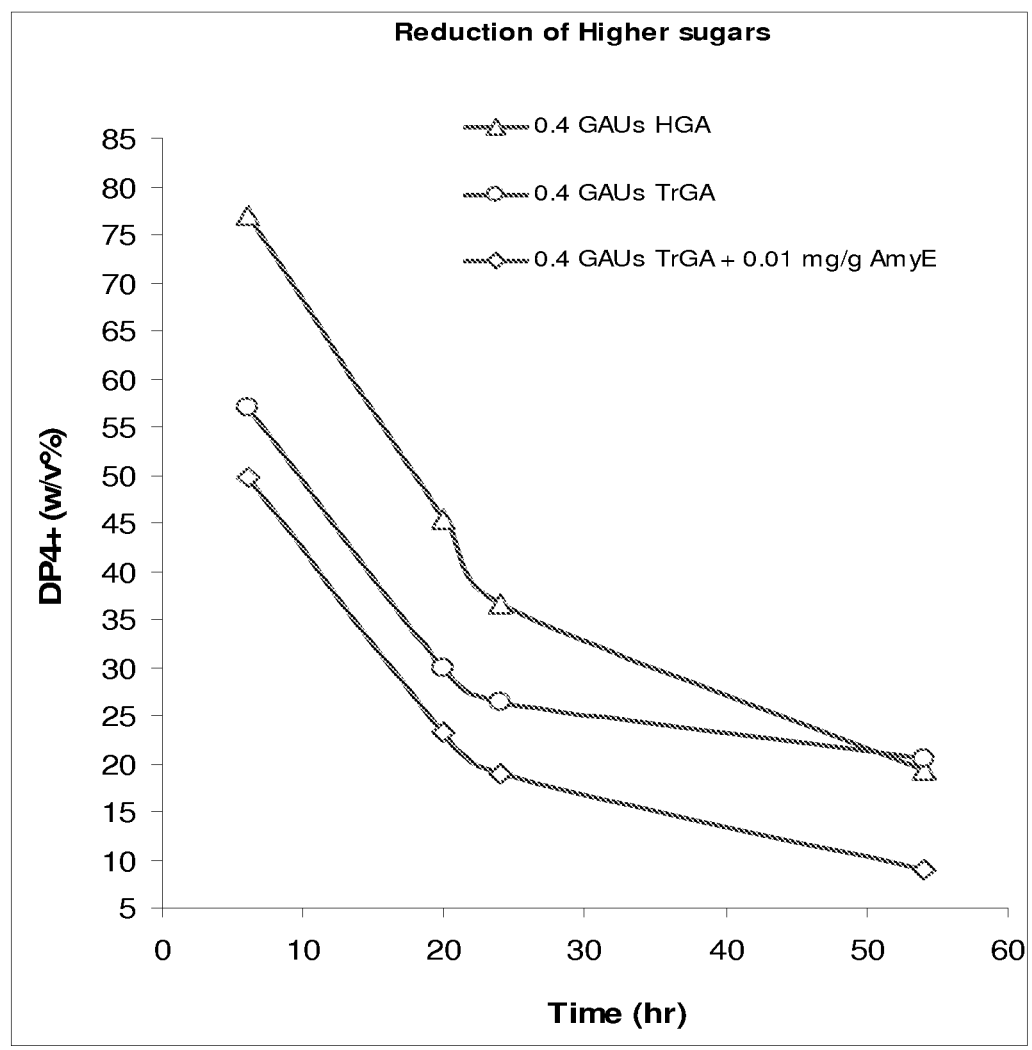
FIG. 18 depicts the levels of higher sugars (DP4+) during 60 min saccharification reaction using (1) HGA (*Humicola grisea* glucoamylase), (2) TrGA (*Trichoderma reesei* glucoamylase), and (3) TrGA supplemented with AmyE.

Furthermore, the primary and secondary slopes for the above saccharification experiments were calculated and compiled in Table 5. The primary and secondary slopes represent the relative velocity of hydrolyzing higher and lower molecular weight substrates, respectfully. The data presented here indicate that supplementation of AmyE significantly accelerates the hydrolysis of low molecular weight substrates, as the value of the secondary slope increased significantly when AmyE was supplemented. See Table 5 and FIG. 18.

TABLE 5

Comparison of primary and secondary slopes for saccharification with AmyE and various glucoamylases.

| Treatments | Primary Slope | Secondary Slope |
|---|---|---|
| 0.4 GAUs A. niger | 2.33 | 0.29 |
| 0.4 GAUs TrGA | 2.32 | 0.21 |
| 0.4 GAUs HGA | 2.62 | 0.58 |
| 0.4 GAUs TrGA + 0.01 mg/g AmyE | 2.03 | 0.34 |
| 0.4 GAUs HGA + 0.01 mg/g AmyE | 2.72 | 0.60 |
| TrGA + HGA @ 0.2 GAUs each | 2.53 | 0.40 |
| TrGA + HGA @ 0.2 GAUs each + 0.01 mg/g AmyE | 2.64 | 0.51 |

Example 12

The advantages of using AmyE as an enzyme in biofuel production were further characterized. Whole ground corn liquefact from Illinois River Energy (Rochelle, Ill.) was thawed at 75° C. before being brought to room temperature. The pH was left at 5.5. The liquefact was dispensed in 150-gram quantities into 250 ml Erlenmeyer flasks. To the liquefact in each flask, 500 μl of 20% yeast/water solution and 600 μl of 10% urea/water solution (400 ppm final concentration) were added. The total enzyme protein dosed for each fermentation experiment was 0.16 mg/g ds. The dosed amount for TrGA is equivalent to the standard GA dose of 0.325 GAU/g ds. Enzymes and/or enzyme combinations were dosed according to the experimental design shown in Table 6.

TABLE 6

Enzyme combination in fermentation

| Flask | Description % Amy E:TrGA | GAU/g DS Dose | mg/g DS GA protein | mg/g DS Amy E protein |
|---|---|---|---|---|
| 1, 2 | AnGA Ctrl | 0.325 |  |  |
| 3, 4 | TrGA Ctrl | 0.325 | 0.1625 |  |
| 5, 6 | 25 AmyE/75 TrGA |  | 0.121 | 0.04 |
| 7, 8 | 50 AmyE/50 TrGA |  | 0.08 | 0.08 |
| 9, 10 | 75 AmyE/25 TrGA |  | 0.04 | 0.121 |

Figure 19:
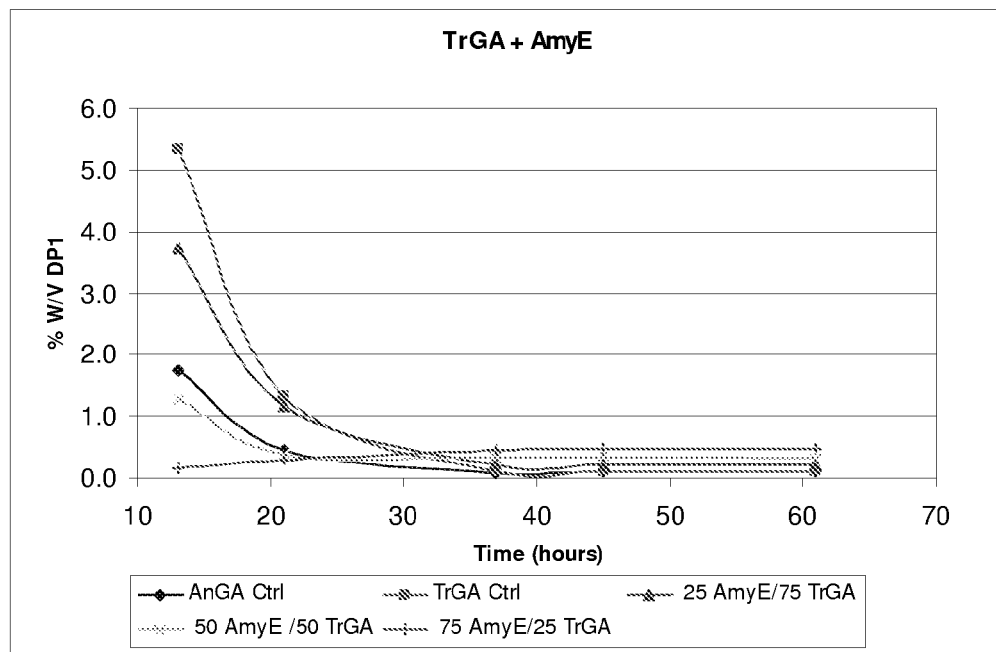
FIG. 19 depicts the glucose level during fermentation with various glucoamylases and/or various combinations of glucoamylase and AmyE.
Figure 20:
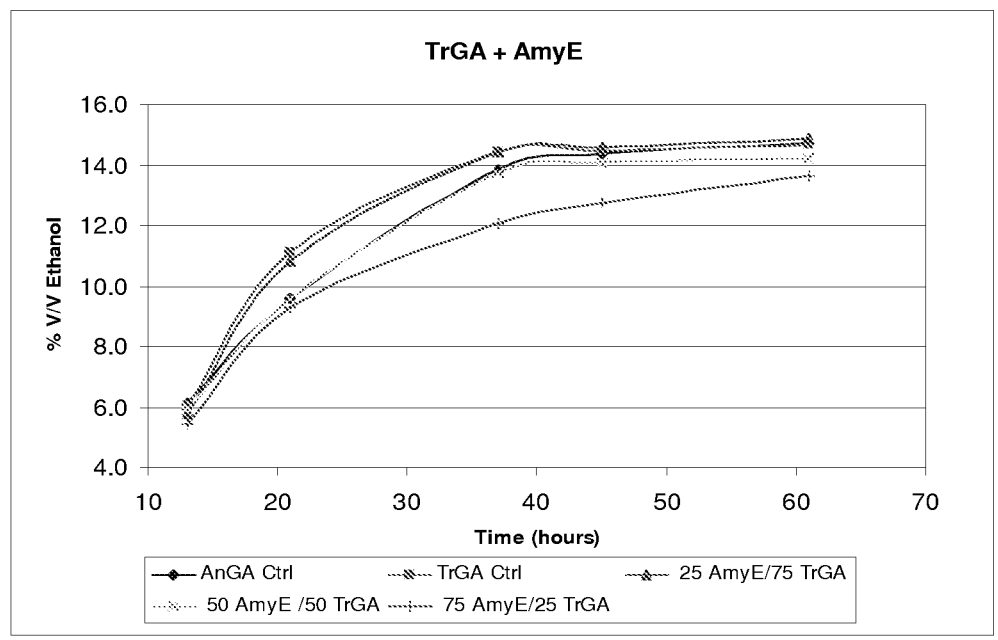
FIG. 20 depicts the ethanol percentage present after fermentation with various glucoamylases and/or various combinations of glucoamylase and AmyE.

The flasks were incubated at 32° C. in a forced air shaker at 150 rpm. Samples were removed at scheduled intervals for HPLC analysis and at the end of the fermentation for starch analysis. The results were compiled in Table 7 and shown in FIG. 19 and FIG. 20.

TABLE 7

Composition analysis of fermentation using different enzymes or enzyme combinations
Average HPLC Data

| Flask | Description | hrs | % W/V DP > 3 | % W/V DP-3 | % W/V DP-2 | % W/V DP-1 | % W/V Lactic | % W/V Glycerol | % W/V Acetic | % V/V Ethanol | % Residual Starch |
|---|---|---|---|---|---|---|---|---|---|---|---|
| 1, 2 | AnGA Ctrl | 13 | 8.67 | 0.56 | 4.84 | 1.76 | 0.21 | 1.42 | 0.04 | 6.13 | |
| | | 21 | 6.67 | 0.12 | 2.32 | 0.46 | 0.22 | 1.65 | 0.05 | 9.59 | |
| | | 37 | 1.35 | 0.17 | 0.22 | 0.09 | 0.16 | 1.77 | 0.09 | 13.85 | |
| | | 45 | 0.89 | 0.14 | 0.21 | 0.11 | 0.12 | 1.79 | 0.10 | 14.35 | |
| | | 61 | 0.73 | 0.12 | 0.26 | 0.10 | 0.06 | 1.81 | 0.14 | 14.71 | 4.86 |
| 3, 4 | TrGA Ctrl | 13 | 7.23 | 0.12 | 2.49 | 5.33 | 0.21 | 1.38 | 0.05 | 6.04 | |
| | | 21 | 4.44 | 0.15 | 0.51 | 1.32 | 0.21 | 1.74 | 0.08 | 11.12 | |
| | | 37 | 0.86 | 0.11 | 0.19 | 0.10 | 0.12 | 1.81 | 0.10 | 14.40 | |
| | | 45 | 0.82 | 0.11 | 0.18 | 0.10 | 0.08 | 1.80 | 0.11 | 14.45 | |
| | | 61 | 0.82 | 0.10 | 0.16 | 0.11 | 0.05 | 1.83 | 0.13 | 14.66 | 6.35 |
| 5, 6 | 25 AmyE/75 TrGA | 13 | 6.45 | 0.48 | 5.02 | 3.72 | 0.19 | 1.32 | 0.04 | 5.76 | |
| | | 21 | 3.60 | 0.38 | 2.43 | 1.17 | 0.22 | 1.72 | 0.07 | 10.80 | |
| | | 37 | 0.93 | 0.17 | 0.38 | 0.22 | 0.16 | 1.82 | 0.09 | 14.42 | |
| | | 45 | 0.84 | 0.16 | 0.36 | 0.22 | 0.11 | 1.82 | 0.10 | 14.59 | |
| | | 61 | 0.80 | 0.15 | 0.35 | 0.21 | 0.06 | 1.81 | 0.12 | 14.87 | 4.87 |
| 7, 8 | 50 AmyE/50 TrGA | 13 | 7.33 | 1.43 | 5.84 | 1.28 | 0.20 | 1.33 | 0.04 | 5.92 | |
| | | 21 | 5.14 | 0.53 | 3.60 | 0.36 | 0.20 | 1.57 | 0.05 | 9.59 | |
| | | 37 | 1.26 | 0.30 | 0.54 | 0.35 | 0.16 | 1.66 | 0.09 | 13.73 | |
| | | 45 | 0.98 | 0.21 | 0.41 | 0.33 | 0.12 | 1.67 | 0.10 | 14.08 | |
| | | 61 | 0.82 | 0.17 | 0.39 | 0.33 | 0.05 | 1.67 | 0.10 | 14.24 | 5.42 |
| 9, 10 | 75 AmyE/25 TrGA | 13 | 13.58 | 2.31 | 1.25 | 0.15 | 0.21 | 1.13 | 0.03 | 5.41 | |
| | | 21 | 7.87 | 1.05 | 1.10 | 0.30 | 0.20 | 1.30 | 0.04 | 9.30 | |
| | | 37 | 4.58 | 0.26 | 0.31 | 0.44 | 0.15 | 1.34 | 0.05 | 12.03 | |
| | | 45 | 3.41 | 0.26 | 0.31 | 0.47 | 0.14 | 1.36 | 0.06 | 12.73 | |
| | | 61 | 1.79 | 0.24 | 0.28 | 0.48 | 0.08 | 1.38 | 0.06 | 13.64 | 10.82 |

The data presented in Table 4 show that TrGA alone and the AmyE/TrGA (25/75) blend exhibited nearly identical ethanol production rates as well as the final ethanol yields. The AmyE/TrGA (50/50) blend performed comparable to AnGA alone in terms of ethanol production rate, though both produced ethanol significantly slower than TrGA alone and the AmyE/TrGA (25/75) blend. A comparison of the residual starch data indicates that the AmyE/TrGA (25/75) blend performs equivalently as the AnGA alone in terms of total carbohydrate usage.

FIG. 16 indicates that AmyE is capable of effectively reducing the glucose surge in the lag (yeast growth) phase of the fermentation. The glucose surge, typical in saccharification by TrGA, is believed to slow down further saccharification by a feedback inhibition. FIG. 17, on the other hand, indicates that, in yeast fermentation for alcohol production, AmyE is capable of replacing approximately at least 25% of the total glucoamylase.

SEQUENCE LISTING

```
SEQ ID NO: 1:
Full length Bacillus subtilis AmyE amino acid sequence.
The native signal sequence is not shown.
   1 LTAPSIKSGT ILHAWNWSFN TLKHNMKDIH DAGYTAIQTS PINQVKEGNQ

51 GDKSMSNWYW LYQPTSYQIG NRYLGTEQEF KEMCAAAEEY GIKVIVDAVI

101 NHTTSDYAAI SNEVKSIPNW THGNTQIKNW SDRWDVTQNS LLGLYDWNTQ

151 NTQVQSYLKR FLDRALNDGA DGFRFDAAKH IELPDDGSYG SQFWPNITNT

201 SAEFQYGEIL QDSASRDAAY ANYMDVTASN YGHSIRSALK NRNLGVSNIS

251 HYASDVSADK LVTWVESHDT YANDDEESTW MSDDDIRLGW AVIASRSGST

301 PLFFSRPEGG GNGVRFPGKS QIGDRGSALF EDQAITAVNR FHNVMAGQPE

351 ELSNPNGNNQ IFMNQRGSHG VVLANAGSSS VSINTATKLP DGRYDNKAGA

401 GSFQVNDGKL TGTINARSVA VLYPDDIAKA PHVFLENYKT GVTHSFNDQL

451 TITLRADANT TKAVYQINNG PETAFKDGDQ FTIGKGDPFG KTYTIMLKGT

501 NSDGVTRTEK YSFVKRDPAS AKTIGYQNPN HWSQVNAYIY KHDGSRVIEL

551 TGSWPGKPMT KNADGIYTLT LPADTDTTNA KVIFNNGSAQ VPGQNQPGFD

601 YVLNGLYNDS GLSGSLPH
```

SEQ ID NO: 2:
Truncated *Bacillus subtilis* AmyE (AmyE-tr) amino acid
sequence. The native signal sequence is not shown.

```
  1 LTAPSIKSGT ILHAWNWSFN TLKHNMKDIH DAGYTAIQTS PINQVKEGNQ

51 GDKSMSNWYW LYQPTSYQIG NRYLGTEQEF KEMCAAAEEY GIKVIVDAVI

101 NHTTSDYAAI SNEVKSIPNW THGNTQIKNW SDRWDVTQNS LLGLYDWNTQ

151 NTQVQSYLKR FLDRALNDGA DGFRFDAAKH IELPDDGSYG SQFWPNITNT

201 SAEFQYGEIL QDSASRDAAY ANYMDVTASN YGHSIRSALK NRNLGVSNIS

251 HYASDVSADK LVTWVESHDT YANDDEESTW MSDDDIRLGW AVIASRSGST

301 PLFFSRPEGG GNGVRFPGKS QIGDRGSALF EDQAITAVNR FHNVMAGQPE

351 ELSNPNGNNQ IFMNQRGSHG VVLANAGSSS VSINTATKLP DGRYDNKAGA

401 GSFQVNDGKL TGTINARSVA VLYPD
```

SEQ ID NO: 3:
*Bacillus subtilis* alpha-amylase variant Amy31A amino acid
sequence (UniProtKB/TrEMBL Accession No. O82953).
The native signal sequence is shown in bold.

```
  1 MFEKRFKTSL LPLFAGFLLL FHLVLSGPAA ANAETANKSN KVTASSVKNG

51 TILHAWNWSF NTLTQNMKDI RDAGYAAIQT SPINQVKEGN QGDKSMSNWY

101 WLYQPTSYQI GNRYLGTEQE FKDMCAAAEK YGVKVIVDAV VNHTTSDYGA

151 ISDEIKRIPN WTHGNTQIKN WSDRWDITQN ALLGLYDWNT QNTEVQAYLK

201 GFLERALNDG ADGFRYDAAK HIELPDDGNY GSQFWPNITN TSAEFQYGEI

251 LQDSASRDTA YANYMNVTAS NYGHSIRSAL KNRILSVSNI SHYASDVSAD

301 KLVTWVESHD TYANDDEEST WMSDDDIRLG WAVIGSRSGS TPLFFSRPEG

351 GGNGVRFPGK SQIGDRGSAL FKDQAITAVN QFHNEMAGQP EELSNPNGNN

401 QIFMNQRGSK GVVLANAGSS SVTINTSTKL PDGRYDNRAG AGSFQVANGK

451 LTGTINARSA AVLYPDDIGN APHVFLENYQ TEAVHSFNDQ LTVTLRANAK

501 TTKAVYQINN GQETAFKDGD RLTIGKEDPI GTTYNVKLTG TNGEGASRTQ

551 EYTFVKKDPS QTNIIGYQNP DHWGNVNAYI YKHDGGGAIE LTGSWPGKAM

601 TKNADGIYTL TLPANADTAD AKVIFNNGSA QVPGQNHPGF DYVQNGLYNN

651 SGLNGYLPH
```

SEQ ID NO: 4:
Truncated *Geobacillus stearothermophilus* alpha-amylase
(AmyS, a/k/a "Ethyl3") protein sequence.
The signal sequence is shown in bold.

```
  1 MLTFHRIIRK GWMFLLAFLL TASLFCPTGQ HAKAAAPFNG TMMQYFEWYL

51 PDDGTLWTKV ANEANNLSSL GITALWLPPA YKGTSRSDVG YGVYDLYDLG

101 EFNQKGTVRT KYGTKAQYLQ AIQAAHAAGM QVYADVVFDH KGGADGTEWV

151 DAVEVNPSDR NQEISGTYQI QAWTKFDFPG RGNTYSSFKW RWYHFDGVDW

201 DESRKLSRIY KFIGKAWDWE VDTENGNYDY LMYADLDMDH PEVVTELKNW

251 GKWYVNTTNI DGFRLDAVKH IKFSFFPDWL SYVRSQTGKP LFTVGEYWSY

301 DINKLHNYIT KTNGTMSLFD APLHNKFYTA SKSGGAFDMR TLMTNTLMKD

351 QPTLAVTFVD NHDTEPGQAL QSWVDPWFKP LAYAFILTRQ EGYPCVFYGD

401 YYGIPQYNIP SLKSKIDPLL IARRDYAYGT QHDYLDHSDI IGWTREGVTE

451 KPGSGLAALI TDGPGGSKWM YVGKQHAGKV FYDLTGNRSD TVTINSDGWG

501 EFKVNGGSVS VWVPRKTT
```

-continued

SEQ ID NO: 5:
Geobacillus stearothermophilus alpha-amylase
(AmyR; SPEZYME> XTRA amylase) amino acid sequence.
```
  1 AAPFNGTMMQ YFEWYLPDDG TLWTKVANEA NNLSSLGITA LWLPPAYKGT

51 SRSDVGYGVY DLYDLGEFNQ KGTVRTKYGT KAQYLQAIQA AHAAGMQVYA

101 DVVFDHKGGA DGTEWVDAVE VNPSDRNQEI SGTYQIQAWT KFDFPGRGNT

151 YSSFKWRWYH FDGVDWDESR KLSRIYKFRG IGKAWDWEVD TENGNYDYLM

201 YADLDMDHPE VVTELKNWGK WYVNTTNIDG FRLDAVKHIK FSFFPDWLSY

251 VRSQTGKPLF TVGEYWSYDI NKLHNYITKT NGTMSLFDAP LHNKFYTASK

301 SGGAFDMRTL MTNTLMKDQP TLAVTFVDNH DTEPGQALQS WVDPWFKPLA

351 YAFILTRQEG YPCVFYGDYY GIPQYNIPSL KSKIDPLLIA RRDYAYGTQH

401 DYLDHSDIIG WTREGVTEKP GSGLAALITD GPGGSKWMYV GKQHAGKVFY

451 DLTGNRSDTV TINSDGWGEF KVNGGSVSVW VPRKTT
```

SEQ ID NO: 6:
Aspergillus kawachii alpha-amylase (AkAA) amino acid sequence.
```
  1 MRVSTSSIAL AVSLFGKLAL GLSAAEWRTQ SIYFLLTDRF GRTDNSTTAT

51 CNTGDQIYCG GSWQGIINHL DYIQGMGFTA IWISPITEQL PQDTSDGEAY

101 HGYWQQKIYN VNSNFGTADD LKSLSDALHA RGMYLMVDVV PNHMGYAGNG

151 NDVDYSVFDP FDSSSYFHPY CLITDWDNLT MVQDCWEGDT IVSLPDLNTT

201 ETAVRTIWYD WVADLVSNYS VDGLRIDSVE EVEPDFFPGY QEAAGVYCVG

251 EVDNGNPALD CPYQKYLDGV LNYPIYWQLL YAFESSSGSI SNLYNMIKSV

301 ASDCSDPTLL GNFIENHDNP RFASYTSDYS QAKNVLSYIF LSDGIPIVYA

351 GEEQHYSGGD VPYNREATWL SGYDTSAELY TWIATTNAIR KLAISADSDY

401 ITYANDPIYT DSNTIAMRKG TSGSQIITVL SNKGSSGSSY TLTLSGSGYT

451 SGTKLIEAYT CTSVTVDSNG DIPVPMASGL PRVLLPASVV DSSSLCGGSG

501 NTTTTTTAAT STSKATTSSS SSSAAATTSS SCTATSTTLP ITFEELVTTT

551 YGEEVYLSGS ISQLGEWDTS DAVKLSADDY TSSNPEWSVT VSLPVGTTFE

601 YKFIKVDEGG SVTWESDPNR EYTVPECGSG SGETVVDTWR
```

SEQ ID NO: 7:
Trichoderma reesei glucoamylase (TrGA) amino acid sequence
(SEQ ID NO: 3 of WO 2006/060062).
The pro-sequence is italicized.
```
  1 MHVLSTAVLL GSVAVQKVLG RPGSSGLSDV TKRSVDDFIS TETPIALNNL

51 LCNVGPDGCR AFGTSAGAVI ASPSTIDPDY YYMWTRDSAL VFKNLIDRFT

100 ETYDAGLQRR IEQYITAQVT LQGLSNPSGS LADGSGLGEP KFELTLKPFT

151 GNWGRPQRDG PALRAIALIG YSKWLINNNY QSTVSNVIWP IVRNDLNYVA

201 QYWNQTGFDL WEEVNGSSFF TVANQHRALV EGATLAATLG QSGSAYSSVA

251 PQVLCFLQRF WVSSGGYVDS NINTNEGRTG KDVNSVLTSI HTFDPNLGCD

301 AGTFQPCSDK ALSNLKVVVD SFRSIYGVNK GIPAGAAVAI GRYAEDVYYN

351 GNPWYLATFA AAEQLYDAIY VWKKTGSITV TATSLAFFQE LVPGVTAGTY

401 SSSSSTFTNI INAVSTYADG FLSEAAKYVP ADGSLAEQFD RNSGTPLSAL

451 HLTWSYASFL TATARRAGIV PPSWANSSAS TIPSTCSGAS VVGSYSRPTA

501 TSFPPSQTPK PGVPSGTPYT PLPCATPTSV AVTFHELVST QFGQTVKVAG

551 NAAALGNWST SAAVALDAVN YADNHPLWIG TVNLEAGDVV EYKYINVGQD

601 GSVTWESDPN HTYTVPAVAC VTQVVKEDTW QS
```

-continued

SEQ ID NO: 8:
SPEZYME® FRED alpha-amylase amino acid sequence.
```
  1 ANLNGTLMQY FEWYTPNDGQ HWKRLQNDSA YLAEHGITAV WIPPAYKGTS

51 QADVGYGAYD LYDLGEFHQK GTVRTKYGTK GELQSAIKSL HSRDINVYGD

101 VVINHKGGAD ATEDVTAVEV DPADRNRVIS GEYLIKAWTH FHFPGRGSTY

151 SDFKWHWYHF DGTDWDESRK LNRIYKFQGK AWDWEVSSEN GNYDYLMYAD

201 IDYDHPDVVA EIKRWGTWYA NELQLDGFRL DAVKHIKFSF LRDWVNHVRE

251 KTGKEMFTVA EYWQNDLGAL ENYLNKTNFN HSVFDVPLHY QFHAASTQGG

301 GYDMRKLLNG TVVSKHPLKS VTFVDNHDTQ PGQSLESTVQ TWFKPLAYAF

351 ILTRESGYPQ VFYGDMYGTK GDSQREIPAL KHKIEPILKA RKQYAYGAQH

401 DYFDHHDIVG WTREGDSSVA NSGLAALITD GPGGAKRMYV GRQNAGETWH

451 DITGNRSEPV VINSEGWGEF HVNGGSVSIY VQR
```

SEQ ID NO: 9:
Nucleotide sequence encoding the AmyE of SEQ ID NO: 1.
```
CTTACAGCACCGTCGATCAAAAGCGGAACCATTCTTCATGCATGGAATTGGTCGTTCAATACGTT

AAAACACAATATGAAGGATATTCATGATGCAGGATATACAGCCATTCAGACATCTCCGATTAACC

AAGTAAAGGAAGGGAATCAAGGAGATAAAAGCATGTCGAACTGGTACTGGCTGTATCAGCCGACA

TCGTATCAAATTGGCAACCGTTACTTAGGTACTGAACAAGAATTTAAAGAAATGTGTGCAGCCGC

TGAAGAATATGGCATAAAGGTCATTGTTGACGCGGTCATCAATCATACCACCAGTGATTATGCCG

CGATTTCCAATGAGGTTAAGAGTATTCCAAACTGGACACATGGAAACACACAAATTAAAAACTGG

TCTGATCGATGGGATGTCACGCAGAATTCATTGCTCGGGCTGTATGACTGGAATACACAAAATAC

ACAAGTACAGTCCTATCTGAAACGGTTCTTAGACAGGGCATTGAATGACGGGGCAGACGGTTTTC

GATTTGATGCCGCCAAACATATAGAGCTTCCAGATGATGGCAGTTACGGCAGTCAATTTTGGCCG

AATATCACAAATACATCAGCAGAGTTCCAATACGGAGAAATCCTTCAGGATAGTGCCTCCAGAGA

TGCTGCATATGCGAATTATATGGATGTGACAGCGTCTAACTATGGGCATTCCATAAGGTCCGCTT

TAAAGAATCGTAATCTGGGCGTGTCGAATATCTCCCACTATGCATCTGATGTGTCTGCGGACAAG

CTAGTGACATGGGTAGAGTCGCATGATACGTATGCCAATGATGATGAAGAGTCGACATGGATGAG

CGATGATGATATCCGTTTAGGCTGGGCGGTGATAGCTTCTCGTTCAGGCAGTACGCCTCTTTTCT

TTTCCAGACCTGAGGGAGGCGGAAATGGTGTGAGGTTCCCGGGGAAAAGCCAAATAGGCGATCGC

GGGAGTGCTTTATTTGAAGATCAGGCTATCACTGCGGTCAATAGATTTCACAATGTGATGGCTGG

ACAGCCTGAGGAACTCTCGAACCCGAATGGAAACAACCAGATATTTATGAATCAGCGCGGCTCAC

ATGGCGTTGTGCTGGCAAATGCAGGTTCATCCTCTGTCTCTATCAATACGGCAACAAAATTGCCT

GATGGCAGGTATGACAATAAAGCTGGAGCGGGTTCATTTCAAGTGAACGATGGTAAACTGACAGG

CACGATCAATGCCAGGTCTGTAGCTGTGCTTTATCCTGATGATATTGCAAAAGCGCCTCATGTTT

TCCTTGAGAATTACAAAACAGGTGTAACACATTCTTTCAATGATCAACTGACGATTACCTTGCGT

GCAGATGCGAATACAACAAAAGCCGTTTATCAAATCAATAATGGACCAGAGACGGCGTTTAAGGA

TGGAGATCAATTCACAATCGGAAAAGGAGATCCATTTGGCAAAACATACACCATCATGTTAAAAG

GAACGAACAGTGATGGTGTAACGAGGACCGAGAAATACAGTTTTGTTAAAAGAGATCCAGCGTCG

GCCAAAACCATCGGCTATCAAAATCCGAATCATTGGAGCCAGGTAAATGCTTATATCTATAAACA

TGATGGGAGCCGAGTAATTGAATTGACCGGATCTTGGCCTGGAAAACCAATGACTAAAAATGCAG
```

-continued
ACGGAATTTACACGCTGACGCTGCCTGCGGACACGGATACAACCAACGCAAAAGTGATTTTTAAT

AATGGCAGCGCCCAAGTGCCCGGTCAGAATCAGCCTGGCTTTGATTACGTGCTAAATGGTTTATA

TAATGACTCGGGCTTAAGCGGTTCTCTTCCCCAT

SEQ ID NO: 10:
Nucleotide sequence encoding AmyE-tr (SEQ ID NO: 2).
CTTACAGCACCGTCGATCAAAAGCGGAACCATTCTTCATGCATGGAATTGGTCGTTCAATACGTT

AAAACACAATATGAAGGATATTCATGATGCAGGATATACAGCCATTCAGACATCTCCGATTAACC

AAGTAAAGGAAGGGAATCAAGGAGATAAAAGCATGTCGAACTGGTACTGGCTGTATCAGCCGACA

TCGTATCAAATTGGCAACCGTTACTTAGGTACTGAACAAGAATTTAAAGAAATGTGTGCAGCCGC

TGAAGAATATGGCATAAAGGTCATTGTTGACGCGGTCATCAATCATACCACCAGTGATTATGCCG

CGATTTCCAATGAGGTTAAGAGTATTCCAAACTGGACACATGGAAACACACAAATTAAAAACTGG

TCTGATCGATGGGATGTCACGCAGAATTCATTGCTCGGGCTGTATGACTGGAATACACAAAATAC

ACAAGTACAGTCCTATCTGAAACGGTTCTTAGACAGGGCATTGAATGACGGGGCAGACGGTTTTC

GATTTGATGCCGCCAAACATATAGAGCTTCCAGATGATGGCAGTTACGGCAGTCAATTTTGGCCG

AATATCACAAATACATCAGCAGAGTTCCAATACGGAGAAATCCTTCAGGATAGTGCCTCCAGAGA

TGCTGCATATGCGAATTATATGGATGTGACAGCGTCTAACTATGGGCATTCCATAAGGTCCGCTT

TAAAGAATCGTAATCTGGGCGTGTCGAATATCTCCCACTATGCATCTGATGTGTCTGCGGACAAG

CTAGTGACATGGGTAGAGTCGCATGATACGTATGCCAATGATGATGAAGAGTCGACATGGATGAG

CGATGATGATATCCGTTTAGGCTGGGCGGTGATAGCTTCTCGTTCAGGCAGTACGCCTCTTTTCT

TTTCCAGACCTGAGGGAGGCGGAAATGGTGTGAGGTTCCCGGGGAAAAGCCAAATAGGCGATCGC

GGGAGTGCTTTATTTGAAGATCAGGCTATCACTGCGGTCAATAGATTTCACAATGTGATGGCTGG

ACAGCCTGAGGAACTCTCGAACCCGAATGGAAACAACCAGATATTTATGAATCAGCGCGGCTCAC

ATGGCGTTGTGCTGGCAAATGCAGGTTCATCCTCTGTCTCTATCAATACGGCAACAAAATTGCCT

GATGGCAGGTATGACAATAAAGCTGGAGCGGGTTCATTTCAAGTGAACGATGGTAAACTGACAGG

CACGATCAATGCCAGGTCTGTAGCTGTGCTTTATCCTGAT

SEQ ID NO: 11:
Nucleotide sequence encoding B. subtilis Amy31A (SEQ ID NO: 3).
TCTGTTAAAAACGGCACTATTCTGCATGCATGGAACTGGAGCTTTAACACGCTGACCCAGAACAT

GAAAGATATTCGTGACGCGGGCTATGCTGCGATCCAAACCAGCCCTATCAACCAGGTCAAAGAAG

GCAACCAAGGCGACAAATCCATGTCCAACTGGTACTGGCTGTATCAACCGACGTCCTATCAGATT

GGCAACCGTTATCTGGGCACGGAGCAAGAGTTCAAAGACATGTGTGCTGCGGCTGAGAAATATGG

TGTGAAAGTTATCGTGGACGCTGTGGTAAACCACACGACCTCTGATTATGGTGCTATTAGCGACG

AGATTAAACGTATTCCAAATTGGACCCATGGTAATACCCAGATCAAAAATTGGAGCGACCGCTGG

GACATTACCCAGAATGCGCTGCTGGGTCTGTATGACTGGAACACGCAAAACACCGAAGTACAGGC

ATATCTGAAGGGCTTCCTGGAACGCGCTCTGAACGATGGTGCTGATGGTTTTCGCTACGACGCCG

CAAAGCATATTGAGCTGCCGGATGACGGCAACTACGGTTCCCAATTCTGGCCGAACATCACCAAC

ACCTCTGCCGAATTCCAGTACGGCGAGATCCTGCAAGACTCCGCGAGCCGTGACACCGCTTATGC

CAACTATATGAACGTAACTGCCTCTAACTATGGCCATTCCATTCGTTCTGCGCTGAAAAATCGTA

TCCTGTCCGTGTCCAATATCTCCCACTATGCATCCGACGTTTCTGCTGACAAACTGGTAACTTGG

GTCGAGTCTCACGACACCTATGCAAATGATGACGAGGAGAGCACCTGGATGAGCGATGATGATAT

TCGTCTGGGTTGGGCGGTTATTGGTTCTCGCTCTGGTTCTACTCCGCTGTTCTTTAGCCGTCCGG

AAGGTGGCGGCAATGGCGTTCGTTTCCCGGGTAAATCTCAAATTGGTGATCGTGGCTCTGCACTG

TTTAAAGATCAAGCTATTACGGCGGTGAATCAGTTCCATAATGAGATGGCAGGTCAACCTGAAGA

ACTGTCCAATCCAAACGGTAACAACCAAATCTTCATGAACCAGCGTGGCAGCAAAGGCGTCGTCC

TGGCGAACGCCGGTAGCTCTTCTGTTACCATCAACACGTCTACCAAACTGCCAGACGGCCGCTAT

GATAACCGTGCGGGTGCTGGTTCCTTTCAGGTAGCCAACGGCAAGCTGACGGGCACCATCAACGC

TCGTTCTGCTGCTGTTCTGTACCCGGACGACATTGGCAACGCTCCGCACGTGTTCCTGGAGAATT

ACCAGACCGAAGCGGTACATAGCTTTAATGACCAGCTGACCGTCACTCTGCGTGCCAACGCAAAA

ACCACGAAAGCAGTCTATCAGATCAATAATGGTCAAGAAACTGCTTTCAAGGATGGCGACCGTCT

GACTATTGGTAAGGAGGACCCGATTGGCACCACTTATAACGTTAAACTGACTGGCACCAATGGCG

AGGGCGCTAGCCGCACTCAAGAGTATACGTTCGTAAAGAAAGACCCGTCTCAAACCAACATCATC

GGTTACCAGAATCCTGACCACTGGGGTAATGTGAACGCTTACATCTATAAACATGATGGTGGCGG

TGCTATCGAACTGACCGGCTCTTGGCCAGGTAAAGCCATGACGAAAAACGCGGATGGCATCTATA

CCCTGACCCTGCCGGCCAATGCGGATACCGCAGATGCGAAGGTTATCTTCAATAACGGCTCCGCG

CAGGTTCCGGGCCAAAACCATCCGGGCTTTGACTACGTACAAAATGGTCTGTATAACAACTCTGG

CCTGAACGGTTACCTGCCGCAC

SEQ ID NO: 12:
Nucleotide sequence encoding Geobacillus stearothermophilus AmyS
(SEQ ID NO: 4).
GCCGCACCGTTTAACGGTACCATGATGCAGTATTTTGAATGGTACTTGCCGGATGATGGCACGTT

ATGGACCAAAGTGGCCAATGAAGCCAACAACTTATCCAGCCTTGGCATCACCGCTCTTTGGCTGC

CGCCCGCTTACAAAGGAACAAGCCGCAGCGACGTAGGGTACGGAGTATACGACTTGTATGACCTC

GGCGAATTCAATCAAAAAGGGACCGTCCGCACAAAATATGGAACAAAAGCTCAATATCTTCAAGC

CATTCAAGCCGCCCACGCCGCTGGAATGCAAGTGTACGCCGATGTCGTGTTCGACCATAAAGGCG

GCGCTGACGGCACGGAATGGGTGGACGCCGTCGAAGTCAATCCGTCCGACCGCAACCAAGAAATC

TCGGGCACCTATCAAATCCAAGCATGGACGAAATTTGATTTTCCCGGGCGGGGCAACACCTACTC

CAGCTTTAAGTGGCGCTGGTACCATTTTGACGGCGTTGACTGGGACGAAAGCCGAAAATTAAGCC

GCATTTACAAATTCATCGGCAAAGCGTGGGATTGGGAAGTAGACACAGAAAACGGAAACTATGAC

TACTTAATGTATGCCGACCTTGATATGGATCATCCCGAAGTCGTGACCGAGCTGAAAAACTGGGG

GAAATGGTATGTCAACACAACGAACATTGATGGGTTCCGGCTTGATGCCGTCAAGCATATTAAGT

TCAGTTTTTTTCCTGATTGGTTGTCGTATGTGCGTTCTCAGACTGGCAAGCCGCTATTTACCGTC

GGGGAATATTGGAGCTATGACATCAACAAGTTGCACAATTACATTACGAAAACAAACGGAACGAT

GTCTTTGTTTGATGCCCCGTTACACAACAAATTTTATACCGCTTCCAAATCAGGGGGCGCATTTG

ATATGCGCACGTTAATGACCAATACTCTCATGAAAGATCAACCGACATTGGCCGTCACCTTCGTT

GATAATCATGACACCGAACCCGGCCAAGCGCTGCAGTCATGGGTCGACCCATGGTTCAAACCGTT

GGCTTACGCCTTTATTCTAACTCGGCAGGAAGGATACCCGTGCGTCTTTTATGGTGACTATTATG

GCATTCCACAATATAACATTCCTTCGCTGAAAAGCAAATCGATCCGCTCCTCATCGCGCGCAGG

GATTATGCTTACGGAACGCAACATGATTATCTTGATCACTCCGACATCATCGGGTGGACAAGGGA

AGGGGTCACTGAAAAACCAGGATCCGGGCTGGCCGCACTGATCACCGATGGGCCGGGAGGAAGCA

AATGGATGTACGTTGGCAAACAACACGCTGGAAAAGTGTTCTATGACCTTACCGGCAACCGGAGT

GACACCGTCACCATCAACAGTGATGGATGGGGGGAATTCAAAGTCAATGGCGGTTCGGTTTCGGT

TTGGGTTCCTAGAAAAACGACC

SEQ ID NO: 13:
Nucleotide sequence for SPEZYME® XTRA amylase gene
(SEQ ID NO: 5).
GCCGCACCGTTTAACGGTACCATGATGCAGTATTTTGAATGGTACTTGCCGGATGATGGCACGTT

ATGGACCAAAGTGGCCAATGAAGCCAACAACTTATCCAGCCTTGGCATCACCGCTCTTTGGCTGC

CGCCCGCTTACAAAGGAACAAGCCGCAGCGACGTAGGGTACGGAGTATACGACTTGTATGACCTC

GGCGAATTCAATCAAAAGGGACCGTCCGCACAAAATATGGAACAAAAGCTCAATATCTTCAAGC

CATTCAAGCCGCCCACGCCGCTGGAATGCAAGTGTACGCCGATGTCGTGTTCGACCATAAAGGCG

GCGCTGACGGCACGGAATGGGTGGACGCCGTCGAAGTCAATCCGTCCGACCGCAACCAAGAAATC

TCGGGCACCTATCAAATCCAAGCATGGACGAAATTTGATTTTCCCGGGCGGGGCAACACCTACTC

CAGCTTTAAGTGGCGCTGGTACCATTTTGACGGCGTTGATTGGGACGAAAGCCGAAAATTAAGCC

GCATTTACAAATTCAGGGGCATCGGCAAAGCGTGGGATTGGGAAGTAGACACAGAAAACGGAAAC

TATGACTACTTAATGTATGCCGACCTTGATATGGATCATCCCGAAGTCGTGACCGAGCTGAAAAA

CTGGGGGAAATGGTATGTCAACACAACGAACATTGATGGGTTCCGGCTTGATGCCGTCAAGCATA

TTAAGTTCAGTTTTTTTCCTGATTGGTTGTCGTATGTGCGTTCTCAGACTGGCAAGCCGCTATTT

ACCGTCGGGGAATATTGGAGCTATGACATCAACAAGTTGCACAATTACATTACGAAAACAAACGG

AACGATGTCTTTGTTTGATGCCCCGTTACACAACAAATTTTATACCGCTTCCAAATCAGGGGGCG

CATTTGATATGCGCACGTTAATGACCAATACTCTCATGAAAGATCAACCGACATTGGCCGTCACC

TTCGTTGATAATCATGACACCGAACCCGGCCAAGCGCTTCAGTCATGGGTCGACCCATGGTTCAA

ACCGTTGGCTTACGCCTTTATTCTAACTCGGCAGGAAGGATACCCGTGCGTCTTTTATGGTGACT

ATTATGGCATTCCACAATATAACATTCCTTCGCTGAAAAGCAAAATCGATCCGCTCCTCATCGCG

CGCAGGGATTATGCTTACGGAACGCAACATGATTATCTTGATCACTCCGACATCATCGGGTGGAC

AAGGGAAGGGGTCACTGAAAAACCAGGATCCGGGCTGGCCGCACTGATCACCGATGGGCCGGGAG

GAAGCAAATGGATGTACGTTGGCAAACAACACGCTGGAAAAGTGTTCTATGACCTTACCGGCAAC

CGGAGTGACACCGTCACCATCAACAGTGATGGATGGGGGGAATTCAAAGTCAATGGCGGTTCGGT

TTCGGTTTGGGTTCCTAGAAAACGACC

SEQ ID NO: 14:
Nucleotide sequence for Aspergillus kawachii alpha amylase (AkAA)
gene (SEQ ID NO: 6).
ATGAGAGTGTCGACTTCAAGTATTGCCCTTGCTGTGTCCCTTTTTGGGAAGCTGGCCCTTGGGCT

GTCAGCTGCAGAATGGCGCACTCAATCCATCTACTTCCTTTTGACGGATCGGTTCGGTAGGACGG

ACAATTCGACTACAGCTACGTGCAATACGGGTGACCAAATCTACTGTGGTGGAAGTTGGCAAGGA

ATTATCAACCATCTGGACTATATCCAGGGCATGGGATTCACAGCTATCTGGATCTCGCCTATCAC

TGAGCAGCTACCCCAGGATACTTCGGATGGTGAAGCCTACCATGGATACTGGCAGCAGAAGATAT

ACAATGTGAACTCCAACTTCGGCACGGCAGATGATCTGAAGTCCCTCTCCGATGCTCTTCACGCC

CGCGGAATGTACCTCATGGTCGACGTCGTCCCTAACCACATGGGCTACGCAGGTAACGGCAACGA

TGTGGATTACAGCGTCTTCGACCCCTTCGACTCCTCCTCCTACTTCCATCCATACTGCCTCATCA

CAGATTGGGACAACTTGACCATGGTCCAAGACTGTTGGGAGGGTGACACCATCGTGTCTCTGCCA

GATCTGAACACCACGGAAACCGCCGTGAGAACCATTTGGTACGATTGGGTAGCCGACCTGGTATC

CAACTACTCAGTCGACGGCCTCCGTATCGACAGTGTCGAAGAAGTCGAACCCGACTTCTTCCCGG

GCTACCAAGAAGCAGCAGGAGTCTACTGCGTCGGTGAAGTCGACAACGGCAACCCTGCTCTCGAC

TGCCCATACCAAAAATATCTAGATGGTGTTCTCAACTATCCCATCTACTGGCAACTCCTCTACGC

CTTTGAATCCTCCAGCGGCAGCATCAGCAACCTCTACAACATGATCAAATCCGTCGCCAGCGACT

GCTCCGATCCGACCCTCCTGGGCAACTTTATCGAAAACCACGACAACCCCCGCTTCGCCTCCTAC

-continued

```
ACATCCGACTACTCCCAAGCCAAAAACGTCCTCAGCTACATCTTCCTCTCCGACGGCATCCCCAT

CGTCTACGCCGGCGAAGAACAGCACTACTCCGGCGGCGACGTGCCCTACAACCGCGAAGCTACCT

GGCTATCAGGCTACGACACCTCCGCGGAGCTCTACACCTGGATAGCCACCACAAACGCGATCCGG

AAACTAGCTATCTCAGCAGACTCGGACTACATTACTTACGCGAACGACCCAATCTACACAGACAG

CAACACCATCGCGATGCGCAAAGGCACCTCCGGCTCCCAAATCATCACCGTCCTCTCCAACAAAG

GCTCCTCCGGAAGCAGCTACACCCTCACCCTCAGCGGAAGCGGCTACACGTCCGGCACGAAGCTC

ATCGAAGCGTACACCTGCACGTCCGTGACGGTGGACTCGAACGGGGATATCCCTGTGCCGATGGC

TTCGGGATTACCTAGAGTTCTCCTCCCTGCTTCGGTGGTTGATAGTTCTTCGCTTTGTGGGGGGA

GTGGTAACACAACCACGACCACAACTGCTGCTACCTCCACATCCAAAGCCACCACCTCCTCTTCT

TCTTCTTCTGCTGCTGCTACTACTTCTTCATCATGCACCGCAACAAGCACCACCCTCCCCATCAC

CTTCGAAGAACTCGTCACCACTACCTACGGGAAGAAGTCTACCTCAGCGGATCTATCTCCCAGC

TCGGAGAGTGGGATACGAGTGACGCGGTGAAGTTGTCCGCGGATGATTATACCTCGAGTAACCCC

GAGTGGTCTGTTACTGTGTCGTTGCCGGTGGGGACGACCTTCGAGTATAAGTTTATTAAGGTCGA

TGAGGGTGGAAGTGTGACTTGGGAAAGTGATCCGAATAGGGAGTATACTGTGCCTGAATGTGGGA

GTGGGAGTGGGGAGACGGTGGTTGATACGTGGAGGTAG
```

SEQ ID NO: 15:
Nucleotide sequence for *Trichoderma reesei* glucoamylase gene
(SEQ ID NO: 7).

```
   1 ATGCACGTCC TGTCGACTGC GGTGCTGCTC GGCTCCGTTG CCGTTCAAAA GGTCCTGGGA

61 AGACCAGGAT CAAGCGGTCT GTCCGACGTC ACCAAGAGGT CTGTTGACGA CTTCATCAGC

121 ACCGAGACGC CTATTGCACT GAACAATCTT CTTTGCAATG TTGGTCCTGA TGGATGCCGT

181 GCATTCGGCA CATCAGCTGG TGCGGTGATT GCATCTCCCA GCACAATTGA CCCGGACTAC

241 TATTACATGT GGACGCGAGA TAGCGCTCTT GTCTTCAAGA ACCTCATCGA CCGCTTCACC

301 GAAACGTACG ATGCGGGCCT GCAGCGCCGC ATCGAGCAGT ACATTACTGC CAGGTCACT

361 CTCCAGGGCC TCTCTAACCC CTCGGGCTCC CTCGCGGACG GCTCTGGTCT CGGCGAGCCC

421 AAGTTTGAGT TGACCCTGAA GCCTTTCACC GGCAACTGGG GTCGACCGCA GCGGGATGGC

481 CCAGCTCTGC GAGCCATTGC CTTGATTGGA TACTCAAAGT GGCTCATCAA CAACAACTAT

541 CAGTCGACTG TGTCCAACGT CATCTGGCCT ATTGTGCGCA ACGACCTCAA CTATGTTGCC

601 CAGTACTGGA ACCAAACCGG CTTTGACCTC TGGGAAGAAG TCAATGGGAG CTCATTCTTT

661 ACTGTTGCCA ACCAGCACCG AGCACTTGTC GAGGGCGCCA CTCTTGCTGC CACTCTTGGC

721 CAGTCGGGAA GCGCTTATTC ATCTGTTGCT CCCCAGGTTT TGTGCTTTCT CCAACGATTC

781 TGGGTGTCGT CTGGTGGATA CGTCGACTCC AACATCAACA CCAACGAGGG CAGGACTGGC

841 AAGGATGTCA ACTCCGTCCT GACTTCCATC CACACCTTCG ATCCCAACCT TGGCTGTGAC

901 GCAGGCACCT TCCAGCCATG CAGTGACAAA GCGCTCTCCA ACCTCAAGGT TGTTGTCGAC

961 TCCTTCCGCT CCATCTACGG CGTGAACAAG GGCATTCCTG CCGGTGCTGC CGTCGCCATT

1021 GGCCGGTATG CAGAGGATGT GTACTACAAC GGCAACCCTT GGTATCTTGC TACATTTGCT

1081 GCTGCCGAGC AGCTGTACGA TGCCATCTAC GTCTGGAAGA AGACGGGCTC CATCACGGTG

1141 ACCGCCACCT CCCTGGCCTT CTTCCAGGAG CTTGTTCCTG GCGTGACGGC CGGGACCTAC

1201 TCCAGCAGCT CTTCGACCTT TACCAACATC ATCAACGCCG TCTCGACATA CGCCGATGGC

1261 TTCCTCAGCG AGGCTGCCAA GTACGTCCCC GCCGACGGTT CGCTGGCCGA GCAGTTTGAC

1321 CGCAACAGCG GCACTCCGCT GTCTGCGCTT CACCTGACGT GGTCGTACGC CTCGTTCTTG

1381 ACAGCCACGG CCCGTCGGGC TGGCATCGTG CCCCCCTCGT GGGCCAACAG CAGCGCTAGC
```

-continued

```
1441 ACGATCCCCT CGACGTGCTC CGGCGCGTCC GTGGTCGGAT CCTACTCGCG TCCCACCGCC

1501 ACGTCATTCC CTCCGTCGCA GACGCCCAAG CCTGGCGTGC CTTCCGGTAC TCCCTACACG

1561 CCCCTGCCCT GCGCGACCCC AACCTCCGTG GCCGTCACCT TCCACGAGCT CGTGTCGACA

1621 CAGTTTGGCC AGACGGTCAA GGTGGCGGGC AACGCCGCGG CCCTGGGCAA CTGGAGCACG

1681 AGCGCCGCCG TGGCTCTGGA CGCCGTCAAC TATGCCGATA CCACCCCCT GTGGATTGGG

1741 ACGGTCAACC TCGAGGCTGG AGACGTCGTG GAGTACAAGT ACATCAATGT GGGCCAAGAT

1801 GGCTCCGTGA CCTGGGAGAG TGATCCCAAC CACACTTACA CGGTTCCTGC GGTGGCTTGT

1861 GTGACGCAGG TTGTCAAGGA GGACACCTGG CAGTCGTAA
```

SEQ ID NO: 16:
Nucleotide sequence for AmyL gene (SEQ ID NO: 8).
ACAAATCTTAATGGGACGCTGATGCAGTATTTTGAATGGTACACGCCCAATGACGGCCAACATTG

GAAGCGTCTGCAAAACGACTCGGCATATTTGGCTGAACACGGTATTACTGCCGTCTGGATTCCCC

CGGCATATAAGGGAACGAGCCAAGCGGATGTGGGCTACGGTGCTTACGACCTTTATGATTTAGGG

GAGTTTCATCAAAAAGGGACGGTTCGGACAAAGTACGGCACAAAAGGAGAGCTGCAATCTGCGAT

CAAAAGTCTTCATTCCCGCGACATTAACGTTTACGGGGATGTGGTCATCAACCACAAAGGCGGCG

CTGATGCGACCGAAGATGTAACCGCGGTTGAAGTCGATCCCGCTGACCGCAACCGCGTAATTTCC

GGAGAATACCTAATTAAAGCCTGGACACATTTTCATTTTCCGGGGCGCGGCAGCACATACAGCGA

TTTTAAATGGCATTGGTACCATTTTGACGGAACCGATTGGGACGAGTCCCGAAAGCTGAACCGCA

TCTATAAGTTTCAAGGAAAGGCTTGGGATTGGGAAGTTTCCAGTGAAAACGGCAACTATGATTAT

TTGATGTATGCCGACATCGATTATGACCATCCTGATGTCGTAGCAGAAATTAAGAGATGGGGCAC

TTGGTATGCCAATGAGCTCCAATTGGACGGTTTCCGTCTTGATGCTGTCAAACACATTAAATTTT

CTTTTTTGCGGGATTGGGTTAATCATGTCAGGGAAAAAACGGGGAAGGAAATGTTTACGGTAGCT

GAATATTGGCAGAATGACTTGGGCGCGCTGGAAAACTATTTGAACAAAACAAATTTTAATCATTC

AGTGTTTGACGTGCCGCTTCATTATCAGTTCCATGCTGCATCGACACAGGGAGGCGGCTATGATA

TGAGGAAATTGCTGAACGTACGGTCGTTTCCAAGCATCCGTTGAAATCGGTTACATTTGTCGAT

AACCATGATACACAGCCGGGGCAGTCGCTTGAGTCGACTGTCCAAACATGGTTTAAGCCGCTTGC

TTACGCTTTTATTCTCACAAGGGAATCTGGATACCCTCAGGTTTTCTACGGGGATATGTACGGGA

CGAAAGGAGACTCCCAGCGCGAAATTCCTGCCTTGAAACACAAATTGAACCGATCTTAAAAGCG

AGAAAACAGTATGCGTACGGAGCACAGCATGATTATTTCGACCACCATGACATTGTCGGCTGGAC

AAGGGAAGGCGACAGCTCGGTTGCAAATTCAGGTTTGCGGCATTAATAACAGACGGACCCGGTG

GGGCAAAGCGAATGTATGTCGGCCGGCAAAACGCCGGTGAGACATGGCATGACATTACCGGAAAC

CGTTCGGAGCCGGTTGTCATCAATTCGGAAGGCTGGGGAGAGTTTCACGTAAACGGCGGGTCGGT

TTCAATTTATGTTCAAAGA

SEQ ID NO: 17:
Native signal sequence of the AmyL of SEQ ID NO: 1.
MFAKRFKTSLLPLFAGFLLLFHLVLAGPAAASAETANKSNE SEQ ID NO: 18:
Primer PSTAMYE-F
CTTCTTGCTGCCTCATTCTGCAGCTTCAGCACTTACAGCACCGTCGATCAAAAGCGGAAC SEQ ID NO: 19:
Primer AMYENOPST-R
CTGGAGGCACTATCCTGAAGGATTTCTCCGTATTGGAACTCTGCTGATGTATTTGTG SEQ ID NO: 20:
Primer AMYENOPST-F
CACAAATACATCAGCAGAGTTCCAATACGGAGAAATCCTTCAGGATAGTGCCTCCAG -continued SEQ ID NO: 21:
Primer HPAIAMYE-R
CAGGAAATCCGTCCTCTGTTAACTCAATGGGGAAGAGAACCGCTTAAGCCCGAGTC SEQ ID NO: 22:
Primer HPAIAMYE466-R
CAGGAAATCCGTCCTCTGTTAACTCAATCAGGATAAAGCACAGCTACAGACCTGG SEQ ID NO: 23:
Primer AMYE SEQ-F1
TACACAAGTACAGTCCTATCTG SEQ ID NO: 24:
Primer AMYE SEQ-F2
CATCCTCTGTCTCTATCAATAC SEQ ID NO: 25:
Full length *Geobacillus stearothermophilus* alpha-amylase
(AmyS; P06279) protein sequence.
The signal sequence is shown in bold.
  1 MLTFHRIIRK GWMFLLAFLL TALLFCPTGQ PAKAAAPFNG TMMQYFEWYL

51 PDDGTLWTKV ANEANNLSSL GITALWLPPA YKGTSRSDVG YGVYDLYDLG

101 EFNQKGAVRT KYGTKAQYLQ AIQAAHAAGM QVYADVVFDH KGGADGTEWV

151 DAVEVNPSDR NQEISGTYQI QAWTKFDFPG RGNTYSSFKW RWYHFDGVDW

201 DESRKLSRIY KFRGIGKAWD WEVDTENGNY DYLMYADLDM DHPEVVTELK

251 SWGKWYVNTT NIDGFRLDAV KHIKFSFFPD WLSDVRSQTG KPLFTVGEYW

301 SYDINKLHNY IMKTNGTMSL FDAPLHNKFY TASKSGGTFD MRTLMTNTLM

351 KDQPTLAVTF VDNHDTEPGQ ALQSWVDPWF KPLAYAFILT RQEGYPCVFY

401 GDYYGIPQYN IPSLKSKIDP LLIARRDYAY GTQHDYLDHS DIIGWTREGV

451 TEKPGSGLAA LITDGPGGSK WMYVGKQHAG KVFYDLTGNR SDTVTINSDG

501 WGEFKVNGGS VSVWVPRKTT VSTIAWSITT RPWIDEFVRW TEPRLVAWP

SEQ ID NO: 26:
Full length *Bacillus licheniformis* alpha-amylase
(AmyL; P06278) protein sequence.
The signal sequence is shown in bold.
  1 MKQQKRLYAR LLTLLFALIF LLPHSAAAAA NLNGTLMQYF EWYMPNDGQH

51 WKRLQNDSAY LAEHGITAVW IPPAYKGTSQ ADVGYGAYDL YDLGEFHQKG

101 TVRTKYGTKG ELQSAIKSLH SRDINVYGDV VINHKGGADA TEDVTAVEVD

151 PADRNRVISG EHRIKAWTHF HFPGRGSTYS DFKWHWYHFD GTDWDESRKL

201 NRIYKFQGKA WDWEVSNENG NYDYLMYADI DYDHPDVAAE IKRWGTWYAN

251 ELQLDGFRLD AVKHIKFSFL RDWVNHVREK TGKEMFTVAE YWQNDLGALE

301 NYLNKTNFNH SVFDVPLHYQ FHAASTQGGG YDMRKLLNST VVSKHPLKAV

351 TFVDNHDTQP GQSLESTVQT WFKPLAYAFI LTRESGYPQV FYGDMYGTKG

401 DSQREIPALK HKIEPILKAR KQYAYGAQHD YFDHHDIVGW TREGDSSVAN

451 SGLAALITDG PGGAKRMYVG RQNAGETWHD ITGNRSEPVV INSEGWGEFH

501 VNGGSVSIYV QR

SEQ ID NO: 27:
Full length *Bacillus subtilis* alpha-amylase (AmyL; NP_988186).
The signal sequence is shown in bold.
  1 MFAKRFKTSL LPLFAGFLLL FHLVLAGPAA ASAETANKSN ELTAPSIKSG

51 TILHAWNWSF NTLKHNMKDI HDAGYTAIQT SPINQVKEGN QGDKSMSNWY

101 WLYQPTSYQI GNRYLGTEQE FKEMCAAAEE YGIKVIVDAV INHTTSDYAA

151 ISNEVKSIPN WTHGNTQIKN WSDRWDVTQN SLLGLYDWNT QNTQVQSYLK

201 RFLDRALNDG ADGFRFDAAK HIELPDDGSY GSQFWPNITN TSAEFQYGEI

```
251 LQDSASRDAA YANYMDVTAS NYGHSIRSAL KNRNLGVSNI SHYASDVSAD

301 KLVTWVESHD TYANDDEEST WMSDDDIRLG WAVIASRSGS TPLFFSRPEG

351 GGNGVRFPGK SQIGDRGSAL FEDQAITAVN RFHNVMAGQP EELSNPNGNN

401 QIFMNQRGSH GVVLANAGSS SVSINTATKL PDGRYDNKAG AGSFQVNDGK

451 LTGTINARSV AVLYPDDIAK APHVFLENYK TGVTHSFNDQ LTITLRADAN

501 TTKAVYQINN GPDDRRLRME INSQSEKEIQ FGKTYTIMLK GTNSDGVTRT

551 EKYSFVKRDP ASAKTIGYQN PNHWSQVNAY IYKHDGSRVI ELTGSWPGKP

601 MTKNADGIYT LTLPADIDTT NAKVIFNNGS AQVPGQNQPG FDYVLNGLYN

651 DSGLSGSLPH

SEQ ID NO: 28:
Full length Bacillus subtilis alpha-amylase
(AmyL; NCBI Accession No. ABW75769)
  1 MFAKRFKTSL LPLFAGFLLL FHLVLAGPAA ASAETANKSN ELTAPSIKSG

51 TILHAWNWSF NTLKHNMKDI HDAGYTAIQT SPINQVKEGN QGNKSMSNWY

101 WLYQPTSYQI GNRYLGTEQE FKEMCAAAEE YGIKVIVDAV INHTTSDYAA

151 ISNEIKSIPN WTHGNTQIKN WSDRWDVTQN SLLGLYDWNT QNTQVQSYLK

201 RFLERALNDG ADGFRFDAAK HIELPDDGSY GSQFWPNITN TSAEFQYGEI

251 LQDSASRDAA YANYMNVTAS NYGHSIRSAL KNRNLGVSNI SHYASDVSAD

301 KLVTWVESHD TYANDDEEST WMSDDDIRLG WAVIASRSGS TPLFFSRPEG

351 GGNGVRFPGK SQIGDRGSAL FEDQAITAVN RFHNVMAGQP EELSNPNGNN

401 QIFMNQRGSH GVVLANAGSS SVSINTPTKL PDGRYDNKAG AGSFQVNDGK

451 LTGTINARSV AVLYPDDIAK APHVFLENYK TGVTHSFNDQ LTITLRADAN

501 TTKAVYQINN GPETAFKDGD QFTIGKGDPF GKTYTIMLKG TNSNGVTKAE

551 EYSFVKRDPA SAKTIGYQNP NHWSQVNAYI YKHDGSRAIE LTGSWPGKPM

601 TKNADGIYTL TLPADIDTTN AKVIFNNGSA QVPGQNQPGF DYVQNGLYND

651 SGLSGSLPH

SEQ ID NO: 29:
Full length Bacillus subtilis alpha-amylase
(AmyL; NCBI Accession No. ABK54355)
  1 MFAKRFKTSL LPLFAGFLLL FHLVLAGPAA ASAETANKSN ELTAPSIKSG

51 TILHAWNWSF NTLKHNMKDI HDAGYTAIQT SPINQVKEGN QGDKSMSNWY

101 WLYQPTSYQI GNRYLGTEQE FKEMCAAAEE YGIKVIVDAV INHTTSDYAA

151 ISNEIKSIPN WTHGNTQIKN WSDRWDVTQN SLLGLYDWNT QNTQVQSYLK

201 RFLERALNDG ADGFRFDAAK HIELPDDGSY GSQFWPTITN TSAEFQYGEI

251 LQDSASRDAA YANYMDVTAS NYGHSIRSAL KNRNLGVSNL SHYASDVSAD

301 KLVTWVESHD TYANDDEEST WMSDDDIRLG WAVIASRSGS TPLFFSRPEG

351 GGNGVRFPGK SQIGDRGSAL FEDQAITAVN RFHNVMAGQP EELSNPNGNN

401 QIFMNQRGSH GVVLANAGSS SVSINTATKL PDGRYDNKAG AGSFQVNDGK

451 LTGTINARSV AVLYPDDIAK APHVFLENYK TGVTHSFNDQ LTITLRADAN

501 TTKAVYQINN GPETAFKDGD QFTIGKGDPF GKTYTIMLKG TNSDGVTRAE

551 EYSFVKRDPA SAKTIGYQNP NHWSQVNAYI YKHDGGRAIE LTGSWPGKPM

601 TKNADGIYTL TLPADIDTTN AKVIFNNGSA QVPGQNQPGF DYVQNGLYND

651 SGLSGSLPH
```

-continued

SEQ ID NO: 30:
Full length *Bacillus subtilis* alpha-amylase
(AmyL; NCBI Accession No. AAF14358)
```
  1 MFAKRFKTSL LPLFAGFLLL FHLVLAGPAA ASAETANKSN ELTAPSIKSG

51 TILHAWNWSF NTLKHNMKDI HDAGYTAIQT SPINQVKEGN QGDKSMSNWY

101 WLYQPTSYQI GNRYLGTEQE FKEMCAAAEE YGIKVIVDAV INHTTSDYAA

151 ISNEIKSIPN WTHGNTQIKN WSDRWDVTQN SLLGLYDWNT QNTQVQSYLK

201 RFLERALNDG ADGFRFDAAK HIELPDDGSY GSQFWPTITN TSAEFQYGEI

251 LQDSASRDAA YANYMDVTAS NYGHSIRSAL KNRNLGVSNL SHYASDVSAD

301 KLVTWVESHD TYANDDEEST WMSDDDIRLG WAVIASRSGS TPLFFSRPEG

351 GGNGVRFPGK SQIGDRGSAL FEDQAITAVN RFHNVMAGQP EELSNPNGNN

401 QIFMNQRGSH GVVLANAGSS SVSINTATKL PDGRYDNKAG AGSFQVNDGK

451 LTGTINARSV AVLYPDDIAK APHVFLENYK TGVTHSFNDQ LTITLRADAN

501 TTKAVYQINN GPETAFKDGD QFTIGKGDPF GKTYTIMLKG TNSDGVTRAE

551 EYSFVKRDPA SAKTIGYQNP NHWSQVNAYI YKHDGGRAIE LTGSWPGKPM

601 TKNADGIYTL TLPADIDTTN AKVIFNNGSA QVPGQNQPGF DYVQNGLYND

651 SGLSGSLPH
```

SEQ ID NO: 31:
Full length *Bacillus subtilis* alpha-amylase
(AmyL; NCBI Accession No. AAT01440)
```
  1 MFAKRFKTSL LPLFAGFLLL FHLVLAGPAA ASAETANKSN ELTAPSIKSG

51 TILHAWNWSF NTLKHNMKDI HDAGYTAIQT SPINQVKEGN QGDKSMSNWY

101 WLYQPTSYQI GNRYLGTEQE FKEMCAAAEE YGIKVIVDAV INHTTSDYAA

151 ISNEVKSIPN WTHGNTQIKN WSDRWDVTQN SLLGLYDWNT QNTQVQSYLK

201 RFLERALNDG ADGFRFDAAK HIELPDDGSY GSQFWPNITN TSAEFQYGEI

251 LQDSASRDAA YANYMDVTAS NYGHSIRSAL KNRNLGVSNI SHYASDVSAD

301 KLVTWVESHD TYANDDEEST WMSDDDIRLG WAVIASRSGS TPLFFSRPEG

351 GGNGVRFPGK SQIGDRGSAL FEDQAITAVN RFHNVMAGQP EELSNPNGNN

401 QIFMNQRGSH GVVLANAGSS SVSINTPTKL PDGRYDNKAG AGSFQVNDGK

451 LTGTINARSV AVLYPDDIAQ APHVFLENYK TGVTHSFNDQ LTITLRADAN

501 TTKAVYQINN GPETAFKDGD QFTIGKGDPF GKTYTIMLKG TNSDGVTRTE

551 EYSFIKRDPA SAKTIGYQNP NHWSQVNAYI YKHDGGQAIE LTGSWPGKPM

601 TKNADGIYTL TLPADIDTTN AKVIFNNGSA QVPGQNQPGF DYVQNGLYND

651 SGLSGSLPY
```

SEQ ID NO: 32:
Full length *Bacillus subtilis* alpha-amylase
(AmyL; NCBI Accession No. AAZ30064)
```
  1 MFAKRFKTSL LPLFAGFLLL FHLVLAGPNA ANAETANKSN ELTAPSIKSG

51 TILHAWNWSF NTLKHNMKDI HDAGYTAIQT SPINQVKEGN QGNKSMLNWY

101 WLYQPTSYQI GNRYLGTEQE FKEMCAAAEE YGIKVIVDAV INHTTSDYAA

151 ISNEIKSIPN WTHGNTQIKN WSDRWDVTQN SLLGLYDWNT QNTQVQSYLK

201 RFLERALNDG ADGFRFDAAK HIELPDDGSY GSQFWPNITN TSAEFQYGEI

251 LQDSASRDAS YANYMNVTAS NYGHSIRSAL KNRNLGVSNI SHYASDVPAD

301 KLVTWVESHD TYANDDEEST WMSDDDIRLG WAVIASRSGS TPLFFSRPEG

351 GGNGVRFPGK SQIGDRGSAL FEDQAITAVN RFHNVMAGQP EELSNPNGNN
```

```
401 QIFMNQRGSH GVVLANAGSS SVSINTPTKL PDGRYDNKAG AGSFQVNDGK

451 LTGTINARSV AVLYPDDIAK APHVFLENYK TGVTHSFNDQ LTITMRADAK

501 TTKAVYQINN GPETAFKDGD QFTIGKGDPF GKTYTIMLKG TNSDGVTRTE

551 EYSFIKRDPA SAKTIGYQNP NHWSQVNAYI YKHDGGQAIE LTGSWPGKPM

601 TKNADGIYTL TLPADIDTTN AKVIFNNGSA QVPGQNQPGF DYVQNGLYND

651 SGLSGSLPH

SEQ ID NO: 33:
Full length Bacillus subtilis alpha-amylase
(AmyL: NCBI Accession No. AAQ83841)
  1 MFAKRFKTSL LPLFAGFLLL FYLVLAGPAA ASAETANKSI ELTAPSIKSG

51 TILHAWNWSF NTLKHNMKDI HDAGYTAIQT SPINQVKEGN QGDKSMSNWY

101 WLYQPTSYQI GNRYLGTEQE FKEMCAAAEE YGIKVIVDAV INHTTSDYAA

151 ISNEVKSIPN WTHGNTQIKN WSDRWDVTQN SLLGLYDWNT QNTQVQSYLK

201 RFLDRALNDG ADGFRFDAAK HIELPDDGSY GSQFWPNITN TSAEFQYGEI

251 LQDSASRDAA YANYMDVTAS NYGHSIRSAL KNRNLGVSNI SHYASDVSAD

301 KLVTWVESHD TYANDDEEST WMSDDDIRLG WAVIASRSGS TPLFFSRPEG

351 GGNGVRFPGK SQIGDRGSAL FEDQAITAVN RFHNVMAGQP EELSNPNGNN

401 QIFMNQRISH GVVLANAGSS SVSINTATKL PDGRYDNKAG AGSFQVNDGK

451 LTGTINARSV AVLYPDDIAK APHVFLENYK TGVTHSFNDQ LTITLRADAN

501 TFIKSIMDQI NXRXRRLRME INSQSEKEIQ FGKTYTIMLK GTNSDGVTRX

551 EKYSLPKRDP ASAKTIGYQN PNHWSQVNAY IYKHDGSREI ELTGSWPGKP

601 MTKNADGIYT LTLPADIDTT NAKVIFNNGY AQVPGQNQPG FDYVLNGLY

SEQ ID NO: 34:
Full length Bacillus subtilis alpha-amylase
(AmyL; NCBI Accession No. BAA31528)
  1 MFEKRFKTSL LPLFAGFLLL FHLVLSGPAA ANAETANKSN KVTASSVKNG

51 TILHAWNWSF NTLTQNMKDI RDAGYAAIQT SPINQVKEGN QGDKSMSNWY

101 WLYQPTSYQI GNRYLGTEQE FKDMCAAAEK YGVKVIVDAV VNHTTSDYGA

151 ISDEIKRIPN WTHGNTQIKN WSDRWDITQN ALLGLYDWNT QNTEVQAYLK

201 GFLERALNDG ADGFRYDAAK HIELPDDGNY GSQFWPNITN TSAEFQYGEI

251 LQDSASRDTA YANYMNVTAS NYGHSIRSAL KNRILSVSNI SHYASDVSAD

301 KLVTWVESHD TYANDDEEST WMSDDDIRLG WAVIGSRSGS TPLFFSRPEG

351 GGNGVRFPGK SQIGDRGSAL FKDQAITAVN QFHNEMAGQP EELSNPNGNN

401 QIFMNQRGSK GVVLANAGSS SVTINTSTKL PDGRYDNRAG AGSFQVANGK

451 LTGTINARSA AVLYPDDIGN APHVFLENYQ TEAVHSFNDQ LTVTLRANAK

501 TTKAVYQINN GQETAFKDGD RLTIGKEDPI GTTYNVKLTG TNGEGASRTQ

551 EYTFVKKDPS QTNIIGYQNP DHWGNVNAYI YKHDGGGAIE LTGSWPGKAM

601 TKNADGIYTL TLPANADTAD AKVIFNNGSA QVPGQNHPGF DYVQNGLYNN

651 SGLNGYLPH
```

What is claimed is:

1. A composition for saccharifying a starch comprising a glucoamylase and an alpha-amylase, wherein the alpha-amylase is a *Bacillus subtilis* alpha-amylase (AmyE) or an AmyE variant, wherein the alpha-amylase consists of the amino acid sequence of SEQ ID NO: 1 and the AmyE variant consists of the amino acid sequence of SEQ ID NO: 2.

2. The composition of claim 1, wherein the alpha-amylase consisting of the amino acid sequence set forth in SEQ ID NO: 1.

3. The composition of claim 1, wherein the AmyE variant has one or more altered properties compared to the AmyE having an amino acid sequence of SEQ ID NO: 1.

4. The composition of claim 3, wherein the one or more altered properties is: substrate specificity, substrate binding, substrate cleavage pattern, thermal stability, pH/activity profile, pH/stability profile, stability towards oxidation, stability at lower level of calcium ion ($Ca^{2+}$), specific activity, or any combination thereof.

5. The composition of claim 1 further comprising a phytase, a pullulanase, a beta-amylase, a fungal alpha-amylase, a protease, a cellulose, a hemicellulase, a lipase, a cutinase, an isoamylase, or any combination thereof.

6. A method of processing a starch comprising admixing the composition of claim 1 for a time sufficient to saccharify the starch.

7. The method of claim 6 further comprising producing high fructose corn syrup.

8. The method of claim 7, wherein high fructose corn syrup production is achieved by admixing a glucose isomerase.

9. The method of claim 6 further comprising fermenting the starch to produce ethanol.

10. The method of claim 9, wherein saccharifying and fermenting are performed simultaneously.

11. The method of claim 9 further comprising recovering the ethanol.

12. The method of claim 9 further comprising distilling the starch to obtain the ethanol, wherein the fermenting and the distilling are carried out simultaneously, separately, or sequentially.

13. A method of saccharifying a starch comprising admixing a composition of claim 1 comprising a glucoamylase and an alpha-amylase with an oligosaccharide or a starch substrate, wherein the alpha-amylase is a *Bacillus subtilis* alpha-amylase (AmyE) or an AmyE variant having the amino acid sequence consisting of SEQ ID NO: 1 or SEQ ID NO: 2.

14. The method of claim 13, wherein the alpha-amylase consists of the amino acid sequence set forth in SEQ ID NO: 1.

15. The method of claim 13, wherein the AmyE variant has one or more altered properties compared to the AmyE having an amino acid sequence of SEQ ID NO: 1.

16. The method of claim 15, wherein the one or more altered properties is: substrate specificity, substrate binding, substrate cleavage pattern, thermal stability, pH/activity profile, pH/stability profile, stability towards oxidation, stability at lower level of calcium ion ($Ca^{2+}$), specific activity, or any combination thereof.

17. The method of claim 13, wherein the glucoamylase is used at an amount no higher than 0.11 glucoamylase units per gram dry solid (GAU/g ds).

18. The method of claim 13 further comprising admixing a phytase, a pullulanase, a beta-amylase, a fungal alpha-amylase, a protease, a cellulose, a hemicellulase, a lipase, a cutinase, an isoamylase, or any combination thereof, with the oligosaccharide or the starch substrate.

19. The method of claim 13 further comprising producing high fructose corn syrup.

20. The method of claim 19, wherein high fructose corn syrup production is achieved by admixing a glucose isomerase.

21. The method of claim 13 further comprising fermenting the starch to produce ethanol.

22. The method of claim 21, wherein saccharifying and fermenting are performed simultaneously.

23. The method of claim 21 further comprising recovering the ethanol.

24. The method of claim 21 further comprising distilling the starch to obtain the ethanol, wherein the fermenting and the distilling are carried out simultaneously, separately, or sequentially.

* * * * *

SEQUENCE LISTING

<160> NUMBER OF SEQ ID NOS: 35

<210> SEQ ID NO 1
<211> LENGTH: 618
<212> TYPE: PRT
<213> ORGANISM: Bacillus subtilis

<400> SEQUENCE: 1

Leu Thr Ala Pro Ser Ile Lys Ser Gly Thr Ile Leu His Ala Trp Asn
1               5                   10                  15

Trp Ser Phe Asn Thr Leu Lys His Asn Met Lys Asp Ile His Asp Ala
            20                  25                  30

Gly Tyr Thr Ala Ile Gln Thr Ser Pro Ile Asn Gln Val Lys Glu Gly
        35                  40                  45

Asn Gln Gly Asp Lys Ser Met Ser Asn Trp Tyr Trp Leu Tyr Gln Pro
    50                  55                  60

Thr Ser Tyr Gln Ile Gly Asn Arg Tyr Leu Gly Thr Glu Gln Glu Phe
65                  70                  75                  80

Lys Glu Met Cys Ala Ala Ala Glu Glu Tyr Gly Ile Lys Val Ile Val
                85                  90                  95

Asp Ala Val Ile Asn His Thr Thr Ser Asp Tyr Ala Ala Ile Ser Asn
            100                 105                 110

Glu Val Lys Ser Ile Pro Asn Trp Thr His Gly Asn Thr Gln Ile Lys
            115                 120                 125

Asn Trp Ser Asp Arg Trp Asp Val Thr Gln Asn Ser Leu Leu Gly Leu
    130                 135                 140

Tyr Asp Trp Asn Thr Gln Asn Thr Gln Val Gln Ser Tyr Leu Lys Arg
145                 150                 155                 160

Phe Leu Asp Arg Ala Leu Asn Asp Gly Ala Asp Gly Phe Arg Phe Asp
                165                 170                 175

Ala Ala Lys His Ile Glu Leu Pro Asp Asp Gly Ser Tyr Gly Ser Gln
            180                 185                 190

Phe Trp Pro Asn Ile Thr Asn Thr Ser Ala Glu Phe Gln Tyr Gly Glu
            195                 200                 205

Ile Leu Gln Asp Ser Ala Ser Arg Asp Ala Ala Tyr Ala Asn Tyr Met
    210                 215                 220

Asp Val Thr Ala Ser Asn Tyr Gly His Ser Ile Arg Ser Ala Leu Lys
225                 230                 235                 240

Asn Arg Asn Leu Gly Val Ser Asn Ile Ser His Tyr Ala Ser Asp Val
                245                 250                 255

Ser Ala Asp Lys Leu Val Thr Trp Val Glu Ser His Asp Thr Tyr Ala
            260                 265                 270

Asn Asp Asp Glu Glu Ser Thr Trp Met Ser Asp Asp Ile Arg Leu
            275                 280                 285

Gly Trp Ala Val Ile Ala Ser Arg Ser Gly Ser Thr Pro Leu Phe Phe
    290                 295                 300

Ser Arg Pro Glu Gly Gly Gly Asn Gly Val Arg Phe Pro Gly Lys Ser
305                 310                 315                 320

Gln Ile Gly Asp Arg Gly Ser Ala Leu Phe Glu Asp Gln Ala Ile Thr
                325                 330                 335

Ala Val Asn Arg Phe His Asn Val Met Ala Gly Gln Pro Glu Glu Leu
            340                 345                 350

Ser Asn Pro Asn Gly Asn Asn Gln Ile Phe Met Asn Gln Arg Gly Ser
            355                 360                 365

```
His Gly Val Val Leu Ala Asn Ala Gly Ser Ser Val Ser Ile Asn
    370                 375                 380

Thr Ala Thr Lys Leu Pro Asp Gly Arg Tyr Asp Asn Lys Ala Gly Ala
385                 390                 395                 400

Gly Ser Phe Gln Val Asn Asp Gly Lys Leu Thr Gly Thr Ile Asn Ala
                405                 410                 415

Arg Ser Val Ala Val Leu Tyr Pro Asp Asp Ile Ala Lys Ala Pro His
            420                 425                 430

Val Phe Leu Glu Asn Tyr Lys Thr Gly Val Thr His Ser Phe Asn Asp
        435                 440                 445

Gln Leu Thr Ile Thr Leu Arg Ala Asp Ala Asn Thr Thr Lys Ala Val
    450                 455                 460

Tyr Gln Ile Asn Asn Gly Pro Glu Thr Ala Phe Lys Asp Gly Asp Gln
465                 470                 475                 480

Phe Thr Ile Gly Lys Gly Asp Pro Phe Gly Lys Thr Tyr Thr Ile Met
                485                 490                 495

Leu Lys Gly Thr Asn Ser Asp Gly Val Thr Arg Thr Glu Lys Tyr Ser
            500                 505                 510

Phe Val Lys Arg Asp Pro Ala Ser Ala Lys Thr Ile Gly Tyr Gln Asn
        515                 520                 525

Pro Asn His Trp Ser Gln Val Asn Ala Tyr Ile Tyr Lys His Asp Gly
    530                 535                 540

Ser Arg Val Ile Glu Leu Thr Gly Ser Trp Pro Gly Lys Pro Met Thr
545                 550                 555                 560

Lys Asn Ala Asp Gly Ile Tyr Thr Leu Thr Leu Pro Ala Asp Thr Asp
                565                 570                 575

Thr Thr Asn Ala Lys Val Ile Phe Asn Asn Gly Ser Ala Gln Val Pro
            580                 585                 590

Gly Gln Asn Gln Pro Gly Phe Asp Tyr Val Leu Asn Gly Leu Tyr Asn
        595                 600                 605

Asp Ser Gly Leu Ser Gly Ser Leu Pro His
    610                 615

<210> SEQ ID NO 2
<211> LENGTH: 425
<212> TYPE: PRT
<213> ORGANISM: Bacillus subtilis

<400> SEQUENCE: 2

Leu Thr Ala Pro Ser Ile Lys Ser Gly Thr Ile Leu His Ala Trp Asn
1               5                   10                  15

Trp Ser Phe Asn Thr Leu Lys His Asn Met Lys Asp Ile His Asp Ala
                20                  25                  30

Gly Tyr Thr Ala Ile Gln Thr Ser Pro Ile Asn Gln Val Lys Glu Gly
            35                  40                  45

Asn Gln Gly Asp Lys Ser Met Ser Asn Trp Tyr Trp Leu Tyr Gln Pro
        50                  55                  60

Thr Ser Tyr Gln Ile Gly Asn Arg Tyr Leu Gly Thr Glu Gln Glu Phe
65                  70                  75                  80

Lys Glu Met Cys Ala Ala Ala Glu Glu Tyr Gly Ile Lys Val Ile Val
                85                  90                  95

Asp Ala Val Ile Asn His Thr Thr Ser Asp Tyr Ala Ala Ile Ser Asn
            100                 105                 110

Glu Val Lys Ser Ile Pro Asn Trp Thr His Gly Asn Thr Gln Ile Lys
        115                 120                 125
```

```
Asn Trp Ser Asp Arg Trp Asp Val Thr Gln Asn Ser Leu Leu Gly Leu
    130                 135                 140

Tyr Asp Trp Asn Thr Gln Asn Thr Gln Val Gln Ser Tyr Leu Lys Arg
145                 150                 155                 160

Phe Leu Asp Arg Ala Leu Asn Asp Gly Ala Asp Gly Phe Arg Phe Asp
                165                 170                 175

Ala Ala Lys His Ile Glu Leu Pro Asp Asp Gly Ser Tyr Gly Ser Gln
            180                 185                 190

Phe Trp Pro Asn Ile Thr Asn Thr Ser Ala Glu Phe Gln Tyr Gly Glu
        195                 200                 205

Ile Leu Gln Asp Ser Ala Ser Arg Asp Ala Ala Tyr Ala Asn Tyr Met
210                 215                 220

Asp Val Thr Ala Ser Asn Tyr Gly His Ser Ile Arg Ser Ala Leu Lys
225                 230                 235                 240

Asn Arg Asn Leu Gly Val Ser Asn Ile Ser His Tyr Ala Ser Asp Val
                245                 250                 255

Ser Ala Asp Lys Leu Val Thr Trp Val Glu Ser His Asp Thr Tyr Ala
            260                 265                 270

Asn Asp Asp Glu Glu Ser Thr Trp Met Ser Asp Asp Ile Arg Leu
        275                 280                 285

Gly Trp Ala Val Ile Ala Ser Arg Ser Gly Ser Thr Pro Leu Phe Phe
290                 295                 300

Ser Arg Pro Glu Gly Gly Gly Asn Gly Val Arg Phe Pro Gly Lys Ser
305                 310                 315                 320

Gln Ile Gly Asp Arg Gly Ser Ala Leu Phe Glu Asp Gln Ala Ile Thr
                325                 330                 335

Ala Val Asn Arg Phe His Asn Val Met Ala Gly Gln Pro Glu Glu Leu
            340                 345                 350

Ser Asn Pro Asn Gly Asn Asn Gln Ile Phe Met Asn Gln Arg Gly Ser
        355                 360                 365

His Gly Val Val Leu Ala Asn Ala Gly Ser Ser Ser Val Ser Ile Asn
370                 375                 380

Thr Ala Thr Lys Leu Pro Asp Gly Arg Tyr Asp Asn Lys Ala Gly Ala
385                 390                 395                 400

Gly Ser Phe Gln Val Asn Asp Gly Lys Leu Thr Gly Thr Ile Asn Ala
                405                 410                 415

Arg Ser Val Ala Val Leu Tyr Pro Asp
            420                 425

<210> SEQ ID NO 3
<211> LENGTH: 659
<212> TYPE: PRT
<213> ORGANISM: Bacillus subtilis

<400> SEQUENCE: 3

Met Phe Glu Lys Arg Phe Lys Thr Ser Leu Leu Pro Leu Phe Ala Gly
1               5                   10                  15

Phe Leu Leu Leu Phe His Leu Val Leu Ser Gly Pro Ala Ala Ala Asn
                20                  25                  30

Ala Glu Thr Ala Asn Lys Ser Asn Lys Val Thr Ala Ser Ser Val Lys
            35                  40                  45

Asn Gly Thr Ile Leu His Ala Trp Asn Trp Ser Phe Asn Thr Leu Thr
        50                  55                  60

Gln Asn Met Lys Asp Ile Arg Asp Ala Gly Tyr Ala Ala Ile Gln Thr
```

```
            65                  70                  75                  80
Ser Pro Ile Asn Gln Val Lys Glu Gly Asn Gln Gly Asp Lys Ser Met
                    85                  90                  95

Ser Asn Trp Tyr Trp Leu Tyr Gln Pro Thr Ser Tyr Gln Ile Gly Asn
                100                 105                 110

Arg Tyr Leu Gly Thr Glu Gln Glu Phe Lys Asp Met Cys Ala Ala Ala
                115                 120                 125

Glu Lys Tyr Gly Val Lys Val Ile Val Asp Ala Val Asn His Thr
130                 135                 140

Thr Ser Asp Tyr Gly Ala Ile Ser Asp Glu Ile Lys Arg Ile Pro Asn
145                 150                 155                 160

Trp Thr His Gly Asn Thr Gln Ile Lys Asn Trp Ser Asp Arg Trp Asp
                165                 170                 175

Ile Thr Gln Asn Ala Leu Leu Gly Leu Tyr Asp Trp Asn Thr Gln Asn
                180                 185                 190

Thr Glu Val Gln Ala Tyr Leu Lys Gly Phe Leu Glu Arg Ala Leu Asn
                195                 200                 205

Asp Gly Ala Asp Gly Phe Arg Tyr Asp Ala Ala Lys His Ile Glu Leu
210                 215                 220

Pro Asp Asp Gly Asn Tyr Gly Ser Gln Phe Trp Pro Asn Ile Thr Asn
225                 230                 235                 240

Thr Ser Ala Glu Phe Gln Tyr Gly Glu Ile Leu Gln Asp Ser Ala Ser
                245                 250                 255

Arg Asp Thr Ala Tyr Ala Asn Tyr Met Asn Val Thr Ala Ser Asn Tyr
                260                 265                 270

Gly His Ser Ile Arg Ser Ala Leu Lys Asn Arg Ile Leu Ser Val Ser
                275                 280                 285

Asn Ile Ser His Tyr Ala Ser Asp Val Ser Ala Asp Lys Leu Val Thr
                290                 295                 300

Trp Val Glu Ser His Asp Thr Tyr Ala Asn Asp Asp Glu Glu Ser Thr
305                 310                 315                 320

Trp Met Ser Asp Asp Asp Ile Arg Leu Gly Trp Ala Val Ile Gly Ser
                325                 330                 335

Arg Ser Gly Ser Thr Pro Leu Phe Phe Ser Arg Pro Glu Gly Gly Gly
                340                 345                 350

Asn Gly Val Arg Phe Pro Gly Lys Ser Gln Ile Gly Asp Arg Gly Ser
                355                 360                 365

Ala Leu Phe Lys Asp Gln Ala Ile Thr Ala Val Asn Gln Phe His Asn
                370                 375                 380

Glu Met Ala Gly Gln Pro Glu Glu Leu Ser Asn Pro Asn Gly Asn Asn
385                 390                 395                 400

Gln Ile Phe Met Asn Gln Arg Gly Ser Lys Gly Val Val Leu Ala Asn
                405                 410                 415

Ala Gly Ser Ser Ser Val Thr Ile Asn Thr Ser Thr Lys Leu Pro Asp
                420                 425                 430

Gly Arg Tyr Asp Asn Arg Ala Gly Ala Gly Ser Phe Gln Val Ala Asn
                435                 440                 445

Gly Lys Leu Thr Gly Thr Ile Asn Ala Arg Ser Ala Ala Val Leu Tyr
                450                 455                 460

Pro Asp Asp Ile Gly Asn Ala Pro His Val Phe Leu Glu Asn Tyr Gln
465                 470                 475                 480

Thr Glu Ala Val His Ser Phe Asn Asp Gln Leu Thr Val Thr Leu Arg
                485                 490                 495
```

```
Ala Asn Ala Lys Thr Thr Lys Ala Val Tyr Gln Ile Asn Asn Gly Gln
            500                 505                 510

Glu Thr Ala Phe Lys Asp Gly Asp Arg Leu Thr Ile Gly Lys Glu Asp
            515                 520                 525

Pro Ile Gly Thr Thr Tyr Asn Val Lys Leu Thr Gly Thr Asn Gly Glu
            530                 535                 540

Gly Ala Ser Arg Thr Gln Glu Tyr Thr Phe Val Lys Lys Asp Pro Ser
545                 550                 555                 560

Gln Thr Asn Ile Ile Gly Tyr Gln Asn Pro Asp His Trp Gly Asn Val
            565                 570                 575

Asn Ala Tyr Ile Tyr Lys His Asp Gly Gly Ala Ile Glu Leu Thr
            580                 585                 590

Gly Ser Trp Pro Gly Lys Ala Met Thr Lys Asn Ala Asp Gly Ile Tyr
            595                 600                 605

Thr Leu Thr Leu Pro Ala Asn Ala Asp Thr Ala Asp Ala Lys Val Ile
            610                 615                 620

Phe Asn Asn Gly Ser Ala Gln Val Pro Gly Gln Asn His Pro Gly Phe
625                 630                 635                 640

Asp Tyr Val Gln Asn Gly Leu Tyr Asn Asn Ser Gly Leu Asn Gly Tyr
            645                 650                 655

Leu Pro His

<210> SEQ ID NO 4
<211> LENGTH: 518
<212> TYPE: PRT
<213> ORGANISM: Geobacillus stearothermophilus

<400> SEQUENCE: 4

Met Leu Thr Phe His Arg Ile Ile Arg Lys Gly Trp Met Phe Leu Leu
1               5                   10                  15

Ala Phe Leu Leu Thr Ala Ser Leu Phe Cys Pro Thr Gly Gln His Ala
            20                  25                  30

Lys Ala Ala Ala Pro Phe Asn Gly Thr Met Met Gln Tyr Phe Glu Trp
            35                  40                  45

Tyr Leu Pro Asp Asp Gly Thr Leu Trp Thr Lys Val Ala Asn Glu Ala
        50                  55                  60

Asn Asn Leu Ser Ser Leu Gly Ile Thr Ala Leu Trp Leu Pro Pro Ala
65                  70                  75                  80

Tyr Lys Gly Thr Ser Arg Ser Asp Val Gly Tyr Gly Val Tyr Asp Leu
            85                  90                  95

Tyr Asp Leu Gly Glu Phe Asn Gln Lys Gly Thr Val Arg Thr Lys Tyr
            100                 105                 110

Gly Thr Lys Ala Gln Tyr Leu Gln Ala Ile Gln Ala Ala His Ala Ala
            115                 120                 125

Gly Met Gln Val Tyr Ala Asp Val Val Phe Asp His Lys Gly Gly Ala
            130                 135                 140

Asp Gly Thr Glu Trp Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
            165                 170                 175

Asp Phe Pro Gly Arg Gly Asn Thr Tyr Ser Ser Phe Lys Trp Arg Trp
            180                 185                 190

Tyr His Phe Asp Gly Val Asp Trp Asp Glu Ser Arg Lys Leu Ser Arg
            195                 200                 205
```

-continued

Ile Tyr Lys Phe Ile Gly Lys Ala Trp Asp Trp Glu Val Asp Thr Glu
             210                 215                 220

Asn Gly Asn Tyr Asp Tyr Leu Met Tyr Ala Asp Leu Asp Met Asp His
225                 230                 235                 240

Pro Glu Val Val Thr Glu Leu Lys Asn Trp Gly Lys Trp Tyr Val Asn
                245                 250                 255

Thr Thr Asn Ile Asp Gly Phe Arg Leu Asp Ala Val Lys His Ile Lys
            260                 265                 270

Phe Ser Phe Phe Pro Asp Trp Leu Ser Tyr Val Arg Ser Gln Thr Gly
        275                 280                 285

Lys Pro Leu Phe Thr Val Gly Glu Tyr Trp Ser Tyr Asp Ile Asn Lys
    290                 295                 300

Leu His Asn Tyr Ile Thr Lys Thr Asn Gly Thr Met Ser Leu Phe Asp
305                 310                 315                 320

Ala Pro Leu His Asn Lys Phe Tyr Thr Ala Ser Lys Ser Gly Gly Ala
                325                 330                 335

Phe Asp Met Arg Thr Leu Met Thr Asn Thr Leu Met Lys Asp Gln Pro
            340                 345                 350

Thr Leu Ala Val Thr Phe Val Asp Asn His Asp Thr Glu Pro Gly Gln
        355                 360                 365

Ala Leu Gln Ser Trp Val Asp Pro Trp Phe Lys Pro Leu Ala Tyr Ala
    370                 375                 380

Phe Ile Leu Thr Arg Gln Glu Gly Tyr Pro Cys Val Phe Tyr Gly Asp
385                 390                 395                 400

Tyr Tyr Gly Ile Pro Gln Tyr Asn Ile Pro Ser Leu Lys Ser Lys Ile
                405                 410                 415

Asp Pro Leu Leu Ile Ala Arg Arg Asp Tyr Ala Tyr Gly Thr Gln His
            420                 425                 430

Asp Tyr Leu Asp His Ser Asp Ile Ile Gly Trp Thr Arg Glu Gly Val
        435                 440                 445

Thr Glu Lys Pro Gly Ser Gly Leu Ala Ala Leu Ile Thr Asp Gly Pro
    450                 455                 460

Gly Gly Ser Lys Trp Met Tyr Val Gly Lys Gln His Ala Gly Lys Val
465                 470                 475                 480

Phe Tyr Asp Leu Thr Gly Asn Arg Ser Asp Thr Val Thr Ile Asn Ser
                485                 490                 495

Asp Gly Trp Gly Glu Phe Lys Val Asn Gly Gly Ser Val Ser Val Trp
            500                 505                 510

Val Pro Arg Lys Thr Thr
        515

<210> SEQ ID NO 5
<211> LENGTH: 486
<212> TYPE: PRT
<213> ORGANISM: Geobacillus stearothermophilus

<400> SEQUENCE: 5

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp

-continued

```
            50                  55                  60
Leu Gly Glu Phe Asn Gln Lys Gly Thr Val Arg Thr Lys Tyr Gly Thr
 65                  70                  75                  80
Lys Ala Gln Tyr Leu Gln Ala Ile Gln Ala His Ala Ala Gly Met
                     85                  90                  95
Gln Val Tyr Ala Asp Val Val Phe Asp His Lys Gly Gly Ala Asp Gly
                    100                 105                 110
Thr Glu Trp Val Asp Ala Val Glu Val Asn Pro Ser Asp Arg Asn Gln
                    115                 120                 125
Glu Ile Ser Gly Thr Tyr Gln Ile Gln Ala Trp Thr Lys Phe Asp Phe
                    130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                    165                 170                 175
Lys Phe Arg Gly Ile Gly Lys Ala Trp Asp Trp Glu Val Asp Thr Glu
                    180                 185                 190
Asn Gly Asn Tyr Asp Tyr Leu Met Tyr Ala Asp Leu Asp Met Asp His
                    195                 200                 205
Pro Glu Val Val Thr Glu Leu Lys Asn Trp Gly Lys Trp Tyr Val Asn
210                 215                 220
Thr Thr Asn Ile Asp Gly Phe Arg Leu Asp Ala Val Lys His Ile Lys
225                 230                 235                 240
Phe Ser Phe Phe Pro Asp Trp Leu Ser Tyr Val Arg Ser Gln Thr Gly
                    245                 250                 255
Lys Pro Leu Phe Thr Val Gly Glu Tyr Trp Ser Tyr Asp Ile Asn Lys
                    260                 265                 270
Leu His Asn Tyr Ile Thr Lys Thr Asn Gly Thr Met Ser Leu Phe Asp
                    275                 280                 285
Ala Pro Leu His Asn Lys Phe Tyr Thr Ala Ser Lys Ser Gly Gly Ala
                    290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                    325                 330                 335
Ala Leu Gln Ser Trp Val Asp Pro Trp Phe Lys Pro Leu Ala Tyr Ala
                    340                 345                 350
Phe Ile Leu Thr Arg Gln Glu Gly Tyr Pro Cys Val Phe Tyr Gly Asp
                    355                 360                 365
Tyr Tyr Gly Ile Pro Gln Tyr Asn Ile Pro Ser Leu Lys Ser Lys Ile
                    370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
                    405                 410                 415
Thr Glu Lys Pro Gly Ser Gly Leu Ala Ala Leu Ile Thr Asp Gly Pro
                    420                 425                 430
Gly Gly Ser Lys Trp Met Tyr Val Gly Lys Gln His Ala Gly Lys Val
                    435                 440                 445
Phe Tyr Asp Leu Thr Gly Asn Arg Ser Asp Thr Val Thr Ile Asn Ser
                    450                 455                 460
Asp Gly Trp Gly Glu Phe Lys Val Asn Gly Gly Ser Val Ser Val Trp
465                 470                 475                 480
```

Val Pro Arg Lys Thr Thr
                485

<210> SEQ ID NO 6
<211> LENGTH: 640
<212> TYPE: PRT
<213> ORGANISM: Aspergillus kawachii

<400> SEQUENCE: 6

Met Arg Val Ser Thr Ser Ser Ile Ala Leu Ala Val Ser Leu Phe Gly
1               5                   10                  15

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
        35                  40                  45

Ala Thr Cys Asn Thr Gly Asp Gln Ile Tyr Cys Gly Gly Ser Trp Gln
    50                  55                  60

Gly Ile Ile Asn His Leu Asp Tyr Ile Gln Gly Met Gly Phe Thr Ala
65                  70                  75                  80

Ile Trp Ile Ser Pro Ile Thr Glu Gln Leu Pro Gln Asp Thr Ser Asp
                85                  90                  95

Gly Glu Ala Tyr His Gly Tyr Trp Gln Gln Lys Ile Tyr Asn Val Asn
            100                 105                 110

Ser Asn Phe Gly Thr Ala Asp Asp Leu Lys Ser Leu Ser Asp Ala Leu
        115                 120                 125

His Ala Arg Gly Met Tyr Leu Met Val Asp Val Val Pro Asn His Met
    130                 135                 140

Gly Tyr Ala Gly Asn Gly Asn Asp Val Asp Tyr Ser Val Phe Asp Pro
145                 150                 155                 160

Phe Asp Ser Ser Ser Tyr Phe His Pro Tyr Cys Leu Ile Thr Asp Trp
                165                 170                 175

Asp Asn Leu Thr Met Val Gln Asp Cys Trp Glu Gly Asp Thr Ile Val
            180                 185                 190

Ser Leu Pro Asp Leu Asn Thr Thr Glu Thr Ala Val Arg Thr Ile Trp
        195                 200                 205

Tyr Asp Trp Val Ala Asp Leu Val Ser Asn Tyr Ser Val Asp Gly Leu
    210                 215                 220

Arg Ile Asp Ser Val Glu Glu Val Glu Pro Asp Phe Phe Pro Gly Tyr
225                 230                 235                 240

Gln Glu Ala Ala Gly Val Tyr Cys Val Gly Glu Val Asp Asn Gly Asn
                245                 250                 255

Pro Ala Leu Asp Cys Pro Tyr Gln Lys Tyr Leu Asp Gly Val Leu Asn
            260                 265                 270

Tyr Pro Ile Tyr Trp Gln Leu Leu Tyr Ala Phe Glu Ser Ser Ser Gly
        275                 280                 285

Ser Ile Ser Asn Leu Tyr Asn Met Ile Lys Ser Val Ala Ser Asp Cys
    290                 295                 300

Ser Asp Pro Thr Leu Leu Gly Asn Phe Ile Glu Asn His Asp Asn Pro
305                 310                 315                 320

Arg Phe Ala Ser Tyr Thr Ser Asp Tyr Ser Gln Ala Lys Asn Val Leu
                325                 330                 335

Ser Tyr Ile Phe Leu Ser Asp Gly Ile Pro Ile Val Tyr Ala Gly Glu
            340                 345                 350

Glu Gln His Tyr Ser Gly Gly Asp Val Pro Tyr Asn Arg Glu Ala Thr

```
                355                 360                 365
Trp Leu Ser Gly Tyr Asp Thr Ser Ala Glu Leu Tyr Thr Trp Ile Ala
370                 375                 380

Thr Thr Asn Ala Ile Arg Lys Leu Ala Ile Ser Ala Asp Ser Asp Tyr
385                 390                 395                 400

Ile Thr Tyr Ala Asn Asp Pro Ile Tyr Thr Asp Ser Asn Thr Ile Ala
                405                 410                 415

Met Arg Lys Gly Thr Gly Ser Gln Ile Ile Thr Val Leu Ser Asn
            420                 425                 430

Lys Gly Ser Ser Gly Ser Ser Tyr Thr Leu Thr Leu Ser Gly Ser Gly
        435                 440                 445

Tyr Thr Ser Gly Thr Lys Leu Ile Glu Ala Tyr Thr Cys Thr Ser Val
    450                 455                 460

Thr Val Asp Ser Asn Gly Asp Ile Pro Val Pro Met Ala Ser Gly Leu
465                 470                 475                 480

Pro Arg Val Leu Leu Pro Ala Ser Val Val Asp Ser Ser Ser Leu Cys
                485                 490                 495

Gly Gly Ser Gly Asn Thr Thr Thr Thr Thr Ala Ala Thr Ser Thr
            500                 505                 510

Ser Lys Ala Thr Thr Ser Ser Ser Ser Ser Ala Ala Ala Thr Thr
        515                 520                 525

Ser Ser Ser Cys Thr Ala Thr Ser Thr Thr Leu Pro Ile Thr Phe Glu
530                 535                 540

Glu Leu Val Thr Thr Thr Tyr Gly Glu Glu Val Tyr Leu Ser Gly Ser
545                 550                 555                 560

Ile Ser Gln Leu Gly Glu Trp Asp Thr Ser Asp Ala Val Lys Leu Ser
                565                 570                 575

Ala Asp Asp Tyr Thr Ser Ser Asn Pro Glu Trp Ser Val Thr Val Ser
            580                 585                 590

Leu Pro Val Gly Thr Thr Phe Glu Tyr Lys Phe Ile Lys Val Asp Glu
        595                 600                 605

Gly Gly Ser Val Thr Trp Glu Ser Asp Pro Asn Arg Glu Tyr Thr Val
    610                 615                 620

Pro Glu Cys Gly Ser Gly Ser Gly Glu Thr Val Val Asp Thr Trp Arg
625                 630                 635                 640

<210> SEQ ID NO 7
<211> LENGTH: 632
<212> TYPE: PRT
<213> ORGANISM: Trichoderma reesei

<400> SEQUENCE: 7

Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Ile Asp Pro Asp Tyr
65                  70                  75                  80

Tyr Tyr Met Trp Thr Arg Asp Ser Ala Leu Val Phe Lys Asn Leu Ile
                85                  90                  95
```

```
Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
        115                 120                 125

Gly Ser Leu Ala Asp Gly Ser Gly Leu Gly Glu Pro Lys Phe Glu Leu
    130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Val Ile Trp Pro Ile Val
            180                 185                 190

Arg Asn Asp Leu Asn Tyr Val Ala Gln Tyr Trp Asn Gln Thr Gly Phe
        195                 200                 205

Asp Leu Trp Glu Glu Val Asn Gly Ser Ser Phe Phe Thr Val Ala Asn
    210                 215                 220

Gln His Arg Ala Leu Val Glu Gly Ala Thr Leu Ala Ala Thr Leu Gly
225                 230                 235                 240

Gln Ser Gly Ser Ala Tyr Ser Ser Val Ala Pro Gln Val Leu Cys Phe
                245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Val Leu Thr
        275                 280                 285

Ser Ile His Thr Phe Asp Pro Asn Leu Gly Cys Asp Ala Gly Thr Phe
    290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
                325                 330                 335

Ala Val Ala Ile Gly Arg Tyr Ala Glu Asp Val Tyr Tyr Asn Gly Asn
            340                 345                 350

Pro Trp Tyr Leu Ala Thr Phe Ala Ala Ala Glu Gln Leu Tyr Asp Ala
        355                 360                 365

Ile Tyr Val Trp Lys Lys Thr Gly Ser Ile Thr Val Thr Ala Thr Ser
    370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Asn Ile Ile Asn Ala Val Ser Thr
                405                 410                 415

Tyr Ala Asp Gly Phe Leu Ser Glu Ala Ala Lys Tyr Val Pro Ala Asp
            420                 425                 430

Gly Ser Leu Ala Glu Gln Phe Asp Arg Asn Ser Gly Thr Pro Leu Ser
        435                 440                 445

Ala Leu His Leu Thr Trp Ser Tyr Ala Ser Phe Leu Thr Ala Thr Ala
    450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
                485                 490                 495

Arg Pro Thr Ala Thr Ser Phe Pro Pro Ser Gln Thr Pro Lys Pro Gly
            500                 505                 510

Val Pro Ser Gly Thr Pro Tyr Thr Pro Leu Pro Cys Ala Thr Pro Thr
```

```
            515                 520                 525
Ser Val Ala Val Thr Phe His Glu Leu Val Ser Thr Gln Phe Gly Gln
530                 535                 540

Thr Val Lys Val Ala Gly Asn Ala Ala Leu Gly Asn Trp Ser Thr
545                 550                 555                 560

Ser Ala Ala Val Ala Leu Asp Ala Val Asn Tyr Ala Asp Asn His Pro
                565                 570                 575

Leu Trp Ile Gly Thr Val Asn Leu Glu Ala Gly Asp Val Val Glu Tyr
            580                 585                 590

Lys Tyr Ile Asn Val Gly Gln Asp Gly Ser Val Thr Trp Glu Ser Asp
                595                 600                 605

Pro Asn His Thr Tyr Thr Val Pro Ala Val Ala Cys Val Thr Gln Val
            610                 615                 620

Val Lys Glu Asp Thr Trp Gln Ser
625                 630

<210> SEQ ID NO 8
<211> LENGTH: 483
<212> TYPE: PRT
<213> ORGANISM: Artificial
<220> FEATURE:
<223> OTHER INFORMATION: Synthetic AmyL

<400> SEQUENCE: 8

Ala Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu Tyr Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Ser Glu Asn Gly Asn
            180                 185                 190

Tyr Asp Tyr Leu Met Tyr Ala Asp Ile Asp Tyr Asp His Pro Asp Val
        195                 200                 205

Val Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
```

```
                245                 250                 255
Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Asp Ser Gln Arg Glu Ile Pro Ala Leu Lys His Lys Ile
            370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                    405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 9
<211> LENGTH: 1854
<212> TYPE: DNA
<213> ORGANISM: Bacillus subtilis

<400> SEQUENCE: 9
cttacagcac cgtcgatcaa aagcggaacc attcttcatg catggaattg gtcgttcaat      60
acgttaaaac acaatatgaa ggatattcat gatgcaggat atacagccat tcagacatct     120
ccgattaacc aagtaaagga agggaatcaa ggagataaaa gcatgtcgaa ctggtactgg     180
ctgtatcagc cgacatcgta tcaaattggc aaccgttact taggtactga acaagaattt     240
aaagaaatgt gtgcagccgc tgaagaatat ggcataaagg tcattgttga cgcggtcatc     300
aatcatacca ccagtgatta tgccgcgatt ccaatgagg ttaagagtat tccaaactgg     360
acacatggaa acacacaaat taaaaactgg tctgatcgat gggatgtcac gcagaattca     420
ttgctcgggc tgtatgactg gaatacacaa aatacacaag tacagtccta tctgaaacgg     480
ttcttagaca gggcattgaa tgacggggca gacggttttc gatttgatgc cgccaaacat     540
atagagcttc cagatgatgg cagttacggc agtcaatttt ggccgaatat cacaaataca     600
tcagcagagt ccaatacgg agaaatcctt caggatagtg cctccagaga tgctgcatat     660
gcgaattata tggatgtgac agcgtctaac tatgggcatt ccataaggtc cgcttttaaag    720 aatcgtaatc tgggcgtgtc gaatatctcc cactatgcat ctgatgtgtc tgcggacaag     780
```

```
ctagtgacat gggtagagtc gcatgatacg tatgccaatg atgatgaaga gtcgacatgg      840
atgagcgatg atgatatccg tttaggctgg gcggtgatag cttctcgttc aggcagtacg      900
cctcttttct tttccagacc tgagggaggc ggaaatggtg tgaggttccc ggggaaaagc      960
caaataggcg atcgcgggag tgctttattt gaagatcagg ctatcactgc ggtcaataga     1020
tttcacaatg tgatggctgg acagcctgag gaactctcga acccgaatgg aaacaaccag     1080
atatttatga atcagcgcgg ctcacatggc gttgtgctgg caaatgcagg ttcatcctct     1140
gtctctatca atacggcaac aaaattgcct gatggcaggt atgacaataa agctggagcg     1200
ggttcatttc aagtgaacga tggtaaactg acaggcacga tcaatgccag gtctgtagct     1260
gtgctttatc ctgatgatat tgcaaaagcg cctcatgttt tccttgagaa ttacaaaaca     1320
ggtgtaacac attctttcaa tgatcaactg acgattacct gcgtgcaga tgcgaataca      1380 acaaaagccg tttatcaaat caataatgga ccagagacgg cgtttaagga tggagatcaa     1440
ttcacaatcg gaaaggaga tccatttggc aaaacataca ccatcatgtt aaaaggaacg      1500
aacagtgatg gtgtaacgag gaccgagaaa tacagttttg ttaaaagaga tccagcgtcg     1560
gccaaaacca tcggctatca aaatccgaat cattggagcc aggtaaatgc ttatatctat     1620
aaacatgatg ggagccgagt aattgaattg accggatctt ggcctggaaa accaatgact     1680
aaaaatgcag acggaattta cacgctgacg ctgcctgcgg acacggatac aaccaacgca     1740
aaagtgattt ttaataatgg cagcgcccaa gtgcccggtc agaatcagcc tggctttgat     1800
tacgtgctaa atggtttata taatgactcg ggcttaagcg gttctcttcc ccat            1854
```

<210> SEQ ID NO 10
<211> LENGTH: 1275
<212> TYPE: DNA
<213> ORGANISM: Bacillus subtilis

<400> SEQUENCE: 10

```
cttacagcac cgtcgatcaa aagcggaacc attcttcatg catggaattg gtcgttcaat       60
acgttaaaac acaatatgaa ggatattcat gatgcaggat atacagccat tcagacatct      120
ccgattaacc aagtaaagga agggaatcaa ggagataaaa gcatgtcgaa ctggtactgg      180
ctgtatcagc cgacatcgta tcaaattggc aaccgttact taggtactga acaagaattt      240
aaagaaatgt gtgcagccgc tgaagaatat ggcataaagg tcattgttga cgcggtcatc      300
aatcatacca ccagtgatta tgccgcgatt tccaatgagg ttaagagtat tccaaactgg      360
acacatggaa acacacaaat taaaaactgg tctgatcgat gggatgtcac gcagaattca      420
ttgctcgggc tgtatgactg gaatacacaa aatacacaag tacagtccta tctgaaacgg      480
ttcttagaca gggcattgaa tgacggggca gacggttttc gatttgatgc cgccaaacat      540
atagagcttc cagatgatgg cagttacggc agtcaatttt ggccgaatat cacaaataca      600
tcagcagagt tccaatacgg agaaatcctt caggatagtg cctccagaga tgctgcatat      660
gcgaattata tggatgtgac agcgtctaac tatgggcatt ccataaggtc cgctttaaag      720
aatcgtaatc tgggcgtgtc gaatatctcc cactatgcat ctgatgtgtc tgcggacaag     780
ctagtgacat gggtagagtc gcatgatacg tatgccaatg atgatgaaga gtcgacatgg      840
atgagcgatg atgatatccg tttaggctgg gcggtgatag cttctcgttc aggcagtacg      900
cctcttttct tttccagacc tgagggaggc ggaaatggtg tgaggttccc ggggaaaagc      960
caaataggcg atcgcgggag tgctttattt gaagatcagg ctatcactgc ggtcaataga     1020
```

```
tttcacaatg tgatggctgg acagcctgag gaactctcga acccgaatgg aaacaaccag      1080
atatttatga atcagcgcgg ctcacatggc gttgtgctgg caaatgcagg ttcatcctct      1140
gtctctatca atacggcaac aaaattgcct gatggcaggt atgacaataa agctggagcg      1200
ggttcatttc aagtgaacga tggtaaactg acaggcacga tcaatgccag gtctgtagct      1260
gtgctttatc ctgat                                                       1275

<210> SEQ ID NO 11
<211> LENGTH: 1842
<212> TYPE: DNA
<213> ORGANISM: Bacillus subtilis

<400> SEQUENCE: 11
tctgttaaaa acggcactat tctgcatgca tggaactgga gctttaacac gctgacccag        60
aacatgaaag atattcgtga cgcgggctat gctgcgatcc aaaccagccc tatcaaccag       120
gtcaaagaag gcaaccaagg cgacaaatcc atgtccaact ggtactggct gtatcaaccg       180
acgtcctatc agattggcaa ccgttatctg ggcacggagc aagagttcaa agacatgtgt       240
gctgcggctg agaaatatgg tgtgaaagtt atcgtggacg ctgtggtaaa ccacacgacc       300
tctgattatg gtgctattag cgacgagatt aaacgtattc caaattggac ccatggtaat       360
acccagatca aaaattggag cgaccgctgg gacattaccc agaatgcgct gctgggtctg       420
tatgactgga acacgcaaaa caccgaagta caggcatatc tgaagggctt cctggaacgc       480
gctctgaacg atggtgctga tggttttcgc tacgacgccg caaagcatat tgagctgccg       540
gatgacggca actacggttc ccaattctgg ccgaacatca ccaacacctc tgccgaattc       600
cagtacggcg agatcctgca agactccgcg agccgtgaca ccgcttatgc caactatatg       660
aacgtaactg cctctaacta tggccattcc attcgttctg cgctgaaaaa tcgtatcctg       720
tccgtgtcca atatctccca ctatgcatcc gacgtttctg ctgacaaact ggtaacttgg       780
gtcgagtctc acgacaccta tgcaaatgat gacgaggaga gcacctggat gagcgatgat       840
gatattcgtc tgggttgggc ggttattggt tctcgctctg gttctactcc gctgttcttt       900
agccgtccgg aaggtggcgg caatggcgtt cgtttcccgg gtaaatctca aattggtgat       960
cgtggctctg cactgtttaa agatcaagct attacggcgg tgaatcagtt ccataatgag      1020
atggcaggtc aacctgaaga actgtccaat ccaaacggta caaccaaat cttcatgaac       1080 cagcgtggca gcaaaggcgt cgtcctggcg aacgccggta gctcttctgt taccatcaac      1140
acgtctacca aactgccaga cggccgctat gataaccgtg cgggtgctgg ttcctttcag      1200
gtagccaacg gcaagctgac gggcaccatc aacgctcgtt ctgctgctgt tctgtacccg      1260
gacgacattg gcaacgctcc gcacgtgttc ctggagaatt accagaccga agcggtacat      1320
agctttaatg accagctgac cgtcactctg cgtgccaacg caaaaaccac gaaagcagtc      1380
tatcagatca ataatggtca agaaactgct ttcaaggatg cgaccgtct  gactattggt      1440 aaggaggacc cgattggcac cacttataac gttaaactga ctggcaccaa tggcgagggc      1500
gctagccgca ctcaagagta acgttcgta aagaaagacc cgtctcaaac caacatcatc       1560
ggttaccaga atcctgacca ctgggtaat gtgaacgctt acatctataa acatgatggt       1620
ggcggtgcta tcgaactgac cggctcttgg ccaggtaaag ccatgacgaa aaacgcggat      1680
ggcatctata ccctgaccct gccggccaat gcggataccg cagatgcgaa ggttatcttc      1740
aataacggct ccgcgcaggt tccgggccaa accatccgg gctttgacta cgtacaaaat      1800
ggtctgtata caactctggg cctgaacggt tacctgccgc ac                        1842
```

<210> SEQ ID NO 12
<211> LENGTH: 1452
<212> TYPE: DNA
<213> ORGANISM: Geobacillus stearothermophilus

<400> SEQUENCE: 12

| | | | | | |
|---|---|---|---|---|---|
| gccgcaccgt | ttaacggtac | catgatgcag | tattttgaat | ggtacttgcc | ggatgatggc | 60 |
| acgttatgga | ccaaagtggc | caatgaagcc | aacaacttat | ccagccttgg | catcaccgct | 120 |
| ctttggctgc | cgcccgctta | caaggaaca | agccgcagcg | acgtagggta | cggagtatac | 180 |
| gacttgtatg | acctcggcga | attcaatcaa | aagggaccg | tccgcacaaa | atatggaaca | 240 |
| aaagctcaat | atcttcaagc | cattcaagcc | gcccacgccg | ctggaatgca | agtgtacgcc | 300 |
| gatgtcgtgt | tcgaccataa | aggcggcgct | gacggcacgg | aatgggtgga | cgccgtcgaa | 360 |
| gtcaatccgt | ccgaccgcaa | ccaagaaatc | tcgggcacct | atcaaatcca | agcatggacg | 420 |
| aaatttgatt | ttcccgggcg | gggcaacacc | tactccagct | ttaagtggcg | ctggtaccat | 480 |
| tttgacggcg | ttgactggga | cgaaagccga | aaattaagcc | gcatttacaa | attcatcggc | 540 |
| aaagcgtggg | attgggaagt | agacacagaa | acggaaact | atgactactt | aatgtatgcc | 600 |
| gaccttgata | tggatcatcc | cgaagtcgtg | accgagctga | aaaactgggg | gaaatggtat | 660 |
| gtcaacacaa | cgaacattga | tgggttccgg | cttgatgccg | tcaagcatat | taagttcagt | 720 |
| ttttttcctg | attggttgtc | gtatgtgcgt | tctcagactg | gcaagccgct | atttaccgtc | 780 |
| ggggaatatt | ggagctatga | catcaacaag | ttgcacaatt | acattacgaa | aacaaacgga | 840 |
| acgatgtctt | tgtttgatgc | cccgttacac | aacaaattt | ataccgcttc | caaatcaggg | 900 |
| ggcgcatttg | atatgcgcac | gttaatgacc | aatactctca | tgaaagatca | accgacattg | 960 |
| gccgtcacct | tcgttgataa | tcatgacacc | gaacccggcc | aagcgctgca | gtcatgggtc | 1020 |
| gacccatggt | tcaaaccgtt | ggcttacgcc | tttattctaa | ctcggcagga | aggatacccg | 1080 |
| tgcgtctttt | atggtgacta | ttatggcatt | ccacaatata | acattccttc | gctgaaaagc | 1140 |
| aaaatcgatc | cgctcctcat | cgcgcgcagg | gattatgctt | acggaacgca | acatgattat | 1200 |
| cttgatcact | ccgacatcat | cgggtggaca | agggaagggg | tcactgaaaa | accaggatcc | 1260 |
| gggctggccg | cactgatcac | cgatgggccg | ggaggaagca | aatggatgta | cgttggcaaa | 1320 |
| caacacgctg | gaaaagtgtt | ctatgacctt | accggcaacc | ggagtgacac | cgtcaccatc | 1380 |
| aacagtgatg | gatgggggga | attcaaagtc | aatggcggtt | cggtttcggt | ttgggttcct | 1440 |
| agaaaaacga | cc | | | | | 1452 |

<210> SEQ ID NO 13
<211> LENGTH: 1458
<212> TYPE: DNA
<213> ORGANISM: Geobacillus stearothermophilus

<400> SEQUENCE: 13

| | | | | | |
|---|---|---|---|---|---|
| gccgcaccgt | ttaacggtac | catgatgcag | tattttgaat | ggtacttgcc | ggatgatggc | 60 |
| acgttatgga | ccaaagtggc | caatgaagcc | aacaacttat | ccagccttgg | catcaccgct | 120 |
| ctttggctgc | cgcccgctta | caaggaaca | agccgcagcg | acgtagggta | cggagtatac | 180 |
| gacttgtatg | acctcggcga | attcaatcaa | aagggaccg | tccgcacaaa | atatggaaca | 240 |
| aaagctcaat | atcttcaagc | cattcaagcc | gcccacgccg | ctggaatgca | agtgtacgcc | 300 |
| gatgtcgtgt | tcgaccataa | aggcggcgct | gacggcacgg | aatgggtgga | cgccgtcgaa | 360 |

-continued

```
gtcaatccgt ccgaccgcaa ccaagaaatc tcgggcacct atcaaatcca agcatggacg    420
aaatttgatt ttcccgggcg gggcaacacc tactccagct ttaagtggcg ctggtaccat    480
tttgacggcg ttgattggga cgaaagccga aaattaagcc gcatttacaa attcaggggc    540
atcggcaaag cgtgggattg ggaagtagac acagaaaacg gaaactatga ctacttaatg    600
tatgccgacc ttgatatgga tcatcccgaa gtcgtgaccg agctgaaaaa ctgggggaaa    660
tggtatgtca acacaacgaa cattgatggg ttccggcttg atgccgtcaa gcatattaag    720
ttcagttttt ttcctgattg gttgtcgtat gtgcgttctc agactggcaa gccgctattt    780
accgtcgggg aatattggag ctatgacatc aacaagttgc acaattacat tacgaaaaca    840
aacggaacga tgtctttgtt tgatgccccg ttacacaaca aattttatac cgcttccaaa    900
tcagggggcg catttgatat gcgcacgtta atgaccaata ctctcatgaa agatcaaccg    960
acattggccg tcaccttcgt tgataatcat gacaccgaac ccggccaagc gcttcagtca   1020
tgggtcgacc catggttcaa accgttggct tacgccttta ttctaactcg gcaggaagga   1080
tacccgtgcg tcttttatgg tgactattat ggcattccac aatataacat tccttcgctg   1140
aaaagcaaaa tcgatccgct cctcatcgcg cgcagggatt atgcttacgg aacgcaacat   1200
gattatcttg atcactccga catcatcggg tggacaaggg aaggggtcac tgaaaaacca   1260
ggatccgggc tggccgcact gatcaccgat gggccgggag aagcaaatg gatgtacgtt   1320 ggcaaacaac acgctggaaa agtgttctat gaccttaccg gcaaccggag tgacaccgtc   1380
accatcaaca gtgatggatg gggggaattc aaagtcaatg gcggttcggt tcggttttgg   1440
gttcctagaa aaacgacc                                                 1458
```

<210> SEQ ID NO 14
<211> LENGTH: 1923
<212> TYPE: DNA
<213> ORGANISM: Aspergillus kawachii

<400> SEQUENCE: 14

```
atgagagtgt cgacttcaag tattgcccctt gctgtgtccc tttttgggaa gctggccctt     60
gggctgtcag ctgcagaatg gcgcactcaa tccatctact tccttttgac ggatcggttc    120
ggtaggacgg acaattcgac tacagctacg tgcaatacgg gtgaccaaat ctactgtggt    180
ggaagttggc aaggaattat caaccatctg gactatatcc agggcatggg attcacagct    240
atctggatct cgcctatcac tgagcagcta ccccaggata cttcggatgg tgaagcctac    300
catggatact ggcagcagaa gatatacaat gtgaactcca acttcggcac ggcagatgat    360
ctgaagtccc tctccgatgc tcttcacgcc cgcggaatgt acctcatggt cgacgtcgtc    420
cctaaccaca tgggctacgc aggtaacggc aacgatgtgg attacagcgt cttcgacccc    480
ttcgactcct cctcctactt ccatccatac tgcctcatca cagattggga caacttgacc    540
atggtccaag actgttggga gggtgacacc atcgtgtctc tgccagatct gaacaccacg    600
gaaaccgccg tgagaaccat ttggtacgat tgggtagccg acctggtatc caactactca    660
gtcgacggcc tccgtatcga cagtgtcgaa gaagtcgaac ccgacttctt cccgggctac    720
caagaagcag caggagtcta ctgcgtcggt gaagtcgaca cggcaaccc tgctctcgac    780 tgcccatacc aaaaatatct agatggtgtt ctcaactatc ccatctactg caactcctc    840 tacgcctttg aatcctccag cggcagcatc agcaacctct acaacatgat caaatcgtc    900 gccagcgact gctccgatcc gacccctcctg ggcaacttta tcgaaaacca cgacaacccc    960
cgcttcgcct cctacacatc cgactactcc caagccaaaa acgtcctcag ctacatcttc   1020
```

```
ctctccgacg gcatccccat cgtctacgcc ggcgaagaac agcactactc cggcggcgac    1080
gtgccctaca accgcgaagc tacctggcta tcaggctacg acacctccgc ggagctctac    1140
acctggatag ccaccacaaa cgcgatccgg aaactagcta tctcagcaga ctcggactac    1200
attacttacg cgaacgaccc aatctacaca gacagcaaca ccatcgcgat gcgcaaaggc    1260
acctccggct cccaaatcat caccgtcctc tccaacaaag gctcctccgg aagcagctac    1320
accctcaccc tcagcggaag cggctacacg tccggcacga agctcatcga agcgtacacc    1380
tgcacgtccg tgacggtgga ctcgaacggg gatatccctg tgccgatggc ttcgggatta    1440
cctagagttc tcctccctgc ttcggtggtt gatagttctt cgcttttgtgg ggggagtggt    1500 aacacaacca cgaccacaac tgctgctacc tccacatcca agccaccac ctcctcttct    1560 tcttcttctg ctgctgctac tacttcttca tcatgcaccg caacaagcac acccctcccc    1620
atcaccttcg aagaactcgt caccactacc tacggggaag aagtctacct cagcggatct    1680
atctcccagc tcggagagtg ggatacgagt gacgcgtgtga agttgtccgc ggatgattat    1740
acctcgagta accccgagtg gtctgttact gtgtcgttgc cggtggggac gaccttcgag    1800
tataagttta ttaaggtcga tgagggtgga agtgtgactt gggaaagtga tccgaatagg    1860
gagtatactg tgcctgaatg tgggagtggg agtgggggaga cggtggttga tacgtggagg    1920
tag                                                                1923

<210> SEQ ID NO 15
<211> LENGTH: 1899
<212> TYPE: DNA
<213> ORGANISM: Trichoderma reesei

<400> SEQUENCE: 15
atgcacgtcc tgtcgactgc ggtgctgctc ggctccgttg ccgttcaaaa ggtcctggga      60
agaccaggat caagcggtct gtccgacgtc accaagaggt ctgttgacga cttcatcagc    120
accgagacgc ctattgcact gaacaatctt cttttgcaatg ttggtcctga tggatgccgt    180
gcattcggca catcagctgg tgcggtgatt gcatctccca gcacaattga cccggactac    240
tattacatgt ggacgcgaga tagcgctctt gtcttcaaga acctcatcga ccgcttcacc    300
gaaacgtacg atgcgggcct gcagcgccgc atcgagcagt acattactgc ccaggtcact    360
ctccagggcc tctctaaccc ctcgggctcc ctcgcggacg gctctggtct cggcgagccc    420
aagtttgagt tgaccctgaa gcctttcacc ggcaactggg gtcgaccgca gcgggatggc    480
ccagctctgc gagccattgc cttgattgga tactcaaagt ggctcatcaa caacaactat    540
cagtcgactg tgtccaacgt catctggcct attgtgcgca acgacctcaa ctatgttgcc    600
cagtactgga accaaaccgg ctttgacctc tgggaagaag tcaatgggag ctcattcttt    660
actgttgcca accagcaccg agcacttgtc gagggcgcca ctcttgctgc cactcttggc    720
cagtcgggaa gcgcttattc atctgttgct ccccaggttt tgtgctttct ccaacgattc    780
tgggtgtcgt ctggtggata cgtcgactcc aacatcaaca ccaacgaggg caggactggc    840
aaggatgtca actccgtcct gacttccatc cacaccttcg atcccaacct tggctgtgac    900
gcaggcacct tccagccatg cagtgacaaa gcgctctcca acctcaaggt tgttgtcgac    960
tccttccgct ccatctacgg cgtgaacaag ggcattcctg ccggtgctgc cgtcgccatt   1020
ggccggtatg cagaggatgt gtactacaac ggcaaccctt ggtatcttgc acatttgctt   1080
gctgccgagc agctgtacga tgccatctac gtctggaaga agacgggctc catcacggtg   1140
```

-continued

| | |
|---|---|
| accgccacct ccctggcctt cttccaggag cttgttcctg gcgtgacggc cgggacctac | 1200 |
| tccagcagct cttcgacctt taccaacatc atcaacgccg tctcgacata cgccgatggc | 1260 |
| ttcctcagcg aggctgccaa gtacgtcccc gccgacggtt cgctggccga gcagtttgac | 1320 |
| cgcaacagcg gcactccgct gtctgcgctt cacctgacgt ggtcgtacgc ctcgttcttg | 1380 |
| acagccacgg cccgtcgggc tggcatcgtg ccccctcgt gggccaacag cagcgctagc | 1440 |
| acgatcccct cgacgtgctc cggcgcgtcc gtggtcggat cctactcgcg tcccaccgcc | 1500 |
| acgtcattcc ctccgtcgca gacgcccaag cctggcgtgc cttccggtac tccctacacg | 1560 |
| cccctgccct gcgcgacccc aacctccgtg gccgtcacct tccacgagct cgtgtcgaca | 1620 |
| cagtttggcc agacggtcaa ggtggcgggc aacgccgcgg ccctgggcaa ctggagcacg | 1680 |
| agcgccgccg tggctctgga cgccgtcaac tatgccgata accacccct gtggattggg | 1740 |
| acggtcaacc tcgaggctgg agacgtcgtg gagtacaagt acatcaatgt gggccaagat | 1800 |
| ggctccgtga cctgggagag tgatcccaac cacacttaca cggttcctgc ggtggcttgt | 1860 |
| gtgacgcagg ttgtcaagga ggacacctgg cagtcgtaa | 1899 |

<210> SEQ ID NO 16
<211> LENGTH: 1449
<212> TYPE: DNA
<213> ORGANISM: Artificial
<220> FEATURE:
<223> OTHER INFORMATION: Synthetic polynucleotide encoding SEQ ID NO:8

<400> SEQUENCE: 16

| | |
|---|---|
| acaaatctta atgggacgct gatgcagtat tttgaatggt acacgcccaa tgacggccaa | 60 |
| cattggaagc gtctgcaaaa cgactcggca tatttggctg aacacggtat tactgccgtc | 120 |
| tggattcccc cggcatataa gggaacgagc caagcggatg tgggctacgg tgcttacgac | 180 |
| ctttatgatt taggggagtt tcatcaaaaa gggacggttc ggacaaagta cggcacaaaa | 240 |
| ggagagctgc aatctgcgat caaaagtctt cattcccgcg acattaacgt ttacggggat | 300 |
| gtggtcatca accacaaagg cggcgctgat gcgaccgaag atgtaaccgc ggttgaagtc | 360 |
| gatcccgctg accgcaaccg cgtaatttcc ggagaatacc taattaaagc ctggacacat | 420 |
| tttcattttc cggggcgcgg cagcacatac agcgatttta atggcattg gtaccatttt | 480 |
| gacgaaaccg attgggacga gtcccgaaag ctgaaccgca tctataagtt tcaaggaaag | 540 |
| gcttgggatt gggaagtttc cagtgaaaac ggcaactatg attatttgat gtatgccgac | 600 |
| atcgattatg accatcctga tgtcgtagca gaaattaaga gatggggcac ttggtatgcc | 660 |
| aatgagctcc aattggacgg tttccgtctt gatgctgtca acacattaa attttctttt | 720 |
| ttgcgggatt gggttaatca tgtcagggaa aaacgggga aggaaatgtt tacggtagct | 780 |
| gaatattggc agaatgactt gggcgcgctg gaaaactatt tgaacaaaac aaattttaat | 840 |
| cattcagtgt ttgacgtgcc gcttcattat cagttccatg ctgcatcgac acagggaggc | 900 |
| ggctatgata tgaggaaatt gctgaacggt acggtcgttt ccaagcatcc gttgaaatcg | 960 |
| gttacatttg tcgataacca tgatacacag ccggggcagt cgcttgagtc gactgtccaa | 1020 |
| acatggttta gccgcttgc ttacgctttt attctcacaa gggaatctgg ataccctcag | 1080 |
| gttttctacg gggatatgta cgggacgaaa ggagactccc agcgcgaaat tcctgccttg | 1140 |
| aaacacaaaa ttgaaccgat cttaaaagcg agaaaacagt atgcgtacgg agcacagcat | 1200 |
| gattatttcg accaccatga cattgtcggc tggacaaggg aaggcgacag ctcggttgca | 1260 |
| aattcaggtt tggcggcatt aataacagac ggacccggtg gggcaaagcg aatgtatgtc | 1320 |

```
ggccggcaaa acgccggtga gacatggcat gacattaccg gaaaccgttc ggagccggtt    1380
gtcatcaatt cggaaggctg gggagagttt cacgtaaacg gcgggtcggt ttcaatttat    1440
gttcaaaga                                                            1449
```

<210> SEQ ID NO 17
<211> LENGTH: 41
<212> TYPE: PRT
<213> ORGANISM: Bacillus subtilis

<400> SEQUENCE: 17

Met Phe Ala Lys Arg Phe Lys Thr Ser Leu Leu Pro Leu Phe Ala Gly
1               5                   10                  15

Phe Leu Leu Leu Phe His Leu Val Leu Ala Gly Pro Ala Ala Ala Ser
            20                  25                  30

Ala Glu Thr Ala Asn Lys Ser Asn Glu
        35                  40

<210> SEQ ID NO 18
<211> LENGTH: 60
<212> TYPE: DNA
<213> ORGANISM: Artificial
<220> FEATURE:
<223> OTHER INFORMATION: Synthetic primer

<400> SEQUENCE: 18
cttcttgctg cctcattctg cagcttcagc acttacagca ccgtcgatca aaagcggaac    60

<210> SEQ ID NO 19
<211> LENGTH: 57
<212> TYPE: DNA
<213> ORGANISM: Artificial
<220> FEATURE:
<223> OTHER INFORMATION: Synthetic primer

<400> SEQUENCE: 19
ctggaggcac tatcctgaag gatttctccg tattggaact ctgctgatgt atttgtg       57

<210> SEQ ID NO 20
<211> LENGTH: 57
<212> TYPE: DNA
<213> ORGANISM: Artificial
<220> FEATURE:
<223> OTHER INFORMATION: Synthetic primer

<400> SEQUENCE: 20
cacaaataca tcagcagagt tccaatacgg agaaatcctt caggatagtg cctccag       57

<210> SEQ ID NO 21
<211> LENGTH: 56
<212> TYPE: DNA
<213> ORGANISM: Artificial
<220> FEATURE:
<223> OTHER INFORMATION: Synthetic primer

<400> SEQUENCE: 21
caggaaatcc gtcctctgtt aactcaatgg ggaagagaac cgcttaagcc cgagtc        56

<210> SEQ ID NO 22
<211> LENGTH: 55
<212> TYPE: DNA
<213> ORGANISM: Artificial
<220> FEATURE:
<223> OTHER INFORMATION: Synthetic primer

```
<400> SEQUENCE: 22
caggaaatcc gtcctctgtt aactcaatca ggataaagca cagctacaga cctgg        55

<210> SEQ ID NO 23
<211> LENGTH: 22
<212> TYPE: DNA
<213> ORGANISM: Artificial
<220> FEATURE:
<223> OTHER INFORMATION: Synthetic primer

<400> SEQUENCE: 23
tacacaagta cagtcctatc tg                                             22

<210> SEQ ID NO 24
<211> LENGTH: 22
<212> TYPE: DNA
<213> ORGANISM: Artificial
<220> FEATURE:
<223> OTHER INFORMATION: Synthetic primer

<400> SEQUENCE: 24
catcctctgt ctctatcaat ac                                             22

<210> SEQ ID NO 25
<211> LENGTH: 549
<212> TYPE: PRT
<213> ORGANISM: Geobacillus stearothermophilus

<400> SEQUENCE: 25
```

Met Leu Thr Phe His Arg Ile Ile Arg Lys Gly Trp Met Phe Leu Leu
1               5                   10                  15

Ala Phe Leu Leu Thr Ala Leu Leu Phe Cys Pro Thr Gly Gln Pro Ala
            20                  25                  30

Lys Ala Ala Pro Phe Asn Gly Thr Met Met Gln Tyr Phe Glu Trp
        35                  40                  45

Tyr Leu Pro Asp Asp Gly Thr Leu Trp Thr Lys Val Ala Asn Glu Ala
    50                  55                  60

Asn Asn Leu Ser Ser Leu Gly Ile Thr Ala Leu Trp Leu Pro Pro Ala
65                  70                  75                  80

Tyr Lys Gly Thr Ser Arg Ser Asp Val Gly Tyr Gly Val Tyr Asp Leu
                85                  90                  95

Tyr Asp Leu Gly Glu Phe Asn Gln Lys Gly Ala Val Arg Thr Lys Tyr
            100                 105                 110

Gly Thr Lys Ala Gln Tyr Leu Gln Ala Ile Gln Ala Ala His Ala Ala
        115                 120                 125

Gly Met Gln Val Tyr Ala Asp Val Val Phe Asp His Lys Gly Gly Ala
    130                 135                 140

Asp Gly Thr Glu Trp Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
                165                 170                 175

Asp Phe Pro Gly Arg Gly Asn Thr Tyr Ser Ser Phe Lys Trp Arg Trp
            180                 185                 190

Tyr His Phe Asp Gly Val Asp Trp Asp Glu Ser Arg Lys Leu Ser Arg
        195                 200                 205

Ile Tyr Lys Phe Arg Gly Ile Gly Lys Ala Trp Asp Trp Glu Val Asp
    210                 215                 220

```
Thr Glu Asn Gly Asn Tyr Asp Tyr Leu Met Tyr Ala Asp Leu Asp Met
225                 230                 235                 240

Asp His Pro Glu Val Val Thr Glu Leu Lys Ser Trp Gly Lys Trp Tyr
            245                 250                 255

Val Asn Thr Thr Asn Ile Asp Gly Phe Arg Leu Asp Ala Val Lys His
                260                 265                 270

Ile Lys Phe Ser Phe Phe Pro Asp Trp Leu Ser Asp Val Arg Ser Gln
            275                 280                 285

Thr Gly Lys Pro Leu Phe Thr Val Gly Glu Tyr Trp Ser Tyr Asp Ile
            290                 295                 300

Asn Lys Leu His Asn Tyr Ile Met Lys Thr Asn Gly Thr Met Ser Leu
305                 310                 315                 320

Phe Asp Ala Pro Leu His Asn Lys Phe Tyr Thr Ala Ser Lys Ser Gly
                325                 330                 335

Gly Thr Phe Asp Met Arg Thr Leu Met Thr Asn Thr Leu Met Lys Asp
                340                 345                 350

Gln Pro Thr Leu Ala Val Thr Phe Val Asp Asn His Asp Thr Glu Pro
            355                 360                 365

Gly Gln Ala Leu Gln Ser Trp Val Asp Pro Trp Phe Lys Pro Leu Ala
370                 375                 380

Tyr Ala Phe Ile Leu Thr Arg Gln Glu Gly Tyr Pro Cys Val Phe Tyr
385                 390                 395                 400

Gly Asp Tyr Tyr Gly Ile Pro Gln Tyr Asn Ile Pro Ser Leu Lys Ser
                405                 410                 415

Lys Ile Asp Pro Leu Leu Ile Ala Arg Arg Asp Tyr Ala Tyr Gly Thr
            420                 425                 430

Gln His Asp Tyr Leu Asp His Ser Asp Ile Ile Gly Trp Thr Arg Glu
            435                 440                 445

Gly Val Thr Glu Lys Pro Gly Ser Gly Leu Ala Ala Leu Ile Thr Asp
            450                 455                 460

Gly Pro Gly Gly Ser Lys Trp Met Tyr Val Gly Lys Gln His Ala Gly
465                 470                 475                 480

Lys Val Phe Tyr Asp Leu Thr Gly Asn Arg Ser Asp Thr Val Thr Ile
                485                 490                 495

Asn Ser Asp Gly Trp Gly Glu Phe Lys Val Asn Gly Gly Ser Val Ser
                500                 505                 510

Val Trp Val Pro Arg Lys Thr Thr Val Ser Thr Ile Ala Trp Ser Ile
            515                 520                 525

Thr Thr Arg Pro Trp Thr Asp Glu Phe Val Arg Trp Thr Glu Pro Arg
            530                 535                 540

Leu Val Ala Trp Pro
545

<210> SEQ ID NO 26
<211> LENGTH: 512
<212> TYPE: PRT
<213> ORGANISM: Bacillus licheniformis

<400> SEQUENCE: 26

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ala Ala Ala Asn Leu
            20                  25                  30

Asn Gly Thr Leu Met Gln Tyr Phe Glu Trp Tyr Met Pro Asn Asp Gly
            35                  40                  45
```

```
Gln His Trp Lys Arg Leu Gln Asn Asp Ser Ala Tyr Leu Ala Glu His
    50                  55                  60
Gly Ile Thr Ala Val Trp Ile Pro Pro Ala Tyr Lys Gly Thr Ser Gln
 65                  70                  75                  80
Ala Asp Val Gly Tyr Gly Ala Tyr Asp Leu Tyr Asp Leu Gly Glu Phe
                     85                  90                  95
His Gln Lys Gly Thr Val Arg Thr Lys Tyr Gly Thr Lys Gly Glu Leu
                100                 105                 110
Gln Ser Ala Ile Lys Ser Leu His Ser Arg Asp Ile Asn Val Tyr Gly
            115                 120                 125
Asp Val Val Ile Asn His Lys Gly Gly Ala Asp Ala Thr Glu Asp Val
130                 135                 140
Thr Ala Val Glu Val Asp Pro Ala Asp Arg Asn Arg Val Ile Ser Gly
145                 150                 155                 160
Glu His Arg Ile Lys Ala Trp Thr His Phe His Phe Pro Gly Arg Gly
                165                 170                 175
Ser Thr Tyr Ser Asp Phe Lys Trp His Trp Tyr His Phe Asp Gly Thr
                180                 185                 190
Asp Trp Asp Glu Ser Arg Lys Leu Asn Arg Ile Tyr Lys Phe Gln Gly
                195                 200                 205
Lys Ala Trp Asp Trp Glu Val Ser Asn Glu Asn Gly Asn Tyr Asp Tyr
210                 215                 220
Leu Met Tyr Ala Asp Ile Asp Tyr Asp His Pro Asp Val Ala Ala Glu
225                 230                 235                 240
Ile Lys Arg Trp Gly Thr Trp Tyr Ala Asn Glu Leu Gln Leu Asp Gly
                245                 250                 255
Phe Arg Leu Asp Ala Val Lys His Ile Lys Phe Ser Phe Leu Arg Asp
                260                 265                 270
Trp Val Asn His Val Arg Glu Lys Thr Gly Lys Glu Met Phe Thr Val
                275                 280                 285
Ala Glu Tyr Trp Gln Asn Asp Leu Gly Ala Leu Glu Asn Tyr Leu Asn
290                 295                 300
Lys Thr Asn Phe Asn His Ser Val Phe Asp Val Pro Leu His Tyr Gln
305                 310                 315                 320
Phe His Ala Ala Ser Thr Gln Gly Gly Gly Tyr Asp Met Arg Lys Leu
                325                 330                 335
Leu Asn Ser Thr Val Val Ser Lys His Pro Leu Lys Ala Val Thr Phe
                340                 345                 350
Val Asp Asn His Asp Thr Gln Pro Gly Gln Ser Leu Glu Ser Thr Val
                355                 360                 365
Gln Thr Trp Phe Lys Pro Leu Ala Tyr Ala Phe Ile Leu Thr Arg Glu
            370                 375                 380
Ser Gly Tyr Pro Gln Val Phe Tyr Gly Asp Met Tyr Gly Thr Lys Gly
385                 390                 395                 400
Asp Ser Gln Arg Glu Ile Pro Ala Leu Lys His Lys Ile Glu Pro Ile
                405                 410                 415
Leu Lys Ala Arg Lys Gln Tyr Ala Tyr Gly Ala Gln His Asp Tyr Phe
                420                 425                 430
Asp His His Asp Ile Val Gly Trp Thr Arg Glu Gly Asp Ser Ser Val
            435                 440                 445
Ala Asn Ser Gly Leu Ala Ala Leu Ile Thr Asp Gly Pro Gly Gly Ala
450                 455                 460
```

```
Lys Arg Met Tyr Val Gly Arg Gln Asn Ala Gly Glu Thr Trp His Asp
465                 470                 475                 480

Ile Thr Gly Asn Arg Ser Glu Pro Val Val Ile Asn Ser Glu Gly Trp
                485                 490                 495

Gly Glu Phe His Val Asn Gly Gly Ser Val Ser Ile Tyr Val Gln Arg
            500                 505                 510

<210> SEQ ID NO 27
<211> LENGTH: 660
<212> TYPE: PRT
<213> ORGANISM: Bacillus subtilis

<400> SEQUENCE: 27

Met Phe Ala Lys Arg Phe Lys Thr Ser Leu Leu Pro Leu Phe Ala Gly
1               5                   10                  15

Phe Leu Leu Leu Phe His Leu Val Leu Ala Gly Pro Ala Ala Ala Ser
            20                  25                  30

Ala Glu Thr Ala Asn Lys Ser Asn Glu Leu Thr Ala Pro Ser Ile Lys
        35                  40                  45

Ser Gly Thr Ile Leu His Ala Trp Asn Trp Ser Phe Asn Thr Leu Lys
50                  55                  60

His Asn Met Lys Asp Ile His Asp Ala Gly Tyr Thr Ala Ile Gln Thr
65                  70                  75                  80

Ser Pro Ile Asn Gln Val Lys Glu Gly Asn Gln Gly Asp Lys Ser Met
                85                  90                  95

Ser Asn Trp Tyr Trp Leu Tyr Gln Pro Thr Ser Tyr Gln Ile Gly Asn
            100                 105                 110

Arg Tyr Leu Gly Thr Glu Gln Glu Phe Lys Glu Met Cys Ala Ala Ala
        115                 120                 125

Glu Glu Tyr Gly Ile Lys Val Ile Val Asp Ala Val Ile Asn His Thr
130                 135                 140

Thr Ser Asp Tyr Ala Ala Ile Ser Asn Glu Val Lys Ser Ile Pro Asn
145                 150                 155                 160

Trp Thr His Gly Asn Thr Gln Ile Lys Asn Trp Ser Asp Arg Trp Asp
                165                 170                 175

Val Thr Gln Asn Ser Leu Leu Gly Leu Tyr Asp Trp Asn Thr Gln Asn
            180                 185                 190

Thr Gln Val Gln Ser Tyr Leu Lys Arg Phe Leu Asp Arg Ala Leu Asn
        195                 200                 205

Asp Gly Ala Asp Gly Phe Arg Phe Asp Ala Ala Lys His Ile Glu Leu
210                 215                 220

Pro Asp Asp Gly Ser Tyr Gly Ser Gln Phe Trp Pro Asn Ile Thr Asn
225                 230                 235                 240

Thr Ser Ala Glu Phe Gln Tyr Gly Glu Ile Leu Gln Asp Ser Ala Ser
                245                 250                 255

Arg Asp Ala Ala Tyr Ala Asn Tyr Met Asp Val Thr Ala Ser Asn Tyr
            260                 265                 270

Gly His Ser Ile Arg Ser Ala Leu Lys Asn Arg Asn Leu Gly Val Ser
        275                 280                 285

Asn Ile Ser His Tyr Ala Ser Asp Val Ser Ala Asp Lys Leu Val Thr
290                 295                 300

Trp Val Glu Ser His Asp Thr Tyr Ala Asn Asp Asp Glu Glu Ser Thr
305                 310                 315                 320

Trp Met Ser Asp Asp Asp Ile Arg Leu Gly Trp Ala Val Ile Ala Ser
                325                 330                 335
```

```
Arg Ser Gly Ser Thr Pro Leu Phe Phe Ser Arg Pro Glu Gly Gly
            340                 345                 350

Asn Gly Val Arg Phe Pro Gly Lys Ser Gln Ile Gly Asp Arg Gly Ser
            355                 360                 365

Ala Leu Phe Glu Asp Gln Ala Ile Thr Ala Val Asn Arg Phe His Asn
        370                 375                 380

Val Met Ala Gly Gln Pro Glu Glu Leu Ser Asn Pro Asn Gly Asn Asn
385                 390                 395                 400

Gln Ile Phe Met Asn Gln Arg Gly Ser His Gly Val Val Leu Ala Asn
                405                 410                 415

Ala Gly Ser Ser Val Ser Ile Asn Thr Ala Thr Lys Leu Pro Asp
            420                 425                 430

Gly Arg Tyr Asp Asn Lys Ala Gly Ala Gly Ser Phe Gln Val Asn Asp
            435                 440                 445

Gly Lys Leu Thr Gly Thr Ile Asn Ala Arg Ser Val Ala Val Leu Tyr
        450                 455                 460

Pro Asp Asp Ile Ala Lys Ala Pro His Val Phe Leu Glu Asn Tyr Lys
465                 470                 475                 480

Thr Gly Val Thr His Ser Phe Asn Asp Gln Leu Thr Ile Thr Leu Arg
                485                 490                 495

Ala Asp Ala Asn Thr Thr Lys Ala Val Tyr Gln Ile Asn Asn Gly Pro
            500                 505                 510

Asp Asp Arg Arg Leu Arg Met Glu Ile Asn Ser Gln Ser Glu Lys Glu
        515                 520                 525

Ile Gln Phe Gly Lys Thr Tyr Thr Ile Met Leu Lys Gly Thr Asn Ser
        530                 535                 540

Asp Gly Val Thr Arg Thr Glu Lys Tyr Ser Phe Val Lys Arg Asp Pro
545                 550                 555                 560

Ala Ser Ala Lys Thr Ile Gly Tyr Gln Asn Pro Asn His Trp Ser Gln
                565                 570                 575

Val Asn Ala Tyr Ile Tyr Lys His Asp Gly Ser Arg Val Ile Glu Leu
            580                 585                 590

Thr Gly Ser Trp Pro Gly Lys Pro Met Thr Lys Asn Ala Asp Gly Ile
            595                 600                 605

Tyr Thr Leu Thr Leu Pro Ala Asp Thr Asp Thr Thr Asn Ala Lys Val
        610                 615                 620

Ile Phe Asn Asn Gly Ser Ala Gln Val Pro Gly Gln Asn Gln Pro Gly
625                 630                 635                 640

Phe Asp Tyr Val Leu Asn Gly Leu Tyr Asn Asp Ser Gly Leu Ser Gly
                645                 650                 655

Ser Leu Pro His
            660

<210> SEQ ID NO 28
<211> LENGTH: 659
<212> TYPE: PRT
<213> ORGANISM: Bacillus subtilis

<400> SEQUENCE: 28

Met Phe Ala Lys Arg Phe Lys Thr Ser Leu Leu Pro Leu Phe Ala Gly
1               5                   10                  15

Phe Leu Leu Leu Phe His Leu Val Leu Ala Gly Pro Ala Ala Ala Ser
            20                  25                  30

Ala Glu Thr Ala Asn Lys Ser Asn Glu Leu Thr Ala Pro Ser Ile Lys
```

```
                 35                  40                  45
Ser Gly Thr Ile Leu His Ala Trp Asn Trp Ser Phe Asn Thr Leu Lys
 50                  55                  60

His Asn Met Lys Asp Ile His Asp Ala Gly Tyr Thr Ala Ile Gln Thr
 65                  70                  75                  80

Ser Pro Ile Asn Gln Val Lys Glu Gly Asn Gln Gly Asn Lys Ser Met
                 85                  90                  95

Ser Asn Trp Tyr Trp Leu Tyr Gln Pro Thr Ser Tyr Gln Ile Gly Asn
                100                 105                 110

Arg Tyr Leu Gly Thr Glu Gln Glu Phe Lys Glu Met Cys Ala Ala Ala
                115                 120                 125

Glu Glu Tyr Gly Ile Lys Val Ile Val Asp Ala Val Ile Asn His Thr
                130                 135                 140

Thr Ser Asp Tyr Ala Ala Ile Ser Asn Glu Ile Lys Ser Ile Pro Asn
145                 150                 155                 160

Trp Thr His Gly Asn Thr Gln Ile Lys Asn Trp Ser Asp Arg Trp Asp
                165                 170                 175

Val Thr Gln Asn Ser Leu Leu Gly Leu Tyr Asp Trp Asn Thr Gln Asn
                180                 185                 190

Thr Gln Val Gln Ser Tyr Leu Lys Arg Phe Leu Glu Arg Ala Leu Asn
                195                 200                 205

Asp Gly Ala Asp Gly Phe Arg Phe Asp Ala Ala Lys His Ile Glu Leu
                210                 215                 220

Pro Asp Asp Gly Ser Tyr Gly Ser Gln Phe Trp Pro Asn Ile Thr Asn
225                 230                 235                 240

Thr Ser Ala Glu Phe Gln Tyr Gly Glu Ile Leu Gln Asp Ser Ala Ser
                245                 250                 255

Arg Asp Ala Ala Tyr Ala Asn Tyr Met Asn Val Thr Ala Ser Asn Tyr
                260                 265                 270

Gly His Ser Ile Arg Ser Ala Leu Lys Asn Arg Asn Leu Gly Val Ser
                275                 280                 285

Asn Ile Ser His Tyr Ala Ser Asp Val Ser Ala Asp Lys Leu Val Thr
                290                 295                 300

Trp Val Glu Ser His Asp Thr Tyr Ala Asn Asp Asp Glu Glu Ser Thr
305                 310                 315                 320

Trp Met Ser Asp Asp Asp Ile Arg Leu Gly Trp Ala Val Ile Ala Ser
                325                 330                 335

Arg Ser Gly Ser Thr Pro Leu Phe Phe Ser Arg Pro Glu Gly Gly Gly
                340                 345                 350

Asn Gly Val Arg Phe Pro Gly Lys Ser Gln Ile Gly Asp Arg Gly Ser
                355                 360                 365

Ala Leu Phe Glu Asp Gln Ala Ile Thr Ala Val Asn Arg Phe His Asn
                370                 375                 380

Val Met Ala Gly Gln Pro Glu Glu Leu Ser Asn Pro Asn Gly Asn Asn
385                 390                 395                 400

Gln Ile Phe Met Asn Gln Arg Gly Ser His Gly Val Val Leu Ala Asn
                405                 410                 415

Ala Gly Ser Ser Ser Val Ser Ile Asn Thr Pro Thr Lys Leu Pro Asp
                420                 425                 430

Gly Arg Tyr Asp Asn Lys Ala Gly Ala Gly Ser Phe Gln Val Asn Asp
                435                 440                 445

Gly Lys Leu Thr Gly Thr Ile Asn Ala Arg Ser Val Ala Val Leu Tyr
                450                 455                 460
```

```
Pro Asp Asp Ile Ala Lys Ala Pro His Val Phe Leu Glu Asn Tyr Lys
465                 470                 475                 480

Thr Gly Val Thr His Ser Phe Asn Asp Gln Leu Thr Ile Thr Leu Arg
                485                 490                 495

Ala Asp Ala Asn Thr Thr Lys Ala Val Tyr Gln Ile Asn Asn Gly Pro
            500                 505                 510

Glu Thr Ala Phe Lys Asp Gly Asp Gln Phe Thr Ile Gly Lys Gly Asp
        515                 520                 525

Pro Phe Gly Lys Thr Tyr Thr Ile Met Leu Lys Gly Thr Asn Ser Asn
    530                 535                 540

Gly Val Thr Lys Ala Glu Glu Tyr Ser Phe Val Lys Arg Asp Pro Ala
545                 550                 555                 560

Ser Ala Lys Thr Ile Gly Tyr Gln Asn Pro Asn His Trp Ser Gln Val
                565                 570                 575

Asn Ala Tyr Ile Tyr Lys His Asp Gly Ser Arg Ala Ile Glu Leu Thr
            580                 585                 590

Gly Ser Trp Pro Gly Lys Pro Met Thr Lys Asn Ala Asp Gly Ile Tyr
        595                 600                 605

Thr Leu Thr Leu Pro Ala Asp Thr Asp Thr Thr Asn Ala Lys Val Ile
    610                 615                 620

Phe Asn Asn Gly Ser Ala Gln Val Pro Gly Gln Asn Gln Pro Gly Phe
625                 630                 635                 640

Asp Tyr Val Gln Asn Gly Leu Tyr Asn Asp Ser Gly Leu Ser Gly Ser
                645                 650                 655

Leu Pro His

<210> SEQ ID NO 29
<211> LENGTH: 659
<212> TYPE: PRT
<213> ORGANISM: Bacillus subtilis

<400> SEQUENCE: 29

Met Phe Ala Lys Arg Phe Lys Thr Ser Leu Leu Pro Leu Phe Ala Gly
1               5                   10                  15

Phe Leu Leu Leu Phe His Leu Val Leu Ala Gly Pro Ala Ala Ala Ser
                20                  25                  30

Ala Glu Thr Ala Asn Lys Ser Asn Glu Leu Thr Ala Pro Ser Ile Lys
            35                  40                  45

Ser Gly Thr Ile Leu His Ala Trp Asn Trp Ser Phe Asn Thr Leu Lys
50                  55                  60

His Asn Met Lys Asp Ile His Asp Ala Gly Tyr Thr Ala Ile Gln Thr
65                  70                  75                  80

Ser Pro Ile Asn Gln Val Lys Glu Gly Asn Gln Gly Asp Lys Ser Met
                85                  90                  95

Ser Asn Trp Tyr Trp Leu Tyr Gln Pro Thr Ser Tyr Gln Ile Gly Asn
            100                 105                 110

Arg Tyr Leu Gly Thr Glu Gln Glu Phe Lys Glu Met Cys Ala Ala Ala
        115                 120                 125

Glu Glu Tyr Gly Ile Lys Val Ile Val Asp Ala Val Ile Asn His Thr
    130                 135                 140

Thr Ser Asp Tyr Ala Ala Ile Ser Asn Glu Ile Lys Ser Ile Pro Asn
145                 150                 155                 160

Trp Thr His Gly Asn Thr Gln Ile Lys Asn Trp Ser Asp Arg Trp Asp
                165                 170                 175
```

Val Thr Gln Asn Ser Leu Leu Gly Leu Tyr Asp Trp Asn Thr Gln Asn
            180                 185                 190

Thr Gln Val Gln Ser Tyr Leu Lys Arg Phe Leu Glu Arg Ala Leu Asn
            195                 200                 205

Asp Gly Ala Asp Gly Phe Arg Phe Asp Ala Ala Lys His Ile Glu Leu
210                 215                 220

Pro Asp Asp Gly Ser Tyr Gly Ser Gln Phe Trp Pro Thr Ile Thr Asn
225                 230                 235                 240

Thr Ser Ala Glu Phe Gln Tyr Gly Glu Ile Leu Gln Asp Ser Ala Ser
            245                 250                 255

Arg Asp Ala Ala Tyr Ala Asn Tyr Met Asp Val Thr Ala Ser Asn Tyr
            260                 265                 270

Gly His Ser Ile Arg Ser Ala Leu Lys Asn Arg Asn Leu Gly Val Ser
            275                 280                 285

Asn Leu Ser His Tyr Ala Ser Asp Val Ser Ala Asp Lys Leu Val Thr
            290                 295                 300

Trp Val Glu Ser His Asp Thr Tyr Ala Asn Asp Asp Glu Glu Ser Thr
305                 310                 315                 320

Trp Met Ser Asp Asp Asp Ile Arg Leu Gly Trp Ala Val Ile Ala Ser
            325                 330                 335

Arg Ser Gly Ser Thr Pro Leu Phe Phe Ser Arg Pro Glu Gly Gly Gly
            340                 345                 350

Asn Gly Val Arg Phe Pro Gly Lys Ser Gln Ile Gly Asp Arg Gly Ser
            355                 360                 365

Ala Leu Phe Glu Asp Gln Ala Ile Thr Ala Val Asn Arg Phe His Asn
            370                 375                 380

Val Met Ala Gly Gln Pro Glu Glu Leu Ser Asn Pro Asn Gly Asn Asn
385                 390                 395                 400

Gln Ile Phe Met Asn Gln Arg Gly Ser His Gly Val Val Leu Ala Asn
            405                 410                 415

Ala Gly Ser Ser Ser Val Ser Ile Asn Thr Ala Thr Lys Leu Pro Asp
            420                 425                 430

Gly Arg Tyr Asp Asn Lys Ala Gly Ala Gly Ser Phe Gln Val Asn Asp
            435                 440                 445

Gly Lys Leu Thr Gly Thr Ile Asn Ala Arg Ser Val Ala Val Leu Tyr
            450                 455                 460

Pro Asp Asp Ile Ala Lys Ala Pro His Val Phe Leu Glu Asn Tyr Lys
465                 470                 475                 480

Thr Gly Val Thr His Ser Phe Asn Asp Gln Leu Thr Ile Thr Leu Arg
            485                 490                 495

Ala Asp Ala Asn Thr Thr Lys Ala Val Tyr Gln Ile Asn Asn Gly Pro
            500                 505                 510

Glu Thr Ala Phe Lys Asp Gly Asp Gln Phe Thr Ile Gly Lys Gly Asp
            515                 520                 525

Pro Phe Gly Lys Thr Tyr Thr Ile Met Leu Lys Gly Thr Asn Ser Asp
            530                 535                 540

Gly Val Thr Arg Ala Glu Glu Tyr Ser Phe Val Lys Arg Asp Pro Ala
545                 550                 555                 560

Ser Ala Lys Thr Ile Gly Tyr Gln Asn Pro Asn His Trp Ser Gln Val
            565                 570                 575

Asn Ala Tyr Ile Tyr Lys His Asp Gly Gly Arg Ala Ile Glu Leu Thr
            580                 585                 590

```
Gly Ser Trp Pro Gly Lys Pro Met Thr Lys Asn Ala Asp Gly Ile Tyr
            595                 600                 605

Thr Leu Thr Leu Pro Ala Asp Thr Asp Thr Thr Asn Ala Lys Val Ile
    610                 615                 620

Phe Asn Asn Gly Ser Ala Gln Val Pro Gly Gln Asn Gln Pro Gly Phe
625                 630                 635                 640

Asp Tyr Val Gln Asn Gly Leu Tyr Asn Asp Ser Gly Leu Ser Gly Ser
                645                 650                 655

Leu Pro His

<210> SEQ ID NO 30
<211> LENGTH: 659
<212> TYPE: PRT
<213> ORGANISM: Bacillus subtilis

<400> SEQUENCE: 30

Met Phe Ala Lys Arg Phe Lys Thr Ser Leu Leu Pro Leu Phe Ala Gly
1               5                   10                  15

Phe Leu Leu Leu Phe His Leu Val Leu Ala Gly Pro Ala Ala Ala Ser
            20                  25                  30

Ala Glu Thr Ala Asn Lys Ser Asn Glu Leu Thr Ala Pro Ser Ile Lys
        35                  40                  45

Ser Gly Thr Ile Leu His Ala Trp Asn Trp Ser Phe Asn Thr Leu Lys
    50                  55                  60

His Asn Met Lys Asp Ile His Asp Ala Gly Tyr Thr Ala Ile Gln Thr
65              70                  75                  80

Ser Pro Ile Asn Gln Val Lys Glu Gly Asn Gln Gly Asp Lys Ser Met
                85                  90                  95

Ser Asn Trp Tyr Trp Leu Tyr Gln Pro Thr Ser Tyr Gln Ile Gly Asn
            100                 105                 110

Arg Tyr Leu Gly Thr Glu Gln Glu Phe Lys Glu Met Cys Ala Ala Ala
        115                 120                 125

Glu Glu Tyr Gly Ile Lys Val Ile Val Asp Ala Val Ile Asn His Thr
130                 135                 140

Thr Ser Asp Tyr Ala Ala Ile Ser Asn Glu Ile Lys Ser Ile Pro Asn
145                 150                 155                 160

Trp Thr His Gly Asn Thr Gln Ile Lys Asn Trp Ser Asp Arg Trp Asp
                165                 170                 175

Val Thr Gln Asn Ser Leu Leu Gly Leu Tyr Asp Trp Asn Thr Gln Asn
            180                 185                 190

Thr Gln Val Gln Ser Tyr Leu Lys Arg Phe Leu Glu Arg Ala Leu Asn
        195                 200                 205

Asp Gly Ala Asp Gly Phe Arg Phe Asp Ala Ala Lys His Ile Glu Leu
210                 215                 220

Pro Asp Asp Gly Ser Tyr Gly Ser Gln Phe Trp Pro Thr Ile Thr Asn
225                 230                 235                 240

Thr Ser Ala Glu Phe Gln Tyr Gly Glu Ile Leu Gln Asp Ser Ala Ser
                245                 250                 255

Arg Asp Ala Ala Tyr Ala Asn Tyr Met Asp Val Thr Ala Ser Asn Tyr
            260                 265                 270

Gly His Ser Ile Arg Ser Ala Leu Lys Asn Arg Asn Leu Gly Val Ser
        275                 280                 285

Asn Leu Ser His Tyr Ala Ser Asp Val Ser Ala Asp Lys Leu Val Thr
290                 295                 300
```

```
Trp Val Glu Ser His Asp Thr Tyr Ala Asn Asp Glu Glu Ser Thr
305                 310                 315                 320

Trp Met Ser Asp Asp Ile Arg Leu Gly Trp Ala Val Ile Ala Ser
            325                 330                 335

Arg Ser Gly Ser Thr Pro Leu Phe Phe Ser Arg Pro Glu Gly Gly
        340                 345                 350

Asn Gly Val Arg Phe Pro Gly Lys Ser Gln Ile Gly Asp Arg Gly Ser
    355                 360                 365

Ala Leu Phe Glu Asp Gln Ala Ile Thr Ala Val Asn Arg Phe His Asn
370                 375                 380

Val Met Ala Gly Gln Pro Glu Glu Leu Ser Asn Pro Asn Gly Asn Asn
385                 390                 395                 400

Gln Ile Phe Met Asn Gln Arg Gly Ser His Gly Val Val Leu Ala Asn
                405                 410                 415

Ala Gly Ser Ser Ser Val Ser Ile Asn Thr Ala Thr Lys Leu Pro Asp
            420                 425                 430

Gly Arg Tyr Asp Asn Lys Ala Gly Ala Gly Ser Phe Gln Val Asn Asp
            435                 440                 445

Gly Lys Leu Thr Gly Thr Ile Asn Ala Arg Ser Val Ala Val Leu Tyr
450                 455                 460

Pro Asp Asp Ile Ala Lys Ala Pro His Val Phe Leu Glu Asn Tyr Lys
465                 470                 475                 480

Thr Gly Val Thr His Ser Phe Asn Asp Gln Leu Thr Ile Thr Leu Arg
                485                 490                 495

Ala Asp Ala Asn Thr Thr Lys Ala Val Tyr Gln Ile Asn Asn Gly Pro
            500                 505                 510

Glu Thr Ala Phe Lys Asp Gly Asp Gln Phe Thr Ile Gly Lys Gly Asp
        515                 520                 525

Pro Phe Gly Lys Thr Tyr Thr Ile Met Leu Lys Gly Thr Asn Ser Asp
530                 535                 540

Gly Val Thr Arg Ala Glu Glu Tyr Ser Phe Val Lys Arg Asp Pro Ala
545                 550                 555                 560

Ser Ala Lys Thr Ile Gly Tyr Gln Asn Pro Asn His Trp Ser Gln Val
                565                 570                 575

Asn Ala Tyr Ile Tyr Lys His Asp Gly Gly Arg Ala Ile Glu Leu Thr
            580                 585                 590

Gly Ser Trp Pro Gly Lys Pro Met Thr Lys Asn Ala Asp Gly Ile Tyr
        595                 600                 605

Thr Leu Thr Leu Pro Ala Asp Thr Asp Thr Thr Asn Ala Lys Val Ile
610                 615                 620

Phe Asn Asn Gly Ser Ala Gln Val Pro Gly Gln Asn Gln Pro Gly Phe
625                 630                 635                 640

Asp Tyr Val Gln Asn Gly Leu Tyr Asn Asp Ser Gly Leu Ser Gly Ser
                645                 650                 655

Leu Pro His

<210> SEQ ID NO 31
<211> LENGTH: 659
<212> TYPE: PRT
<213> ORGANISM: Bacillus subtilis

<400> SEQUENCE: 31

Met Phe Ala Lys Arg Phe Lys Thr Ser Leu Leu Pro Leu Phe Ala Gly
1               5                   10                  15
```

```
Phe Leu Leu Leu Phe His Leu Val Leu Ala Gly Pro Ala Ala Ala Ser
             20                  25                  30

Ala Glu Thr Ala Asn Lys Ser Asn Glu Leu Thr Ala Pro Ser Ile Lys
         35                  40                  45

Ser Gly Thr Ile Leu His Ala Trp Asn Trp Ser Phe Asn Thr Leu Lys
 50                  55                  60

His Asn Met Lys Asp Ile His Asp Ala Gly Tyr Thr Ala Ile Gln Thr
 65                  70                  75                  80

Ser Pro Ile Asn Gln Val Lys Glu Gly Asn Gln Gly Asp Lys Ser Met
                 85                  90                  95

Ser Asn Trp Tyr Trp Leu Tyr Gln Pro Thr Ser Tyr Gln Ile Gly Asn
            100                 105                 110

Arg Tyr Leu Gly Thr Glu Gln Glu Phe Lys Glu Met Cys Ala Ala Ala
        115                 120                 125

Glu Glu Tyr Gly Ile Lys Val Ile Val Asp Ala Val Ile Asn His Thr
130                 135                 140

Thr Ser Asp Tyr Ala Ala Ile Ser Asn Glu Val Lys Ser Ile Pro Asn
145                 150                 155                 160

Trp Thr His Gly Asn Thr Gln Ile Lys Asn Trp Ser Asp Arg Trp Asp
                165                 170                 175

Val Thr Gln Asn Ser Leu Leu Gly Leu Tyr Asp Trp Asn Thr Gln Asn
            180                 185                 190

Thr Gln Val Gln Ser Tyr Leu Lys Arg Phe Leu Glu Arg Ala Leu Asn
        195                 200                 205

Asp Gly Ala Asp Gly Phe Arg Phe Asp Ala Ala Lys His Ile Glu Leu
210                 215                 220

Pro Asp Asp Gly Ser Tyr Gly Ser Gln Phe Trp Pro Asn Ile Thr Asn
225                 230                 235                 240

Thr Ser Ala Glu Phe Gln Tyr Gly Glu Ile Leu Gln Asp Ser Ala Ser
                245                 250                 255

Arg Asp Ala Ala Tyr Ala Asn Tyr Met Asp Val Thr Ala Ser Asn Tyr
            260                 265                 270

Gly His Ser Ile Arg Ser Ala Leu Lys Asn Arg Asn Leu Gly Val Ser
        275                 280                 285

Asn Ile Ser His Tyr Ala Ser Asp Val Ser Ala Asp Lys Leu Val Thr
290                 295                 300

Trp Val Glu Ser His Asp Thr Tyr Ala Asn Asp Asp Glu Glu Ser Thr
305                 310                 315                 320

Trp Met Ser Asp Asp Asp Ile Arg Leu Gly Trp Ala Val Ile Ala Ser
                325                 330                 335

Arg Ser Gly Ser Thr Pro Leu Phe Phe Ser Arg Pro Glu Gly Gly Gly
            340                 345                 350

Asn Gly Val Arg Phe Pro Gly Lys Ser Gln Ile Gly Asp Arg Gly Ser
        355                 360                 365

Ala Leu Phe Glu Asp Gln Ala Ile Thr Ala Val Asn Arg Phe His Asn
370                 375                 380

Val Met Ala Gly Gln Pro Glu Glu Leu Ser Asn Pro Asn Gly Asn Asn
385                 390                 395                 400

Gln Ile Phe Met Asn Gln Arg Gly Ser His Gly Val Val Leu Ala Asn
                405                 410                 415

Ala Gly Ser Ser Ser Val Ser Ile Asn Thr Pro Thr Lys Leu Pro Asp
            420                 425                 430

Gly Arg Tyr Asp Asn Lys Ala Gly Ala Gly Ser Phe Gln Val Asn Asp
```

```
                    435                 440                 445
Gly Lys Leu Thr Gly Thr Ile Asn Ala Arg Ser Val Ala Val Leu Tyr
            450                 455                 460
Pro Asp Asp Ile Ala Gln Ala Pro His Val Phe Leu Glu Asn Tyr Lys
465                 470                 475                 480
Thr Gly Val Thr His Ser Phe Asn Asp Gln Leu Thr Ile Thr Leu Arg
                485                 490                 495
Ala Asp Ala Asn Thr Thr Lys Ala Val Tyr Gln Ile Asn Asn Gly Pro
            500                 505                 510
Glu Thr Ala Phe Lys Asp Gly Asp Gln Phe Thr Ile Gly Lys Gly Asp
        515                 520                 525
Pro Phe Gly Lys Thr Tyr Thr Ile Met Leu Lys Gly Thr Asn Ser Asp
    530                 535                 540
Gly Val Thr Arg Thr Glu Glu Tyr Ser Phe Ile Lys Arg Asp Pro Ala
545                 550                 555                 560
Ser Ala Lys Thr Ile Gly Tyr Gln Asn Pro Asn His Trp Ser Gln Val
                565                 570                 575
Asn Ala Tyr Ile Tyr Lys His Asp Gly Gly Gln Ala Ile Glu Leu Thr
            580                 585                 590
Gly Ser Trp Pro Gly Lys Pro Met Thr Lys Asn Ala Asp Gly Ile Tyr
        595                 600                 605
Thr Leu Thr Leu Pro Ala Asp Thr Asp Thr Thr Asn Ala Lys Val Ile
    610                 615                 620
Phe Asn Asn Gly Ser Ala Gln Val Pro Gly Gln Asn Gln Pro Gly Phe
625                 630                 635                 640
Asp Tyr Val Gln Asn Gly Leu Tyr Asn Asp Ser Gly Leu Ser Gly Ser
                645                 650                 655
Leu Pro Tyr

<210> SEQ ID NO 32
<211> LENGTH: 659
<212> TYPE: PRT
<213> ORGANISM: Bacillus subtilis

<400> SEQUENCE: 32

Met Phe Ala Lys Arg Phe Lys Thr Ser Leu Leu Pro Leu Phe Ala Gly
1               5                   10                  15
Phe Leu Leu Leu Phe His Leu Val Leu Ala Gly Pro Asn Ala Ala Asn
                20                  25                  30
Ala Glu Thr Ala Asn Lys Ser Asn Glu Leu Thr Ala Pro Ser Ile Lys
            35                  40                  45
Ser Gly Thr Ile Leu His Ala Trp Asn Trp Ser Phe Asn Thr Leu Lys
        50                  55                  60
His Asn Met Lys Asp Ile His Asp Ala Gly Tyr Thr Ala Ile Gln Thr
65                  70                  75                  80
Ser Pro Ile Asn Gln Val Lys Glu Gly Asn Gly Asn Lys Ser Met
                85                  90                  95
Leu Asn Trp Tyr Trp Leu Tyr Gln Pro Thr Ser Tyr Gln Ile Gly Asn
            100                 105                 110
Arg Tyr Leu Gly Thr Glu Gln Glu Phe Lys Glu Met Cys Ala Ala Ala
        115                 120                 125
Glu Glu Tyr Gly Ile Lys Val Ile Val Asp Ala Val Ile Asn His Thr
    130                 135                 140
Thr Ser Asp Tyr Ala Ala Ile Ser Asn Glu Ile Lys Ser Ile Pro Asn
```

```
                145                 150                 155                 160
Trp Thr His Gly Asn Thr Gln Ile Lys Asn Trp Ser Asp Arg Trp Asp
                    165                 170                 175
Val Thr Gln Asn Ser Leu Leu Gly Leu Tyr Asp Trp Asn Thr Gln Asn
                180                 185                 190
Thr Gln Val Gln Ser Tyr Leu Lys Arg Phe Leu Glu Arg Ala Leu Asn
            195                 200                 205
Asp Gly Ala Asp Gly Phe Arg Phe Asp Ala Ala Lys His Ile Glu Leu
        210                 215                 220
Pro Asp Asp Gly Ser Tyr Gly Ser Gln Phe Trp Pro Asn Ile Thr Asn
225                 230                 235                 240
Thr Ser Ala Glu Phe Gln Tyr Gly Glu Ile Leu Gln Asp Ser Ala Ser
                245                 250                 255
Arg Asp Ala Ser Tyr Ala Asn Tyr Met Asn Val Thr Ala Ser Asn Tyr
                260                 265                 270
Gly His Ser Ile Arg Ser Ala Leu Lys Asn Arg Asn Leu Gly Val Ser
            275                 280                 285
Asn Ile Ser His Tyr Ala Ser Asp Val Pro Ala Asp Lys Leu Val Thr
        290                 295                 300
Trp Val Glu Ser His Asp Thr Tyr Ala Asn Asp Glu Glu Ser Thr
305                 310                 315                 320
Trp Met Ser Asp Asp Ile Arg Leu Gly Trp Ala Val Ile Ala Ser
                325                 330                 335
Arg Ser Gly Ser Thr Pro Leu Phe Phe Ser Arg Pro Glu Gly Gly Gly
            340                 345                 350
Asn Gly Val Arg Phe Pro Gly Lys Ser Gln Ile Gly Asp Arg Gly Ser
        355                 360                 365
Ala Leu Phe Glu Asp Gln Ala Ile Thr Ala Val Asn Arg Phe His Asn
    370                 375                 380
Val Met Ala Gly Gln Pro Glu Glu Leu Ser Asn Pro Asn Gly Asn Asn
385                 390                 395                 400
Gln Ile Phe Met Asn Gln Arg Gly Ser His Gly Val Val Leu Ala Asn
                405                 410                 415
Ala Gly Ser Ser Ser Val Ser Ile Asn Thr Pro Thr Lys Leu Pro Asp
                420                 425                 430
Gly Arg Tyr Asp Asn Lys Ala Gly Ala Gly Ser Phe Gln Val Asn Asp
            435                 440                 445
Gly Lys Leu Thr Gly Thr Ile Asn Ala Arg Ser Val Ala Val Leu Tyr
        450                 455                 460
Pro Asp Asp Ile Ala Lys Ala Pro His Val Phe Leu Glu Asn Tyr Lys
465                 470                 475                 480
Thr Gly Val Thr His Ser Phe Asn Asp Gln Leu Thr Ile Thr Met Arg
                485                 490                 495
Ala Asp Ala Lys Thr Thr Lys Ala Val Tyr Gln Ile Asn Asn Gly Pro
                500                 505                 510
Glu Thr Ala Phe Lys Asp Gly Asp Gln Phe Thr Ile Gly Lys Gly Asp
            515                 520                 525
Pro Phe Gly Lys Thr Tyr Thr Ile Met Leu Lys Gly Thr Asn Ser Asp
        530                 535                 540
Gly Val Thr Arg Thr Glu Glu Tyr Ser Phe Ile Lys Arg Asp Pro Ala
545                 550                 555                 560
Ser Ala Lys Thr Ile Gly Tyr Gln Asn Pro Asn His Trp Ser Gln Val
                565                 570                 575
```

```
Asn Ala Tyr Ile Tyr Lys His Asp Gly Gln Ala Ile Glu Leu Thr
            580                 585                 590

Gly Ser Trp Pro Gly Lys Pro Met Thr Lys Asn Ala Asp Gly Ile Tyr
        595                 600                 605

Thr Leu Thr Leu Pro Ala Asp Thr Asp Thr Thr Asn Ala Lys Val Ile
610                 615                 620

Phe Asn Asn Gly Ser Ala Gln Val Pro Gly Gln Asn Gln Pro Gly Phe
625                 630                 635                 640

Asp Tyr Val Gln Asn Gly Leu Tyr Asn Asp Ser Gly Leu Ser Gly Ser
            645                 650                 655

Leu Pro His

<210> SEQ ID NO 33
<211> LENGTH: 649
<212> TYPE: PRT
<213> ORGANISM: Bacillus subtilis
<220> FEATURE:
<221> NAME/KEY: misc_feature
<222> LOCATION: (512)..(512)
<223> OTHER INFORMATION: Xaa can be any naturally occurring amino acid
<220> FEATURE:
<221> NAME/KEY: misc_feature
<222> LOCATION: (514)..(514)
<223> OTHER INFORMATION: Xaa can be any naturally occurring amino acid
<220> FEATURE:
<221> NAME/KEY: misc_feature
<222> LOCATION: (550)..(550)
<223> OTHER INFORMATION: Xaa can be any naturally occurring amino acid

<400> SEQUENCE: 33

Met Phe Ala Lys Arg Phe Lys Thr Ser Leu Leu Pro Leu Phe Ala Gly
1               5                   10                  15

Phe Leu Leu Leu Phe Tyr Leu Val Leu Ala Gly Pro Ala Ala Ala Ser
            20                  25                  30

Ala Glu Thr Ala Asn Lys Ser Ile Glu Leu Thr Ala Pro Ser Ile Lys
        35                  40                  45

Ser Gly Thr Ile Leu His Ala Trp Asn Trp Ser Phe Asn Thr Leu Lys
50                  55                  60

His Asn Met Lys Asp Ile His Asp Ala Gly Tyr Thr Ala Ile Gln Thr
65                  70                  75                  80

Ser Pro Ile Asn Gln Val Lys Glu Gly Asn Gln Gly Asp Lys Ser Met
            85                  90                  95

Ser Asn Trp Tyr Trp Leu Tyr Gln Pro Thr Ser Tyr Gln Ile Gly Asn
        100                 105                 110

Arg Tyr Leu Gly Thr Glu Gln Glu Phe Lys Glu Met Cys Ala Ala Ala
        115                 120                 125

Glu Glu Tyr Gly Ile Lys Val Ile Val Asp Ala Val Ile Asn His Thr
130                 135                 140

Thr Ser Asp Tyr Ala Ala Ile Ser Asn Glu Val Lys Ser Ile Pro Asn
145                 150                 155                 160

Trp Thr His Gly Asn Thr Gln Ile Lys Asn Trp Ser Asp Arg Trp Asp
            165                 170                 175

Val Thr Gln Asn Ser Leu Leu Gly Leu Tyr Asp Trp Asn Thr Gln Asn
        180                 185                 190

Thr Gln Val Gln Ser Tyr Leu Lys Arg Phe Leu Asp Arg Ala Leu Asn
        195                 200                 205

Asp Gly Ala Asp Gly Phe Arg Phe Asp Ala Ala Lys His Ile Glu Leu
210                 215                 220
```

```
Pro Asp Asp Gly Ser Tyr Gly Ser Gln Phe Trp Pro Asn Ile Thr Asn
225                 230                 235                 240

Thr Ser Ala Glu Phe Gln Tyr Gly Glu Ile Leu Gln Asp Ser Ala Ser
            245                 250                 255

Arg Asp Ala Ala Tyr Ala Asn Tyr Met Asp Val Thr Ala Ser Asn Tyr
        260                 265                 270

Gly His Ser Ile Arg Ser Ala Leu Lys Asn Arg Asn Leu Gly Val Ser
    275                 280                 285

Asn Ile Ser His Tyr Ala Ser Asp Val Ser Ala Asp Lys Leu Val Thr
290                 295                 300

Trp Val Glu Ser His Asp Thr Tyr Ala Asn Asp Glu Glu Ser Thr
305                 310                 315                 320

Trp Met Ser Asp Asp Ile Arg Leu Gly Trp Ala Val Ile Ala Ser
                325                 330                 335

Arg Ser Gly Ser Thr Pro Leu Phe Phe Ser Arg Pro Glu Gly Gly Gly
            340                 345                 350

Asn Gly Val Arg Phe Pro Gly Lys Ser Gln Ile Gly Asp Arg Gly Ser
        355                 360                 365

Ala Leu Phe Glu Asp Gln Ala Ile Thr Ala Val Asn Arg Phe His Asn
370                 375                 380

Val Met Ala Gly Gln Pro Glu Glu Leu Ser Asn Pro Asn Gly Asn Asn
385                 390                 395                 400

Gln Ile Phe Met Asn Gln Arg Ile Ser His Gly Val Val Leu Ala Asn
                405                 410                 415

Ala Gly Ser Ser Ser Val Ser Ile Asn Thr Ala Thr Lys Leu Pro Asp
            420                 425                 430

Gly Arg Tyr Asp Asn Lys Ala Gly Ala Gly Ser Phe Gln Val Asn Asp
        435                 440                 445

Gly Lys Leu Thr Gly Thr Ile Asn Ala Arg Ser Val Ala Val Leu Tyr
    450                 455                 460

Pro Asp Asp Ile Ala Lys Ala Pro His Val Phe Leu Glu Asn Tyr Lys
465                 470                 475                 480

Thr Gly Val Thr His Ser Phe Asn Asp Gln Leu Thr Ile Thr Leu Arg
                485                 490                 495

Ala Asp Ala Asn Thr Phe Ile Lys Ser Ile Met Asp Gln Ile Asn Xaa
            500                 505                 510

Arg Xaa Arg Arg Leu Arg Met Glu Ile Asn Ser Gln Ser Glu Lys Glu
        515                 520                 525

Ile Gln Phe Gly Lys Thr Tyr Thr Ile Met Leu Lys Gly Thr Asn Ser
    530                 535                 540

Asp Gly Val Thr Arg Xaa Glu Lys Tyr Ser Leu Pro Lys Arg Asp Pro
545                 550                 555                 560

Ala Ser Ala Lys Thr Ile Gly Tyr Gln Asn Pro Asn His Trp Ser Gln
                565                 570                 575

Val Asn Ala Tyr Ile Tyr Lys His Asp Gly Ser Arg Glu Ile Glu Leu
            580                 585                 590

Thr Gly Ser Trp Pro Gly Lys Pro Met Thr Lys Asn Ala Asp Gly Ile
        595                 600                 605

Tyr Thr Leu Thr Leu Pro Ala Asp Thr Asp Thr Thr Asn Ala Lys Val
    610                 615                 620

Ile Phe Asn Asn Gly Tyr Ala Gln Val Pro Gly Gln Asn Gln Pro Gly
625                 630                 635                 640
```

-continued

```
Phe Asp Tyr Val Leu Asn Gly Leu Tyr
                645

<210> SEQ ID NO 34
<211> LENGTH: 659
<212> TYPE: PRT
<213> ORGANISM: Bacillus subtilis

<400> SEQUENCE: 34

Met Phe Glu Lys Arg Phe Lys Thr Ser Leu Leu Pro Leu Phe Ala Gly
1               5                   10                  15

Phe Leu Leu Leu Phe His Leu Val Leu Ser Gly Pro Ala Ala Ala Asn
                20                  25                  30

Ala Glu Thr Ala Asn Lys Ser Asn Lys Val Thr Ala Ser Ser Val Lys
            35                  40                  45

Asn Gly Thr Ile Leu His Ala Trp Asn Trp Ser Phe Asn Thr Leu Thr
    50                  55                  60

Gln Asn Met Lys Asp Ile Arg Asp Ala Gly Tyr Ala Ala Ile Gln Thr
65                  70                  75                  80

Ser Pro Ile Asn Gln Val Lys Glu Gly Asn Gln Gly Asp Lys Ser Met
                85                  90                  95

Ser Asn Trp Tyr Trp Leu Tyr Gln Pro Thr Ser Tyr Gln Ile Gly Asn
                100                 105                 110

Arg Tyr Leu Gly Thr Glu Gln Glu Phe Lys Asp Met Cys Ala Ala Ala
            115                 120                 125

Glu Lys Tyr Gly Val Lys Val Ile Val Asp Ala Val Val Asn His Thr
            130                 135                 140

Thr Ser Asp Tyr Gly Ala Ile Ser Asp Glu Ile Lys Arg Ile Pro Asn
145                 150                 155                 160

Trp Thr His Gly Asn Thr Gln Ile Lys Asn Trp Ser Asp Arg Trp Asp
                165                 170                 175

Ile Thr Gln Asn Ala Leu Leu Gly Leu Tyr Asp Trp Asn Thr Gln Asn
                180                 185                 190

Thr Glu Val Gln Ala Tyr Leu Lys Gly Phe Leu Glu Arg Ala Leu Asn
            195                 200                 205

Asp Gly Ala Asp Gly Phe Arg Tyr Asp Ala Ala Lys His Ile Glu Leu
    210                 215                 220

Pro Asp Asp Gly Asn Tyr Gly Ser Gln Phe Trp Pro Asn Ile Thr Asn
225                 230                 235                 240

Thr Ser Ala Glu Phe Gln Tyr Gly Glu Ile Leu Gln Asp Ser Ala Ser
                245                 250                 255

Arg Asp Thr Ala Tyr Ala Asn Tyr Met Asn Val Thr Ala Ser Asn Tyr
            260                 265                 270

Gly His Ser Ile Arg Ser Ala Leu Lys Asn Arg Ile Leu Ser Val Ser
            275                 280                 285

Asn Ile Ser His Tyr Ala Ser Asp Val Ser Ala Asp Lys Leu Val Thr
    290                 295                 300

Trp Val Glu Ser His Asp Thr Tyr Ala Asn Asp Asp Glu Glu Ser Thr
305                 310                 315                 320

Trp Met Ser Asp Asp Ile Arg Leu Gly Trp Ala Val Ile Gly Ser
                325                 330                 335

Arg Ser Gly Ser Thr Pro Leu Phe Phe Ser Arg Pro Glu Gly Gly Gly
            340                 345                 350

Asn Gly Val Arg Phe Pro Gly Lys Ser Gln Ile Gly Asp Arg Gly Ser
            355                 360                 365
```

```
Ala Leu Phe Lys Asp Gln Ala Ile Thr Ala Val Asn Gln Phe His Asn
        370                 375                 380

Glu Met Ala Gly Gln Pro Glu Glu Leu Ser Asn Pro Asn Gly Asn Asn
385                 390                 395                 400

Gln Ile Phe Met Asn Gln Arg Gly Ser Lys Gly Val Val Leu Ala Asn
                405                 410                 415

Ala Gly Ser Ser Ser Val Thr Ile Asn Thr Ser Thr Lys Leu Pro Asp
            420                 425                 430

Gly Arg Tyr Asp Asn Arg Ala Gly Ala Gly Ser Phe Gln Val Ala Asn
        435                 440                 445

Gly Lys Leu Thr Gly Thr Ile Asn Ala Arg Ser Ala Ala Val Leu Tyr
    450                 455                 460

Pro Asp Asp Ile Gly Asn Ala Pro His Val Phe Leu Glu Asn Tyr Gln
465                 470                 475                 480

Thr Glu Ala Val His Ser Phe Asn Asp Gln Leu Thr Val Thr Leu Arg
                485                 490                 495

Ala Asn Ala Lys Thr Thr Lys Ala Val Tyr Gln Ile Asn Asn Gly Gln
            500                 505                 510

Glu Thr Ala Phe Lys Asp Gly Asp Arg Leu Thr Ile Gly Lys Glu Asp
        515                 520                 525

Pro Ile Gly Thr Thr Tyr Asn Val Lys Leu Thr Gly Thr Asn Gly Glu
530                 535                 540

Gly Ala Ser Arg Thr Gln Glu Tyr Thr Phe Val Lys Lys Asp Pro Ser
545                 550                 555                 560

Gln Thr Asn Ile Ile Gly Tyr Gln Asn Pro Asp His Trp Gly Asn Val
                565                 570                 575

Asn Ala Tyr Ile Tyr Lys His Asp Gly Gly Ala Ile Glu Leu Thr
            580                 585                 590

Gly Ser Trp Pro Gly Lys Ala Met Thr Lys Asn Ala Asp Gly Ile Tyr
        595                 600                 605

Thr Leu Thr Leu Pro Ala Asn Ala Asp Thr Ala Asp Ala Lys Val Ile
    610                 615                 620

Phe Asn Asn Gly Ser Ala Gln Val Pro Gly Gln Asn His Pro Gly Phe
625                 630                 635                 640

Asp Tyr Val Gln Asn Gly Leu Tyr Asn Asn Ser Gly Leu Asn Gly Tyr
                645                 650                 655

Leu Pro His

<210> SEQ ID NO 35
<211> LENGTH: 618
<212> TYPE: PRT
<213> ORGANISM: Bacillus subtilis

<400> SEQUENCE: 35

Val Thr Ala Ser Ser Val Lys Asn Gly Thr Ile Leu His Ala Trp Asn
1               5                   10                  15

Trp Ser Phe Asn Thr Leu Thr Gln Asn Met Lys Asp Ile Arg Asp Ala
                20                  25                  30

Gly Tyr Ala Ala Ile Gln Thr Ser Pro Ile Asn Gln Val Lys Glu Gly
            35                  40                  45

Asn Gln Gly Asp Lys Ser Met Ser Asn Trp Tyr Trp Leu Tyr Gln Pro
        50                  55                  60

Thr Ser Tyr Gln Ile Gly Asn Arg Tyr Leu Gly Thr Glu Gln Glu Phe
65                  70                  75                  80
```

-continued

```
Lys Asp Met Cys Ala Ala Glu Lys Tyr Gly Val Lys Val Ile Val
                85                  90                  95
Asp Ala Val Val Asn His Thr Thr Ser Asp Tyr Gly Ala Ile Ser Asp
            100                 105                 110
Glu Ile Lys Arg Ile Pro Asn Trp Thr His Gly Asn Thr Gln Ile Lys
            115                 120                 125
Asn Trp Ser Asp Arg Trp Asp Ile Thr Gln Asn Ala Leu Leu Gly Leu
130                 135                 140
Tyr Asp Trp Asn Thr Gln Asn Thr Glu Val Gln Ala Tyr Leu Lys Gly
145                 150                 155                 160
Phe Leu Glu Arg Ala Leu Asn Asp Gly Ala Asp Gly Phe Arg Tyr Asp
                165                 170                 175
Ala Ala Lys His Ile Glu Leu Pro Asp Asp Gly Asn Tyr Gly Ser Gln
            180                 185                 190
Phe Trp Pro Asn Ile Thr Asn Thr Ser Ala Glu Phe Gln Tyr Gly Glu
            195                 200                 205
Ile Leu Gln Asp Ser Ala Ser Arg Asp Thr Ala Tyr Ala Asn Tyr Met
        210                 215                 220
Asn Val Thr Ala Ser Asn Tyr Gly His Ser Ile Arg Ser Ala Leu Lys
225                 230                 235                 240
Asn Arg Ile Leu Ser Val Ser Asn Ile Ser His Tyr Ala Ser Asp Val
                245                 250                 255
Ser Ala Asp Lys Leu Val Thr Trp Val Glu Ser His Asp Thr Tyr Ala
            260                 265                 270
Asn Asp Asp Glu Glu Ser Thr Trp Met Ser Asp Asp Ile Arg Leu
            275                 280                 285
Gly Trp Ala Val Ile Gly Ser Arg Ser Gly Ser Thr Pro Leu Phe Phe
290                 295                 300
Ser Arg Pro Glu Gly Gly Gly Asn Gly Val Arg Phe Pro Gly Lys Ser
305                 310                 315                 320
Gln Ile Gly Asp Arg Gly Ser Ala Leu Phe Lys Asp Gln Ala Ile Thr
                325                 330                 335
Ala Val Asn Gln Phe His Asn Glu Met Ala Gly Gln Pro Glu Glu Leu
            340                 345                 350
Ser Asn Pro Asn Gly Asn Asn Gln Ile Phe Met Asn Gln Arg Gly Ser
            355                 360                 365
Lys Gly Val Val Leu Ala Asn Ala Gly Ser Ser Ser Val Thr Ile Asn
370                 375                 380
Thr Ser Thr Lys Leu Pro Asp Gly Arg Tyr Asp Asn Arg Ala Gly Ala
385                 390                 395                 400
Gly Ser Phe Gln Val Ala Asn Gly Lys Leu Thr Gly Thr Ile Asn Ala
                405                 410                 415
Arg Ser Ala Ala Val Leu Tyr Pro Asp Asp Ile Gly Asn Ala Pro His
            420                 425                 430
Val Phe Leu Glu Asn Tyr Gln Thr Glu Ala Val His Ser Phe Asn Asp
            435                 440                 445
Gln Leu Thr Val Thr Leu Arg Ala Asn Ala Lys Thr Thr Lys Ala Val
        450                 455                 460
Tyr Gln Ile Asn Asn Gly Gln Glu Thr Ala Phe Lys Asp Gly Asp Arg
465                 470                 475                 480
Leu Thr Ile Gly Lys Glu Asp Pro Ile Gly Thr Thr Tyr Asn Val Lys
                485                 490                 495
```

-continued

```
Leu Thr Gly Thr Asn Gly Glu Gly Ala Ser Arg Thr Gln Glu Tyr Thr
            500                 505                 510

Phe Val Lys Lys Asp Pro Ser Gln Thr Asn Ile Ile Gly Tyr Gln Asn
        515                 520                 525

Pro Asp His Trp Gly Asn Val Asn Ala Tyr Ile Tyr Lys His Asp Gly
        530                 535                 540

Gly Gly Ala Ile Glu Leu Thr Gly Ser Trp Pro Gly Lys Ala Met Thr
545                 550                 555                 560

Lys Asn Ala Asp Gly Ile Tyr Thr Leu Thr Leu Pro Ala Asn Ala Asp
                565                 570                 575

Thr Ala Asp Ala Lys Val Ile Phe Asn Asn Gly Ser Ala Gln Val Pro
            580                 585                 590

Gly Gln Asn His Pro Gly Phe Asp Tyr Val Gln Asn Gly Leu Tyr Asn
        595                 600                 605

Asn Ser Gly Leu Asn Gly Tyr Leu Pro His
        610                 615
```